United States Patent
Williams et al.

(10) Patent No.: US 10,963,129 B2
(45) Date of Patent: Mar. 30, 2021

(54) DISPLAYING A SCROLLABLE LIST OF AFFORDANCES ASSOCIATED WITH PHYSICAL ACTIVITIES

(71) Applicant: Apple Inc., Cupertino, CA (US)

(72) Inventors: Aled Hywel Williams, San Francisco, CA (US); Gary Ian Butcher, San Jose, CA (US); Stephen O. Lemay, San Francisco, CA (US); Christopher D. Soli, Mountain View, CA (US); Molly Pray Wiebe, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 16/144,753

(22) Filed: Sep. 27, 2018

(65) Prior Publication Data
US 2019/0034050 A1 Jan. 31, 2019

Related U.S. Application Data

(63) Continuation of application No. 15/705,849, filed on Sep. 15, 2017, now Pat. No. 10,845,955.
(Continued)

(51) Int. Cl.
*G06F 3/0482* (2013.01)
*A63B 24/00* (2006.01)
(Continued)

(52) U.S. Cl.
CPC .......... *G06F 3/0482* (2013.01); *A61B 5/0205* (2013.01); *A61B 5/1112* (2013.01);
(Continued)

(58) Field of Classification Search
CPC .................................................... G06F 3/0482
(Continued)

(56) References Cited

U.S. PATENT DOCUMENTS

| 4,205,628 A | 6/1980 | Null |
| 4,842,266 A | 6/1989 | Sweeney et al. |

(Continued)

FOREIGN PATENT DOCUMENTS

| CA | 2815518 A1 | 5/2012 |
| CN | 1337638 A | 2/2002 |

(Continued)

OTHER PUBLICATIONS

"Graphs and Charts", Online available at: <https://www.teachervision.com/lesson-planning/graph-chart-teacher-resources, retrieved on Dec. 12, 2018, 4 pages.

(Continued)

*Primary Examiner* — Reza Nabi
(74) *Attorney, Agent, or Firm* — Dentons US LLP

(57) ABSTRACT

The present disclosure generally relates to managing user interfaces associated with physical activities. The user interface displays a scrollable list of affordances associated with physical activities. The affordances may contain physical activity and heart rate information. A user can launch a physical activity tracking function or an interface to change a workout metric using an affordance. Users can also control the music that is played in response to selecting a workout. Further, the interface can be used to compose a reply message to a received message that contains workout information. The interfaces can show a graph that includes heart data when the user's heart rate meets a heart rate alert criteria.

15 Claims, 71 Drawing Sheets

Related U.S. Application Data

(60) Provisional application No. 62/506,304, filed on May 15, 2017.

(51) Int. Cl.

| | | |
|---|---|---|
| *G06F 3/0481* | (2013.01) | |
| *G06F 3/0484* | (2013.01) | |
| *H04W 4/02* | (2018.01) | |
| *A61B 5/00* | (2006.01) | |
| *G06F 3/0488* | (2013.01) | |
| *G06F 3/0485* | (2013.01) | |
| *A61B 5/11* | (2006.01) | |
| *A61B 5/0205* | (2006.01) | |
| *A63B 69/00* | (2006.01) | |
| *A63B 71/06* | (2006.01) | |
| *G06F 1/16* | (2006.01) | |

(52) U.S. Cl.
CPC ........... *A61B 5/1116* (2013.01); *A61B 5/1118* (2013.01); *A61B 5/1123* (2013.01); *A61B 5/6801* (2013.01); *A61B 5/6898* (2013.01); *A61B 5/7435* (2013.01); *A63B 24/0062* (2013.01); *A63B 24/0075* (2013.01); *G06F 3/0484* (2013.01); *G06F 3/0485* (2013.01); *G06F 3/0488* (2013.01); *G06F 3/04817* (2013.01); *G06F 3/04886* (2013.01); *H04W 4/02* (2013.01); *A61B 2503/10* (2013.01); *A63B 69/0028* (2013.01); *A63B 2024/0065* (2013.01); *A63B 2024/0068* (2013.01); *A63B 2024/0071* (2013.01); *A63B 2071/0658* (2013.01); *A63B 2220/62* (2013.01); *G06F 1/163* (2013.01); *G06F 2203/04105* (2013.01)

(58) Field of Classification Search
USPC ........................................................ 715/784
See application file for complete search history.

(56) References Cited

U.S. PATENT DOCUMENTS

| | | | |
|---|---|---|---|
| 5,423,863 A * | 6/1995 | Felblinger | A61B 5/046 607/5 |
| 5,642,731 A | 7/1997 | Kehr | |
| 5,788,655 A * | 8/1998 | Yoshimura | A61B 5/222 600/587 |
| 6,013,008 A | 1/2000 | Fukushima | |
| 6,095,949 A | 8/2000 | Arai | |
| 6,095,984 A * | 8/2000 | Amano | A61B 5/02438 600/481 |
| 6,097,371 A | 8/2000 | Siddiqui et al. | |
| 6,244,988 B1 | 6/2001 | Delman | |
| 6,416,471 B1 | 7/2002 | Kumar et al. | |
| 6,603,477 B1 | 8/2003 | Tittle | |
| 6,639,584 B1 | 10/2003 | Li | |
| 6,705,972 B1 | 3/2004 | Takano et al. | |
| 6,837,827 B1 * | 1/2005 | Lee | G01S 19/19 482/8 |
| 6,866,613 B1 | 3/2005 | Brown et al. | |
| 7,020,514 B1 | 3/2006 | Wiesel | |
| 7,128,693 B2 | 10/2006 | Brown et al. | |
| 7,251,454 B2 * | 7/2007 | White | A63B 24/0021 455/41.1 |
| 7,662,065 B1 * | 2/2010 | Kahn | G16H 20/30 482/9 |
| 7,739,148 B2 | 6/2010 | Suzuki et al. | |
| 8,105,208 B2 | 1/2012 | Oleson et al. | |
| 8,321,006 B1 | 11/2012 | Snyder et al. | |
| 8,341,557 B2 * | 12/2012 | Pisula | G06F 3/04886 715/863 |
| 8,475,339 B2 | 7/2013 | Hwang et al. | |
| 8,676,170 B2 | 3/2014 | Porrati et al. | |
| 8,784,115 B1 | 7/2014 | Chuang | |
| 8,825,445 B2 | 9/2014 | Hoffman et al. | |
| 8,934,963 B1 * | 1/2015 | Farazi | A61N 1/36592 600/516 |
| 8,990,006 B1 * | 3/2015 | Wallace | G01C 22/006 701/408 |
| 9,020,538 B1 * | 4/2015 | White | G01W 1/00 455/456.3 |
| 9,026,927 B2 | 5/2015 | Brumback et al. | |
| 9,224,291 B2 | 12/2015 | Moll-carrillo et al. | |
| 9,557,881 B1 * | 1/2017 | Jain | G06F 3/0481 |
| 9,589,445 B2 | 3/2017 | White et al. | |
| 9,712,629 B2 | 7/2017 | Molettiere et al. | |
| 9,734,477 B2 | 8/2017 | Weast et al. | |
| 9,801,562 B1 | 10/2017 | Host-Madsen | |
| 9,813,642 B1 | 11/2017 | Chen et al. | |
| 9,817,481 B2 | 11/2017 | Pantelopoulos et al. | |
| 9,854,653 B1 | 12/2017 | Ackmann et al. | |
| 9,880,805 B1 | 1/2018 | Guralnick | |
| 9,940,682 B2 | 4/2018 | Hoffman et al. | |
| 10,175,781 B2 | 1/2019 | Karagozler et al. | |
| 10,300,334 B1 | 5/2019 | Chuang | |
| 10,304,347 B2 | 5/2019 | Wilson et al. | |
| 10,339,830 B2 * | 7/2019 | Han | G09B 5/062 |
| 10,398,381 B1 * | 9/2019 | Heneghan | A61B 5/7282 |
| 10,777,314 B1 | 9/2020 | Williams et al. | |
| 2001/0049470 A1 | 12/2001 | Mault et al. | |
| 2002/0045960 A1 | 4/2002 | Phillips et al. | |
| 2002/0086774 A1 | 7/2002 | Warner | |
| 2002/0118121 A1 | 8/2002 | Lehrman et al. | |
| 2003/0023178 A1 * | 1/2003 | Bischoff | A61B 5/02405 600/515 |
| 2003/0064860 A1 | 4/2003 | Yamashita et al. | |
| 2003/0181291 A1 | 9/2003 | Ogawa | |
| 2003/0182628 A1 | 9/2003 | Lira | |
| 2003/0216971 A1 | 11/2003 | Sick et al. | |
| 2003/0226695 A1 | 12/2003 | Mault | |
| 2004/0014567 A1 | 1/2004 | Mendel | |
| 2004/0017300 A1 | 1/2004 | Kotzin et al. | |
| 2004/0077462 A1 | 4/2004 | Brown et al. | |
| 2004/0128286 A1 | 7/2004 | Yasushi et al. | |
| 2005/0010117 A1 | 1/2005 | Agutter et al. | |
| 2005/0075214 A1 | 4/2005 | Brown et al. | |
| 2005/0079905 A1 | 4/2005 | Martens | |
| 2005/0124324 A1 * | 6/2005 | Thomas | H04M 3/436 455/412.1 |
| 2005/0139852 A1 | 6/2005 | Chen et al. | |
| 2005/0172311 A1 | 8/2005 | Hjelt et al. | |
| 2005/0197063 A1 | 9/2005 | White | |
| 2005/0216867 A1 | 9/2005 | Marvit et al. | |
| 2005/0228735 A1 | 10/2005 | Duquette | |
| 2005/0272564 A1 | 12/2005 | Pyles et al. | |
| 2006/0020174 A1 | 1/2006 | Matsumura et al. | |
| 2006/0052727 A1 * | 3/2006 | Palestrant | A61B 5/681 600/595 |
| 2006/0098109 A1 | 5/2006 | Ooki | |
| 2006/0106741 A1 | 5/2006 | Janarthanan | |
| 2006/0149144 A1 | 7/2006 | Lynn et al. | |
| 2006/0152372 A1 | 7/2006 | Stout | |
| 2006/0235319 A1 | 10/2006 | Belohlavek et al. | |
| 2006/0250524 A1 * | 11/2006 | Roche | A63B 22/00 348/581 |
| 2007/0021269 A1 | 1/2007 | Shum | |
| 2007/0032733 A1 * | 2/2007 | Burton | A61B 5/4812 600/509 |
| 2007/0056727 A1 | 3/2007 | Newman | |
| 2007/0113726 A1 | 5/2007 | Oliver et al. | |
| 2007/0136093 A1 | 6/2007 | Rankin et al. | |
| 2007/0143433 A1 * | 6/2007 | Daigle | H04L 67/24 709/207 |
| 2007/0249949 A1 | 10/2007 | Hadley | |
| 2007/0271065 A1 | 11/2007 | Gupta et al. | |
| 2008/0052945 A1 | 3/2008 | Matas et al. | |
| 2008/0058626 A1 | 3/2008 | Miyata et al. | |
| 2008/0076637 A1 | 3/2008 | Gilley et al. | |
| 2008/0086318 A1 | 4/2008 | Gilley et al. | |
| 2008/0096726 A1 * | 4/2008 | Riley | A63B 24/0075 482/8 |

(56) References Cited

U.S. PATENT DOCUMENTS

| | | |
|---|---|---|
| 2008/0141135 A1 | 6/2008 | Mason et al. |
| 2008/0150731 A1 | 6/2008 | Laukkanen et al. |
| 2008/0161707 A1* | 7/2008 | Farringdon ........ A61B 5/04012 600/509 |
| 2008/0200312 A1 | 8/2008 | Tagliabue |
| 2008/0240519 A1 | 10/2008 | Nagamitsu |
| 2008/0300110 A1 | 12/2008 | Smith et al. |
| 2009/0012988 A1 | 1/2009 | Brown |
| 2009/0118100 A1 | 5/2009 | Oliver et al. |
| 2009/0164567 A1 | 6/2009 | Hara |
| 2009/0192823 A1 | 7/2009 | Hawkins et al. |
| 2009/0210078 A1 | 8/2009 | Crowley |
| 2009/0216556 A1 | 8/2009 | Martin et al. |
| 2009/0222056 A1* | 9/2009 | Lindh ................ A61N 1/37282 607/30 |
| 2009/0233771 A1 | 9/2009 | Quatrochi et al. |
| 2009/0262088 A1 | 10/2009 | Moll-carrillo et al. |
| 2009/0287103 A1 | 11/2009 | Pillai |
| 2009/0319243 A1 | 12/2009 | Suarez-rivera et al. |
| 2010/0003951 A1 | 1/2010 | Ray et al. |
| 2010/0010832 A1 | 1/2010 | Boute et al. |
| 2010/0017489 A1 | 1/2010 | Birnbaum et al. |
| 2010/0031202 A1 | 2/2010 | Morris et al. |
| 2010/0042949 A1 | 2/2010 | Chen |
| 2010/0048358 A1 | 2/2010 | Tchao et al. |
| 2010/0060586 A1* | 3/2010 | Pisula ................ G06F 3/04886 345/169 |
| 2010/0062818 A1 | 3/2010 | Haughay et al. |
| 2010/0062905 A1* | 3/2010 | Rottler .................. G16H 20/30 482/9 |
| 2010/0064255 A1* | 3/2010 | Rottler .................. G06F 3/0482 715/821 |
| 2010/0076331 A1 | 3/2010 | Chan et al. |
| 2010/0079291 A1 | 4/2010 | Kroll et al. |
| 2010/0121700 A1 | 5/2010 | Wigder et al. |
| 2010/0145209 A1* | 6/2010 | Lee ........................ G16H 40/63 600/519 |
| 2010/0179832 A1 | 7/2010 | Van et al. |
| 2010/0194692 A1 | 8/2010 | Orr et al. |
| 2010/0198453 A1 | 8/2010 | Dorogusker et al. |
| 2010/0281374 A1 | 11/2010 | Schulz et al. |
| 2010/0292600 A1 | 11/2010 | Dibenedetto et al. |
| 2010/0298899 A1* | 11/2010 | Donnelly ............. A61B 5/6805 607/6 |
| 2010/0305965 A1 | 12/2010 | Benjamin et al. |
| 2010/0331145 A1 | 12/2010 | Lakovic et al. |
| 2011/0003665 A1 | 1/2011 | Burton et al. |
| 2011/0016120 A1 | 1/2011 | Haughay et al. |
| 2011/0066051 A1 | 3/2011 | Moon et al. |
| 2011/0071869 A1* | 3/2011 | O'Brien ................ G06Q 10/103 705/7.12 |
| 2011/0074699 A1 | 3/2011 | Marr et al. |
| 2011/0098928 A1* | 4/2011 | Hoffman ............ A63B 71/0622 702/5 |
| 2011/0112418 A1* | 5/2011 | Feild ..................... A61B 5/0464 600/509 |
| 2011/0125041 A1* | 5/2011 | Fischell ............... A61B 5/0456 600/515 |
| 2011/0137678 A1* | 6/2011 | Williams ............... G16H 40/67 705/3 |
| 2011/0137836 A1 | 6/2011 | Kuriyama et al. |
| 2011/0167369 A1 | 7/2011 | Van Os |
| 2011/0201911 A1 | 8/2011 | Johnson et al. |
| 2011/0213276 A1 | 9/2011 | Sarussi et al. |
| 2011/0227872 A1 | 9/2011 | Huska et al. |
| 2011/0230169 A1* | 9/2011 | Ohki ................... G08G 1/096838 455/412.1 |
| 2011/0230986 A1 | 9/2011 | Lafortune et al. |
| 2011/0245623 A1 | 10/2011 | Chutani et al. |
| 2011/0246509 A1 | 10/2011 | Migita et al. |
| 2011/0261079 A1* | 10/2011 | Ingrassia, Jr. ....... A63B 71/0622 345/665 |
| 2011/0275940 A1 | 11/2011 | Nims et al. |
| 2011/0306389 A1 | 12/2011 | Nagayama |
| 2011/0307821 A1 | 12/2011 | Martens |
| 2012/0015778 A1* | 1/2012 | Lee ..................... A63B 71/0686 482/8 |
| 2012/0015779 A1* | 1/2012 | Powch ............... A61B 5/02055 482/9 |
| 2012/0029303 A1 | 2/2012 | Shaya |
| 2012/0030623 A1 | 2/2012 | Hoellwarth |
| 2012/0034897 A1* | 2/2012 | Kreitzer ............ H04M 3/42382 455/404.1 |
| 2012/0038651 A1 | 2/2012 | Case et al. |
| 2012/0041767 A1* | 2/2012 | Hoffman ............ A63B 24/0062 705/1.1 |
| 2012/0042039 A1* | 2/2012 | Mark .................... G16H 50/20 709/217 |
| 2012/0065480 A1 | 3/2012 | Badilini et al. |
| 2012/0071770 A1 | 3/2012 | Grey et al. |
| 2012/0092383 A1 | 4/2012 | Hysek et al. |
| 2012/0105225 A1 | 5/2012 | Valtonen |
| 2012/0116550 A1* | 5/2012 | Hoffman ............ A63B 24/0084 700/91 |
| 2012/0232414 A1* | 9/2012 | Mollicone ............ A61B 5/024 600/508 |
| 2012/0245447 A1 | 9/2012 | Karan et al. |
| 2012/0253485 A1 | 10/2012 | Weast et al. |
| 2012/0274508 A1 | 11/2012 | Brown et al. |
| 2012/0283587 A1 | 11/2012 | Gosh et al. |
| 2012/0302840 A1 | 11/2012 | Kubo |
| 2012/0317167 A1 | 12/2012 | Rahman et al. |
| 2012/0326873 A1 | 12/2012 | Utter, II |
| 2013/0054150 A1 | 2/2013 | Sacks et al. |
| 2013/0054720 A1* | 2/2013 | Kang .................... G06Q 50/01 709/206 |
| 2013/0065569 A1 | 3/2013 | Leipzig et al. |
| 2013/0067050 A1* | 3/2013 | Kotteri .................. H04L 65/60 709/223 |
| 2013/0081083 A1 | 3/2013 | Yu et al. |
| 2013/0093715 A1 | 4/2013 | Marsden et al. |
| 2013/0106603 A1 | 5/2013 | Weast et al. |
| 2013/0106684 A1 | 5/2013 | Weast et al. |
| 2013/0110264 A1 | 5/2013 | Weast et al. |
| 2013/0114100 A1 | 5/2013 | Torii et al. |
| 2013/0115583 A1 | 5/2013 | Gordon et al. |
| 2013/0132028 A1 | 5/2013 | Crankson et al. |
| 2013/0137073 A1 | 5/2013 | Nacey et al. |
| 2013/0141233 A1 | 6/2013 | Jacobs et al. |
| 2013/0151285 A1 | 6/2013 | Mclaren et al. |
| 2013/0158416 A1 | 6/2013 | Hatlestad et al. |
| 2013/0184613 A1 | 7/2013 | Homsi et al. |
| 2013/0187923 A1 | 7/2013 | Yoshimoto et al. |
| 2013/0188322 A1 | 7/2013 | Lowe |
| 2013/0197679 A1 | 8/2013 | Balakrishnan et al. |
| 2013/0198672 A1 | 8/2013 | Yoon et al. |
| 2013/0203475 A1 | 8/2013 | Kil et al. |
| 2013/0215042 A1 | 8/2013 | Messerschmidt et al. |
| 2013/0217979 A1 | 8/2013 | Blackadar et al. |
| 2013/0231575 A1 | 9/2013 | Erkkila et al. |
| 2013/0231711 A1* | 9/2013 | Kaib ..................... G16H 40/40 607/5 |
| 2013/0231947 A1 | 9/2013 | Shusterman |
| 2013/0233097 A1 | 9/2013 | Hayner et al. |
| 2013/0262155 A1 | 10/2013 | Hinkamp |
| 2013/0317380 A1 | 11/2013 | Liley et al. |
| 2013/0325394 A1 | 12/2013 | Yuen et al. |
| 2013/0325396 A1 | 12/2013 | Yuen et al. |
| 2013/0332286 A1 | 12/2013 | Medelius et al. |
| 2013/0345978 A1 | 12/2013 | Lush et al. |
| 2014/0038781 A1 | 2/2014 | Foley et al. |
| 2014/0067096 A1 | 3/2014 | Aibara |
| 2014/0081118 A1 | 3/2014 | Reinhold, Jr. et al. |
| 2014/0081666 A1 | 3/2014 | Teller et al. |
| 2014/0108998 A1 | 4/2014 | Chaudhri et al. |
| 2014/0139637 A1 | 5/2014 | Mistry et al. |
| 2014/0142403 A1 | 5/2014 | Brumback et al. |
| 2014/0143678 A1 | 5/2014 | Mistry et al. |
| 2014/0176346 A1 | 6/2014 | Brumback et al. |
| 2014/0176475 A1 | 6/2014 | Myers et al. |
| 2014/0189584 A1 | 7/2014 | Weng et al. |
| 2014/0200691 A1 | 7/2014 | Lee et al. |

(56) References Cited

U.S. PATENT DOCUMENTS

| | | |
|---|---|---|
| 2014/0218369 A1 | 8/2014 | Yuen et al. |
| 2014/0228647 A1 | 8/2014 | Sakamoto et al. |
| 2014/0239065 A1 | 8/2014 | Zhou et al. |
| 2014/0240122 A1 | 8/2014 | Roberts et al. |
| 2014/0240349 A1 | 8/2014 | Tuukkanen |
| 2014/0244009 A1 | 8/2014 | Mestas |
| 2014/0245161 A1 | 8/2014 | Yuen et al. |
| 2014/0257537 A1 | 9/2014 | Stroupe et al. |
| 2014/0266776 A1 | 9/2014 | Miller et al. |
| 2014/0275852 A1 | 9/2014 | Hong et al. |
| 2014/0275854 A1* | 9/2014 | Venkatraman ......... A61B 5/681 600/301 |
| 2014/0277628 A1 | 9/2014 | Nieminen et al. |
| 2014/0278220 A1 | 9/2014 | Yuen |
| 2014/0278229 A1 | 9/2014 | Hong et al. |
| 2014/0282153 A1 | 9/2014 | Christiansen et al. |
| 2014/0288680 A1 | 9/2014 | Hoffman et al. |
| 2014/0336796 A1 | 11/2014 | Agnew |
| 2014/0337450 A1 | 11/2014 | Choudhary et al. |
| 2014/0337451 A1 | 11/2014 | Choudhary et al. |
| 2014/0344723 A1 | 11/2014 | Malik et al. |
| 2014/0344951 A1 | 11/2014 | Brewer |
| 2014/0371887 A1 | 12/2014 | Hoffman et al. |
| 2015/0018632 A1* | 1/2015 | Khair ..................... A61B 5/029 600/301 |
| 2015/0057943 A1 | 2/2015 | Self et al. |
| 2015/0065302 A1 | 3/2015 | Ou et al. |
| 2015/0067513 A1 | 3/2015 | Zambetti et al. |
| 2015/0067811 A1 | 3/2015 | Agnew et al. |
| 2015/0074571 A1 | 3/2015 | Marti et al. |
| 2015/0081059 A1 | 3/2015 | Hwang et al. |
| 2015/0081210 A1 | 3/2015 | Yeh et al. |
| 2015/0083970 A1 | 3/2015 | Koh et al. |
| 2015/0098309 A1 | 4/2015 | Adams et al. |
| 2015/0099991 A1 | 4/2015 | Yamaguchi et al. |
| 2015/0100245 A1 | 4/2015 | Huang et al. |
| 2015/0106025 A1 | 4/2015 | Keller et al. |
| 2015/0112700 A1 | 4/2015 | Sublett et al. |
| 2015/0118657 A1 | 4/2015 | Shrake et al. |
| 2015/0130830 A1* | 5/2015 | Nagasaki ............. A61B 5/7435 345/592 |
| 2015/0142689 A1 | 5/2015 | Squires |
| 2015/0153943 A1 | 6/2015 | Wang |
| 2015/0181314 A1* | 6/2015 | Swanson ................. H04Q 9/00 340/870.07 |
| 2015/0185967 A1 | 7/2015 | Ly et al. |
| 2015/0193805 A1 | 7/2015 | Filipiak |
| 2015/0196804 A1 | 7/2015 | Koduri et al. |
| 2015/0199494 A1 | 7/2015 | Koduri et al. |
| 2015/0205492 A1 | 7/2015 | Nobil |
| 2015/0205930 A1 | 7/2015 | Shaanan et al. |
| 2015/0216448 A1 | 8/2015 | Lotan et al. |
| 2015/0217163 A1 | 8/2015 | Amis et al. |
| 2015/0220883 A1 | 8/2015 | Bfar et al. |
| 2015/0269848 A1* | 9/2015 | Yuen ..................... G06F 3/14 434/236 |
| 2015/0288944 A1 | 10/2015 | Nistico et al. |
| 2015/0293592 A1 | 10/2015 | Cheong et al. |
| 2015/0297134 A1 | 10/2015 | Albert et al. |
| 2015/0301691 A1 | 10/2015 | Qin |
| 2015/0324751 A1 | 11/2015 | Orenstein et al. |
| 2015/0331589 A1 | 11/2015 | Kawakita |
| 2015/0347711 A1 | 12/2015 | Soli et al. |
| 2015/0374310 A1* | 12/2015 | Lee ..................... A61B 5/7285 600/483 |
| 2016/0015275 A1* | 1/2016 | Samadani ............. A61B 5/1118 600/483 |
| 2016/0019360 A1* | 1/2016 | Pahwa ................... G16H 50/30 705/3 |
| 2016/0027282 A1 | 1/2016 | Lee |
| 2016/0048298 A1 | 2/2016 | Choi et al. |
| 2016/0058313 A1 | 3/2016 | Sato |
| 2016/0058336 A1* | 3/2016 | Blahnik ................. G16H 20/30 600/595 |
| 2016/0058337 A1 | 3/2016 | Blahnik et al. |
| 2016/0062582 A1 | 3/2016 | Wilson et al. |
| 2016/0065505 A1 | 3/2016 | Iskander |
| 2016/0085937 A1 | 3/2016 | Dettinger et al. |
| 2016/0089569 A1 | 3/2016 | Blahnik |
| 2016/0109961 A1 | 4/2016 | Parshionikar |
| 2016/0132046 A1 | 5/2016 | Beoughter et al. |
| 2016/0140828 A1* | 5/2016 | DeForest ........... G08B 21/0211 340/539.12 |
| 2016/0156584 A1* | 6/2016 | Hum ..................... G06Q 50/01 715/752 |
| 2016/0174857 A1 | 6/2016 | Eggers et al. |
| 2016/0196635 A1 | 7/2016 | Cho et al. |
| 2016/0220225 A1* | 8/2016 | Wang .................. A61B 8/5223 |
| 2016/0235325 A1 | 8/2016 | Chou |
| 2016/0235374 A1 | 8/2016 | Miller et al. |
| 2016/0249857 A1 | 9/2016 | Choi et al. |
| 2016/0250517 A1 | 9/2016 | Tilvis et al. |
| 2016/0256741 A1* | 9/2016 | Holma ............... A61B 5/02438 |
| 2016/0263435 A1 | 9/2016 | Venkatraman et al. |
| 2016/0275990 A1 | 9/2016 | Vassort |
| 2016/0278659 A1* | 9/2016 | Kaib ..................... A61B 5/0472 |
| 2016/0278667 A1 | 9/2016 | Villard et al. |
| 2016/0292373 A1 | 10/2016 | Spors et al. |
| 2016/0299769 A1 | 10/2016 | Hunter et al. |
| 2016/0301761 A1 | 10/2016 | Sanchez-Sandoval et al. |
| 2016/0301794 A1 | 10/2016 | Schlakman et al. |
| 2016/0302666 A1 | 10/2016 | Shaya |
| 2016/0324457 A1 | 11/2016 | Dagum |
| 2016/0328736 A1* | 11/2016 | Wang ................. G06Q 30/0239 |
| 2016/0332025 A1 | 11/2016 | Repka |
| 2016/0346607 A1* | 12/2016 | Rapfogel ............. A61B 5/4866 |
| 2016/0360100 A1 | 12/2016 | Kim et al. |
| 2016/0375306 A1* | 12/2016 | Gu ..................... G01C 21/3676 701/430 |
| 2016/0379511 A1 | 12/2016 | Dawson et al. |
| 2017/0000359 A1 | 1/2017 | Kohli et al. |
| 2017/0007159 A1 | 1/2017 | Dieffenderfer et al. |
| 2017/0007167 A1 | 1/2017 | Kostic et al. |
| 2017/0011210 A1 | 1/2017 | Cheong et al. |
| 2017/0014037 A1* | 1/2017 | Coppola ............. A61B 5/7285 |
| 2017/0021184 A1* | 1/2017 | Pavel ..................... A61B 7/02 |
| 2017/0024399 A1* | 1/2017 | Boyle ..................... G06F 16/60 |
| 2017/0024539 A1* | 1/2017 | Webb ..................... A61B 5/002 |
| 2017/0032168 A1* | 2/2017 | Kim ..................... G06F 21/00 |
| 2017/0046024 A1 | 2/2017 | Dascola et al. |
| 2017/0053542 A1* | 2/2017 | Wilson ..................... G09B 5/02 |
| 2017/0075551 A1 | 3/2017 | Robinson et al. |
| 2017/0086693 A1 | 3/2017 | Peterson et al. |
| 2017/0095695 A1* | 4/2017 | Mangusson ........ A63B 24/0062 |
| 2017/0127997 A1 | 5/2017 | Hyde et al. |
| 2017/0153606 A1 | 6/2017 | Pitis et al. |
| 2017/0153804 A1 | 6/2017 | Kim et al. |
| 2017/0161014 A1 | 6/2017 | Kikugawa et al. |
| 2017/0172522 A1 | 6/2017 | Insler et al. |
| 2017/0188841 A1 | 7/2017 | Ma et al. |
| 2017/0202496 A1 | 7/2017 | Ramanathan |
| 2017/0209766 A1 | 7/2017 | Riley et al. |
| 2017/0237694 A1 | 8/2017 | Choudhary et al. |
| 2017/0239524 A1* | 8/2017 | Lee ..................... G16H 50/30 |
| 2017/0243508 A1 | 8/2017 | Cheng et al. |
| 2017/0274149 A1 | 9/2017 | Aeschlimann |
| 2017/0274267 A1 | 9/2017 | Blahnik |
| 2017/0281026 A1* | 10/2017 | Nick ..................... A61B 5/7445 |
| 2017/0281057 A1 | 10/2017 | Blahnik et al. |
| 2017/0293727 A1 | 10/2017 | Klaassen et al. |
| 2017/0294174 A1 | 10/2017 | Albadawi et al. |
| 2017/0300186 A1* | 10/2017 | Kuhar ................. A61B 5/7445 |
| 2017/0303844 A1 | 10/2017 | Baker et al. |
| 2017/0319941 A1* | 11/2017 | Smith ................. A63B 21/153 |
| 2017/0330297 A1 | 11/2017 | Cronin et al. |
| 2017/0333752 A1 | 11/2017 | Korkala et al. |
| 2017/0348562 A1 | 12/2017 | Jung et al. |
| 2017/0354845 A1 | 12/2017 | Williams et al. |
| 2017/0357520 A1 | 12/2017 | De vries et al. |
| 2018/0000426 A1 | 1/2018 | Li |
| 2018/0001184 A1* | 1/2018 | Tran ..................... G06F 1/163 |
| 2018/0011686 A1 | 1/2018 | Zhao et al. |
| 2018/0049659 A1 | 2/2018 | Briante et al. |

(56) References Cited

U.S. PATENT DOCUMENTS

| | | |
|---|---|---|
| 2018/0049696 A1 | 2/2018 | Eom et al. |
| 2018/0053200 A1* | 2/2018 | Cronin .............. G06Q 30/0239 |
| 2018/0056132 A1 | 3/2018 | Foley et al. |
| 2018/0060522 A1 | 3/2018 | Petterson et al. |
| 2018/0064356 A1 | 3/2018 | Mendenhall et al. |
| 2018/0074462 A1 | 3/2018 | Helder et al. |
| 2018/0074464 A1 | 3/2018 | Essery et al. |
| 2018/0078182 A1* | 3/2018 | Chen .................... A61B 5/6801 |
| 2018/0126248 A1 | 5/2018 | Dion et al. |
| 2018/0150709 A1 | 5/2018 | Ha |
| 2018/0189077 A1 | 7/2018 | Gupta et al. |
| 2018/0206766 A1 | 7/2018 | Blahnik et al. |
| 2018/0272190 A1* | 9/2018 | Miura .................... G16H 20/10 |
| 2018/0329584 A1* | 11/2018 | Williams ............ G06F 3/04886 |
| 2018/0345078 A1 | 12/2018 | Blahnik et al. |
| 2019/0008467 A1* | 1/2019 | Averina ............... A61B 5/4836 |
| 2019/0025995 A1* | 1/2019 | Williams ............... A61B 5/681 |
| 2019/0034049 A1 | 1/2019 | Williams et al. |
| 2019/0104951 A1 | 4/2019 | Valys et al. |
| 2019/0232110 A1 | 8/2019 | Williams et al. |
| 2019/0232111 A1 | 8/2019 | Williams et al. |
| 2019/0274562 A1 | 9/2019 | Soli et al. |
| 2019/0274563 A1 | 9/2019 | Soli et al. |
| 2019/0274564 A1 | 9/2019 | Soli et al. |
| 2019/0274565 A1 | 9/2019 | Soli et al. |
| 2019/0279520 A1 | 9/2019 | Wilson et al. |
| 2019/0336044 A1 | 11/2019 | Williams et al. |
| 2019/0336045 A1 | 11/2019 | Williams et al. |
| 2019/0339849 A1 | 11/2019 | Williams et al. |
| 2019/0387982 A1* | 12/2019 | Buller ................... A61B 5/1118 |
| 2020/0101365 A1 | 4/2020 | Wilson et al. |
| 2020/0297249 A1 | 9/2020 | Williams et al. |
| 2020/0357522 A1 | 11/2020 | Pahwa et al. |
| 2020/0381100 A1 | 12/2020 | Williams et al. |
| 2020/0382613 A1 | 12/2020 | Sundstrom et al. |
| 2021/0007632 A1 | 1/2021 | Blahnik et al. |
| 2021/0007633 A1 | 1/2021 | Blahnik et al. |

FOREIGN PATENT DOCUMENTS

| | | |
|---|---|---|
| CN | 1397904 A | 2/2003 |
| CN | 1585943 A | 2/2005 |
| CN | 101150810 A | 3/2008 |
| CN | 101541387 A | 9/2009 |
| CN | 101651870 A | 2/2010 |
| CN | 101836894 A | 9/2010 |
| CN | 102339201 A | 2/2012 |
| CN | 102448555 A | 5/2012 |
| CN | 102804238 A | 11/2012 |
| CN | 102989159 A | 3/2013 |
| CN | 103212197 A | 7/2013 |
| CN | 103370924 A | 10/2013 |
| CN | 103403627 A | 11/2013 |
| CN | 104288983 A | 1/2015 |
| CN | 104501043 A | 4/2015 |
| CN | 104720765 A | 6/2015 |
| CN | 106537397 A | 3/2017 |
| CN | 106709235 A | 5/2017 |
| CN | 106725384 A | 5/2017 |
| CN | 106878550 A | 6/2017 |
| CN | 107278138 A | 10/2017 |
| CN | 107591211 A | 1/2018 |
| CN | 107713981 A | 2/2018 |
| EP | 1935339 A1 | 6/2008 |
| EP | 2025368 A2 | 2/2009 |
| EP | 3042606 A1 | 7/2016 |
| JP | 6-187118 A | 7/1994 |
| JP | 2001-76078 A | 3/2001 |
| JP | 2002-190007 A | 7/2002 |
| JP | 2003-337863 A | 11/2003 |
| JP | 2004-102609 A | 4/2004 |
| JP | 2004-113466 A | 4/2004 |
| JP | 2005-79814 A | 3/2005 |
| JP | 2006-230679 A | 9/2006 |
| JP | 2007-260288 A | 10/2007 |
| JP | 2008-104758 A | 5/2008 |
| JP | 2008-183339 A | 8/2008 |
| JP | 2010-12335 A | 1/2010 |
| JP | 2010-122901 A | 6/2010 |
| JP | 2010-181280 A | 8/2010 |
| JP | 2011-125633 A | 6/2011 |
| JP | 2011-183101 A | 9/2011 |
| JP | 2011-192126 A | 9/2011 |
| JP | 2011-198184 A | 10/2011 |
| JP | 2011-206323 A | 10/2011 |
| JP | 2011-259253 A | 12/2011 |
| JP | 2012-59264 A | 3/2012 |
| JP | 2012-524640 A | 10/2012 |
| JP | 2012-230503 A | 11/2012 |
| JP | 2013-103020 A | 5/2013 |
| JP | 2013-117690 A | 6/2013 |
| JP | 2013-544140 A | 12/2013 |
| JP | 2016-502875 A | 2/2016 |
| JP | 2016-177151 A | 10/2016 |
| JP | 2017-134689 A | 8/2017 |
| JP | 2017-532069 A | 11/2017 |
| KR | 10-2011-0017076 A | 2/2011 |
| KR | 10-2012-0023657 A | 3/2012 |
| KR | 10-2013-0111569 A | 10/2013 |
| KR | 10-2013-0111570 A | 10/2013 |
| KR | 10-2013-0135282 A | 12/2013 |
| KR | 10-1594486 B1 | 2/2016 |
| KR | 10-2017-0003608 A | 1/2017 |
| WO | 1999/41682 A2 | 8/1999 |
| WO | 02/27530 A2 | 4/2002 |
| WO | 2005/070289 A1 | 8/2005 |
| WO | 2006/046648 A1 | 5/2006 |
| WO | 2010/126825 A1 | 11/2010 |
| WO | 2012/021507 A2 | 2/2012 |
| WO | 2012/060588 A2 | 5/2012 |
| WO | 2012/061440 A2 | 5/2012 |
| WO | 2012/078079 A2 | 6/2012 |
| WO | 2013/052789 A1 | 4/2013 |
| WO | 2013/109762 A1 | 7/2013 |
| WO | 2013/109777 A1 | 7/2013 |
| WO | 2013109916 A1 | 7/2013 |
| WO | 2013/173838 A2 | 11/2013 |
| WO | 2014/207294 A1 | 12/2014 |
| WO | 2015/187799 A1 | 12/2015 |
| WO | 2015/198488 A1 | 12/2015 |
| WO | 2016/036582 A2 | 3/2016 |
| WO | 2016/151479 A1 | 9/2016 |
| WO | 2016/161152 A1 | 10/2016 |
| WO | 2016/164475 A1 | 10/2016 |
| WO | 2017/003045 A1 | 1/2017 |
| WO | 2017/037242 A1 | 3/2017 |
| WO | 2017/062621 A1 | 4/2017 |
| WO | 2017/087642 A1 | 5/2017 |
| WO | 2017/090810 A1 | 6/2017 |
| WO | 2019/024603 A1 | 2/2019 |

OTHER PUBLICATIONS

International Preliminary Report on Patentability received for PCT Patent Application No. PCT/US2017/035554, dated Dec. 20, 2018, 39 pages.
Corrected Notice of Allowance received for U.S. Appl. No. 15/183,663, dated Mar. 27, 2019, 2 pages.
Non-Final Office Action received for U.S. Appl. No. 16/143,959, dated Apr. 17, 2019, 15 pages.
Non-Final Office Action received for UU.S. Appl. No. 16/144,030, dated Apr. 12, 2019, 8 pages.
Non-Final Office Action received for U.S. Appl. No. 15/925,652, dated Apr. 5, 2019, 28 pages.
Notice of Allowance received for Japanese Patent Application No. 2016-557650, dated Apr. 9, 2019, 4 pages (1 page of English Translation and 3 pages of Official Copy).
Office Action received for Chinese Patent Application No. 201380081349.6, dated Feb. 26, 2019, 12 pages (6 pages of English Translation and 6 pages of Official Copy).
Office Action received for Chinese Patent Application No. 201680047983.1, dated Mar. 18, 2019, 18 pages (6 pages of English

(56) References Cited

OTHER PUBLICATIONS

Translation and 12 pages of Official Copy).
Office Action received for Chinese Patent Application No. 201810105846.X, dated Feb. 25, 2019, 10 pages (5 pages of English Translation and 5 pages of Official copy).
Office Action received for Danish Patent Application No. PA201770423, dated Mar. 29, 2019, 6 pages.
Office Action received for Danish Patent Application No. PA201870601, dated Dec. 13, 2018, 8 pages.
Office Action received for German Patent Application No. 112015002326.7, dated Feb. 20, 2019, 7 pages (2 pages of English Translation and 5 pages of Official Copy).
Search Report and Opinion received for Danish Patent Application No. PA201870599, dated Dec. 21, 2018, 9 pages.
Search Report and Opinion received for Danish Patent Application No. PA201870600, dated Jan. 31, 2019, 8 pages.
Search Report and Opinion received for Danish Patent Application No. PA201870602, dated Dec. 19, 2018, 8 pages.
Supplemental Notice of Allowance received for U.S. Appl. No. 15/616,480, dated Mar. 28, 2019, 2 pages.
"Visual Pace Alarm app", Available Online at: https://apps.garmin.com/en-US/apps/3940f3a2-4847-4078-a911-d77422966c82, Oct. 19, 2016, 1 page.
Teunmo,"Data field: Visual Pace Alarm", Garmin Forum; Available online at: https://forums.garmin.com/forum/developers/connect-iq/connect-iq-showcase/115996-data-field-visual-pace-alarm, Nov. 17, 2015, 10 pages.
Decision to Grant received for Danish Patent Application No. PA201870600, dated Oct. 17, 2019, 2 pages.
Notice of Allowance received for Chinese Patent Application No. 201580037927.5, dated Oct. 17, 2019, 3 pages (1 page of English Translation and 2 pages of Official Copy).
Notice of Allowance received for U.S. Appl. No. 16/143,959, dated Oct. 31, 2019, 10 pages.
Office Action received for Australian Patent Application No. 2019222943, dated Oct. 3, 2019, 3 Pages.
Office Action received for Danish Patent Application No. PA201770191, dated Oct. 25, 2019, 4 pages.
Advisory Action received for U.S. Appl. No. 16/144,849, dated Aug. 12, 2019, 5 pages.
Final Office Action received for U.S. Appl. No. 15/925,652, dated Aug. 1, 2019, 30 Pages.
Invitation to Pay Additional Fees received for PCT Patent Application No. PCT/2019/019694, dated Jul. 10, 2019, 12 pages.
Notice of Acceptance received for Australian Patent Application No. 2019201583, dated Jul. 15, 2019, 3 pages.
Supplementary European Search Report received for European Patent Application No. 17810749.6, dated Aug. 6, 2019, 6 pages.
Office Action received for Australian Patent Application No. 2018200428, dated Nov. 15, 2018, 4 pages.
Office Action received for Danish Patent Application No. PA201770191, dated Nov. 21, 2018, 4 pages.
Office Action received for Japanese Patent Application No. 2016-557650, dated Nov. 9, 2018, 6 pages (3 pages of English Translation and 3 pages of Official copy).
Office Action received for Japanese Patent Application No. 2018-014096, dated Nov. 6, 2018, 15 pages (7 pages of English Translation and 8 pages of Official Copy).
Notice of Allowance received for U.S. Appl. No. 15/183,663, dated Jan. 17, 2019, 6 pages.
Notice of Allowance received for U.S. Appl. No. 15/616,480, dated Jan. 3, 2019, 8 pages.
Advisory Action received for U.S. Appl. No. 16/144,864, dated Jul. 29, 2019, 6 pages.
Decision to Grant received for Danish Patent Application No. PA201870379, dated Jul. 5, 2019, 2 pages.
Intention to Grant received for Danish Patent Application No. PA201870600, dated Jul. 10, 2019, 2 pages.
Applicant Initiated Interview Summary received for U.S. Appl. No. 16/144,849, dated Jan. 21, 2020, 6 pages.

Corrected Notice of Allowance received for U.S. Appl. No. 15/600,243, dated Feb. 5, 2020, 3 pages.
Non-Final Office Action received for U.S. Appl. No. 15/608,848, dated Feb.06, 2020, 12 pages.
Non-Final Office Action received for U.S. Appl. No. 16/144,864, dated Jan. 31, 2020, 29 pages.
Notice of Allowance received for U.S. Appl. No. 16/143,909, dated Jan. 21, 2020, 9 pages.
Office Action received for Danish Patent Application No. PA201870601, dated Jan. 14, 2020, 3 pages.
Certificate of Examination received for Australian Patent Application No. 2019100222, dated Aug. 29, 2019, 2 pages.
International Search Report and Written Opinion received for PCT Patent Application No. PCT/US2019/024570, dated Aug. 8, 2019, 18 pages.
Corrected Notice of Allowance received for U.S. Appl. No. 15/183,663, dated Feb. 25, 2019, 3 pages.
Extended European Search Report received for European Patent Application No. 16837432.0, dated Mar. 11, 2019, 10 pages.
Office Action received for Australian Patent Application No. 2018101855, dated Feb. 22, 2019, 4 pages.
Advisory Action received for U.S. Appl. No. 14/839,922, dated Mar. 24, 2017, 4 pages.
Apple, iPhone User's Guide, Available at <http://mesnotices.20minutes.fr/manuel-notice-mode-emploi/APPLE/IPHONE%2D%5FE#>, Retrieved on Mar. 27, 2008, Jun. 2007, 137 pages.
Certification of Examination received for Australian Patent Application No. 2018100158, dated Oct. 23, 2018, 2 pages.
CNET, "Google Fit's Automatic Activity Tracking Is Getting Smarter on Android Wear", Available online at: https://www.youtube.com/watch?v=lttzlCid_d8, May 18, 2016, 1 page.
Codrington, Simon, "Intuitive Scrolling Interfaces with CSS Scroll Snap Points", Online Available at: https://www.sitepoint.com/intuitive-scrolling-interfaces-with-css-scroll-snap-points/, Dec. 8, 2015, 14 pages.
Decision to Refuse received for European Patent Application No. 13811085.3, dated Sep. 11, 2018, 21 pages.
Decision to Refuse received for European Patent Application No. 15771747.1, dated Aug. 10, 2018, 22 pages.
"DwProgressBar v2: Stepping and Events", davidwalsh.name/dwprogressbar-2-stepping-events-mootools-progress-bar, retrieved from the Wayback Machine, Aug. 31, 2008, 4 pages.
Extended European Search Report received for European Patent Application No. 18154145.9, dated Mar. 2, 2018, 8 pages.
Final Office Action received for U.S. Appl. No. 12/205,847, dated Apr. 25, 2012, 42 pages.
Final Office Action received for U.S. Appl. No. 14/732,773, dated Jul. 13, 2018, 48 pages.
Final Office Action received for U.S. Appl. No. 14/839,922, dated Dec. 14, 2016, 22 pages.
Garmin, "Fenix 5x Owner's Manual", Online Available at :-https://web.archive.org/web/20180127170640/https://static.garmin.com/pumac/fenix5x_OM_EN.pdf, Jul. 2017, 42 pages.
Intention to Grant received for Danish Patent Application No. PA201570668, dated Mar. 27, 2017, 2 pages.
International Preliminary Report on Patentability received for PCT Patent Application No. PCT/US2016/037686, dated Mar. 1, 2018, 12 pages.
International Preliminary Report on Patentability received for PCT Patent Application No. PCT/US2013/073195, dated Jun. 7, 2016, 9 pages.
International Preliminary Report on Patentability received for PCT Patent Application No. PCT/US2015/047282, dated Mar. 16, 2017, 26 pages.
International Search Report and Written Opinion received for PCT Patent Application No. PCT/US2015/047282, dated May 9, 2016, 33 pages.
International Search Report and Written Opinion received for PCT Patent Application No. PCT/US2016/037686, dated Sep. 9, 2016, 19 pages.
International Search Report and Written Opinion received for PCT Patent Application No. PCT/US2017/035554, dated Sep. 22, 2017, 42 pages.

(56) References Cited

OTHER PUBLICATIONS

International Search Report and Written Opinion received for PCT Patent Application No. PCT/US2018/031662, dated Sep. 27, 2018, 19 pages.
International Search Report received for PCT Patent Application No. PCT/US2013/073195, dated Jun. 23, 2014, 3 pages.
International Written Opinion received for PCT Patent Application No. PCT/US2013/073195, dated Jun. 23, 2014, 8 pages.
Invitation to Pay Addition Fees and Partial International Search Report received for PCT Patent Application No. PCT/US2018/031662, dated Jul. 16, 2018, 13 pages.
Invitation to Pay Additional Fees received for PCT Patent Application No. PCT/US2015/047282, dated Dec. 22, 2015, 7 pages.
Invitation to Pay Additional Fees received for PCT Patent Application No. PCT/US2017/035554, dated Jul. 20, 2017, 2 pages.
JENBSJOURNEY, "Wondering About a Fitbit?", Available at: https://jenbsjourney.blogspot.kr/2013/08/wondering-about-fitbit.html, Aug. 6, 2013, 12 pages.
Minutes of Oral Proceedings received for European Patent Application No. 13811085.3, dated Sep. 11, 2018, 3 pages.
Minutes of Oral Proceedings received for European Patent Application No. 15771747.1, dated Aug. 10, 2018, 11 pages.
MUGS, Online Available at: https://web.archive.org/web/20151029034349/http://le-mugs.com/, Oct. 29, 2015.
"My CalStep", Online Available <http://www.surprisesoftware.com/mycalstep/>, retireved from the Wayback Machine, May 9, 2007, 2 pages.
Non-Final Office Action received for U.S. Appl. No. 14/839,916, dated Feb. 4, 2016, 19 pages.
Non-Final Office Action received for U.S. Appl. No. 14/839,922, dated Feb. 25, 2016, 20 pages.
Non-Final Office Action received for U.S. Appl. No. 12/205,847, dated Oct. 3, 2011, 59 pages.
Non-Final Office Action received for U.S. Appl. No. 14/732,773, dated Jan. 19, 2018, 45 pages.
Non-Final Office Action received for U.S. Appl. No. 14/839,916, dated May 1, 2017, 18 pages.
Non-Final Office Action received for U.S. Appl. No. 14/839,922, dated Aug. 17, 2016, 25 pages.
Non-Final Office Action received for U.S. Appl. No. 15/183,663, dated Jul. 9, 2018, 13 pages.
Notice of Acceptance received for Australian Patent Application No. 2015312215, dated Oct. 9, 2017, 3 pages.
Notice of Allowance received for Danish Patent Application No. PA201570666, dated Sep. 15, 2016, 1 page.
Notice of Allowance received for Danish Patent Application No. PA201570668, dated Oct. 30, 2017, 2 pages.
Notice of Allowance received for Japanese Patent Application No. 2016-535045, dated Mar. 2, 2018, 4 pages.
Notice of Allowance received for Korean Patent Application No. 10-2016-7033638, dated May 31, 2017, 5 pages.
Notice of Allowance received for Taiwanese Patent Application No. 104128685, dated May 3, 2017, 3 pages.
Notice of Allowance received for U.S. Appl. No. 12/205,847, dated Aug. 20, 2012, 13 pages.
Notice of Allowance received for U.S. Appl. No. 14/839,916, dated Aug. 31, 2016, 11 pages.
Notice of Allowance received for U.S. Appl. No. 14/839,916, dated Jan. 10, 2018, 19 pages.
Notice of Allowance received for U.S. Appl. No. 14/839,922, dated Jan. 26, 2018, 2 pages.
Notice of Allowance received for U.S. Appl. No. 14/839,922, dated Jul. 6, 2017, 8 pages.
Notice of Allowance received for U.S. Appl. No. 14/839,922, dated Nov. 2, 2017, 8 pages.
Office Action received for Australian Patent Application No. 2015312215, dated Oct. 13, 2016, 3 pages.
Office Action received for Australian Patent Application No. 2017100667, dated Aug. 3, 2017, 9 pages.
Office Action received for Australian Patent Application No. 2018100158, dated Apr. 23, 2018, 5 pages.
Office Action received for Australian Patent Application No. 2018200428, dated Mar. 7, 2018, 4 pages.
Office Action received for Chinese Patent Application No. 201580037927.5, dated Jul. 20, 2018, 21 pages.
Office Action Received for Danish Patent Application No. PA201670656, dated Nov. 3, 2016, 8 pages.
Office Action received for Danish Patent Application No. PA201570666, dated Feb. 2, 2016, 9 pages.
Office Action received for Danish Patent Application No. PA201570666, dated Jun. 27, 2016, 4 pages.
Office Action received for Danish Patent Application No. PA201570668, dated Apr. 8, 2016, 8 pages.
Office Action received for Danish Patent Application No. PA201570668, dated Sep. 9, 2016, 3 pages.
Office Action received for Danish Patent Application No. PA201670656, dated Jun. 14, 2017, 3 pages.
Office Action Received for Danish Patent Application No. PA201670656, dated May 30, 2018, 5 pages.
Office Action received for Danish Patent Application No. PA201770191, dated Jan. 25, 2018, 3 pages.
Office Action received for Danish Patent Application No. PA201770423, dated Jun. 12, 2018, 7 pages.
Office Action received for European Patent Application No. 13811085.3, dated Apr. 20, 2018, 15 pages.
Office Action received for European Patent Application No. 18154145.9, dated Apr. 3, 2018, 6 pages.
Office Action received for European Patent Application No. 15771747.1, dated Oct. 31, 2017, 7 pages.
Office Action received for Japanese Patent Application No. 2016-535045, dated May 12, 2017, 10 pages.
Office Action received for Japanese Patent Application No. 2016-557650, dated Apr. 13, 2018, 9 pages.
Office Action received for Japanese Patent Application No. 2016-557650, dated Aug. 10, 2017, 10 pages.
Office Action received for Japanese Patent Application No. 2018-014096, dated Jun. 29, 2018, 20 pages.
Office Action received for Korean Patent Application No. 10-2016-7014577, dated Dec. 26, 2017, 14 pages.
Office Action received for Korean Patent Application No. 10-2016-7033638, dated Jan. 31, 2017, 6 pages.
Office Action received for Taiwanese Patent Application No. 104128685, dated Jan. 4, 2017, 40 pages.
Rainmaker, "Garmin Fenix3 New Auto Climb Functionality", Available online at: https://www.youtube.com/watch?v=iuavOSNpVRc, Feb. 19, 2015, 1 page.
Razykdreviews, "In Depth Review of Apple Watch Activity and Workout App", available at <URL: https://www.youtube.com/watch?v=GkKI3qIK0ow>, May 11, 2015, 1 page.
Rizknows, "Garmin Connect Mobile App—Review #2", https://www.youtube.com/watch?v=7my3wMpeRbE, Oct. 22, 2015, 1 page.
Rizknows, "Tom Tom Multisport Cardio Review", Online available at :—https://www.youtube.com/watch?v=WoVCzLrSN9A, Sep. 4, 2015, 1 page.
Search report and opinion received for Danish Patent Application No. PA201770191, dated Jun. 30, 2017, 9 pages.
Search Report and Opinion received for Danish Patent Application No. PA201770423, dated Oct. 4, 2017, 10 pages.
Smith, "Garmin Fenix 5 Activity/Smart Watch Review", Online Available at :—https://www.youtube.com/watch?v=6PkQxXQxpoU, Sep. 2, 2017, 1 page.
Sportstechguides, "Garmin Fenix 5: How to Add Power Data Fields", Online Available at :—https://www.youtube.com/watch?v=ZkPptnnXEiQ, Apr. 29, 2017, 2 pages.
Sportstechguides, "Garmin Fenix 5: How to Set Up Run Alerts", Online Available at :—https://www.youtube.com/watch?v=gSMwv8vlhB4, May 13, 2017, 2 pages.
Summons to Attend Oral Proceedings received for European Patent Application No. 13811085.3, dated Jan. 26, 2018, 14 pages.
Summons to Attend Oral Proceedings received for European Patent Application No. 15771747.1, mailed on May 25, 2018, 17 pages.

(56) References Cited

OTHER PUBLICATIONS

"Suunto Spartan Trainer Wrist HR 1.12", Online Available at :—https://web.archive.org/web/20180127155200/https://ns.suunto.com/Manuals/Spartan_Trainer_WristHR/Userguides/Suunto_Spartan_Trainer_WristHR_UserGuide_EN.pdf , Jan. 17, 2018, 47 pages.
Suunto, "Suunto Spartan—Heart Rate Zones", Online Available at :—https://www.youtube.com/watch?v=aixfoCnS0OU, Mar. 19, 2018, 2 page.
Tomtom, "TomTom Runner & Multi-Sport Reference Guide", Online available at :—https://web.archive.org/web/20150908075934/http://download.tomtom.com/open/manuals/Runner_Multi-Sport/refman/TomTom-Runner-Multi-Sport-RG-en-gb.pdf, Sep. 8, 2015, 44 pages.
Utilization of Galaxy S4-S Health, "ChatOn and Samsung Hub", Available at: http://seeit.kr/1263, Jun. 12, 2013, 25 pages.
Zlelik, "Garmin Fenix 5 Open Water Swimming Activity Demo", Online Available at :—https://www.youtube.com/watch?v=iSVhdvw2dcs, Jun. 9, 2017, 1 page.
Advisory Action received for U.S. Appl. No. 16/143,909, dated Nov. 7, 2019, 5 pages.
Applicant Initiated Interview Summary received for U.S. Appl. No. 15/627,069, dated Nov. 4, 2019, 6 pages.
Applicant Initiated Interview Summary received for U.S. Appl. No. 15/600,243, dated Nov. 1, 2019, 6 pages.
Applicant Initiated Interview Summary received for U.S. Appl. No. 15/608,848, dated Nov. 1, 2019, 3 pages.
Non-Final Office Action received for U.S. Appl. No. 15/705,849, dated Nov. 12, 2019, 15 pages.
Advisory Action received for U.S. Appl. No. 14/732,773, dated Nov. 9, 2018, 6 pages.
Cho, H. S., "Satisfactory Innovative Smart-watch (Fitbit Force) Review After Seven Days of Use, Such As the Amount of Sleep and Movement (Improving Sleep Is the Object of X-Blue", Online Available at: < https://x -blueuv.blogspotcom/2013/12/fitbit-force.html>, Dec. 3, 2013, 6 pages (Official Copy Only) (See Communication under 37 CFR § 1.98(a) (3)).
Non-Final Office Action received for U.S. Appl. No. 15/608,848, dated Nov. 2, 2018, 21 pages.
Office Action received for Korean Patent Application No. 10-2016-7014577, dated Oct. 31, 2018, 11 pages (5 pages of English Translation and 6 pages of Official Copy).
Final Office Action received for U.S. Appl. No. 16/144,849, dated Jun. 7, 2019, 29 pages.
Final Office Action received for U.S. Appl. No. 16/144,864, dated May 17, 2019, 24 pages.
Intention to Grant received for Danish Patent Application No. PA201870379, dated May 2, 2019, 2 pages.
Non Final Office Action Received for U.S. Appl. No. 16/144,864, dated Dec. 18, 2018, 19 pages.
Non-Final Office Action received for U.S. Appl. No. 16/144,849, dated Dec. 31, 2018, 28 pages.
Notice of Allowance received for Korean Patent Application No. 10-2016-7014577, dated May 30, 2019, 5 pages (2 pages of English Translation and 3 pages of Official Copy).
Office Action received for Australian Patent Application No. 2019100222, dated May 24, 2019, 6 pages.
Office Action received for Danish Patent Application No. PA201870378, dated Feb. 25, 2019, 3 pages.
Office Action received for Danish Patent Application No. PA201870379, dated Feb. 28, 2019, 3 pages.
Office Action received for Danish Patent Application No. PA201870380, dated Mar. 27, 2019, 4 pages.
Office Action received for Danish Patent Application No. PA201870380, dated Sep. 11, 2018, 9 pages.
Search Report and Opinion received for Danish Patent Application No. PA201870378, dated Sep. 10, 2018, 9 pages.
Search Report and Opinion received for Danish Patent Application No. PA201870379, dated Sep. 14, 2018, 9 pages.
"Multi-Set Bar Chart", The Data Visualization Catalogue, Available Online at: https://datavizcatalogue.com/methods/multiset_barchart.html, Feb. 8, 2014, 3 pages.

Non-Final Office Action received for U.S. Appl. No. 16/143,997, dated May 21, 2019, 15 pages.
Office Action received for Chinese Patent Application No. 201580037927.5, dated Apr. 22, 2019, 9 pages (4 pages of English Translation and 5 pages of Official Copy).
Office Action received for Danish Patent Application No. PA201870600, dated May 8, 2019, 3 pages.
Evergreen et al., "Bar Chart", Better Evaluation, Available Online at: https://www.betterevaluation.org/en/evaluation-options/BarChart, Oct. 31, 2014, 8 pages.
Corrected Notice of Allowance received for U.S. Appl. No. 16/143,959, dated Dec. 13, 2019, 2 pages.
International Preliminary Report on Patentability received for PCT Patent Application No. PCT/US2018/031662, dated Nov. 28, 2019, 12 pages.
Notice of Allowance received for Japanese Patent Application No. 2018-068846, dated Dec. 9, 2019, 4 pages (1 page of English Translation and 3 pages of Official Copy).
Notice of Allowance received for U.S. Appl. No. 14/732,773, dated Dec. 18, 2019, 21 pages.
Notice of Allowance received for U.S. Appl. No. 15/600,243, dated Dec. 12, 2019, 7 pages.
Office Action received for Chinese Patent Application No. 201680047983.1, dated Nov. 28, 2019, 9 pages (4 pages of English Translation and 5 pages of Official Copy).
Office Action received for Korean Patent Application No. 10-2019-7025781, mailed on Nov. 26, 2019, 10 pages (4 pages of English Translation and 6 pages of Official Copy).
Advisory Action received for U.S. Appl. No. 16/143,997, dated Dec. 26, 2019, 7 pages.
Office Action received for Chinese Patent Application No. 201810105846.X, dated Nov. 28, 2019, 9 pages (5 pages of English Translation and 4 pages of Official Copy).
Office Action received for Danish Patent Application No. PA201870378, dated Jan. 6, 2020, 3 pages.
Office Action received for Danish Patent Application No. PA201870599, dated Dec. 20, 2019, 5 pages.
Office Action received for European Patent Application No. 16837432.0, dated Jan. 10, 2020, 7 pages.
Office Action received for European Patent Application No. 19721883.7, dated Jan. 10, 2020, 4 pages.
Advisory Action received for U.S. Appl. No. 14/732,773, dated Aug. 23, 2019, 6 pages.
Certificate of Examination received for Australian Patent Application No. 2018101855, dated Aug. 6, 2019, 2 pages.
Final Office Action received for U.S. Appl. No. 16/143,909, dated Aug. 28, 2019, 20 pages.
Office Action received for Chinese Patent Application No. 201380081349.6, dated Jul. 15, 2019, 10 pages (5 pages of English Translation and 5 pags of Official copy).
Office Action received for European Patent Application No. 17615749.6, dated Aug. 20, 2019, 9 pages.
Final Office Action received for U.S. Appl. No. 15/608,848, dated Jun. 26, 2019, 27 pages.
Final Office Action received for U.S. Appl. No. 14/732,773, dated Jun. 21, 2019, 32 pages.
Non-Final Office Action received for U.S. Appl. No. 15/600,243, dated Jun. 27, 2019, 17 pages.
Non-Final Office Action received for U.S. Appl. No. 15/627,069, dated Jun. 21, 2019, 22 pages.
Office Action received for Danish Patent Application No. PA201870601, dated Jun. 25, 2019, 3 pages.
Office Action received for Danish Patent Application No. PA201870602, dated Jun. 26, 2019, 3 Pages.
Office Action received for Japanese Patent Application No. 2018-014096, dated May 8, 2019, 14 pages (7 pages of English Translation and 7 pages off Official Copy).
Non-Final Office Action received for U.S. Appl. No. 14/732,773, dated Feb. 8, 2019, 32 pages.
Office Action received for Japanese Patent Application No. 2018-068846, dated Jan. 8, 2019, 6 pages (3 pages of English Translation and 3 pages of Official copy).

(56) References Cited

OTHER PUBLICATIONS

Final Office Action received for U.S. Appl. No. 16/143,997, dated Sep. 30, 2019, 16 pages.
Final Office Action received for U.S. Appl. No. 16/144,030, dated Oct. 1, 2019, 13 pages.
"Fitbit App", Available online at: http://web.archive.org/web/20180114083150/https:/ /www.fitbit.com/au/app, Jan. 14, 2018, 8 pages.
International Search Report and Written Opinion received for PCT Patent Application No. PCT/US2019/019694, dated Sep. 2, 2019, 17 pages.
Non-Final Office Action received for U.S. Appl. No. 16/144,849, dated Sep. 17, 2019, 9 pages.
Office Action received for Australian Patent Application No. 2019100495, dated Sep. 17, 2019, 7 pages.
Office Action received for Chinese Patent Application No. 201810105846.X, dated Aug. 27, 2019, 12 pages (5 pages of English Translation and 7 pages of Official Copy).
Non-Final Office Action received for U.S. Appl. No. 16/143,909, dated Apr. 19, 2019, 16 pages.
Office Action Received for Danish Patent Application No. PA201670656, dated May 2, 2019, 4 pages.
Partial Supplementary European Search Report received for European Patent Application No. 17810749.6, dated Apr. 25, 2019, 8 pages.
Corrected Notice of Allowance received for U.S. Appl. No. 15/600,243, dated Mar. 31, 2020, 5 pages.
Office Action received for Australian Patent Application No. 2019100495, dated Mar. 16, 2020, 3 pages.
Supplemental Notice of Allowance received for U.S. Appl. No. 16/144,849, dated Mar. 31, 2020, 2 pages.
Advisory Action received for U.S. Appl. No. 16/144,864, dated Jul. 6, 2020, 6 pages.
Applicant-Initiated Interview Summary received for U.S. Appl. No. 15/705,849, dated Jun. 29, 2020, 3 pages.
Office Action Received for Danish Patent Application No. PA201670656, dated Jul. 1, 2020, 4 pages.
Office Action received for European Patent Application No. 19726205.8, dated Jun. 26, 2020, 9 pages.
Office Action received for Japanese Patent Application No. 2019-044107, dated May 29, 2020, 6 pages (3 pages of English Translation and 3 pages of Official Copy).
Applicant Initiated Interview Summary received for U.S. Appl. No. 16/144,735, dated Jun. 18, 2020, 3 pages.
Applicant-Initiated Interview Summary received for U.S. Appl. No. 16/144,864, dated Jun. 22, 2020, 3 pages.
Office Action received for Australian Patent Application No. 2017277971, dated Jun. 3, 2020, 3 pages.
Decision to Grant received for Danish Patent Application No. PA201870601, dated Aug. 17, 2020, 2 pages.
Decision to Grant received for Danish Patent Application No. PA201870602, dated Aug. 18, 2020, 2 pages.
Extended European Search Report received for European Patent Application No. 20180592.6, dated Aug. 11, 2020, 10 pages.
Final Office Action received for U.S. Appl. No. 15/608,848, dated Aug. 21, 2020, 15 pages.
Final Office Action received for U.S. Appl. No. 16/138,809, dated Aug. 27, 2020, 24 pages.
Office Action received for Australian Patent Application No. 2017277971, dated Aug. 12, 2020, 3 pages.
Office Action received for Chinese Patent Application No. 201380081349.6, dated Jul. 15, 2020, 9 pages (4 pages of English Translation and 5 pages of Official Copy).
Office Action received for Korean Patent Application No. 10-2019-7025538, dated Aug. 15, 2020, 8 pages (4 pages of English Translation and 4 pages of Official Copy).
Applicant Initiated Interview Summary received for U.S. Appl. No. 15/608,848, dated May 12, 2020, 5 pages.
Final Office Action received for U.S. Appl. No. 15/705,849, dated May 1, 2020, 17 pages.
Final Office Action received for U.S. Appl. No. 16/144,735, dated May 4, 2020, 12 pages.
Intention to Grant received for Danish Patent Application No. PA201870601, dated Apr. 24, 2020, 2 pages.
Intention to Grant received for Danish Patent Application No. PA201870602, dated Apr. 24, 2020, 2 pages.
Applicant Initiated Interview Summary received for U.S. Appl. No. 16/144,864, dated Apr. 29, 2020, 4 pages.
Non-Final Office Action received for U.S. Appl. No. 16/418,786, dated Apr. 24, 2020, 16 pages.
Notice of Allowance received for U.S. Appl. No. 16/144,849, dated Apr. 17, 2020, 2 pages.
Office Action received for Chinese Patent Application No. 201710439448.7, dated Mar. 27, 2020, 13 pages (7 pages of English Translation and 6 pages of Official Copy).
Applicant-Initiated Interview Summary received for U.S. Appl. No. 15/705,849, dated Feb. 14, 2020, 3 pages.
Corrected Notice of Allowance received for U.S. Appl. No. 14/732,773, dated Feb. 10, 2020, 3 pages.
Corrected Notice of Allowance received for U.S. Appl. No. 16/143,909, dated Feb. 20, 2020, 3 pages.
Final Office Action received for U.S. Appl. No. 16/144,030, dated Feb. 13, 2020, 11 pages.
Invitation to Pay Search Fees received for European Patent Application No. 19726205.8, dated Feb. 14, 2020, 5 pages.
Non-Final Office Action received for U.S. Appl. No. 16/144,735, dated Feb. 19, 2020, 10 pages.
Notice of Allowance received for U.S. Appl. No. 16/144,671, dated Feb. 10, 2020, 17 pages.
Office Action received for Chinese Patent Application No. 201380081349.6, dated Jan. 16, 2020, 11 pages (6 pages of English Translation and 5 pages of Official Copy).
Office Action received for Danish Patent Application No. PA201870602, dated Feb. 5, 2020, 3 pages.
Office Action received for Japanese Patent Application No. 2018-014096, dated Jan. 6, 2020, 17 pages (8 pages of English Translation and 9 pages of Official Copy).
Non-Final Office Action received for U.S. Appl. No. 16/143,997, dated Jul. 27, 2020, 15 pages.
Notice of Acceptance received for Australian Patent Application No. 2020204153, dated Jul. 6, 2020, 3 pages.
Notice of Allowance received for U.S. Appl. No. 15/705,849, dated Jul. 28, 2020, 10 pages.
Notice of Allowance received for U.S. Appl. No. 16/144,864, dated Jul. 28, 2020, 27 pages.
Office Action received for Chinese Patent Application No. 201680047983.1, dated Jul. 1, 2020, 6 pages (3 pages of English Translation and 3 pages of Official Copy).
Corrected Notice of Allowance received for U.S. Appl. No. 15/600,243, dated Mar. 13, 2020, 3 pages.
Corrected Notice of Allowance received for U.S. Appl. No. 16/143,909, dated Mar. 18, 2020, 3 pages.
Final Office Action received for U.S. Appl. No. 15/627,069, dated Mar. 2, 2020, 22 pages.
Non-Final Office Action received for U.S. Appl. No. 16/138,809, dated Feb. 28, 2020, 22 pages.
Notice of Allowance received for Chinese Patent Application No. 201810105846.X, dated Feb. 18, 2020, 2 pages (1 page of English Translation and 1 page of Official Copy).
Notice of Allowance received for U.S. Appl. No. 16/144,849, dated Mar. 6, 2020, 9 pages.
Office Action received for Australian Patent Application No. 2019100495, dated Mar. 6, 2020, 3 pages.
Office Action received for Danish Patent Application No. PA201870380, dated Mar. 5, 2020, 2 pages.
Office Action received for Japanese Patent Application No. 2019-162293, dated Jan. 31, 2020, 8 pages (4 pages of English Translation and 4 pages of Official Copy).
Office Action received for Korean Patent Application No. 10-2019-7025538, dated Feb. 17, 2020, 12 pages (6 pages of English Translation and 6 pages of Official Copy).

(56) References Cited

OTHER PUBLICATIONS

Wesley, "Apple Watch Series 1", Online available at: http://toolbox.info/blog/archives/1737-unknown.html, May 28, 2015, 5 pages (Official copy only) (See Communication under 37 CFR § 1.98(a) (3)).
Youtube, "Apple Watch Series 3", Online available at: https://www.youtube.com/watch?v=iBPr9gEfkK8, Nov. 21, 2017, 15 pages (Official copy only) (See Communication under 37 CFR § 1.98(a) (3)).
Applicant-Initiated Interview Summary received for U.S. Appl. No. 15/627,069, dated Jul. 20, 2020, 5 pages.
Cyclespeed Tours, "The Most Useful Data Fields to Display on Your Garmin", Online Available at: https://www.youtube.com/watch?v=AN0Eo50yxdg, Nov. 16, 2016, 3 pages.
Notice of Allowance received for U.S. Appl. No. 16/144,735, dated Jul. 21, 2020, 13 pages.
Office Action received for Australian Patent Application No. 2018268972, dated Jul. 9, 2020, 4 pages.
Office Action received for Chinese Patent Application No. 201910972529.2, dated Jun. 28, 2020, 8 pages (1 page of English Translation and 7 pages of Official Copy).
Corrected Notice of Allowance received for U.S. Appl. No. 14/732,773, dated Mar. 24, 2020, 3 pages.
Applicant-Initiated Interview Summary received for U.S. Appl. No. 16/138,809, dated Jun. 9, 2020, 4 pages.
Final Office Action received for U.S. Appl. No. 16/144,864, dated May 28, 2020, 29 pages.
Non-Final Office Action received for U.S. Appl. No. 16/378,136, dated Jun. 2, 2020, 8 pages.
Office Action received for European Patent Application No. 19721883.7, dated May 28, 2020, 11 pages.
Non-Final Office Action received for U.S. Appl. No. 15/627,069, dated May 26, 2020, 25 pages.
Non-Final Office Action received for U.S. Appl. No. 16/377,892, dated May 21, 2020, 9 pages.
Notice of Acceptance received for Australian Patent Application No. 2019222943, dated May 5, 2020, 3 pages.
Applicant Initiated Interview Summary received for U.S. Appl. No. 16/143,997, dated Aug. 13, 2020, 3 pages.
Extended European Search Report received for European Patent Application No. 20180581.9, dated Aug. 12, 2020, 9 pages.
Non-Final Office Action received for U.S. Appl. No. 15/925,652, dated Aug. 7, 2020, 39 pages.
Office Action received for Australian Patent Application No. 2019250251, dated Aug. 6, 2020, 3 pages.
Summons to Attend Oral Proceedings received for European Patent Application No. 17810749.6, dated Aug. 12, 2020, 11 pages.
Applicant-Initiated Interview Summary received for U.S. Appl. No. 15/608,848, dated Oct. 26, 2020, 3 pages.
Applicant-Initiated Interview Summary received for U.S. Appl. No. 16/377,892, dated Oct. 13, 2020, 5 pages.
Applicant-Initiated Interview Summary received for U.S. Appl. No. 16/378,136, dated Oct. 13, 2020, 4 pages.
European Search Report received for European Patent Application No. 20182116.2, dated Oct. 21, 2020, 4 pages.
Final Office Action received for U.S. Appl. No. 15/627,069, dated Oct. 20, 2020, 25 pages.
International Preliminary Report on Patentability received for PCT Patent Application No. PCT/US2019/019694, dated Sep. 24, 2020, 12 pages.
International Search Report and Written Opinion received for PCT Patent Application No. PCT/US2020/025997, dated Jul. 1, 2020, 16 pages.
International Search Report and Written Opinion received for PCT Patent Application No. PCT/US2020/025997, dated Jul. 14, 2020, 15 pages.
Non-Final Office Action received for U.S. Appl. No. 16/894,309, dated Oct. 15, 2020, 24 pages.
Notice of Allowance received for Chinese Patent Application No. 201910972529.2, dated Sep. 14, 2020, 6 pages (3 pages of English Translation and 3 pages of Official Copy).
Notice of Allowance received for U.S. Appl. No. 15/705,849, dated Oct. 16, 2020, 14 pages.
Notice of Allowance received for UU.S. Appl. No. 16/144,735, dated Oct. 28, 2020, 13 pages.
Notice of Allowance received for U.S. Appl. No. 16/144,864, dated Sep. 10, 2020, 3 pages.
Notice of Allowance received for U.S. Appl. No. 16/144,864, dated Sep. 16, 2020, 2 pages.
Notice of Allowance received for U.S. Appl. No. 16/144,864, dated Sep. 29, 2020, 2 pages.
Notice of Allowance received for U.S. Appl. No. 16/556,023, dated Oct. 15, 2020, 8 pages.
Notice of Allowance received for U.S. Appl. No. 16/588,950, dated Feb. 10, 2020, 9 pages.
Notice of Allowance received for U.S. Appl. No. 16/588,950, dated May 5, 2020, 9 pages.
Office Action received for Chinese Patent Application No. 201910858933.7, dated Aug. 18, 2020, 14 pages (7 pages of English Translation and 7 pages of Official Copy).
Office Action received for Danish Patent Application No. PA201970532, dated May 29, 2020, 3 pages.
Office Action received for Japanese Patent Application No. 2018-014096, dated Aug. 28, 2020, 4 pages (2 pages of English Translation and 2 pages of Official Copy).
Office Action received for Japanese Patent Application No. 2019-162293, dated Jul. 27, 2020, 9 pages (5 pages of English Translation and 4 pages of Official Copy).
Office Action received for Japanese Patent Application No. 2020-104679, dated Sep. 18, 2020, 13 pages (7 pages of English Translation and 6 pages of Official Copy).
Result of Consultation received for European Patent Application No. 18154145.9, dated Sep. 4, 2020, 3 pages.
Result of Consultation received for European Patent Application No. 19721883.7, dated Oct. 7, 2020, 3 pages.
Search Report and Opinion received for Danish Patent Application No. PA201970532, dated Nov. 8, 2019, 9 pages.
Summons to Attend Oral Proceedings received for European Patent Application No. 18154145.9, mailed on Sep. 17, 2020, 11 pages.
Summons to Attend Oral Proceedings received for European Patent Application No. 19726205.8, mailed on Oct. 29, 2020, 13 pages.
Supplemental Notice of Allowance received for U.S. Appl. No. 16/588,950, dated Apr. 1, 2020, 2 pages.
Supplemental Notice of Allowance received for U.S. Appl. No. 16/588,950, dated Jul. 29, 2020, 2 pages.
Supplemental Notice of Allowance received for U.S. Appl. No. 16/588,950, dated Jun. 18, 2020, 2 pages.
Notice of Acceptance received for Australian Patent Application No. 2018268972, dated Dec. 18, 2020, 3 pages.
Applicant-Initiated Interview Summary received for U.S. Appl. No. 15/627,069, dated Jan. 22, 2021, 4 pages.
Applicant-Initiated Interview Summary received for U.S. Appl. No. 15/925,652, dated Nov. 3, 2020, 4 pages.
Applicant-Initiated Interview Summary received for U.S. Appl. No. 16/138,809, dated Dec. 16, 2020, 7 pages.
Board Decision received for Chinese Patent Application No. 201380081349.6, dated Nov. 23, 2020, 2 pages (1 page of English Translation and 1 page of Official Copy).
Final Office Action received for U.S. Appl. No. 16/418,786, dated Jan. 13, 2021, 14 pages.
Intention to Grant received for Danish Patent Application No. PA201670656, dated Jan. 18, 2021, 2 pages.
International Preliminary Report on Patentability received for PCT Patent Application No. PCT/US2019/024570, dated Nov. 19, 2020, 10 pages.
International Search Report and Written Opinion received for PCT Patent Application No. PCT/US2020/035199, dated Oct. 30, 2020, 20 pages.
Invitation to Pay Additional Fees received for PCT Patent Application No. PCT/US2020/035199, dated Sep. 8, 2020, 12 pages.
Non-Final Office Action received for U.S. Appl. No. 16/144,030, dated Nov. 5, 2020, 5 pages.
Non-Final Office Action received for U.S. Appl. No. 16/820,383, dated Dec. 14, 2020, 11 pages.

(56) References Cited

OTHER PUBLICATIONS

Non-Final Office Action received for U.S. Appl. No. 17/031,859, dated Dec. 15, 2020, 13 pages.
Non-Final Office Action received for U.S. Appl. No. 17/031,874, dated Dec. 28, 2020, 14 pages.
Notice of Allowance received for Japanese Patent Application No. 2018-014096, dated Jan. 5, 2021, 3 pages (1 page of English Translation and 2 pages of Official Copy).
Notice of Allowance received for Japanese Patent Application No. 2020-104679, dated Jan. 4, 2021, 4 pages (1 page of English Translation and 3 pages of Official Copy).
Notice of Allowance received for U.S. Appl. No. 15/925,652, dated Nov. 20, 2020, 9 pages.
Notice of Allowance received for U.S. Appl. No. 16/556,023, dated Jan. 13, 2021, 8 pages.
Office Action received for Australian Patent Application No. 2019234289, dated Nov. 2, 2020, 6 pages.
Office Action received for Australian Patent Application No. 2020230340, dated Nov. 2, 2020, 5 pages.
Office Action received for Chinese Patent Application No. 201710439448.7, dated Oct. 10, 2020, 19 pages (8 pages of English Translation and 11 pages of Official Copy).
Office Action received for European Patent Application No. 20182116.2, dated Nov. 6, 2020, 9 pages.
Office Action received for Japanese Patent Application No. 2020-000492, dated Dec. 11, 2020, 6 pages (3 pages English Translation and 3 pages of Official Copy).
Office Action received for Korean Patent Application No. 10-2019-7025781, dated Oct. 30, 2020, 10 pages (4 pages of English Translation and 6 pages of Official Copy).
Result of Consultation received for European Patent Application No. 17810749.6, dated Dec. 15, 2020, 3 pages.
Result of Consultation received for European Patent Application No. 17810749.6, dated Jan. 18, 2021, 3 pages.
Result of Consultation received for European Patent Application No. 17810749.6, dated Jan. 21, 2021, 18 pages.
Result of Consultation received for European Patent Application No. 18154145.9, dated Nov. 30, 2020, 17 pages.
Search Report and Opinion received for Danish Patent Application No. PA202070395, dated Nov. 24, 2020, 10 pages.
Search Report and Opinion received for Danish Patent Application No. PA202070614, dated Jan. 14, 2021, 9 pages.
Supplemental Notice of Allowance received for U.S. Appl. No. 15/925,652, dated Jan. 6, 2021, 3 pages.
Bagala et al., "Evaluation of Accelerometer-Based Fall Detection Algorithms on Real-World Falls", PloS One, vol. 7, No. 5, May 16, 2012, 9 pages.
Office Action received for Korean Patent Application No. 10-2019-7033834, dated Jan. 22, 2021, 13 pages (6 pages of English Translation and 7 pages of Official Copy).

* cited by examiner

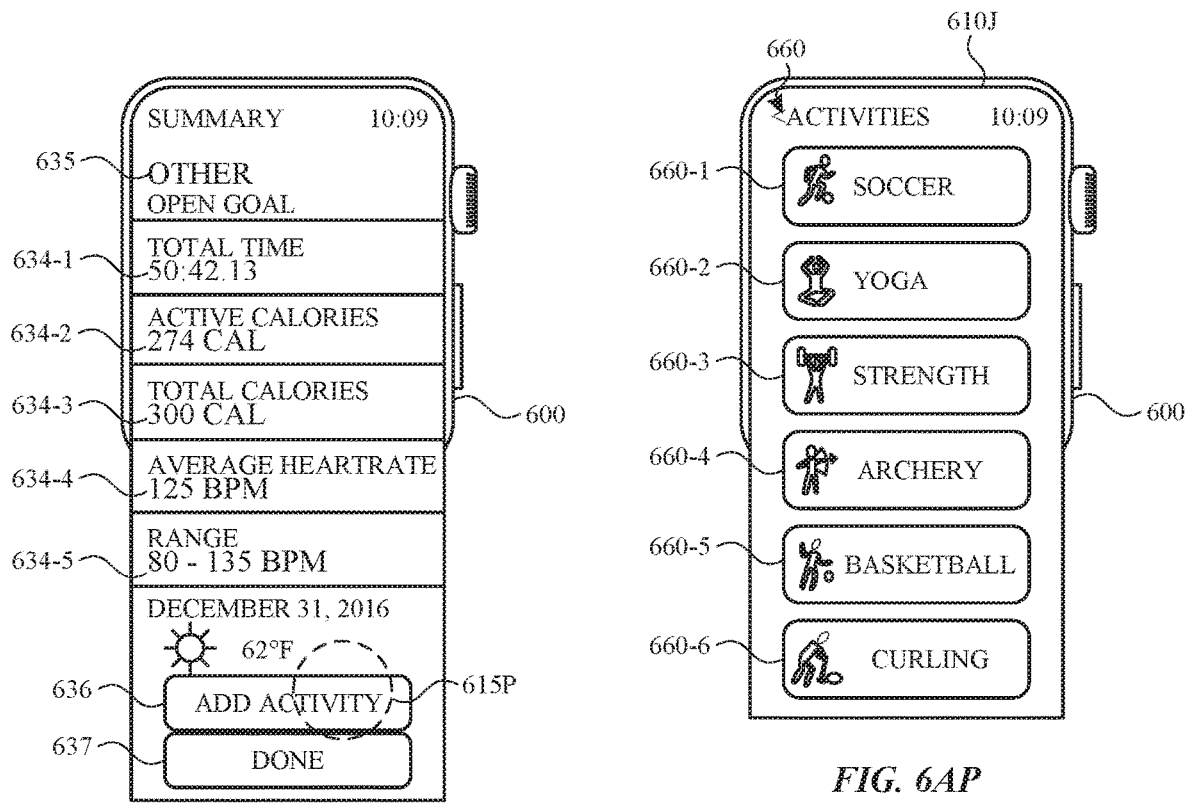
FIG. 6AO
FIG. 6AP
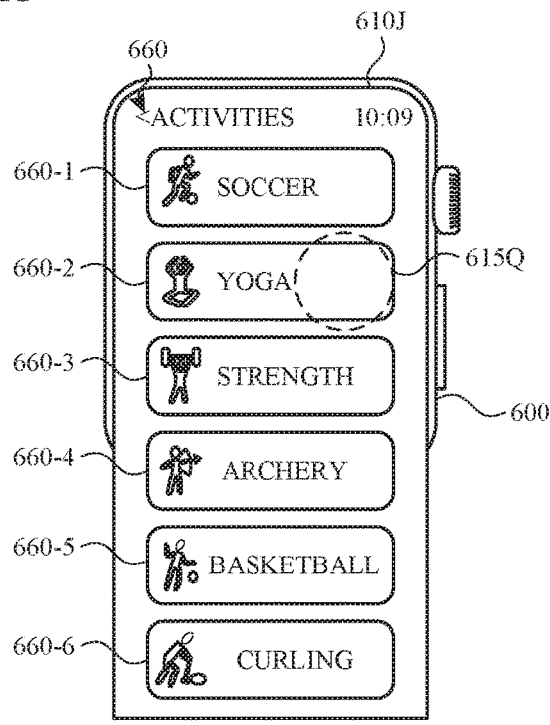
FIG. 6AQ

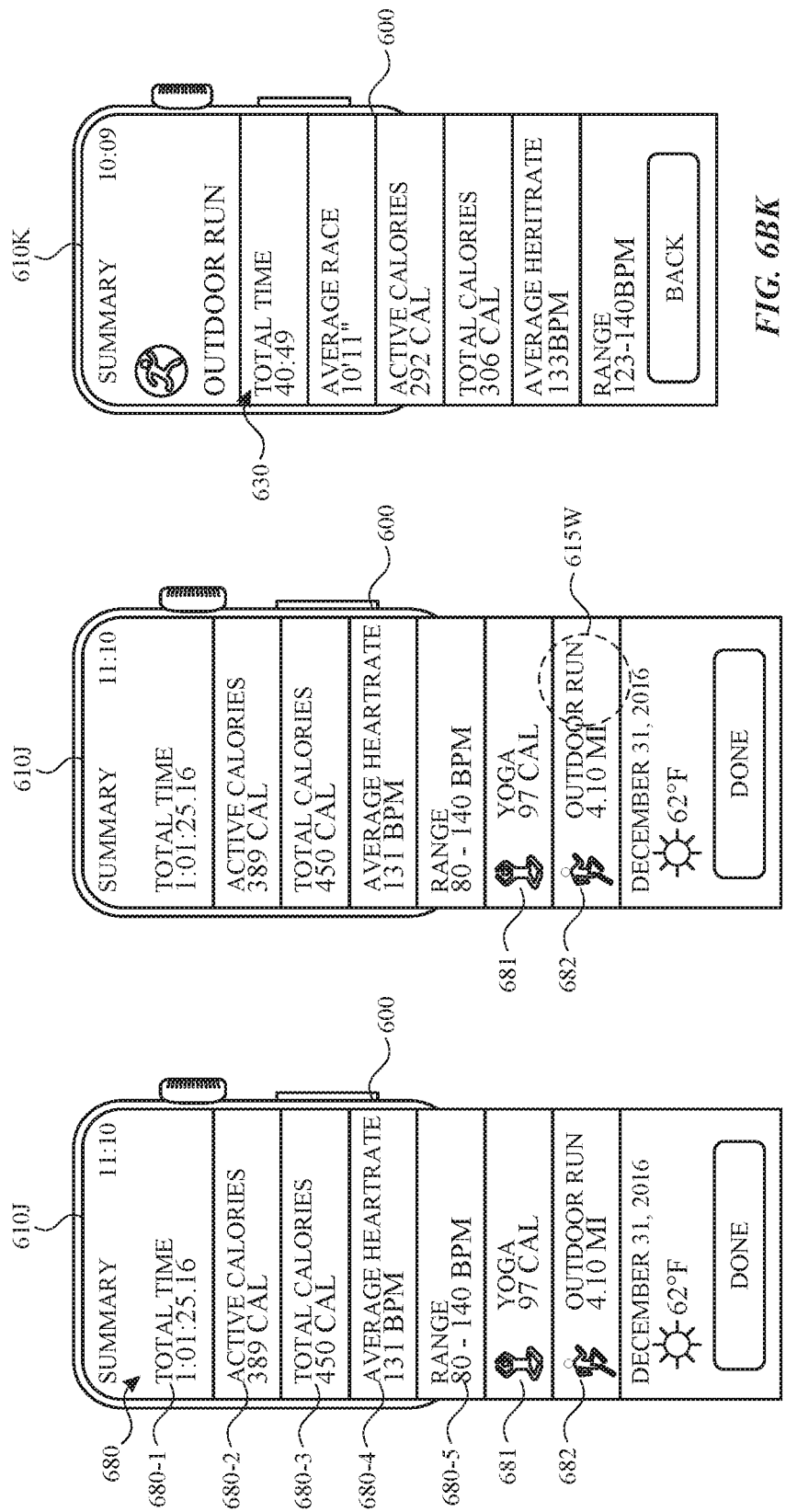

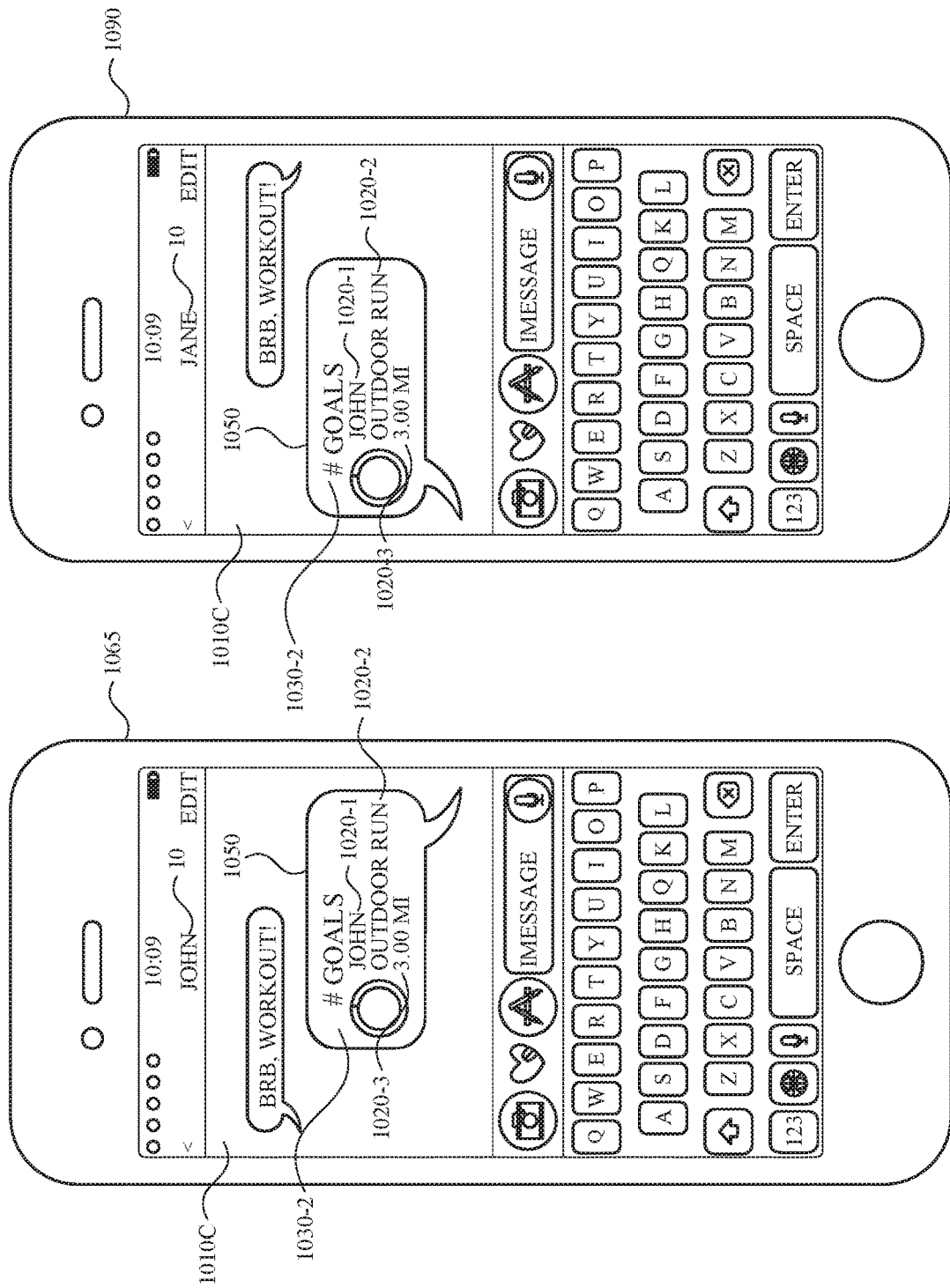

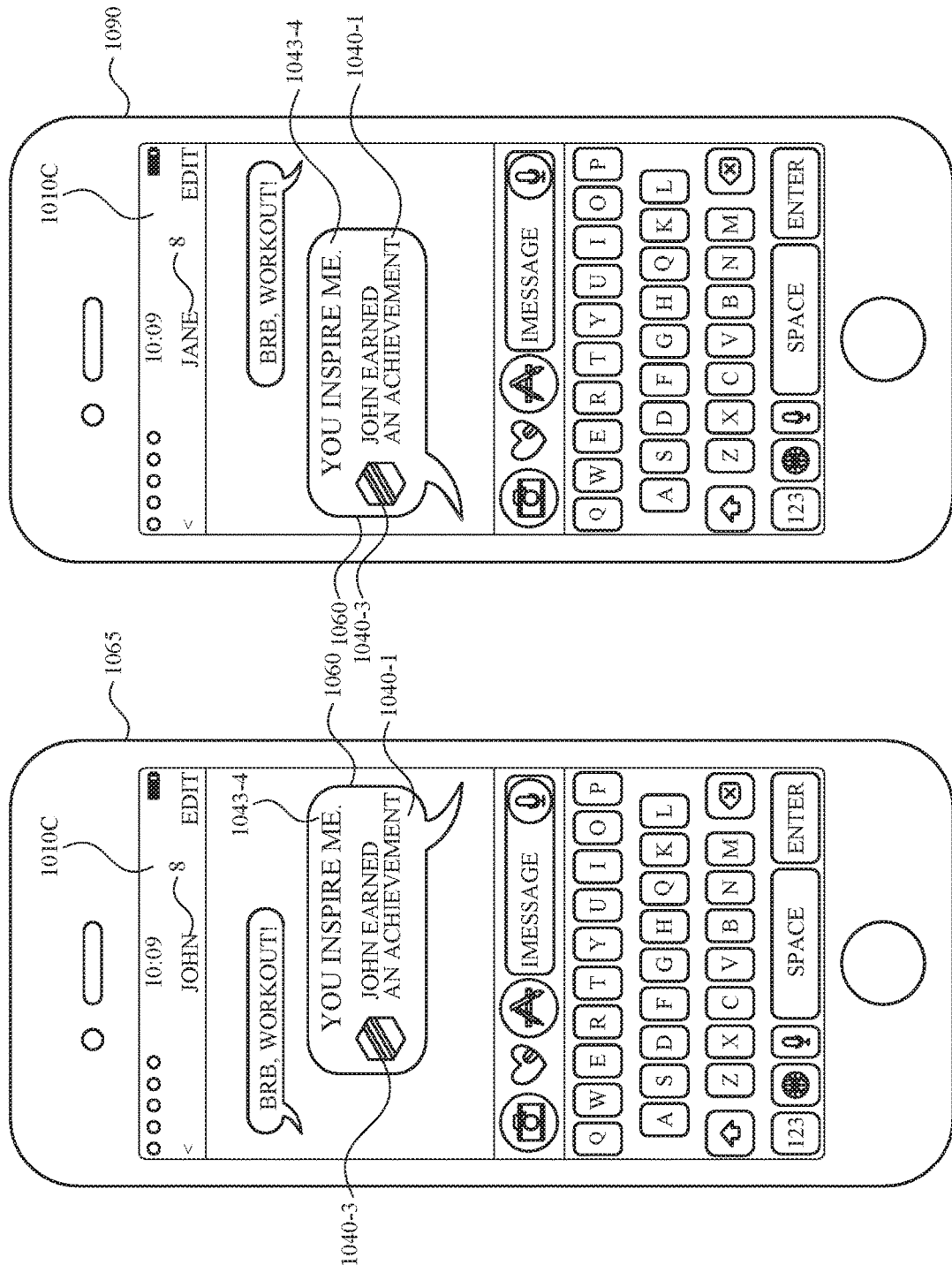

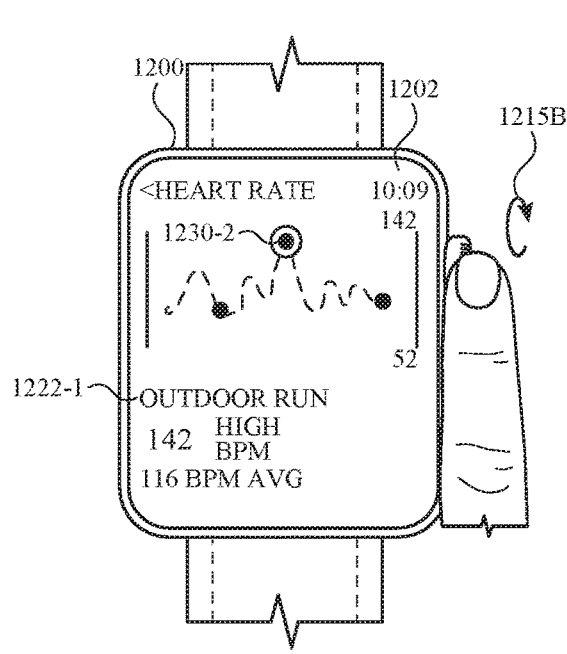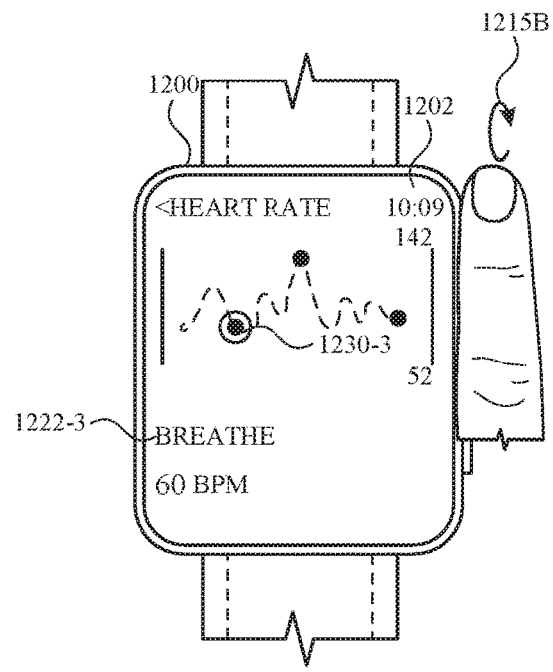
FIG. 12E
FIG. 12F
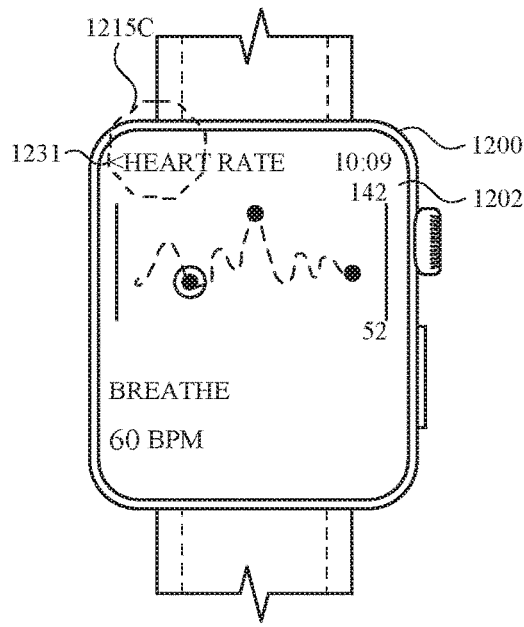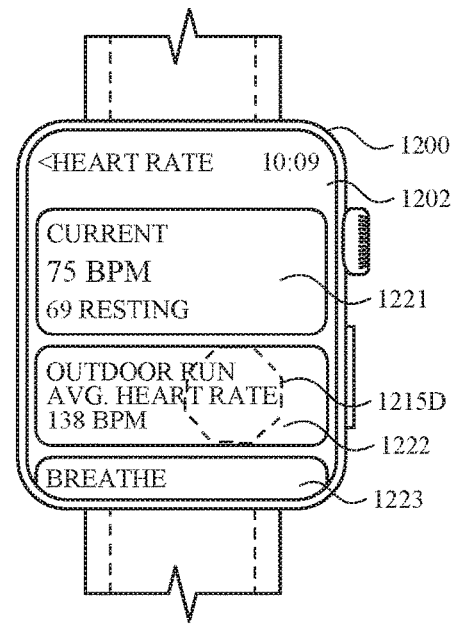
FIG. 12G
FIG. 12H

DISPLAYING A SCROLLABLE LIST OF AFFORDANCES ASSOCIATED WITH PHYSICAL ACTIVITIES

This application is a continuation of U.S. patent application Ser. No. 15/705,849, entitled "DISPLAYING A SCROLLABLE LIST OF AFFORDANCES ASSOCIATED WITH PHYSICAL ACTIVITIES", filed Sep. 15, 2017, which claims priority to U.S. Provisional Patent Application No. 62/506,304, entitled "DISPLAYING A SCROLLABLE LIST OF AFFORDANCES ASSOCIATED WITH PHYSICAL ACTIVITIES", filed on May 15, 2017, the content of which are hereby incorporated by reference in their entirety.

FIELD

The present disclosure relates generally to computer user interfaces and more specifically to techniques for displaying affordances associated with a physical activity.

BACKGROUND

Many modern electronic devices provide the capability of controlling a workout tracking function. Some techniques for controlling a workout tracking function require multiple user inputs. These techniques can be cumbersome and inefficient.

BRIEF SUMMARY

Some techniques for displaying affordances associated with a physical activity using electronic devices, however, are generally cumbersome and inefficient. For example, some existing techniques use a complex and time-consuming user interface, which may include multiple key presses or keystrokes. Existing techniques require more time than necessary, wasting user time and device energy. This latter consideration is particularly important in battery-operated devices.

Accordingly, the present technique provides electronic devices with faster, more efficient methods and interfaces for displaying affordances associated with a physical activity. Such methods and interfaces optionally complement or replace other methods for displaying affordances associated with a physical activity. Such methods and interfaces reduce the cognitive burden on a user and produce a more efficient human-machine interface. For battery-operated computing devices, such methods and interfaces conserve power and increase the time between battery charges.

In some embodiments, a method, comprising: at an electronic device with a display, a touch-sensitive surface, and a physical activity tracking sensor: displaying a scrollable list of affordances associated with physical activities; displaying a first change workout metrics affordance corresponding to a first affordance of the scrollable list of affordances; receiving a user input; in accordance with a determination that the user input is detected at the first affordance in the scrollable list of affordances, launching a physical activity tracking function associated with the selected first affordance; and in accordance with a determination that the user input is detected at the first change workout metrics affordance, displaying a user interface configured to change a workout metric.

In some embodiments, a non-transitory computer-readable storage medium storing one or more programs configured to be executed by one or more processors of an electronic device with a display, a touch-sensitive surface, and a physical activity tracking sensor, the one or more programs including instructions for: displaying a scrollable list of affordances associated with physical activities; displaying a first change workout metrics affordance corresponding to a first affordance of the scrollable list of affordances; receiving a user input; in accordance with a determination that the user input is detected at the first affordance in the scrollable list of affordances, launching a physical activity tracking function associated with the selected first affordance; and in accordance with a determination that the user input is detected at the first change workout metrics affordance, displaying a user interface configured to change a workout metric.

In some embodiments, a transitory computer-readable storage medium storing one or more programs configured to be executed by one or more processors of an electronic device with a display, a touch-sensitive surface, and a physical activity tracking sensor, the one or more programs including instructions for: displaying a scrollable list of affordances associated with physical activities; displaying a first change workout metrics affordance corresponding to a first affordance of the scrollable list of affordances; receiving a user input; in accordance with a determination that the user input is detected at the first affordance in the scrollable list of affordances, launching a physical activity tracking function associated with the selected first affordance; and in accordance with a determination that the user input is detected at the first change workout metrics affordance, displaying a user interface configured to change a workout metric.

In some embodiments, an electronic device, comprising: a display; a touch-sensitive surface; a physical activity tracking sensor; one or more processors; and memory storing one or more programs configured to be executed by the one or more processors, the one or more programs including instructions for: displaying a scrollable list of affordances associated with physical activities; displaying a first change workout metrics affordance corresponding to a first affordance of the scrollable list of affordances; receiving a user input; in accordance with a determination that the user input is detected at the first affordance in the scrollable list of affordances, launching a physical activity tracking function associated with the selected first affordance; and in accordance with a determination that the user input is detected at the first change workout metrics affordance, displaying a user interface configured to change a workout metric.

In some embodiments, an electronic device, comprising: a display; a touch-sensitive surface; a physical activity tracking sensor; means for displaying a scrollable list of affordances associated with physical activities; means for displaying a first change workout metrics affordance corresponding to a first affordance of the scrollable list of affordances; means for receiving a user input; means for in accordance with a determination that the user input is detected at the first affordance in the scrollable list of affordances, launching a physical activity tracking function associated with the selected first affordance; and means for in accordance with a determination that the user input is detected at the first change workout metrics affordance, displaying a user interface configured to change a workout metric.

In some embodiments, a method, comprising: at an electronic device with a display and a touch-sensitive surface: while an audio application is playing audio content, displaying a scrollable list of affordances associated with physical activities; while the audio application is playing the audio content, receiving a user input at an affordance of the scrollable list of affordances; and in response to receiving the user input at the affordance: launching a physical activity tracking function associated with the selected affordance, and determining whether a workout audio playlist setting is enabled; in accordance with a determination that the workout audio playlist setting is enabled: stop playing the audio content on the device, and initiate playing a workout audio playlist on the device; and in accordance with a determination that the workout audio playlist setting is disabled, continue playing the audio content on the device.

In some embodiments, a non-transitory computer-readable storage medium storing one or more programs configured to be executed by one or more processors of an electronic device with a display and a touch-sensitive surface, the one or more programs including instructions for: while an audio application is playing audio content, displaying a scrollable list of affordances associated with physical activities; while the audio application is playing the audio content, receiving a user input at an affordance of the scrollable list of affordances; and in response to receiving the user input at the affordance: launching a physical activity tracking function associated with the selected affordance, and determining whether a workout audio playlist setting is enabled; in accordance with a determination that the workout audio playlist setting is enabled: stop playing the audio content on the device, and initiate playing a workout audio playlist on the device; and in accordance with a determination that the workout audio playlist setting is disabled, continue playing the audio content on the device.

In some embodiments, a transitory computer-readable storage medium storing one or more programs configured to be executed by one or more processors of an electronic device with a display and a touch-sensitive surface, the one or more programs including instructions for: while an audio application is playing audio content, displaying a scrollable list of affordances associated with physical activities; while the audio application is playing the audio content, receiving a user input at an affordance of the scrollable list of affordances; and in response to receiving the user input at the affordance: launching a physical activity tracking function associated with the selected affordance, and determining whether a workout audio playlist setting is enabled; in accordance with a determination that the workout audio playlist setting is enabled: stop playing the audio content on the device, and initiate playing a workout audio playlist on the device; and in accordance with a determination that the workout audio playlist setting is disabled, continue playing the audio content on the device.

In some embodiments, an electronic device, comprising: a display; a touch-sensitive surface; one or more processors; and memory storing one or more programs configured to be executed by the one or more processors, the one or more programs including instructions for: while an audio application is playing audio content, displaying a scrollable list of affordances associated with physical activities; while the audio application is playing the audio content, receiving a user input at an affordance of the scrollable list of affordances; and in response to receiving the user input at the affordance: launching a physical activity tracking function associated with the selected affordance, and determining whether a workout audio playlist setting is enabled; in accordance with a determination that the workout audio playlist setting is enabled: stop playing the audio content on the device, and initiate playing a workout audio playlist on the device; and in accordance with a determination that the workout audio playlist setting is disabled, continue playing the audio content on the device.

In some embodiments, an electronic device, comprising: a display; a touch-sensitive surface; means for, while an audio application is playing audio content, displaying a scrollable list of affordances associated with physical activities; means for, while the audio application is playing the audio content, receiving a user input at an affordance of the scrollable list of affordances; and means for, in response to receiving the user input at the affordance: means for launching a physical activity tracking function associated with the selected affordance, and means for determining whether a workout audio playlist setting is enabled; means for, in accordance with a determination that the workout audio playlist setting is enabled: means for stop playing the audio content on the device, and means for initiate playing a workout audio playlist on the device; and means for, in accordance with a determination that the workout audio playlist setting is disabled, continue playing the audio content on the device.

In some embodiments, a method, comprising: at an electronic device with a display and a touch-sensitive surface: receiving, from an external device, a message; and in accordance with a determination that the message contains workout information: displaying one or more predefined responses to the received message; receiving user input corresponding to selecting a predefined response of the one or more predefined responses; and subsequent to receiving the user input, composing a reply message, wherein the reply message comprises: the selected predefined response; and the workout information.

In some embodiments, a non-transitory computer-readable storage medium storing one or more programs configured to be executed by one or more processors of an electronic device with a display and a touch-sensitive surface, the one or more programs including instructions for: receiving, from an external device, a message; and in accordance with a determination that the message contains workout information: displaying one or more predefined responses to the received message; receiving user input corresponding to selecting a predefined response of the one or more predefined responses; and subsequent to receiving the user input, composing a reply message, wherein the reply message comprises: the selected predefined response; and the workout information.

In some embodiments, a transitory computer-readable storage medium storing one or more programs configured to be executed by one or more processors of an electronic device with a display and a touch-sensitive surface, the one or more programs including instructions for: receiving, from an external device, a message; and in accordance with a determination that the message contains workout information: displaying one or more predefined responses to the received message; receiving user input corresponding to selecting a predefined response of the one or more predefined responses; and subsequent to receiving the user input, composing a reply message, wherein the reply message comprises: the selected predefined response; and the workout information.

In some embodiments, an electronic device, comprising: a display; a touch-sensitive surface; one or more processors; and memory storing one or more programs configured to be executed by the one or more processors, the one or more programs including instructions for: receiving, from an external device, a message; and in accordance with a determination that the message contains workout information: displaying one or more predefined responses to the received message; receiving user input corresponding to selecting a predefined response of the one or more predefined responses; and subsequent to receiving the user input, composing a reply message, wherein the reply message comprises: the selected predefined response; and the workout information.

In some embodiments, an electronic device, comprising: a display; a touch-sensitive surface; means for receiving, from an external device, a message; and means for, in accordance with a determination that the message contains workout information: means for displaying one or more predefined responses to the received message; means for receiving user input corresponding to selecting a predefined response of the one or more predefined responses; and means for, subsequent to receiving the user input, composing a reply message, wherein the reply message comprises: the selected predefined response; and the workout information.

In some embodiments, a method, comprising: at an electronic device with a display, a touch-sensitive surface, and a physical activity tracking sensor: displaying a scrollable list of affordances associated with heart rate information, the scrollable list of affordances comprising: a first affordance identifying: a first physical activity, and first heart rate information associated with the first physical activity, wherein the first heart rate information is measured by the physical activity tracking sensor; and a second affordance identifying: a second physical activity, and second heart rate information associated with the second physical activity, wherein the second heart rate information is different than the first heart rate information, and wherein the second heart rate information is measured by the physical activity tracking sensor; receiving user input; in accordance to a determination that the user input corresponds to the first affordance, displaying additional first heart rate information; and in accordance to a determination that the user input corresponds to the second affordance, displaying additional second heart rate information, wherein the additional second rate information is different than the additional first heart rate information.

In some embodiments, a non-transitory computer-readable storage medium storing one or more programs configured to be executed by one or more processors of an electronic device with a display, a touch-sensitive surface, and a physical activity tracking sensor, the one or more programs including instructions for: displaying a scrollable list of affordances associated with heart rate information, the scrollable list of affordances comprising: a first affordance identifying: a first physical activity, and first heart rate information associated with the first physical activity, wherein the first heart rate information is measured by the physical activity tracking sensor; and a second affordance identifying: a second physical activity, and second heart rate information associated with the second physical activity, wherein the second heart rate information is different than the first heart rate information, and wherein the second heart rate information is measured by the physical activity tracking sensor; receiving user input; in accordance to a determination that the user input corresponds to the first affordance, displaying additional first heart rate information; and in accordance to a determination that the user input corresponds to the second affordance, displaying additional second heart rate information, wherein the additional second rate information is different than the additional first heart rate information.

In some embodiments, a transitory computer-readable storage medium storing one or more programs configured to be executed by one or more processors of an electronic device with a display, a touch-sensitive surface, and a physical activity tracking sensor, the one or more programs including instructions for: displaying a scrollable list of affordances associated with heart rate information, the scrollable list of affordances comprising: a first affordance identifying: a first physical activity, and first heart rate information associated with the first physical activity, wherein the first heart rate information is measured by the physical activity tracking sensor; and a second affordance identifying: a second physical activity, and second heart rate information associated with the second physical activity, wherein the second heart rate information is different than the first heart rate information, and wherein the second heart rate information is measured by the physical activity tracking sensor; receiving user input; in accordance to a determination that the user input corresponds to the first affordance, displaying additional first heart rate information; and in accordance to a determination that the user input corresponds to the second affordance, displaying additional second heart rate information, wherein the additional second rate information is different than the additional first heart rate information.

In some embodiments, an electronic device, comprising: a display; a touch-sensitive surface; a physical activity tracking sensor; one or more processors; and memory storing one or more programs configured to be executed by the one or more processors, the one or more programs including instructions for: displaying a scrollable list of affordances associated with heart rate information, the scrollable list of affordances comprising: a first affordance identifying: a first physical activity, and first heart rate information associated with the first physical activity, wherein the first heart rate information is measured by the physical activity tracking sensor; and a second affordance identifying: a second physical activity, and second heart rate information associated with the second physical activity, wherein the second heart rate information is different than the first heart rate information, and wherein the second heart rate information is measured by the physical activity tracking sensor; receiving user input; in accordance to a determination that the user input corresponds to the first affordance, displaying additional first heart rate information; and in accordance to a determination that the user input corresponds to the second affordance, displaying additional second heart rate information, wherein the additional second rate information is different than the additional first heart rate information.

In some embodiments, an electronic device, comprising: a display; a touch-sensitive surface; a physical activity tracking sensor; means for displaying a scrollable list of affordances associated with heart rate information, the scrollable list of affordances comprising: a first affordance identifying: a first physical activity, and first heart rate information associated with the first physical activity, wherein the first heart rate information is measured by the physical activity tracking sensor; and a second affordance identifying: a second physical activity, and second heart rate information associated with the second physical activity, wherein the second heart rate information is different than the first heart rate information, and wherein the second heart rate information is measured by the physical activity tracking sensor; means for receiving user input; means for, in accordance to a determination that the user input corresponds to the first affordance, displaying additional first heart rate information; and means for, in accordance to a determination that the user input corresponds to the second affordance, displaying additional second heart rate information, wherein the additional second rate information is different than the additional first heart rate information.

In some embodiments, a method, comprising: at an electronic device with a display, a touch-sensitive surface, and a physical activity tracking sensor: while tracking heart rate data corresponding to data received from the physical activity tracking sensor: determining whether the heart rate data satisfies a heart rate alert criteria; in accordance to determining that the heart rate data satisfies the heart rate alert criteria: displaying a heart rate alert affordance; receiving user input corresponding to the heart rate alert affordance; and subsequent to receiving the user input corresponding to the heart rate alert affordance, causing display of a graph comprising the heart rate data that satisfies the heart rate alert criteria over a period of time; and in accordance to determining that the heart rate data does not satisfy the heart rate alert criteria, forgo causing display of the heart rate alert affordance.

In some embodiments, a non-transitory computer-readable storage medium storing one or more programs configured to be executed by one or more processors of an electronic device with a display, a touch-sensitive surface, a physical activity tracking sensor, and the one or more programs including instructions for: while tracking heart rate data corresponding to data received from the physical activity tracking sensor: determining whether the heart rate data satisfies a heart rate alert criteria; in accordance to determining that the heart rate data satisfies the heart rate alert criteria: displaying a heart rate alert affordance; receiving user input corresponding to the heart rate alert affordance; and subsequent to receiving the user input corresponding to the heart rate alert affordance, causing display of a graph comprising the heart rate data that satisfies the heart rate alert criteria over a period of time; and in accordance to determining that the heart rate data does not satisfy the heart rate alert criteria, forgo causing display of the heart rate alert affordance.

In some embodiments, a transitory computer-readable storage medium storing one or more programs configured to be executed by one or more processors of an electronic device with a display, a touch-sensitive surface, a physical activity tracking sensor, and the one or more programs including instructions for: while tracking heart rate data corresponding to data received from the physical activity tracking sensor: determining whether the heart rate data satisfies a heart rate alert criteria; in accordance to determining that the heart rate data satisfies the heart rate alert criteria: displaying a heart rate alert affordance; receiving user input corresponding to the heart rate alert affordance; and subsequent to receiving the user input corresponding to the heart rate alert affordance, causing display of a graph comprising the heart rate data that satisfies the heart rate alert criteria over a period of time; and in accordance to determining that the heart rate data does not satisfy the heart rate alert criteria, forgo causing display of the heart rate alert affordance.

In some embodiments, an electronic device, comprising: a display; a touch-sensitive surface; a physical activity tracking sensor; one or more processors; and memory storing one or more programs configured to be executed by the one or more processors, the one or more programs including instructions for: while tracking heart rate data corresponding to data received from the physical activity tracking sensor: determining whether the heart rate data satisfies a heart rate alert criteria; in accordance to determining that the heart rate data satisfies the heart rate alert criteria: displaying a heart rate alert affordance; receiving user input corresponding to the heart rate alert affordance; and subsequent to receiving the user input corresponding to the heart rate alert affordance, causing display of a graph comprising the heart rate data that satisfies the heart rate alert criteria over a period of time; and in accordance to determining that the heart rate data does not satisfy the heart rate alert criteria, forgo causing display of the heart rate alert affordance.

In some embodiments, an electronic device, comprising: a display; a touch-sensitive surface; a physical activity tracking sensor; means for, while tracking heart rate data corresponding to data received from the physical activity tracking sensor: means for determining whether the heart rate data satisfies a heart rate alert criteria; means for, in accordance to determining that the heart rate data satisfies the heart rate alert criteria: means for displaying a heart rate alert affordance; means for receiving user input corresponding to the heart rate alert affordance; and means for, subsequent to receiving the user input corresponding to the heart rate alert affordance, causing display of a graph comprising the heart rate data that satisfies the heart rate alert criteria over a period of time; and means for, in accordance to determining that the heart rate data does not satisfy the heart rate alert criteria, forgo causing display of the heart rate alert affordance.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for displaying affordances associated with a physical activity, thereby increasing the effectiveness, efficiency, and user satisfaction with such devices. Such methods and interfaces may complement or replace other methods for displaying affordances associated with a physical activity.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIGS. 12A-12M illustrate exemplary user interfaces in accordance with some embodiments.

DESCRIPTION OF EMBODIMENTS

The following description sets forth exemplary methods, parameters, and the like. It should be recognized, however, that such description is not intended as a limitation on the scope of the present disclosure but is instead provided as a description of exemplary embodiments.

There is a need for electronic devices that provide efficient methods and interfaces for displaying affordances associated with a physical activity. Such techniques can reduce the cognitive burden on a user who access the affordances associated with a physical activity, thereby enhancing productivity. Further, such techniques can reduce processor and battery power otherwise wasted on redundant user inputs.

Figure 6A:
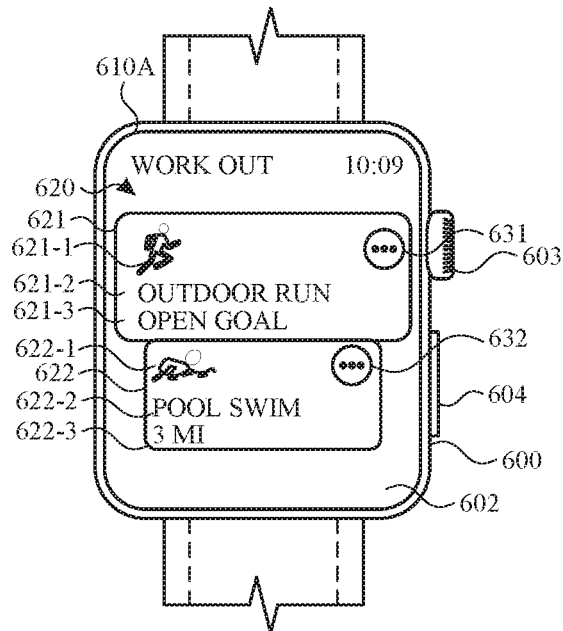
FIGS. 6A-6BN illustrate exemplary user interfaces in accordance with some embodiments.
Figure 6B:
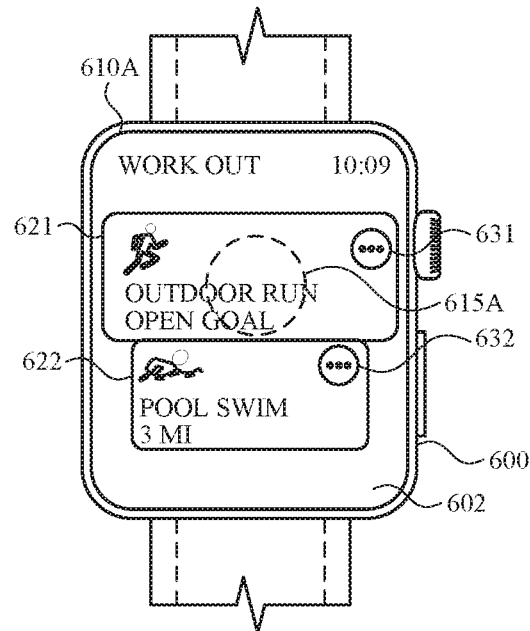
Figure 6C:
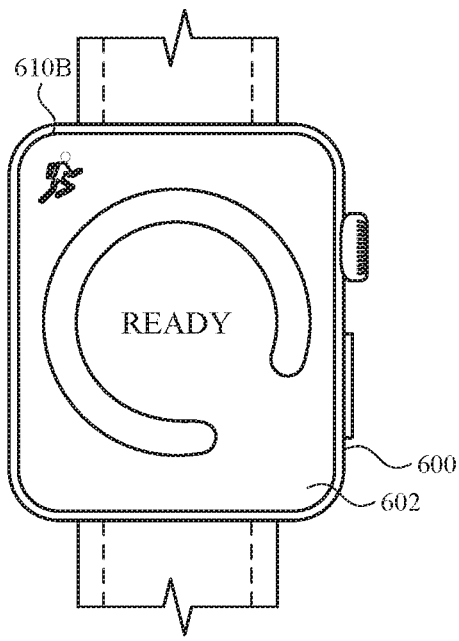
Figure 6D:
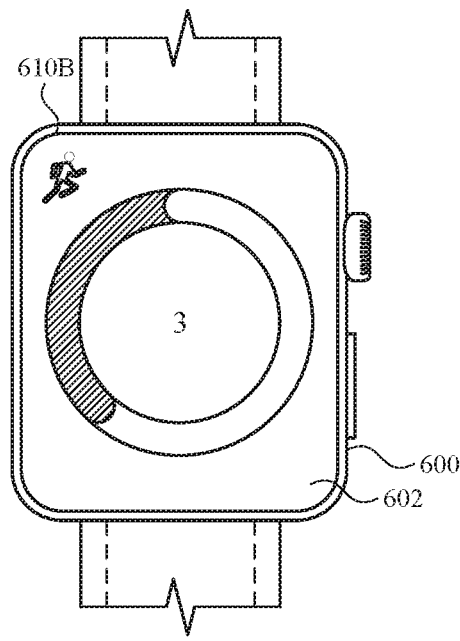
Figure 6E:
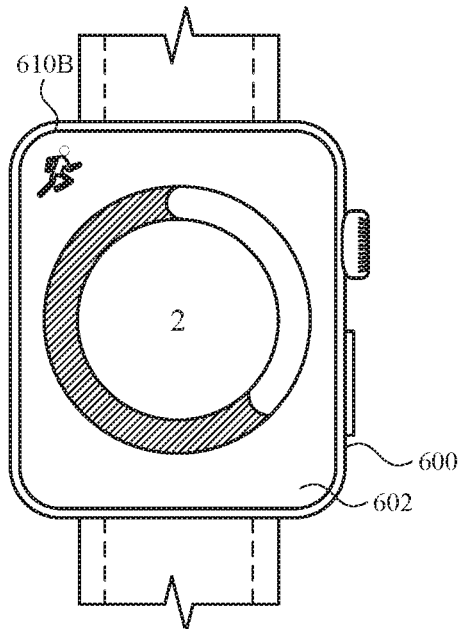
Figure 7:
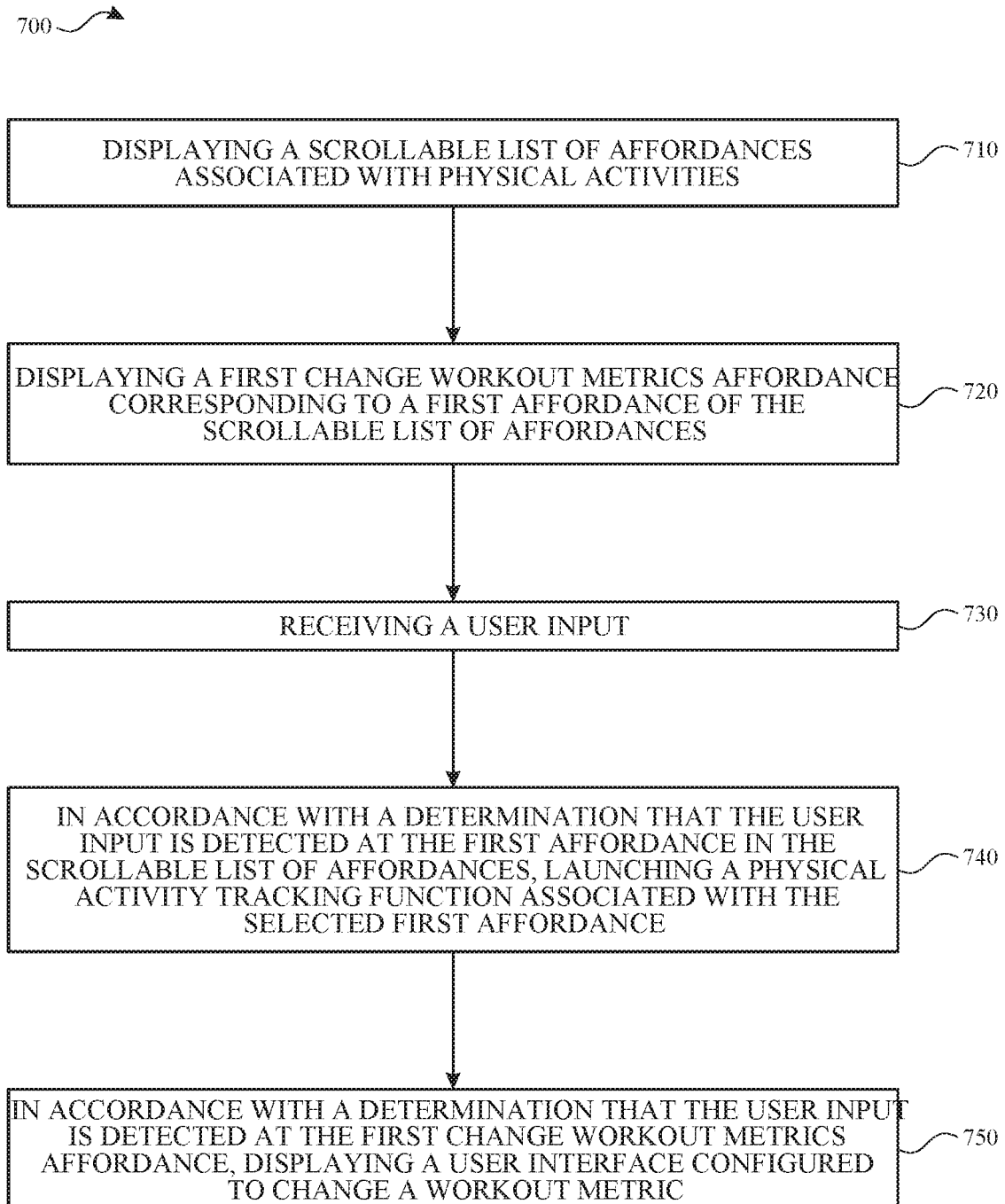
FIG. 7 is a flow diagram illustrating a method for operating an electronic device in accordance with some embodiments.

Below, FIGS. 1A-1B, 2, 3, 4A-4B, and 5A-5H provide a description of exemplary devices for performing the techniques for managing event notifications. FIGS. 6A-6BH illustrate exemplary user interfaces for displaying affordances associated with a physical activity. FIG. 7 is a flow diagram illustrating methods of displaying affordances associated with a physical activity in accordance with some embodiments. The user interfaces in FIGS. 6A-6BH are used to illustrate the processes described below, including the processes in FIG. 7.

Figure 8A:
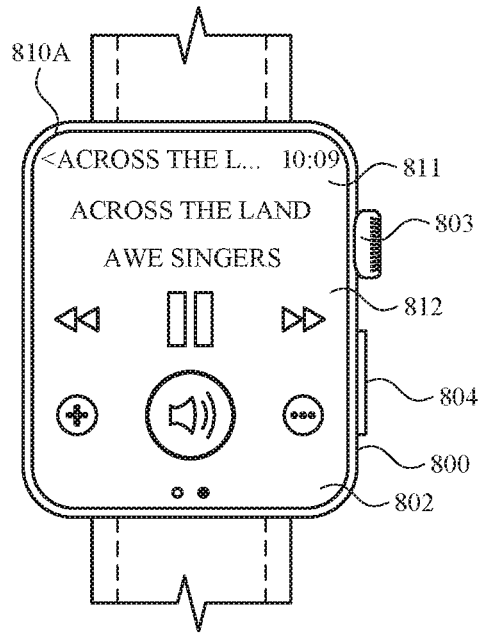
FIGS. 8A-8T illustrate exemplary user interfaces in accordance with some embodiments.
Figure 8B:
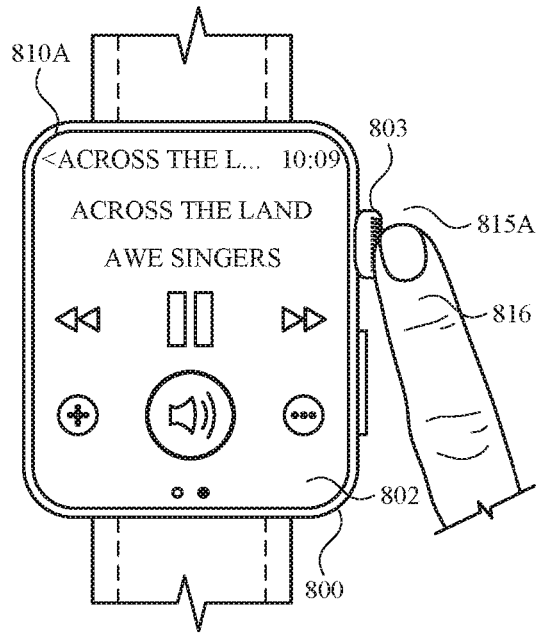
Figure 8C:
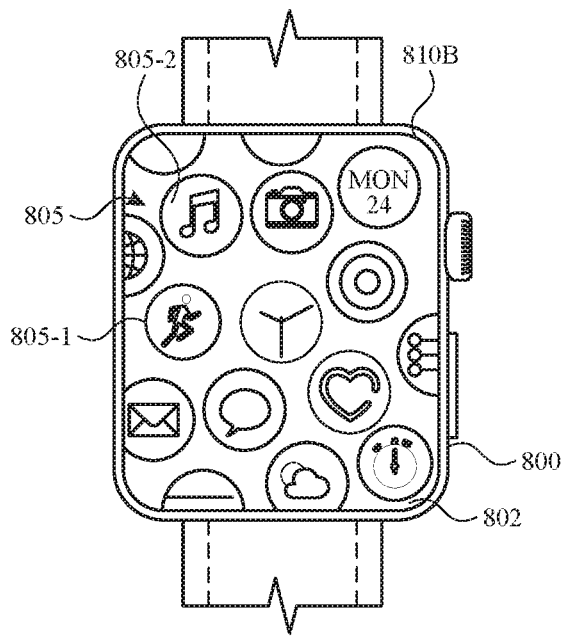
Figure 8D:
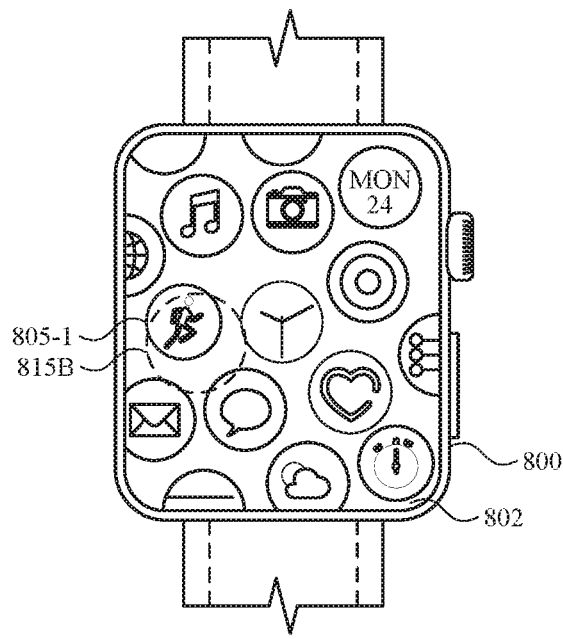
Figure 8E:
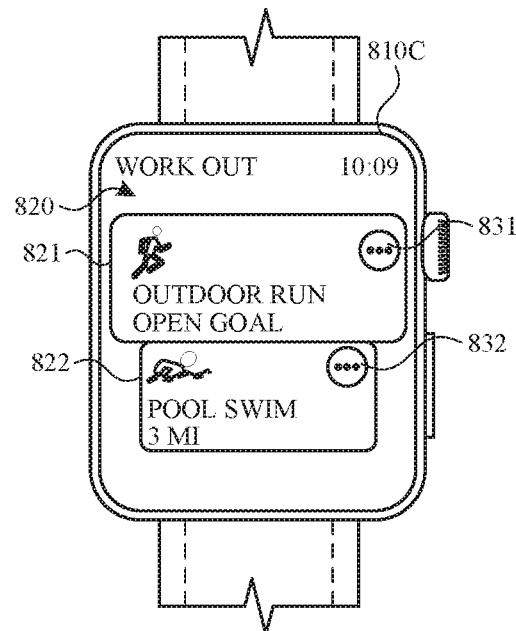
Figure 8F:
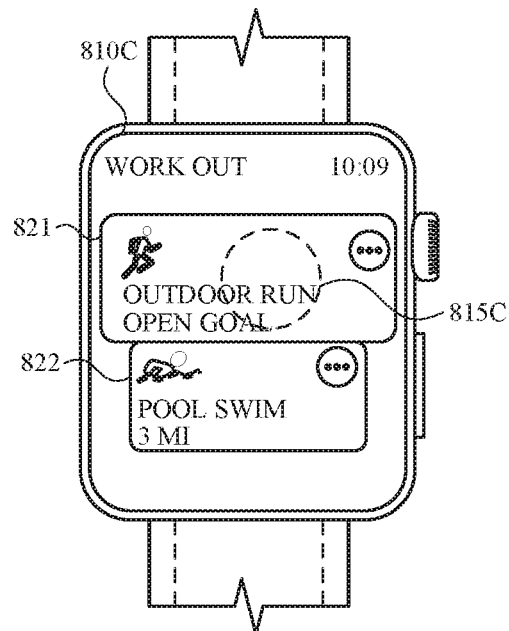
Figure 8G:
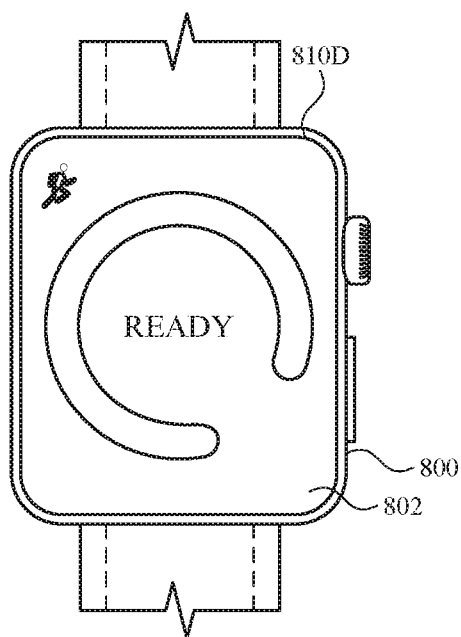
Figure 8H:
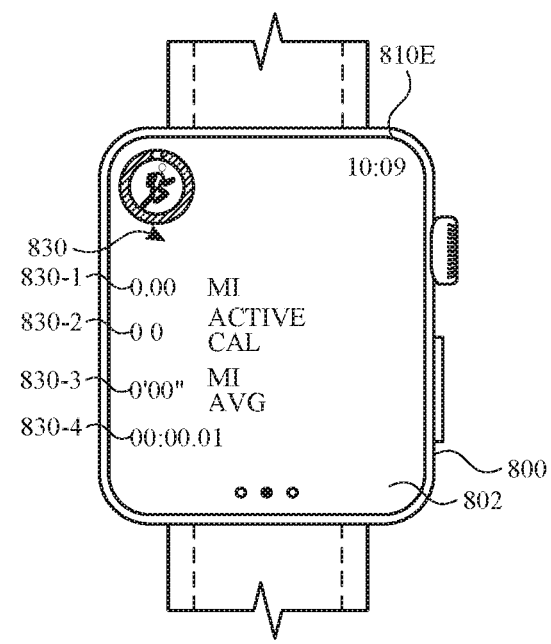
Figure 8I:
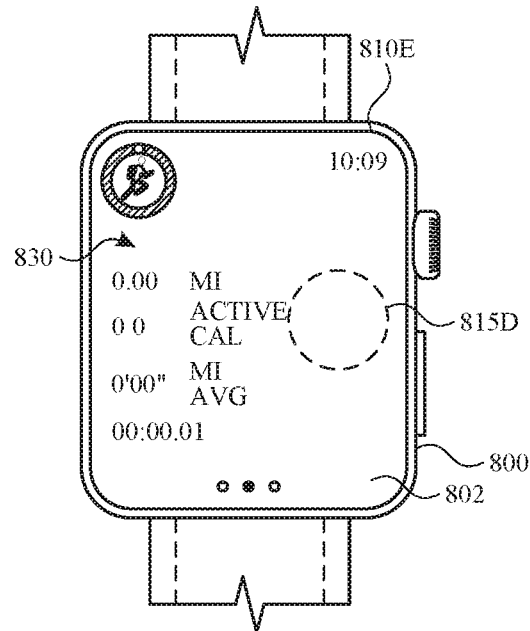
Figure 8J:
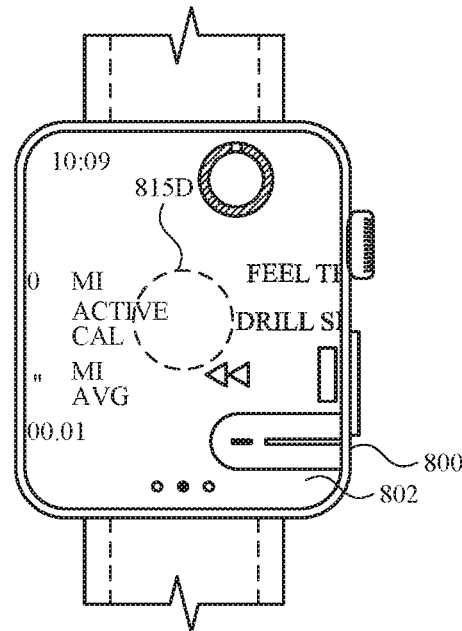
Figure 8K:
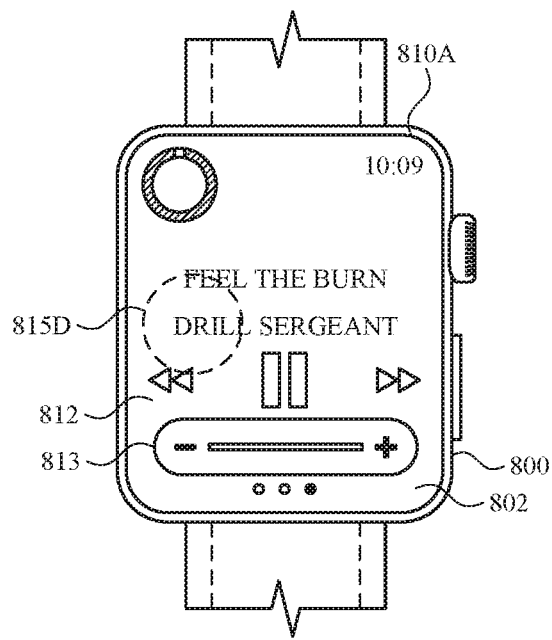
Figure 8L:
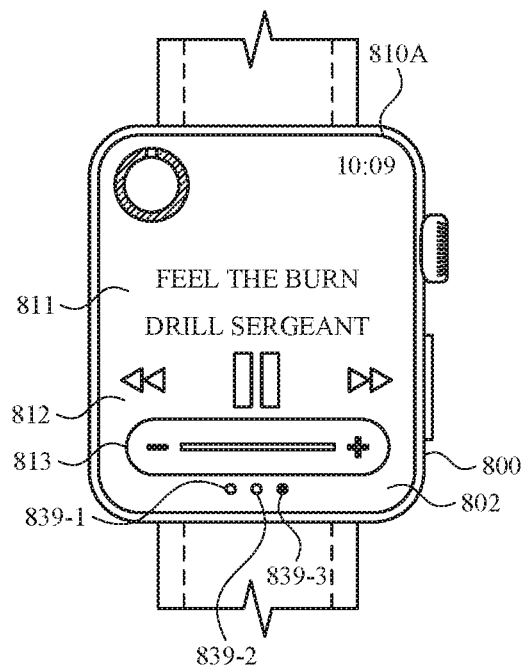
Figures 8M, 8N:
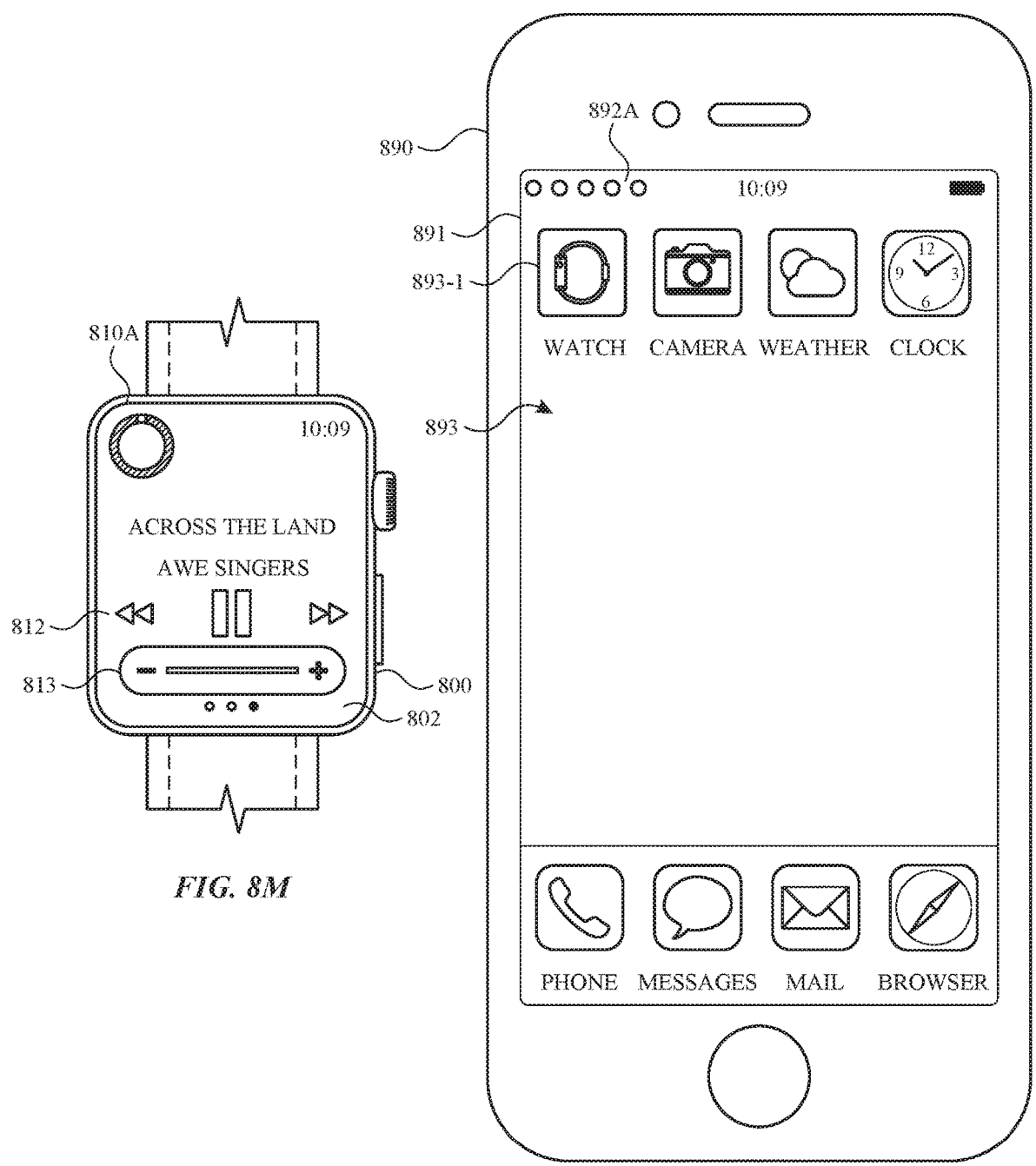
Figure 8O:
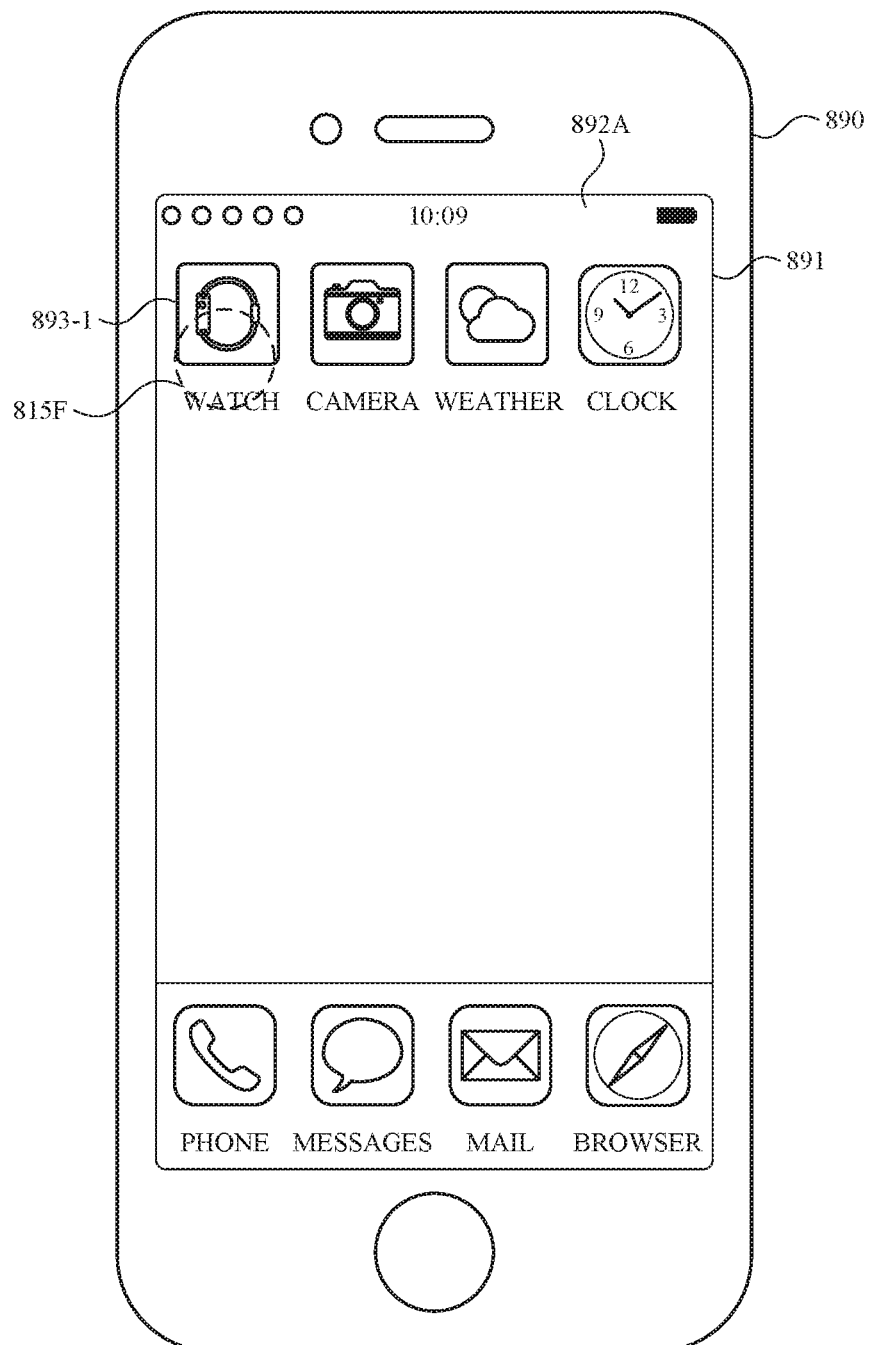
Figure 8P:
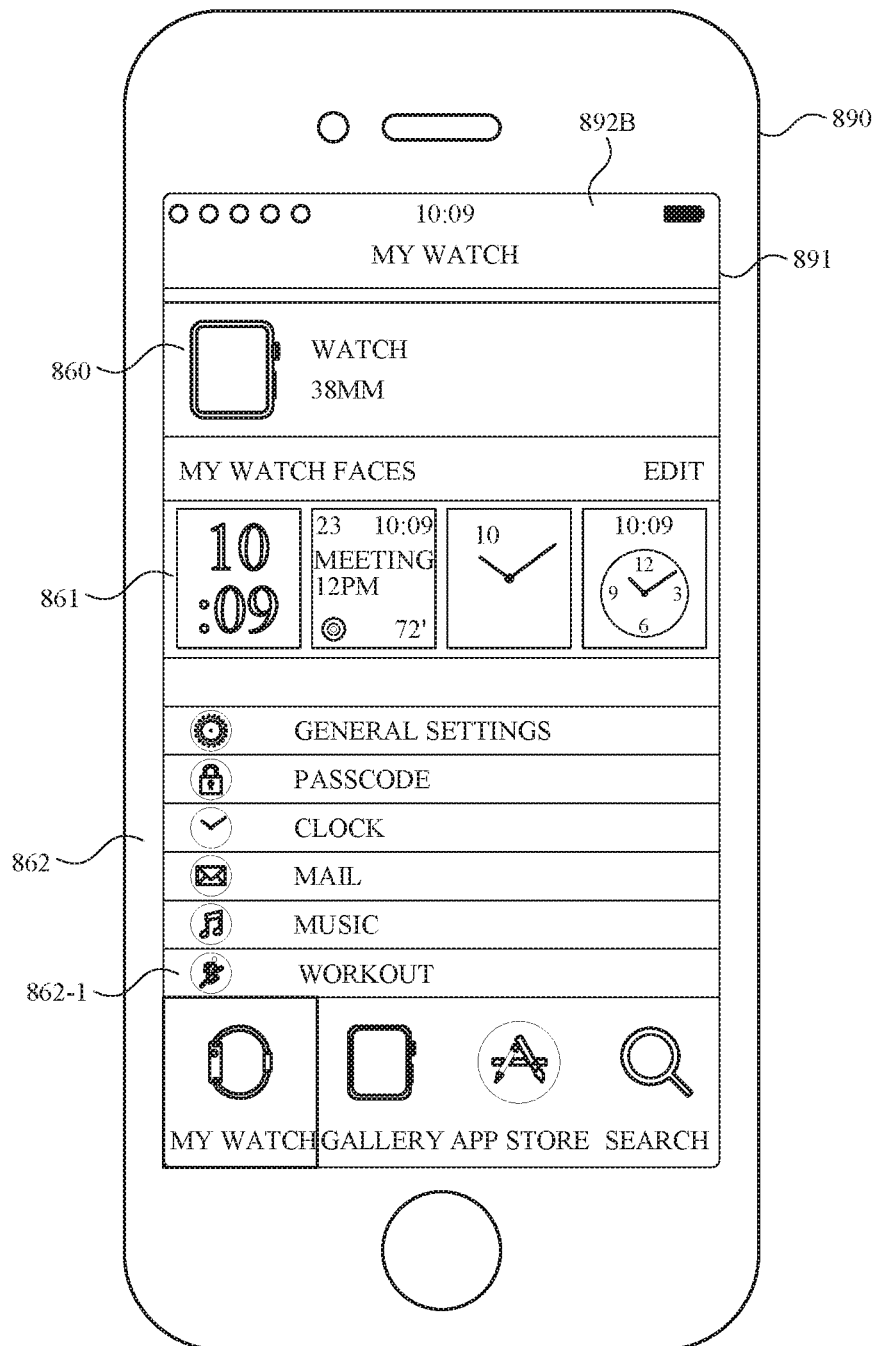
Figure 8Q:
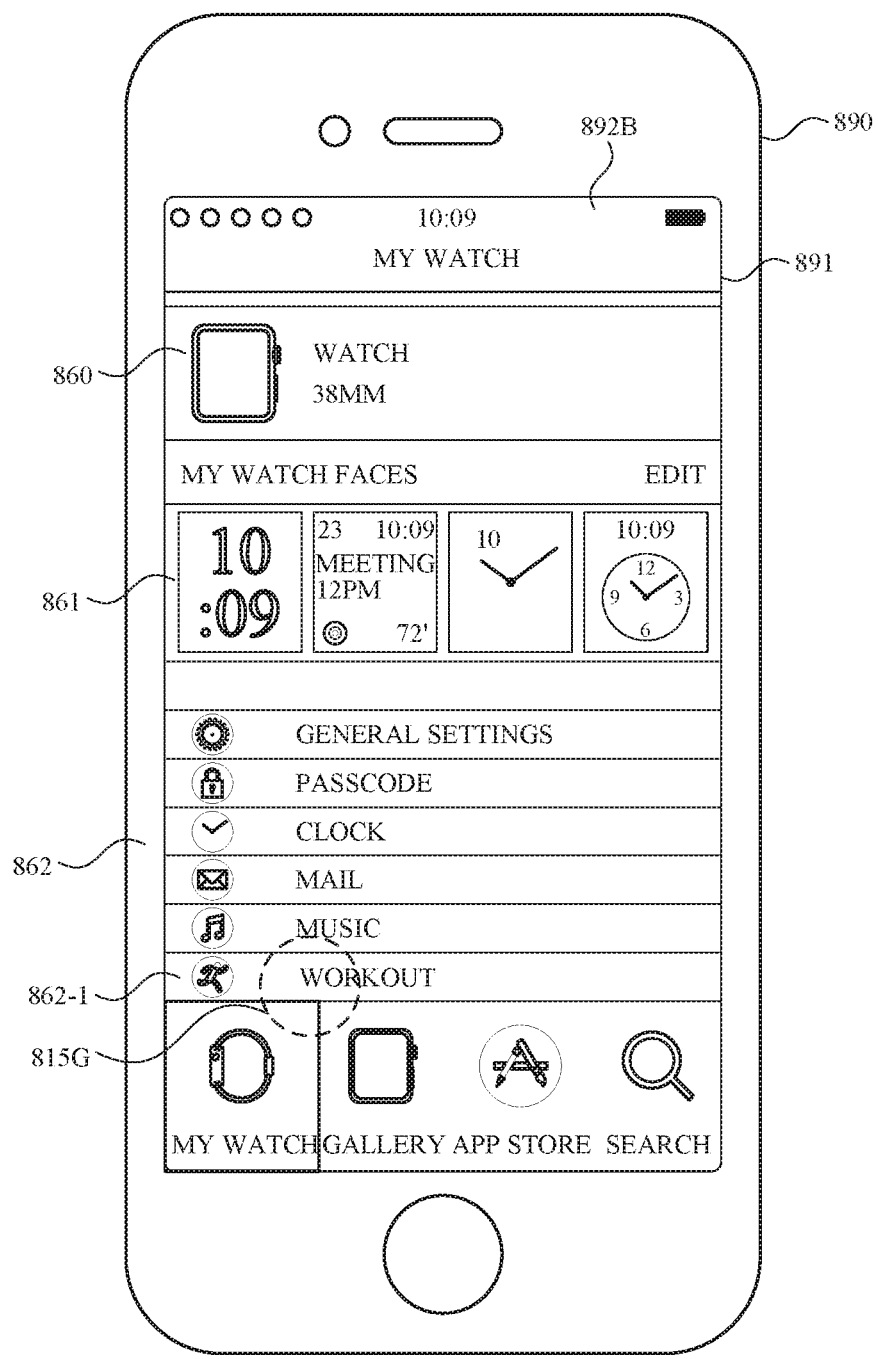
Figure 8R:
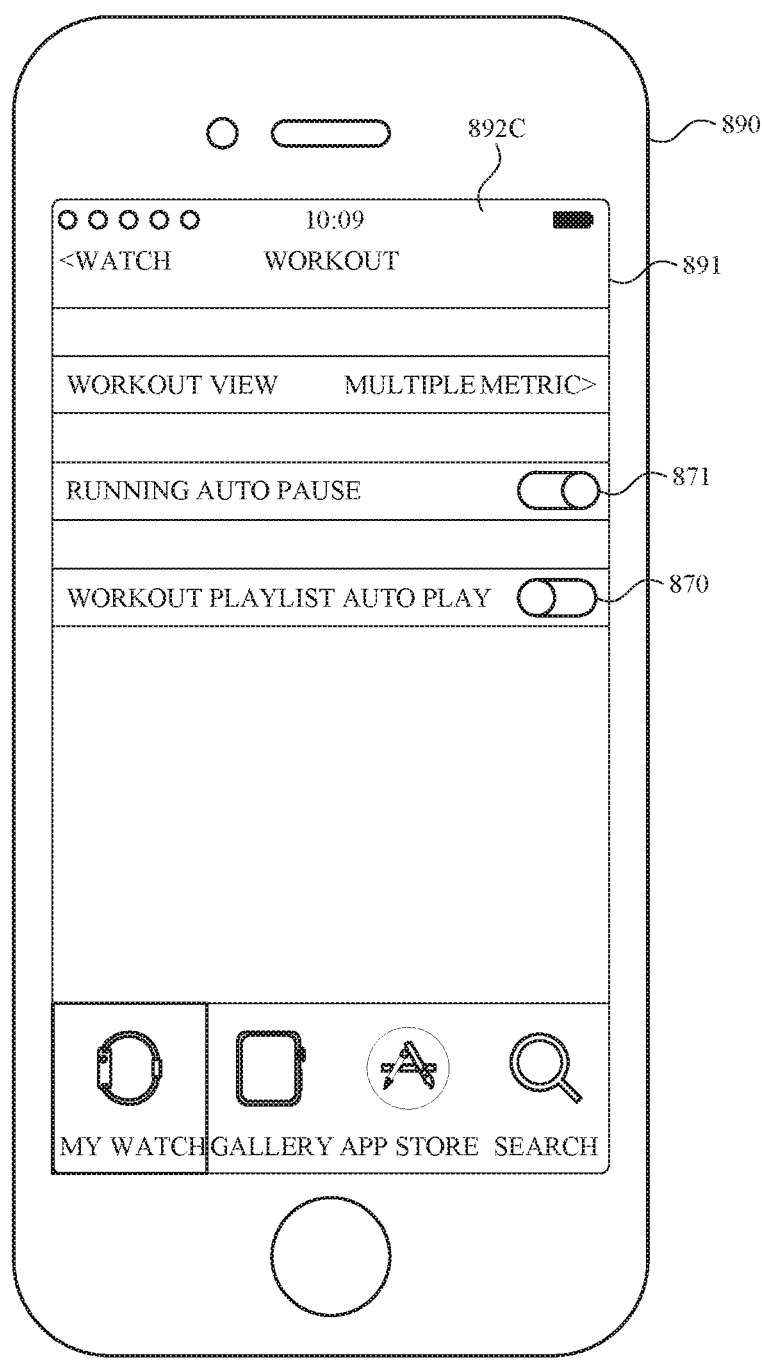
Figure 8S:
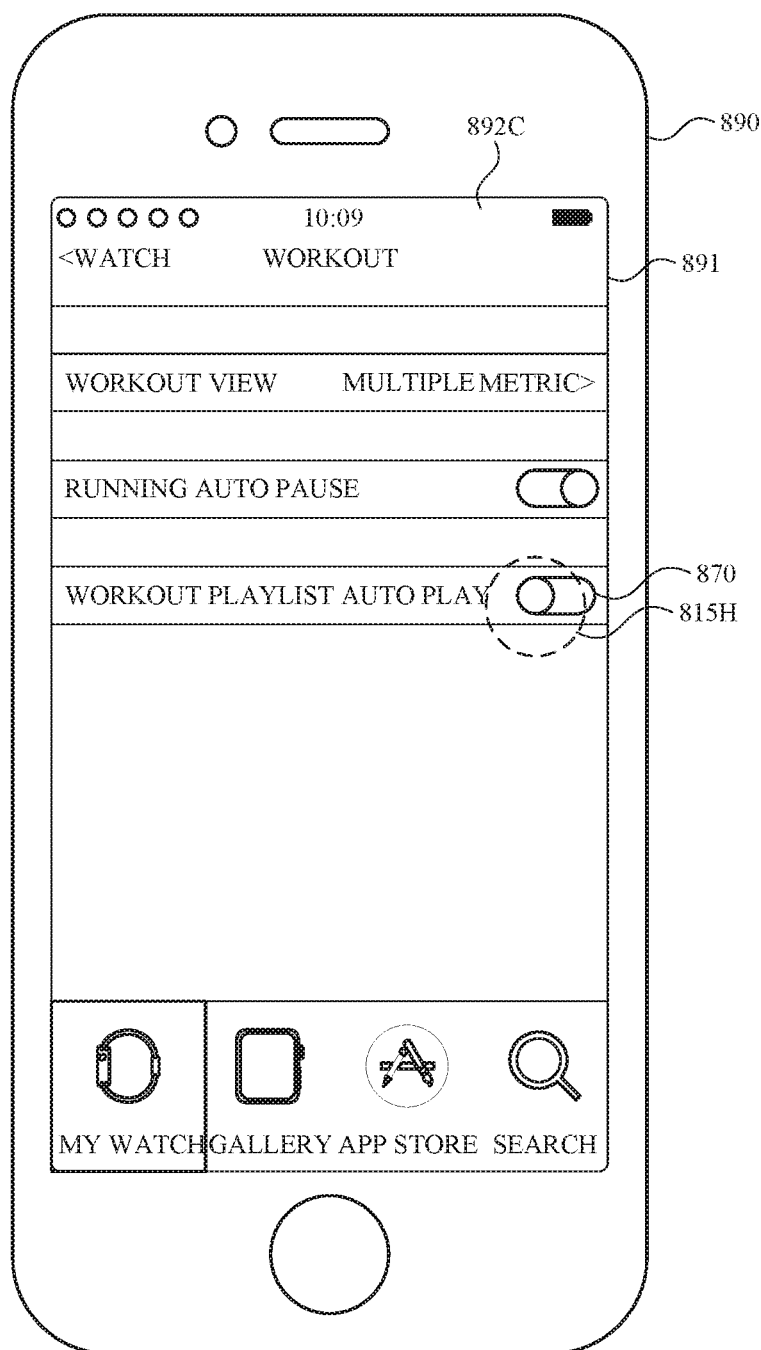
Figure 8T:
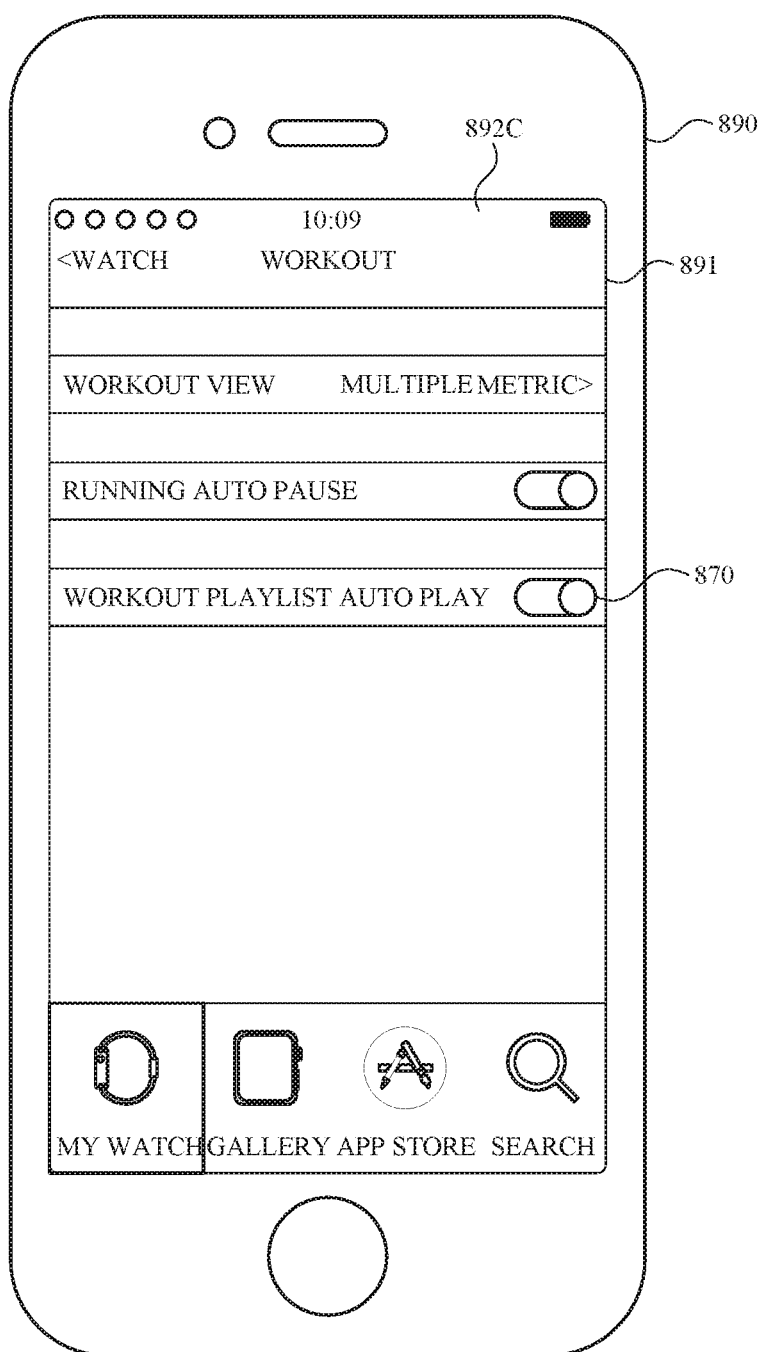
Figure 9:
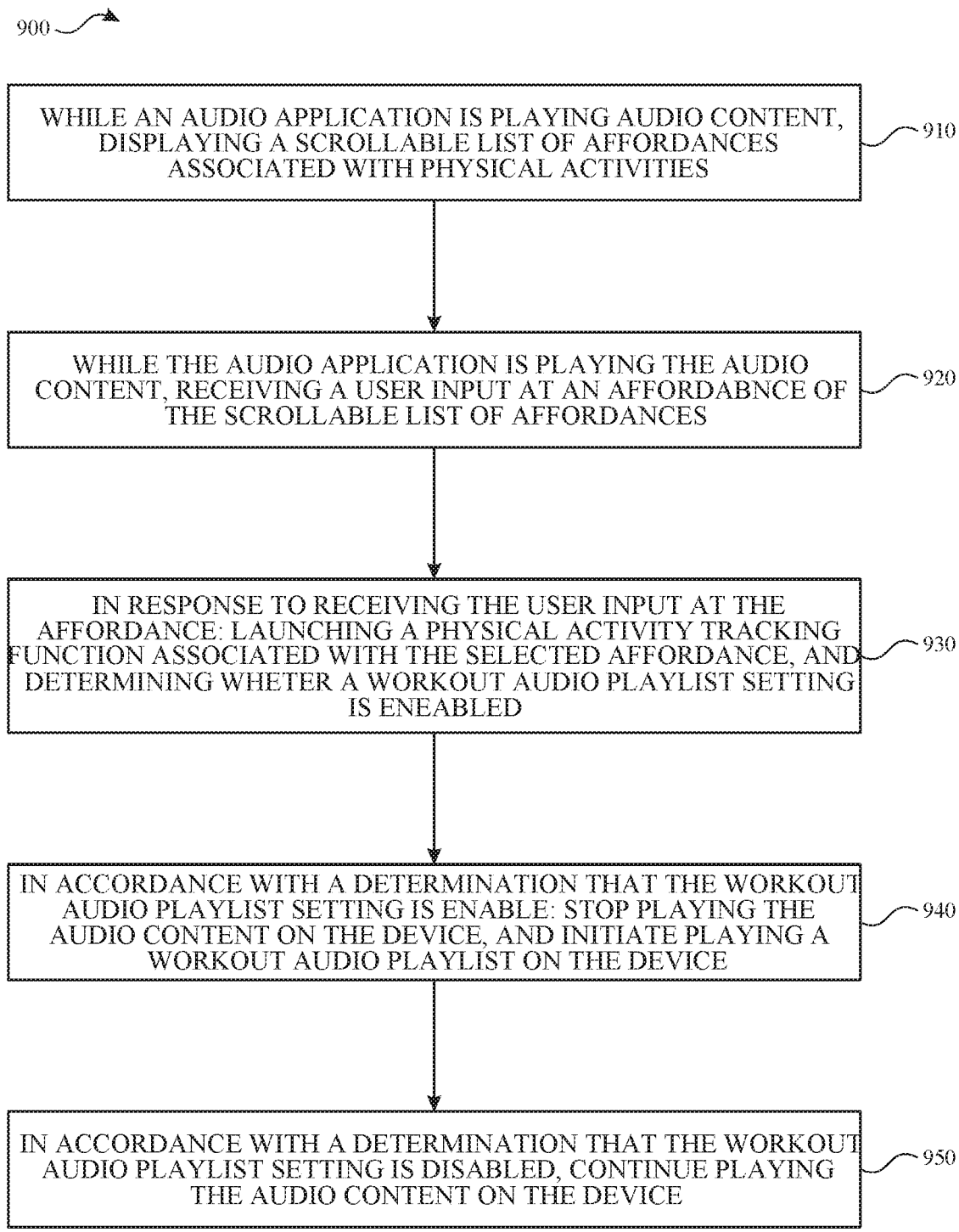
FIG. 9 is a flow diagram illustrating a method for operating an electronic device in accordance with some embodiments.

FIGS. 8A-8T illustrate exemplary user interfaces for continuing or not continuing playing a currently playing song in response to selecting a workout. FIG. 9 is a flow diagram illustrating methods of continuing or not continuing playing a currently playing song in response to selecting a workout in accordance with some embodiments. The user interfaces in FIGS. 8A-8T are used to illustrate the processes described below, including the processes in FIG. 9.

Figure 10A:
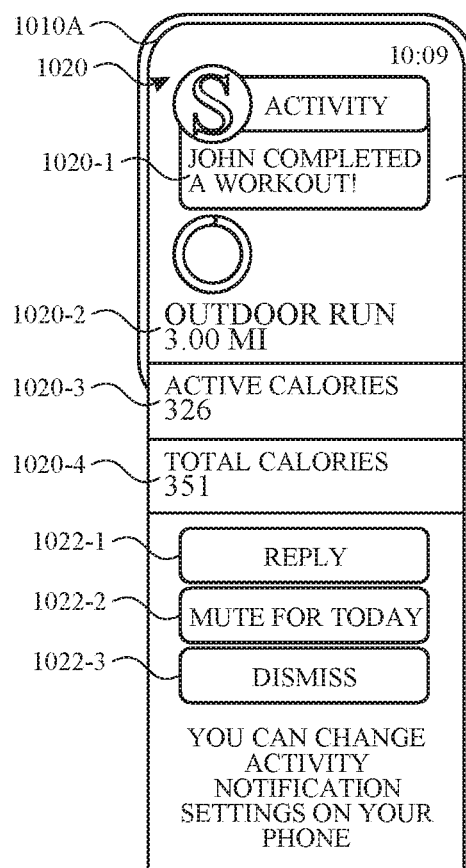
FIGS. 10A-10N illustrate exemplary user interfaces in accordance with some embodiments.
Figure 10B:
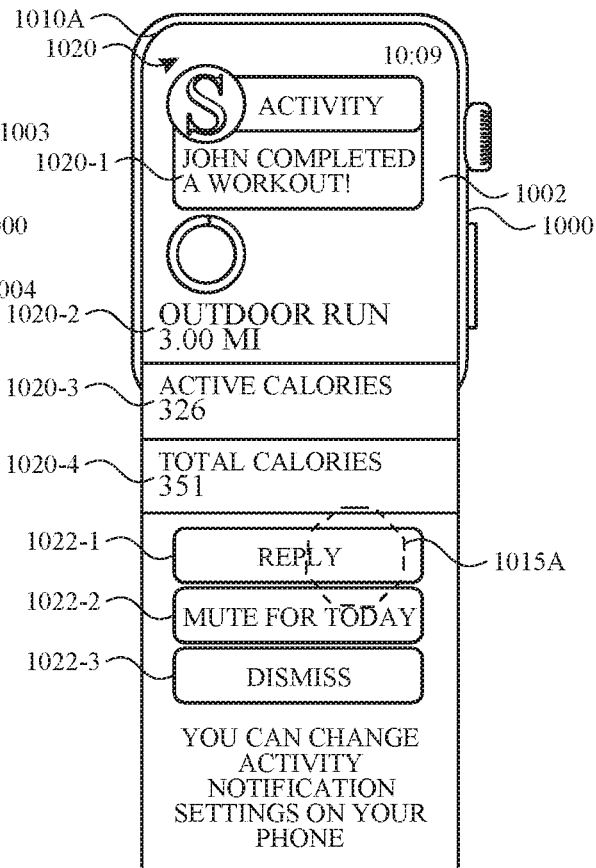
Figure 10C:
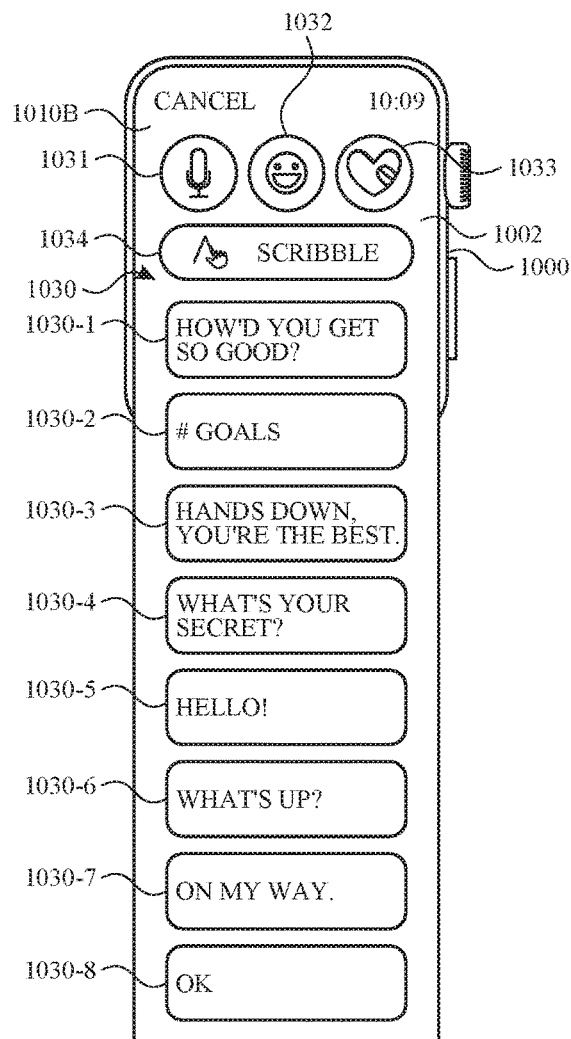
Figure 10D:
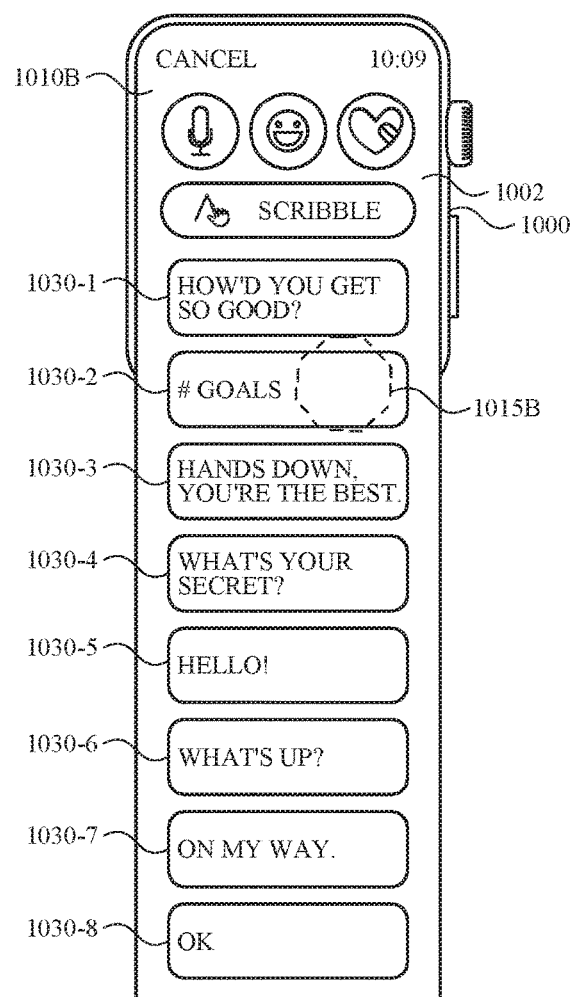
Figure 10G:
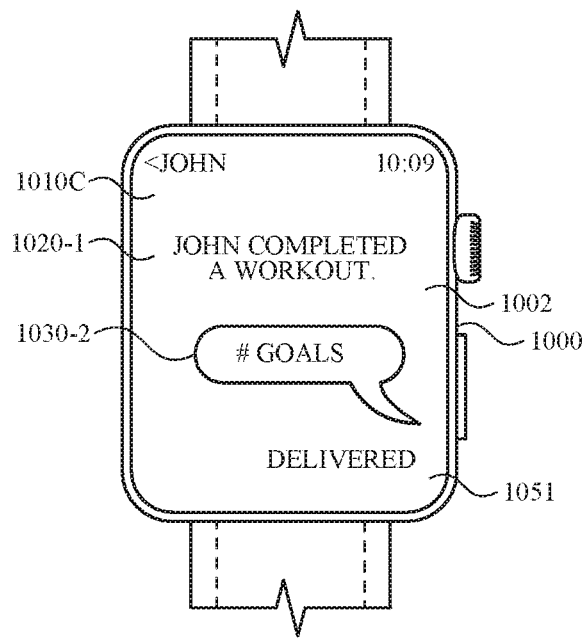
Figure 10H:
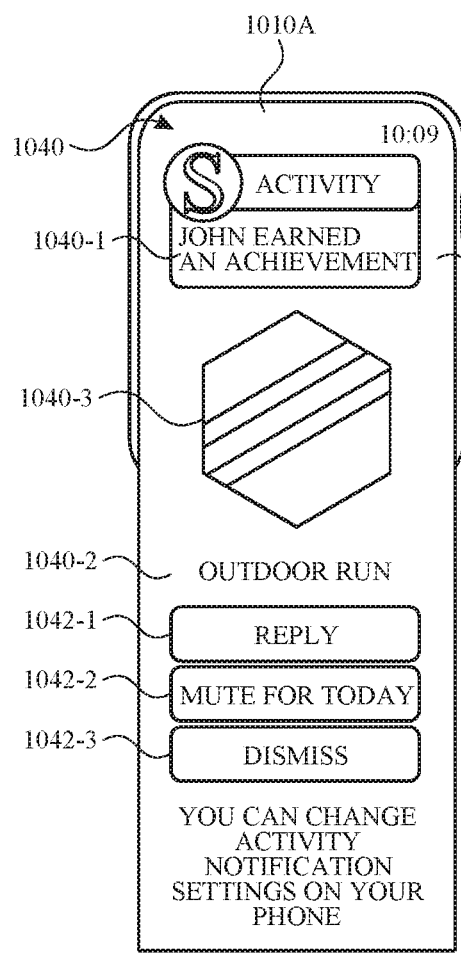
Figure 10I:
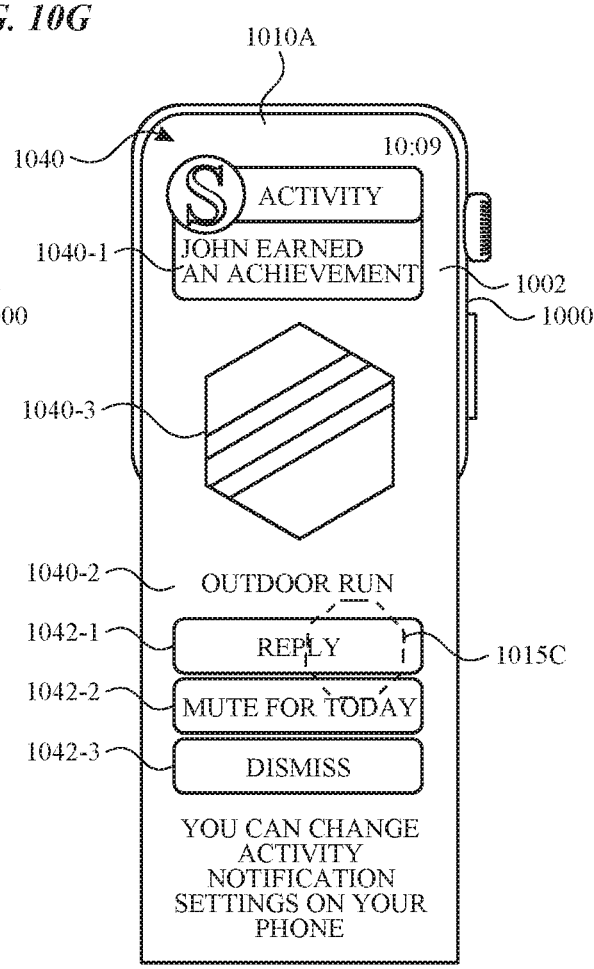
Figure 10J:
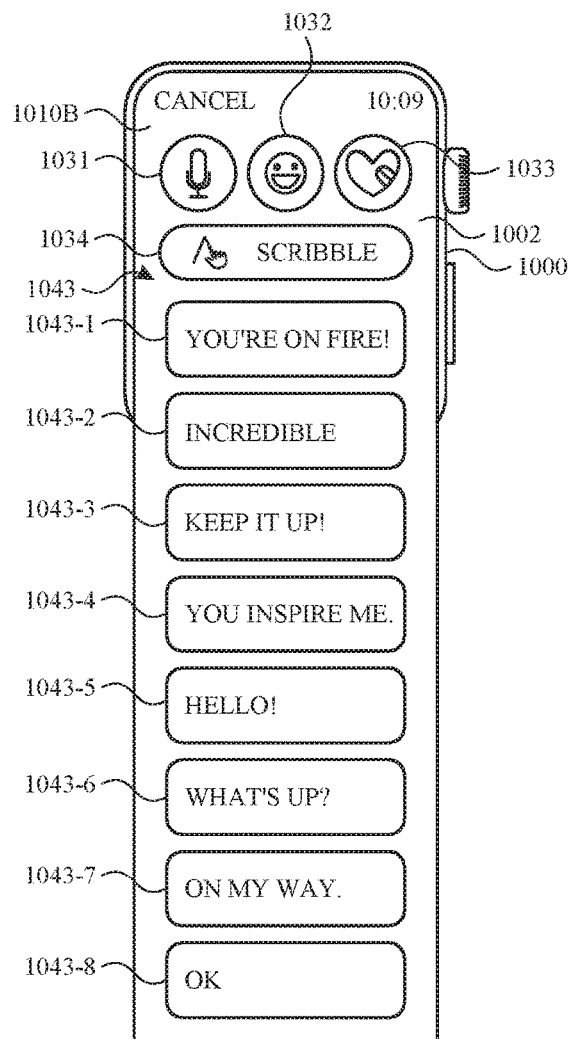
Figure 10K:
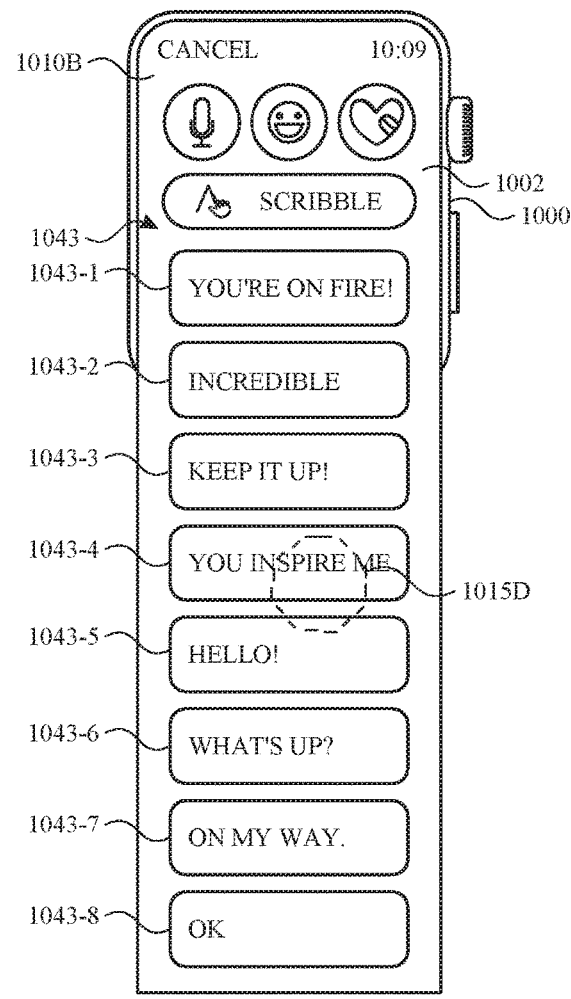
Figure 10N:
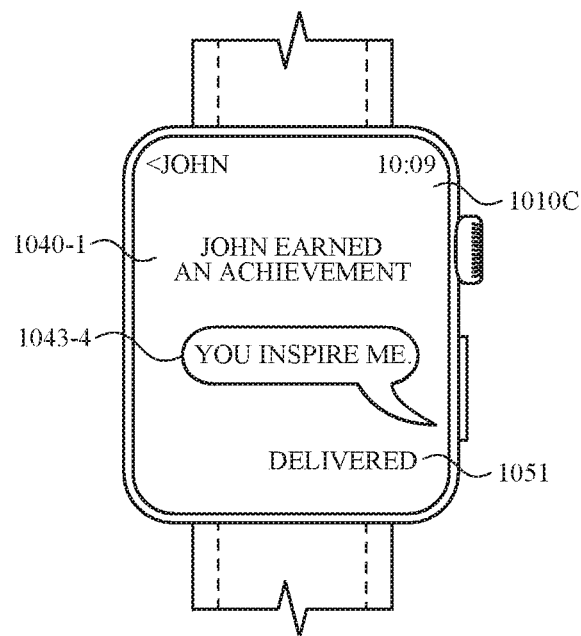
Figure 11:
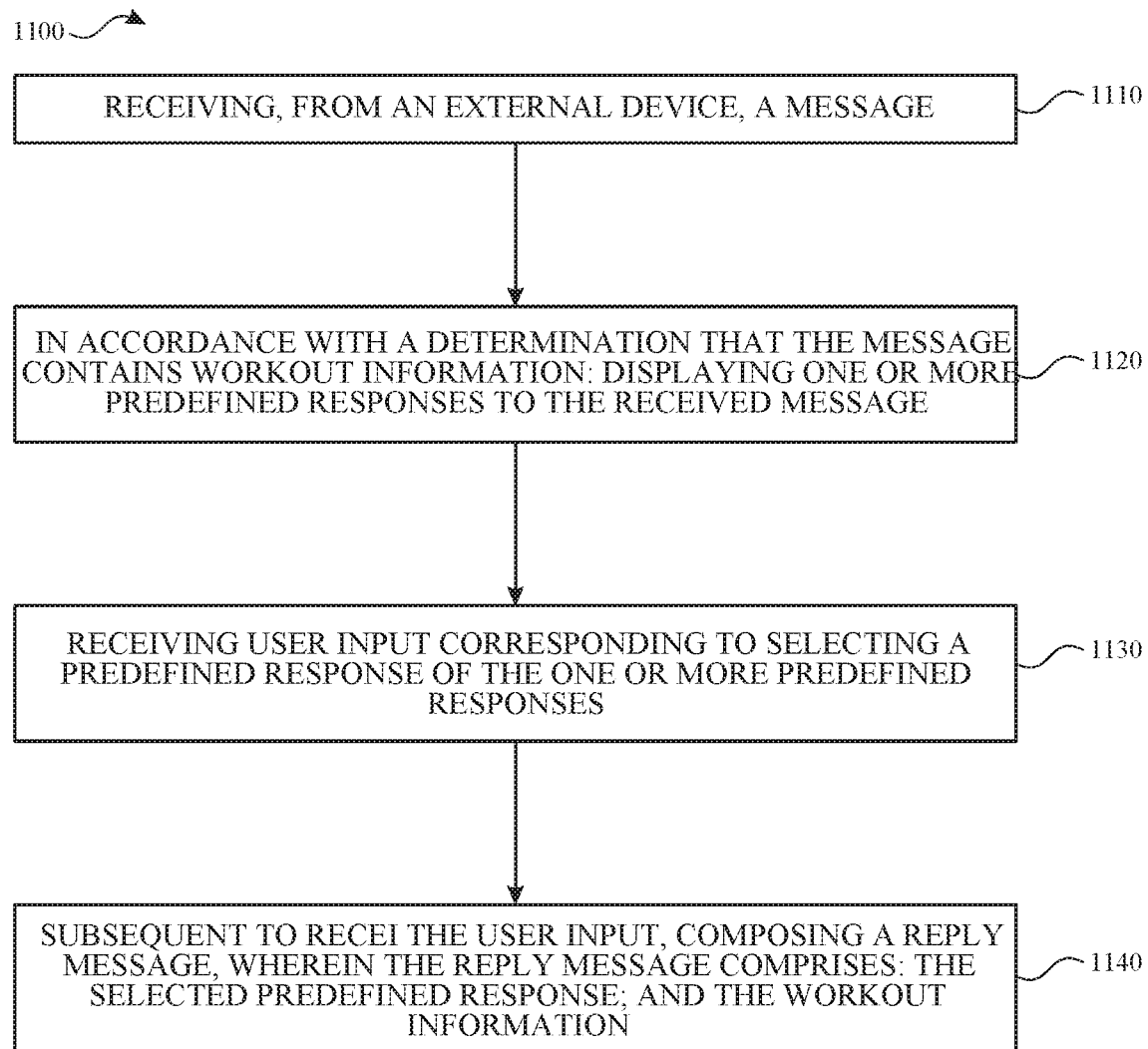
FIG. 11 is a flow diagram illustrating a method for operating an electronic device in accordance with some embodiments.

FIGS. 10A-10N illustrate exemplary user interfaces for composing a reply message that includes a predefined response and workout information. FIG. 11 is a flow diagram illustrating methods of composing a reply message that includes a predefined response and workout information in accordance with some embodiments. The user interfaces in FIGS. 10A-10N are used to illustrate the processes described below, including the processes in FIG. 11.

FIGS. 12A-12M illustrate exemplary user interfaces for displaying affordances associated with heart rate information. FIG. 13 is a flow diagram illustrating methods of displaying affordances associated with heart rate information in accordance with some embodiments. The user interfaces in FIGS. 12A-12M are used to illustrate the processes described below, including the processes in FIG. 13.

Figure 14A:
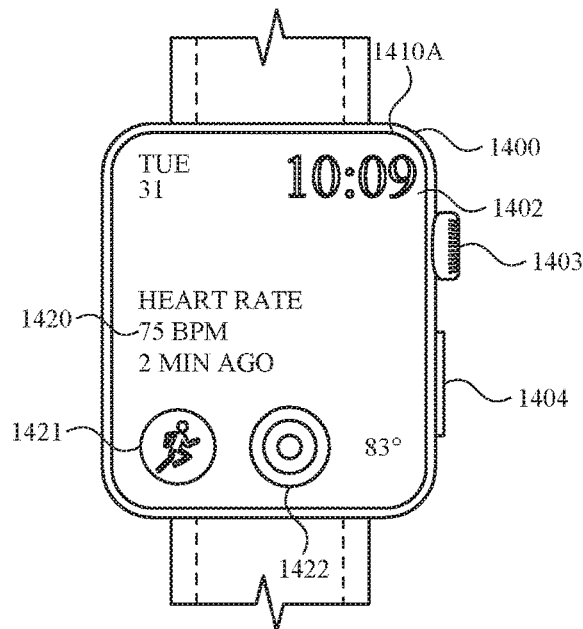
FIGS. 14A-14O illustrate exemplary user interfaces in accordance with some embodiments.
Figure 14B:
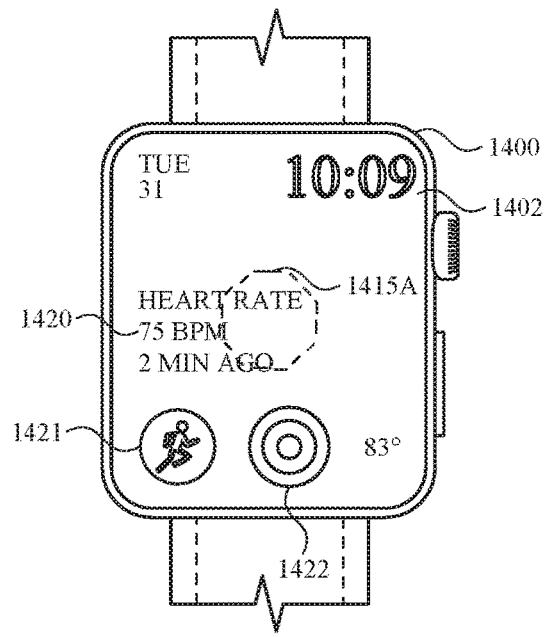
Figure 14C:
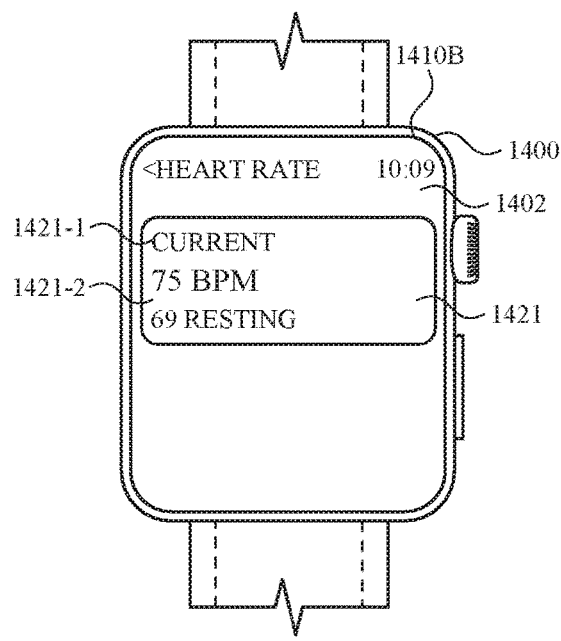
Figure 14D:
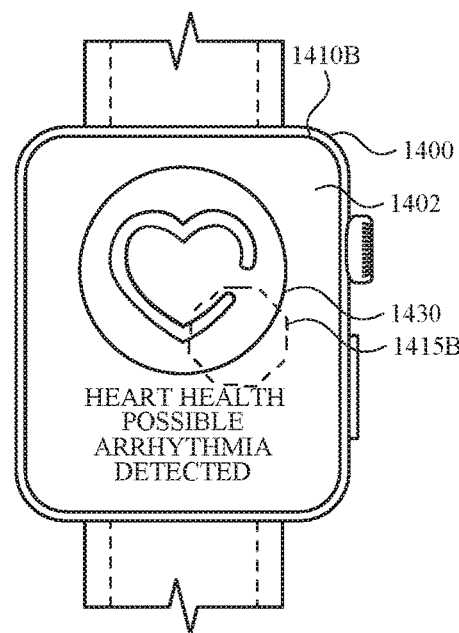
Figure 14E:
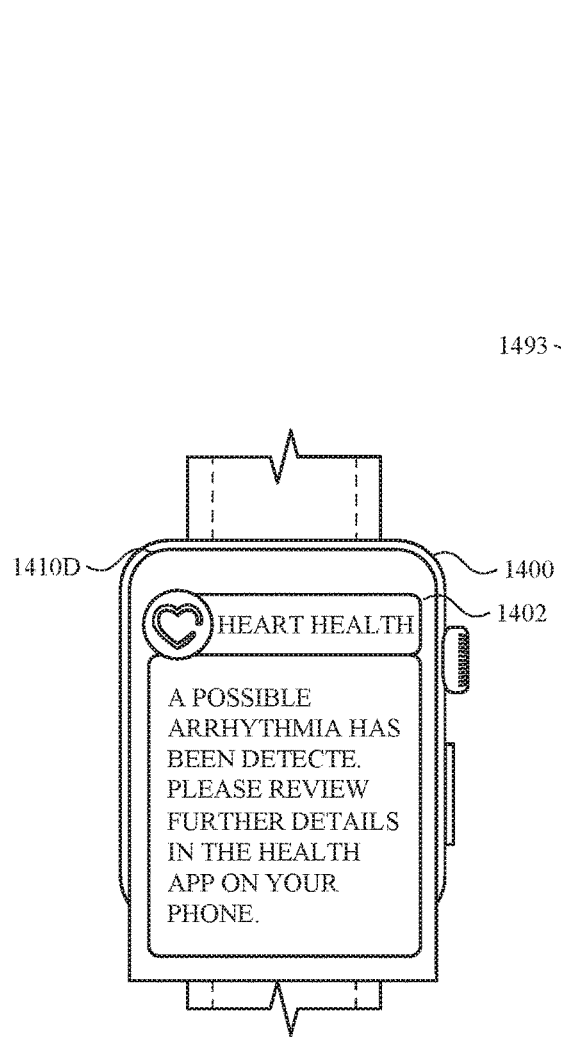
Figure 14F:
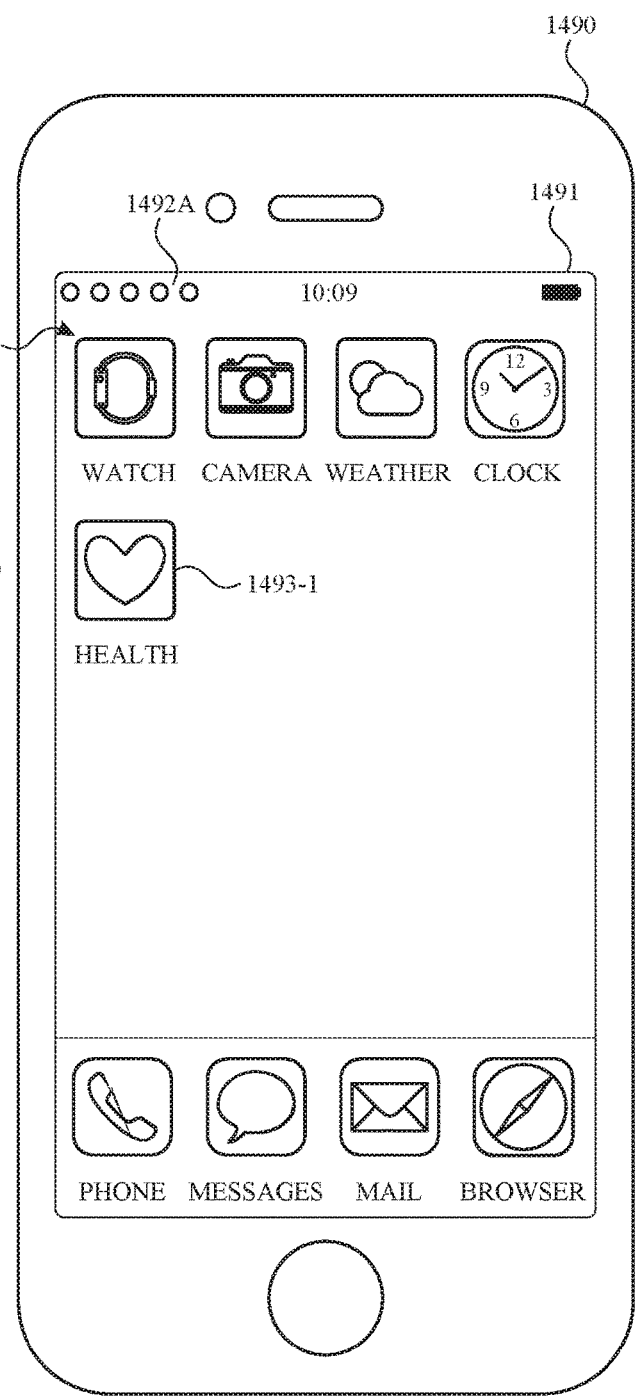
Figure 14G:
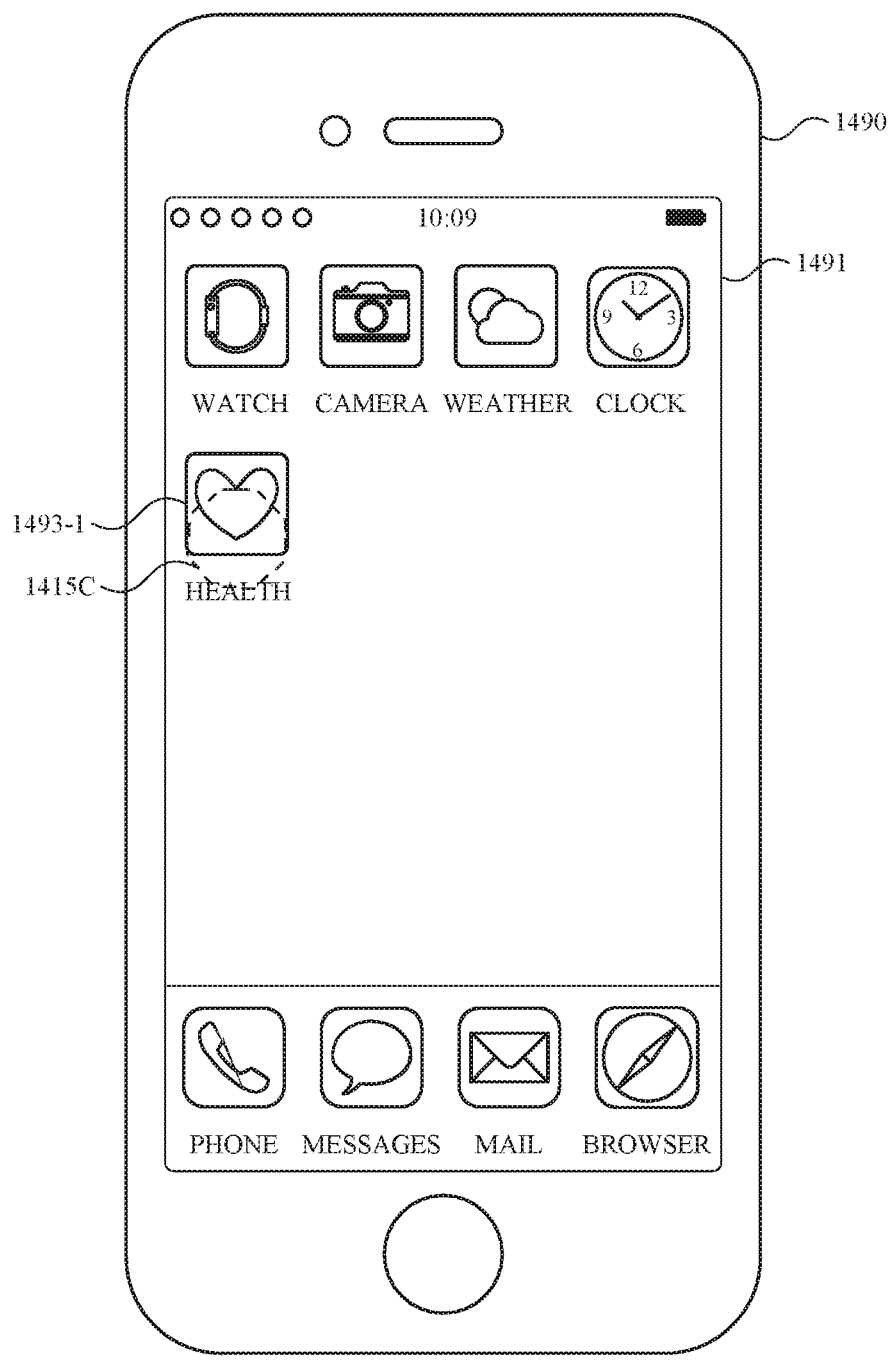
Figure 14H:
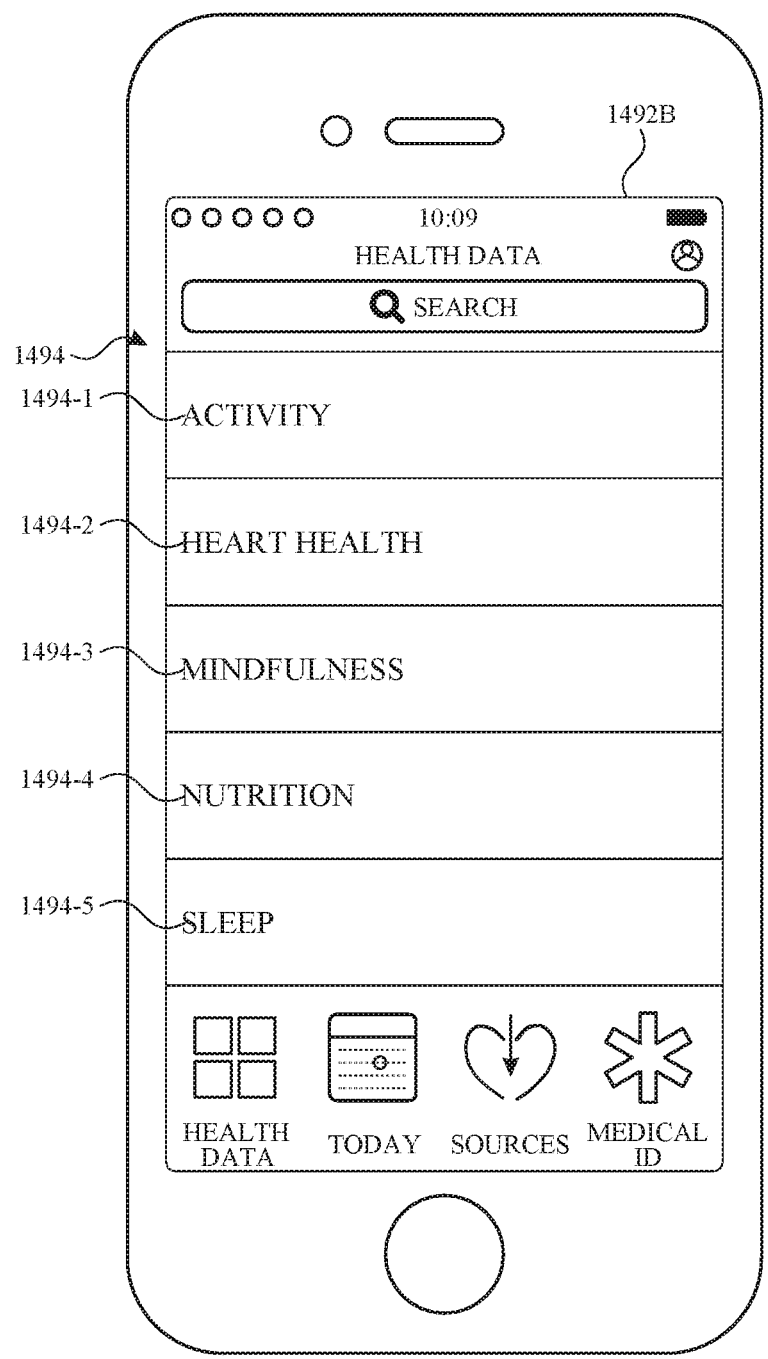
Figure 14I:
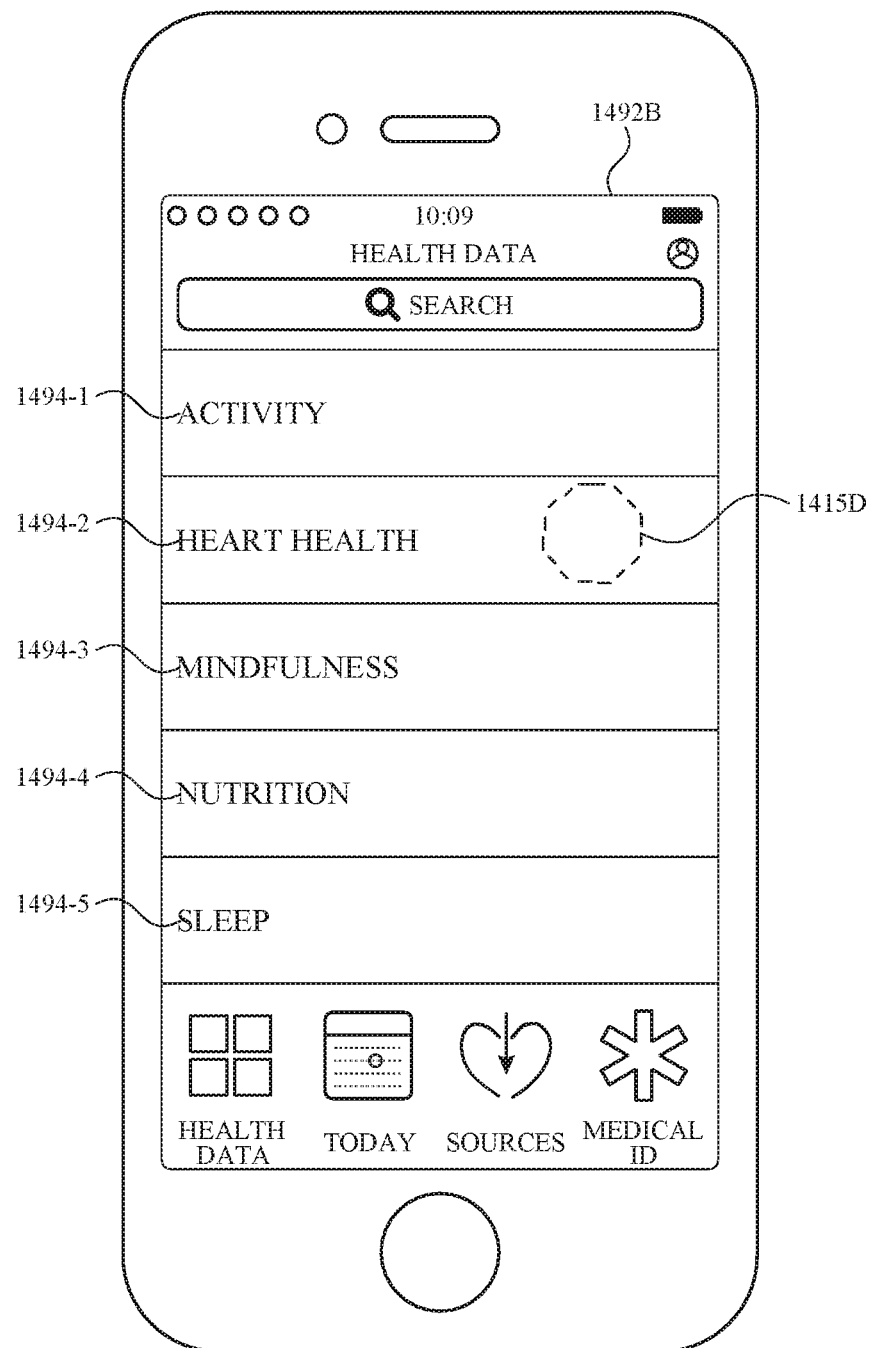
Figure 14J:
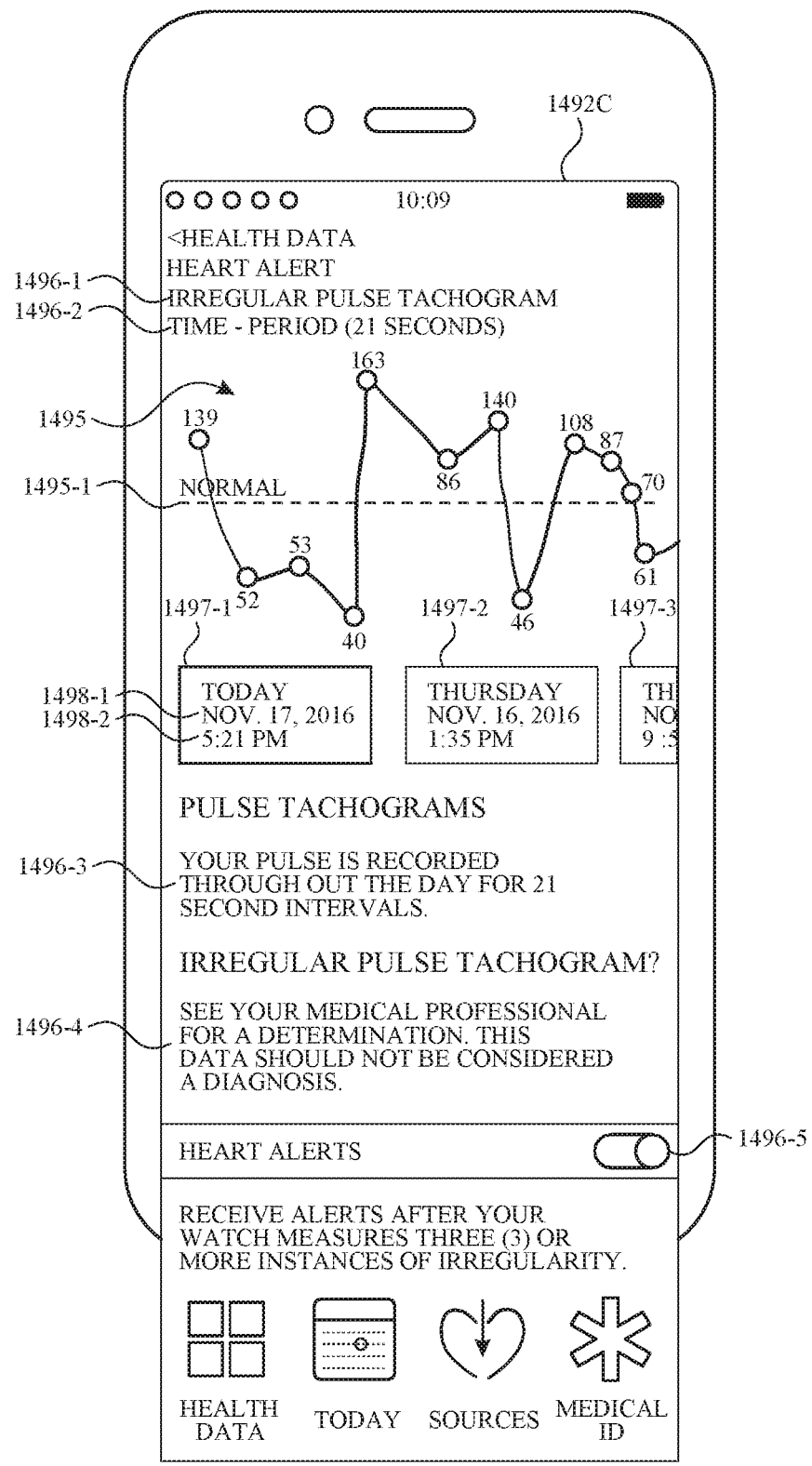
Figure 14K:
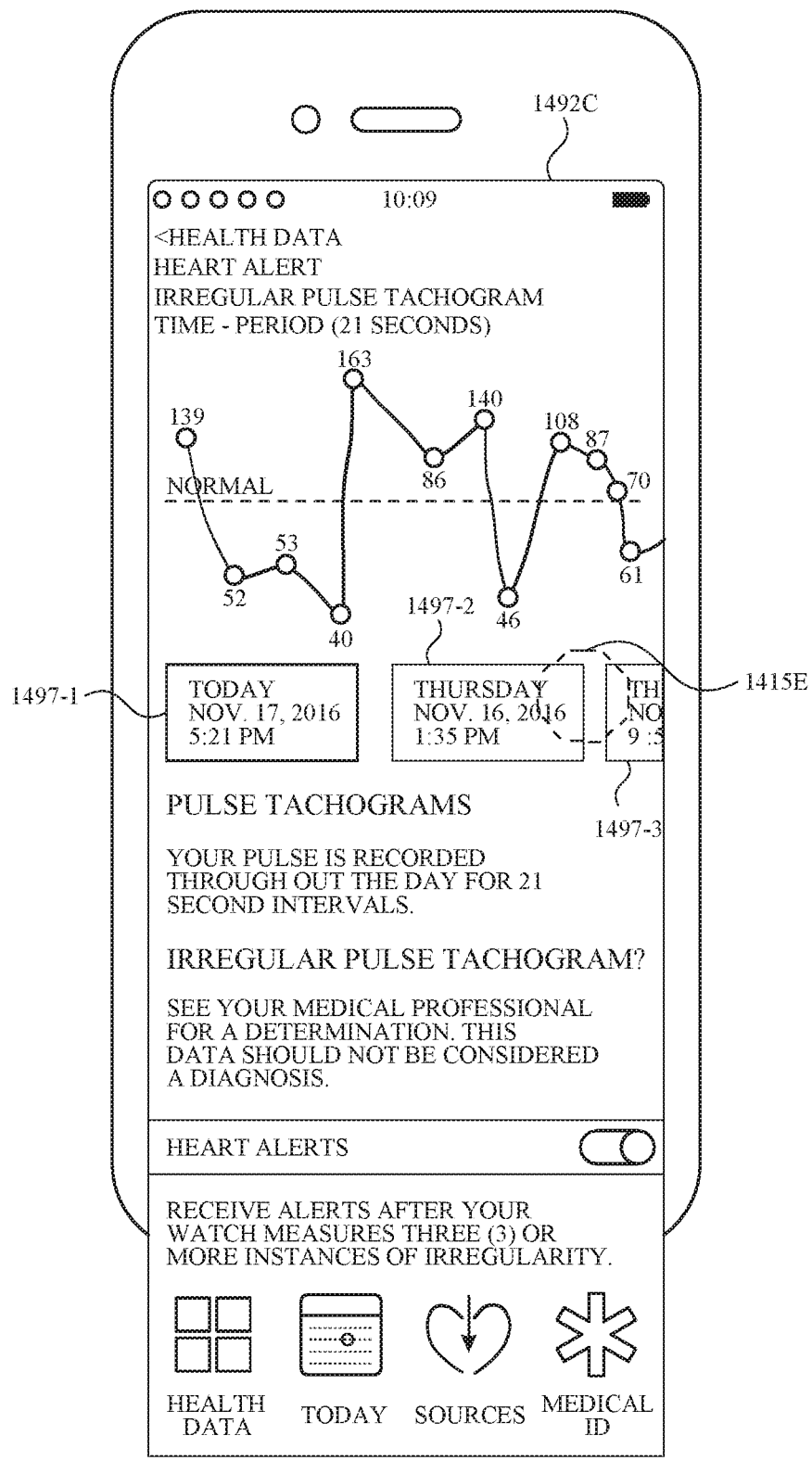
Figure 14L:
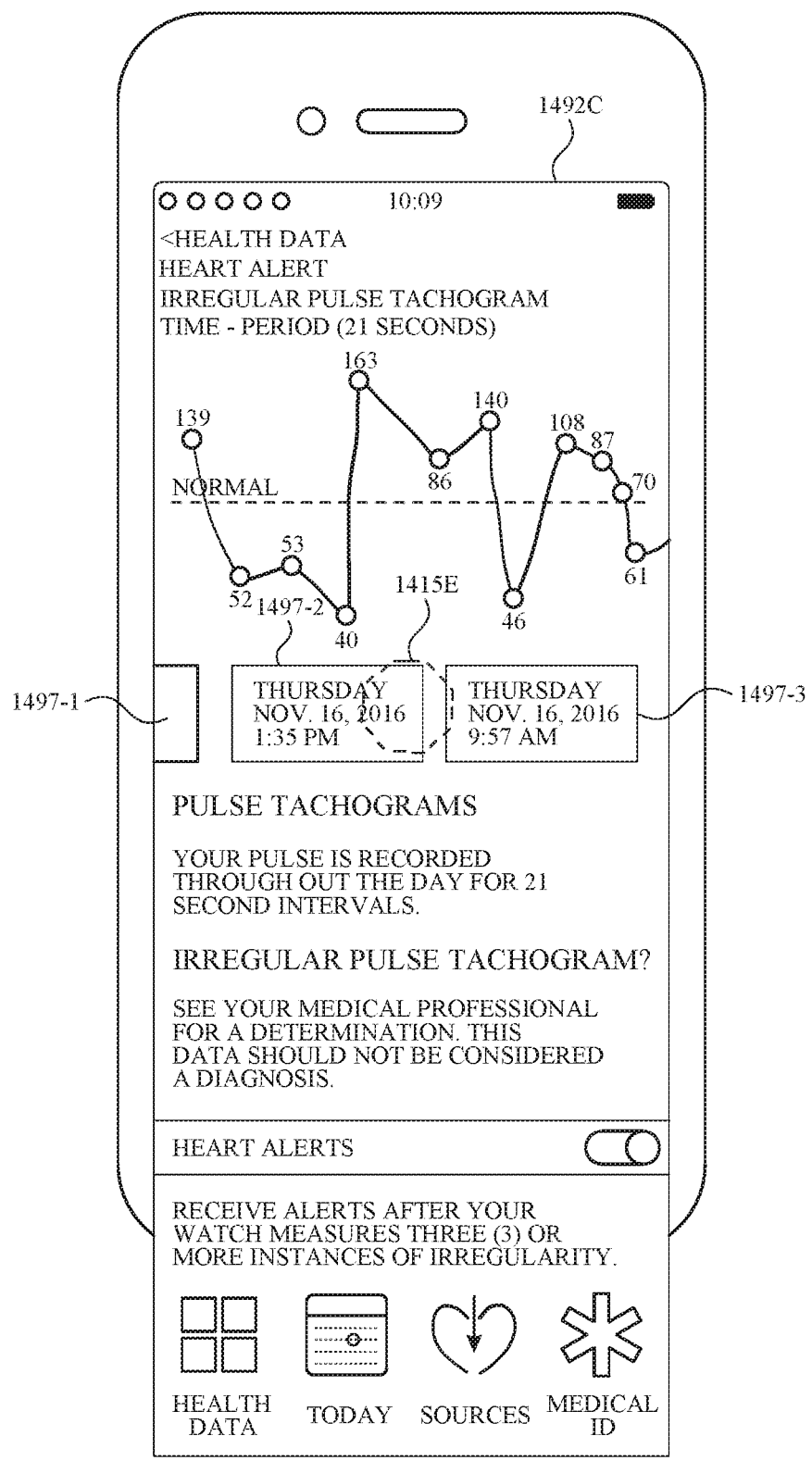
Figure 14M:
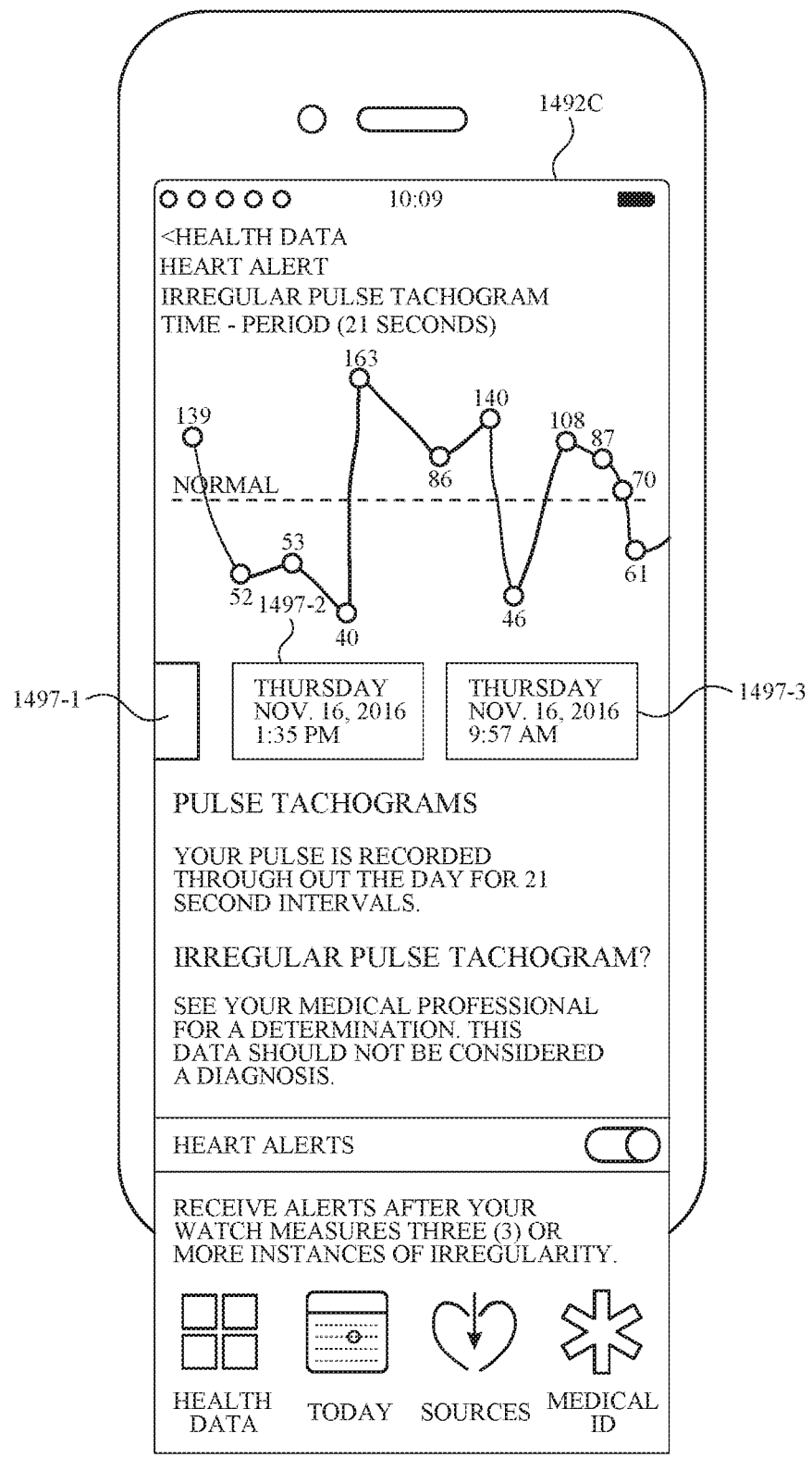
Figure 14N:
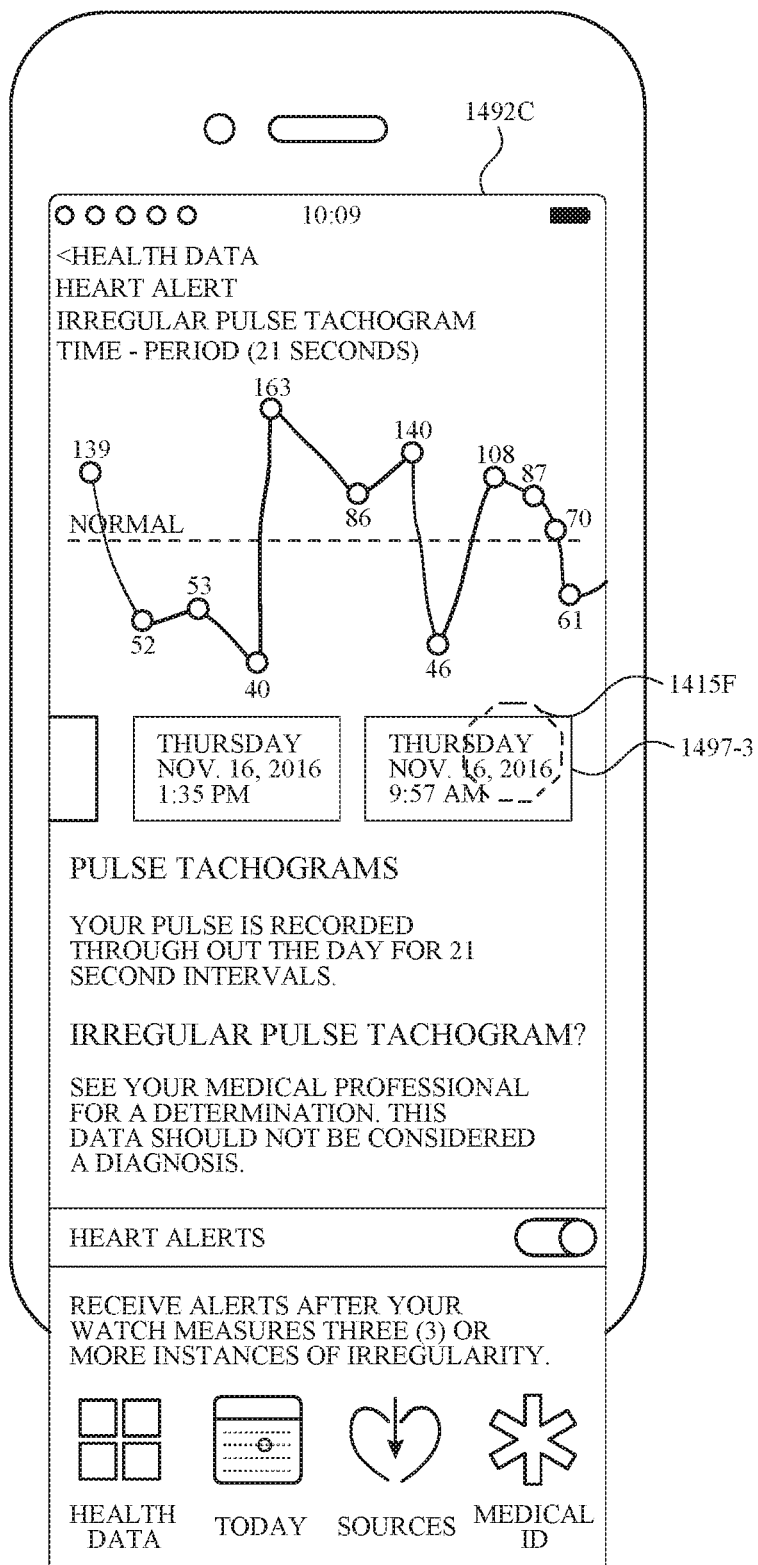
Figure 14O:
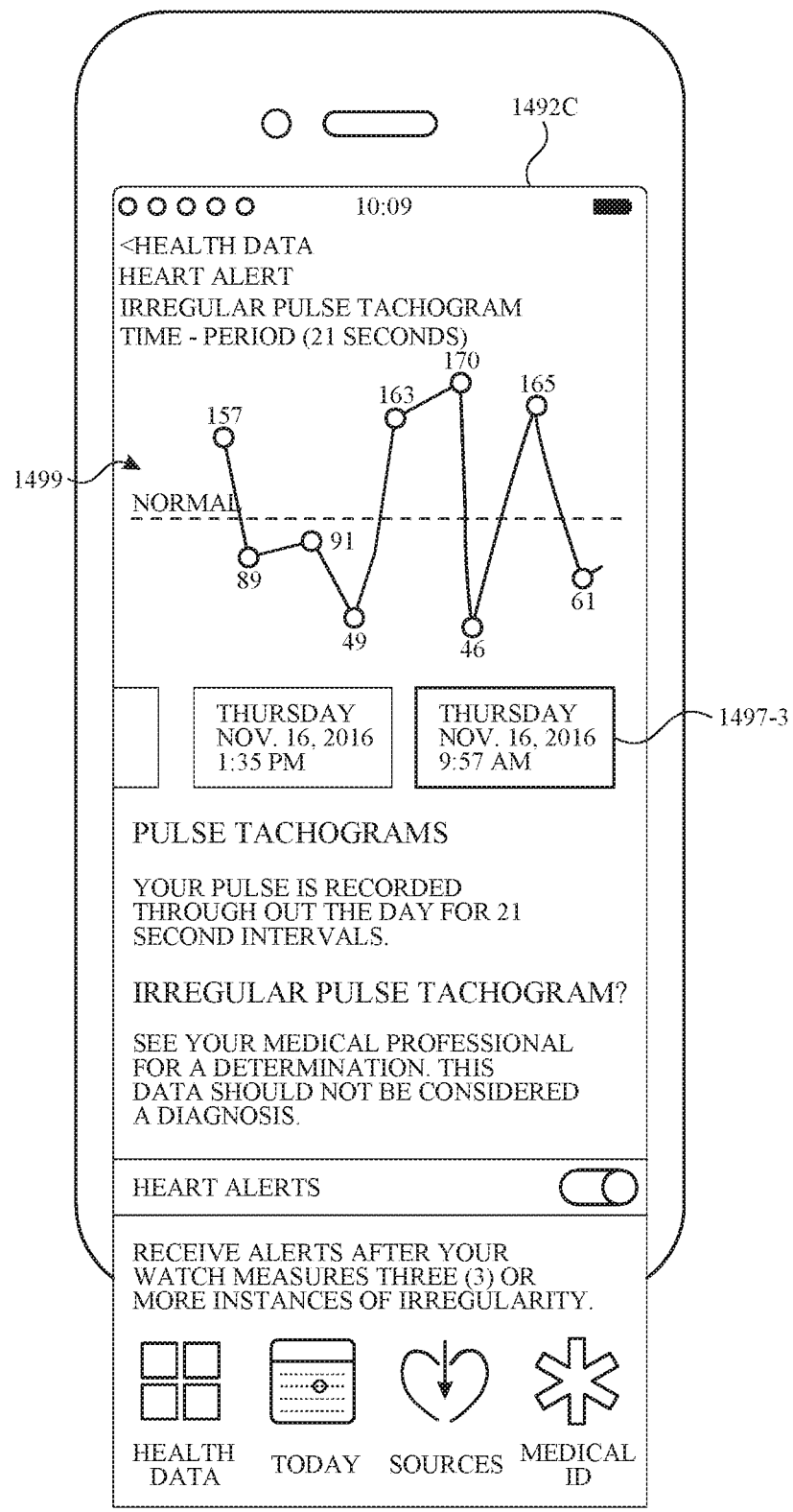
Figure 15:
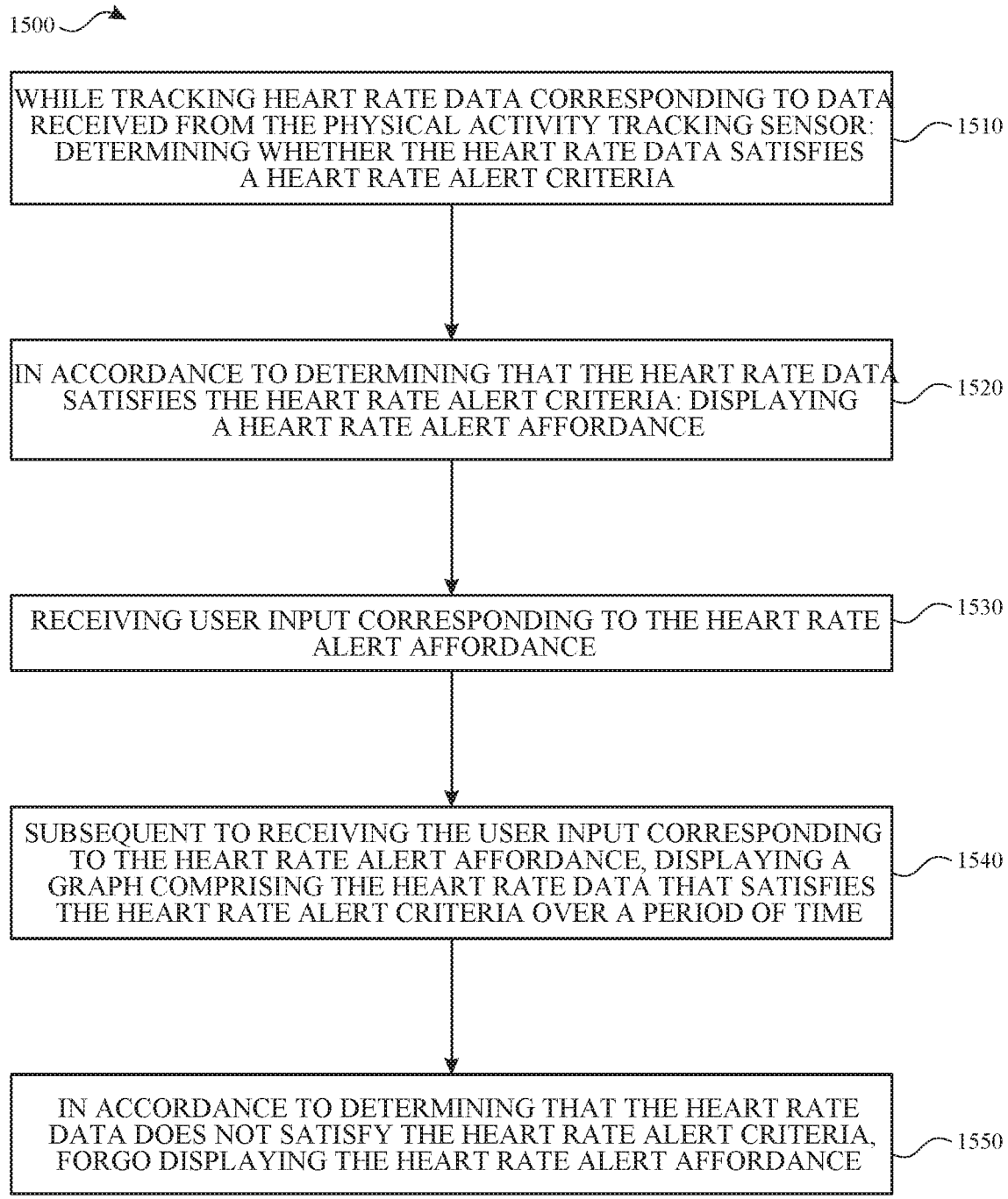
FIG. 15 is a flow diagram illustrating a method for operating an electronic device in accordance with some embodiments.

FIGS. 14A-14O illustrate exemplary user interfaces for displaying a heart rate alert. FIG. 15 is a flow diagram illustrating methods of displaying a heart rate alert in accordance with some embodiments. The user interfaces in FIGS. 14A-14O are used to illustrate the processes described below, including the processes in FIG. 15.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, Calif. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad).

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
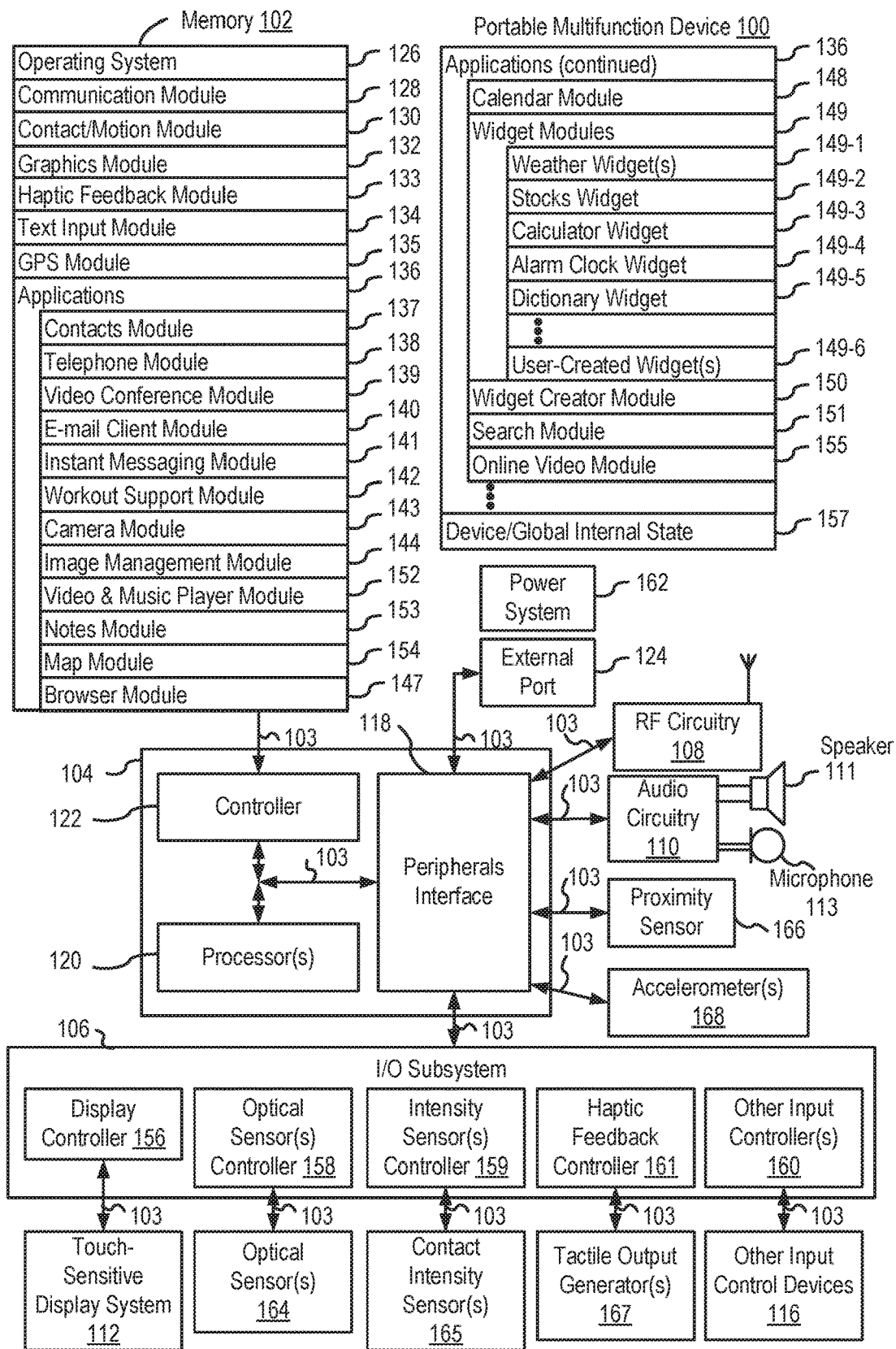
FIG. 1A is a block diagram illustrating a portable multifunction device with a touch-sensitive display in accordance with some embodiments.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some alternate embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2).

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, Calif.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad (not shown) for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals,"

which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer (not shown) and a GPS (or GLONASS or other global navigation system) receiver (not shown) for obtaining information concerning the location and orientation (e.g., portrait or landscape) of device 100.

Figure 3:
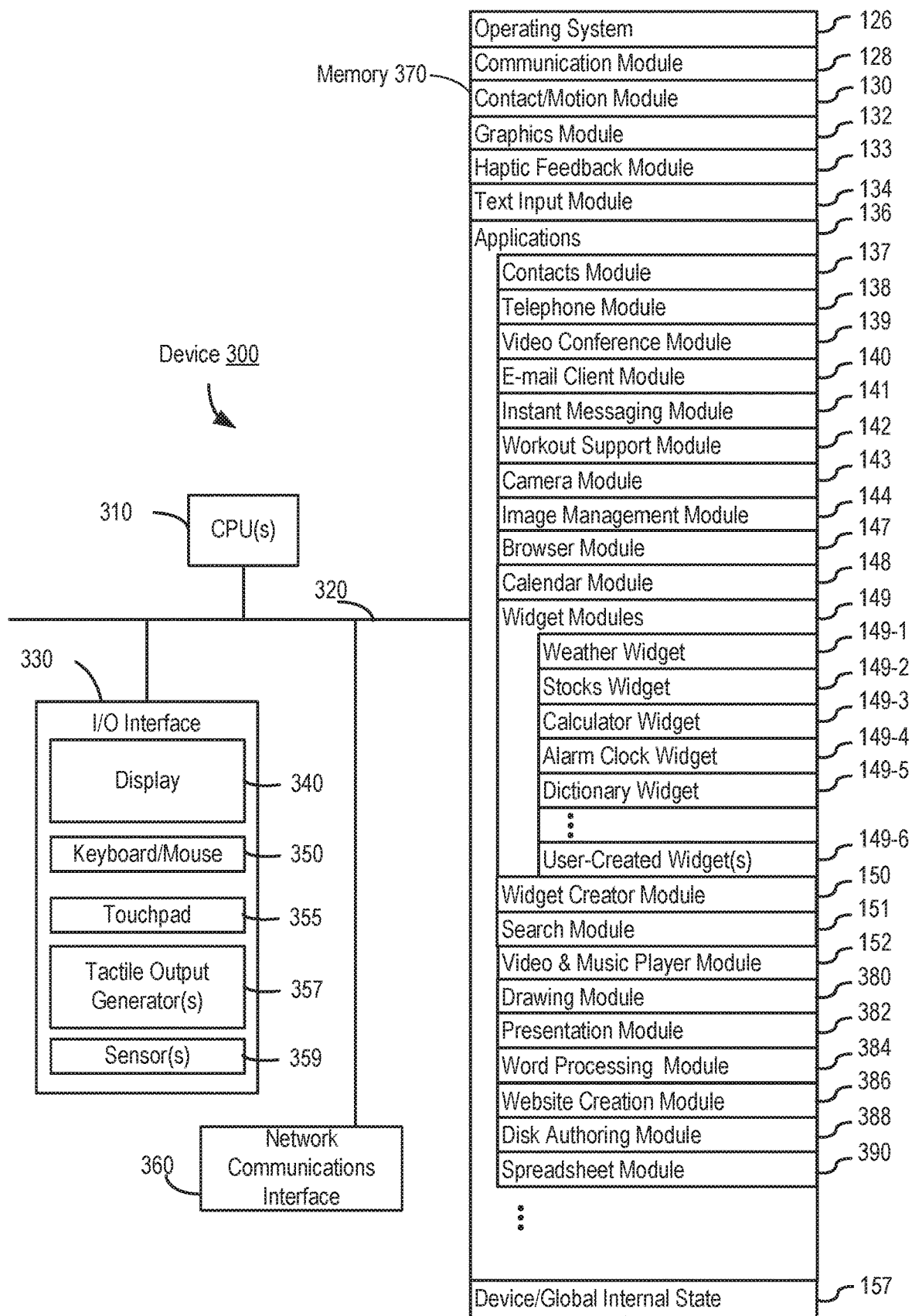
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIRE-WIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing; to camera 143 as picture/video metadata; and to applications that provide location-based services such as weather widgets, local yellow page widgets, and map/navigation widgets).

Applications 136 optionally include the following modules (or sets of instructions), or a subset or superset thereof:
  Contacts module 137 (sometimes called an address book or contact list);
  Telephone module 138;
  Video conference module 139;
  E-mail client module 140;
  Instant messaging (IM) module 141;
  Workout support module 142;
  Camera module 143 for still and/or video images;
  Image management module 144;
  Video player module;
  Music player module;
  Browser module 147;
  Calendar module 148;
  Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
  Widget creator module 150 for making user-created widgets 149-6;
  Search module 151;
  Video and music player module 152, which merges video player module and music player module;
  Notes module 153;
  Map module 154; and/or
  Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
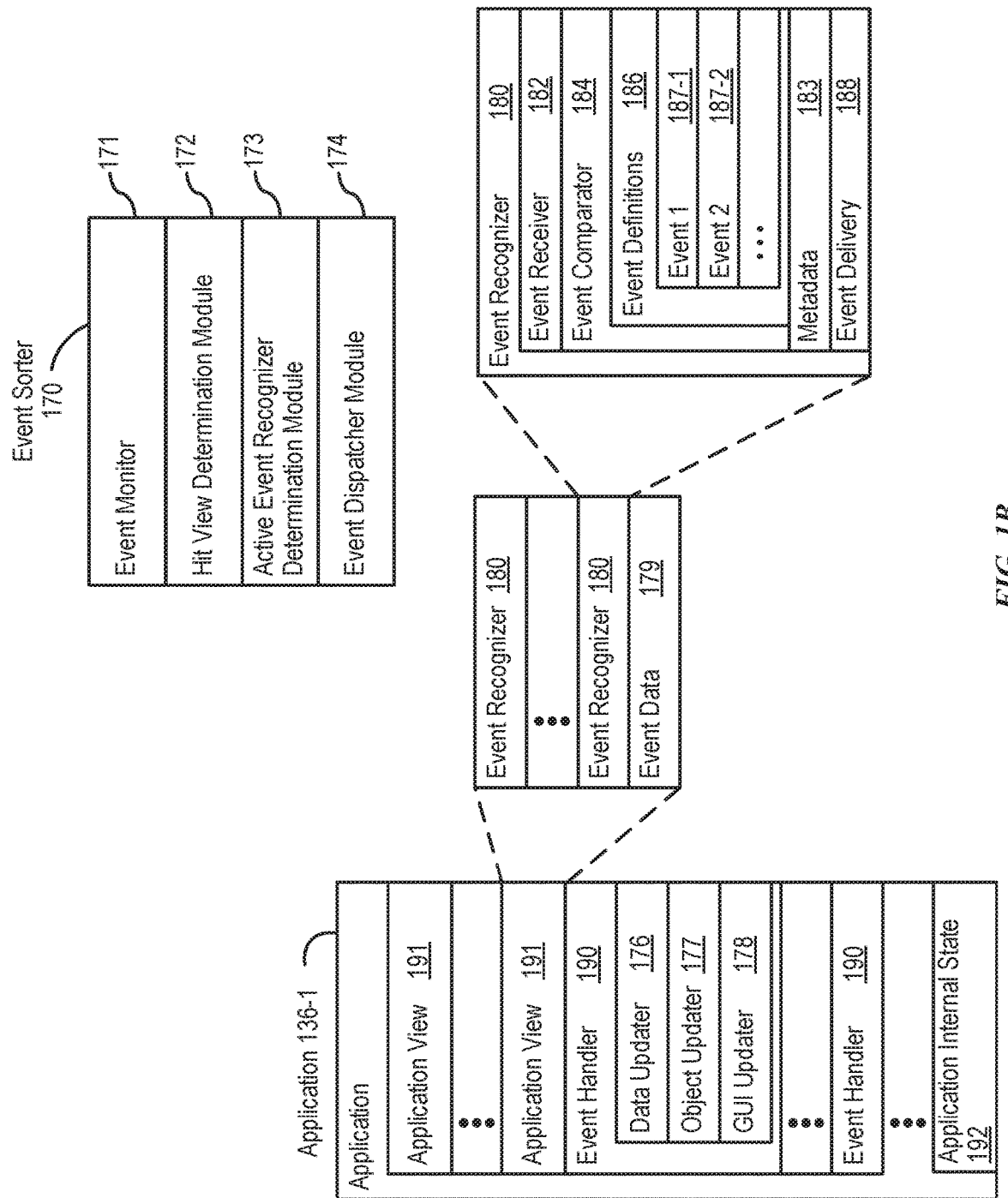
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit (not shown) or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
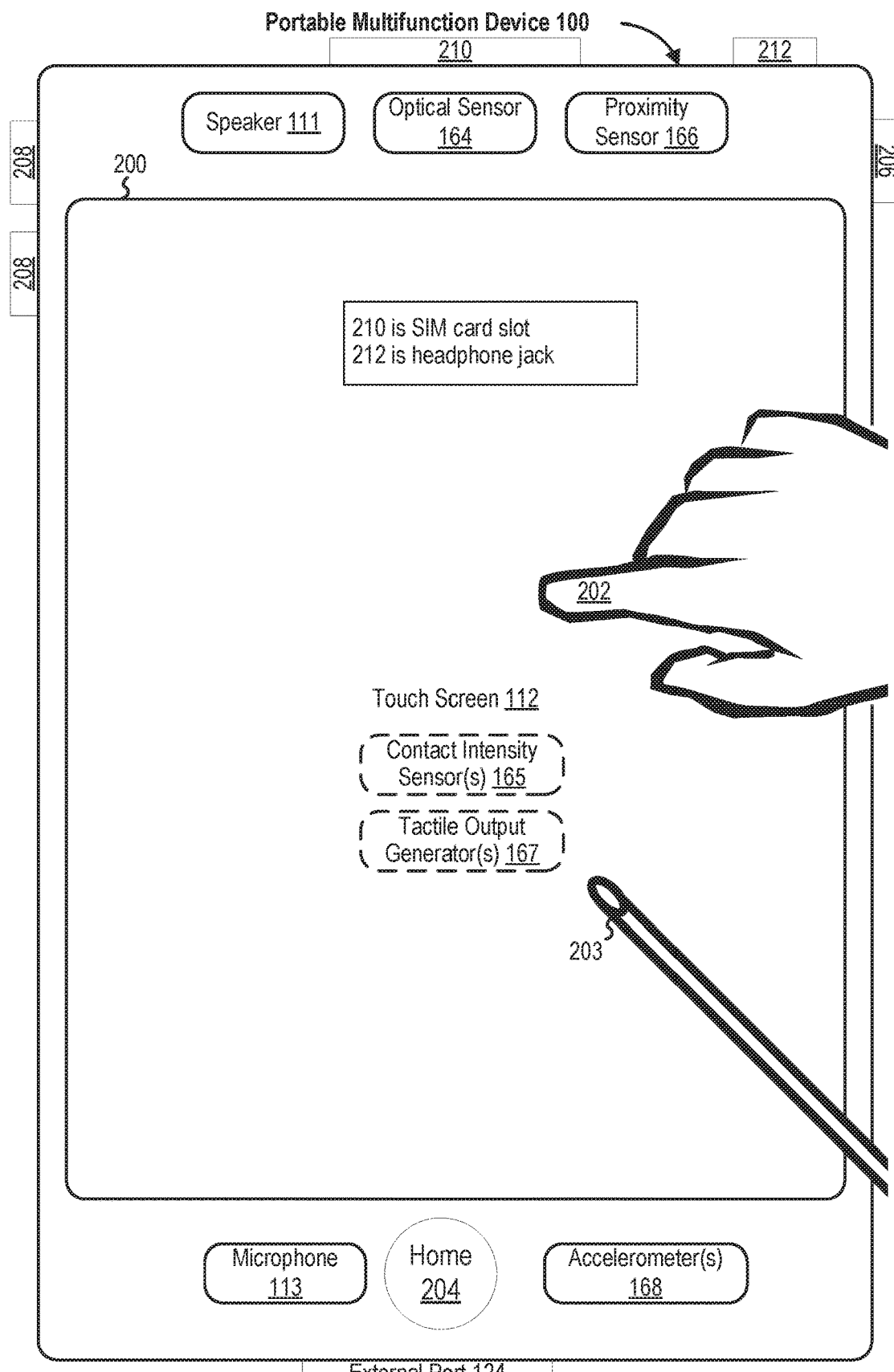
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
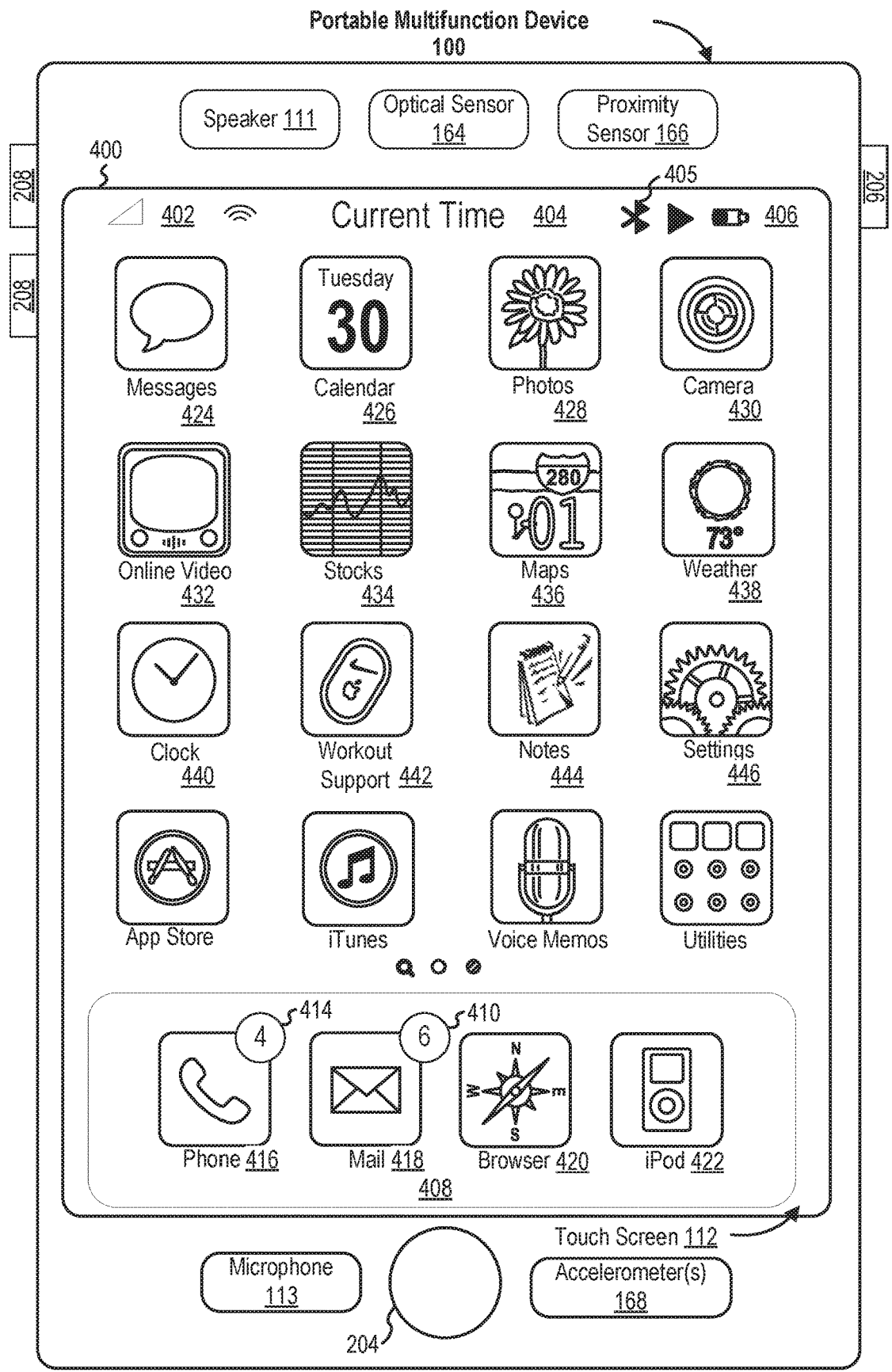
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;

Time 404;
Bluetooth indicator 405;
Battery status indicator 406;
Tray 408 with icons for frequently used applications, such as:
  Icon 416 for telephone module 138, labeled "Phone," which optionally includes an indicator 414 of the number of missed calls or voicemail messages;
  Icon 418 for e-mail client module 140, labeled "Mail," which optionally includes an indicator 410 of the number of unread e-mails;
  Icon 420 for browser module 147, labeled "Browser;" and
  Icon 422 for video and music player module 152, also referred to as iPod (trademark of Apple Inc.) module 152, labeled "iPod;" and
Icons for other applications, such as:
  Icon 424 for IM module 141, labeled "Messages;"
  Icon 426 for calendar module 148, labeled "Calendar;"
  Icon 428 for image management module 144, labeled "Photos;"
  Icon 430 for camera module 143, labeled "Camera;"
  Icon 432 for online video module 155, labeled "Online Video;"
  Icon 434 for stocks widget 149-2, labeled "Stocks;"
  Icon 436 for map module 154, labeled "Maps;"
  Icon 438 for weather widget 149-1, labeled "Weather;"
  Icon 440 for alarm clock widget 149-4, labeled "Clock;"
  Icon 442 for workout support module 142, labeled "Workout Support;"
  Icon 444 for notes module 153, labeled "Notes;" and
  Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

Figure 4B:
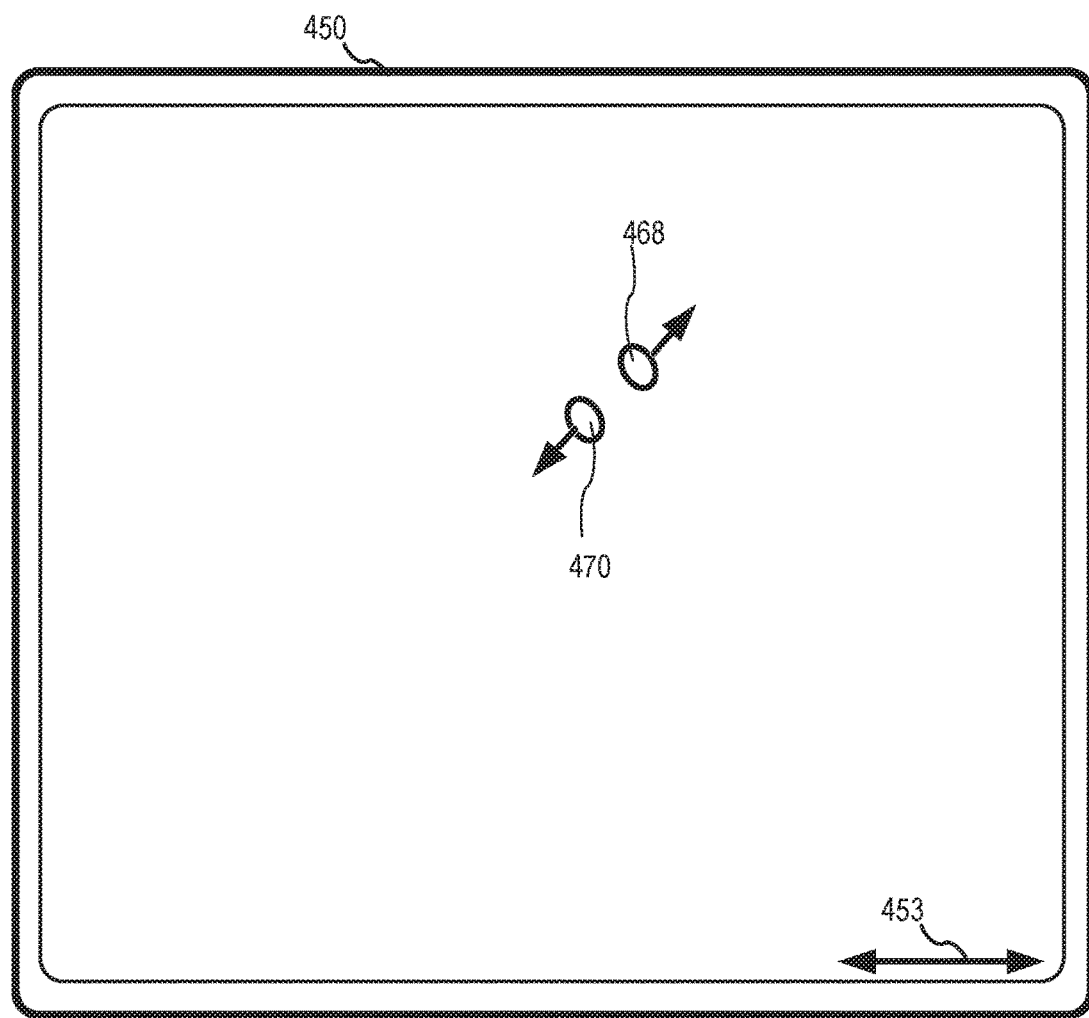
FIG. 4B illustrates an exemplary user interface for a multifunction device with a touch-sensitive surface that is separate from the display in accordance with some embodiments.
Figure 4B:
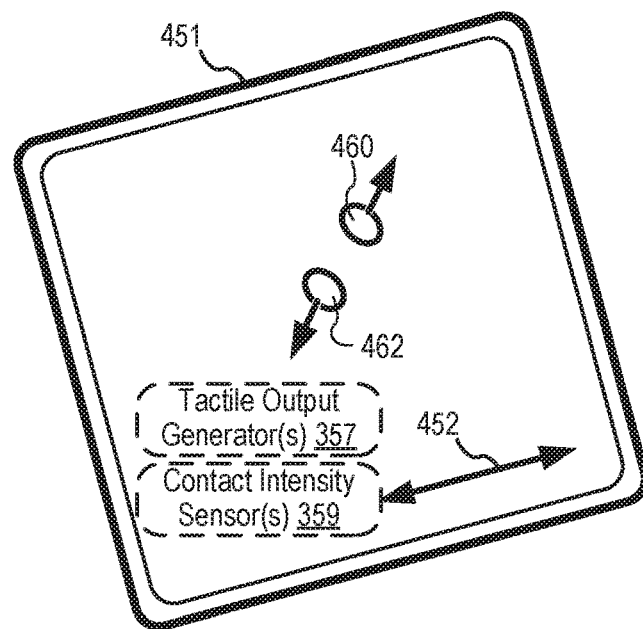

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
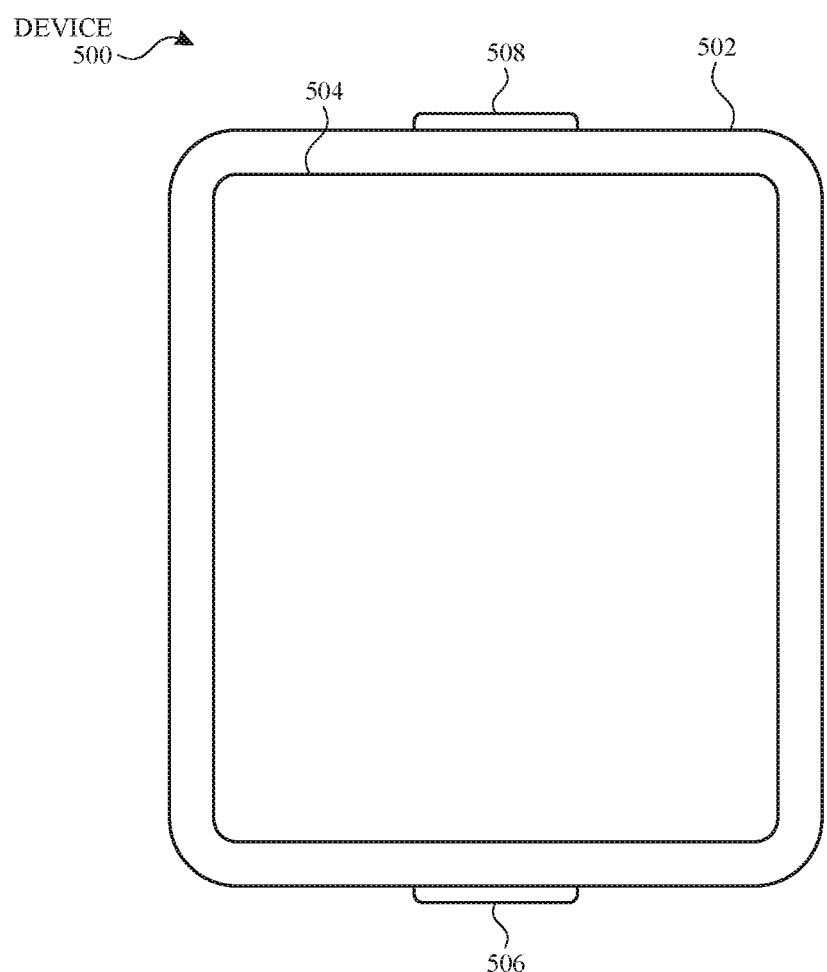
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
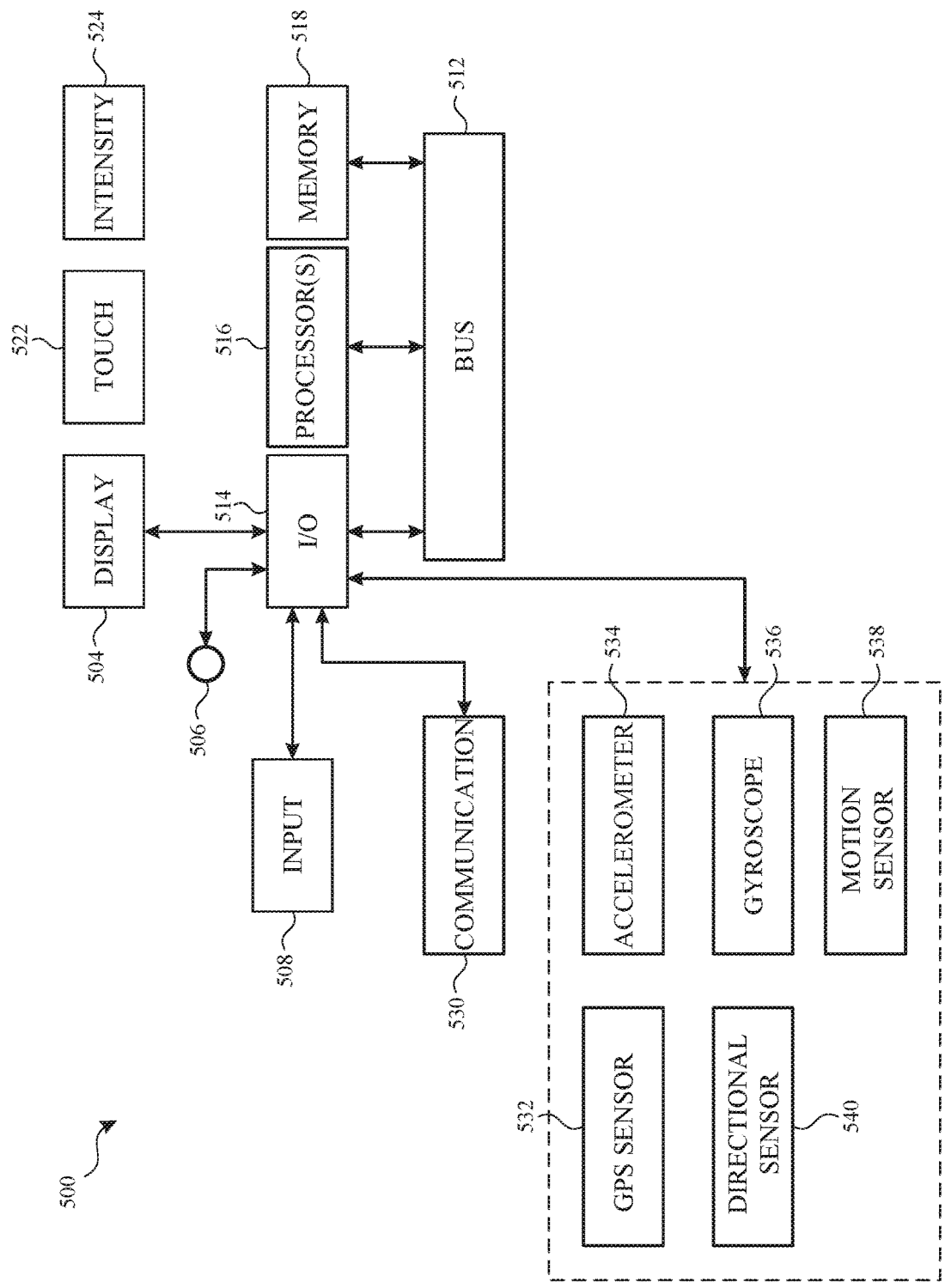
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 700, 900, 1100, 1300 and 1500 (FIGS. 7, 9, 11, 13, and 15). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

Figure 5C:
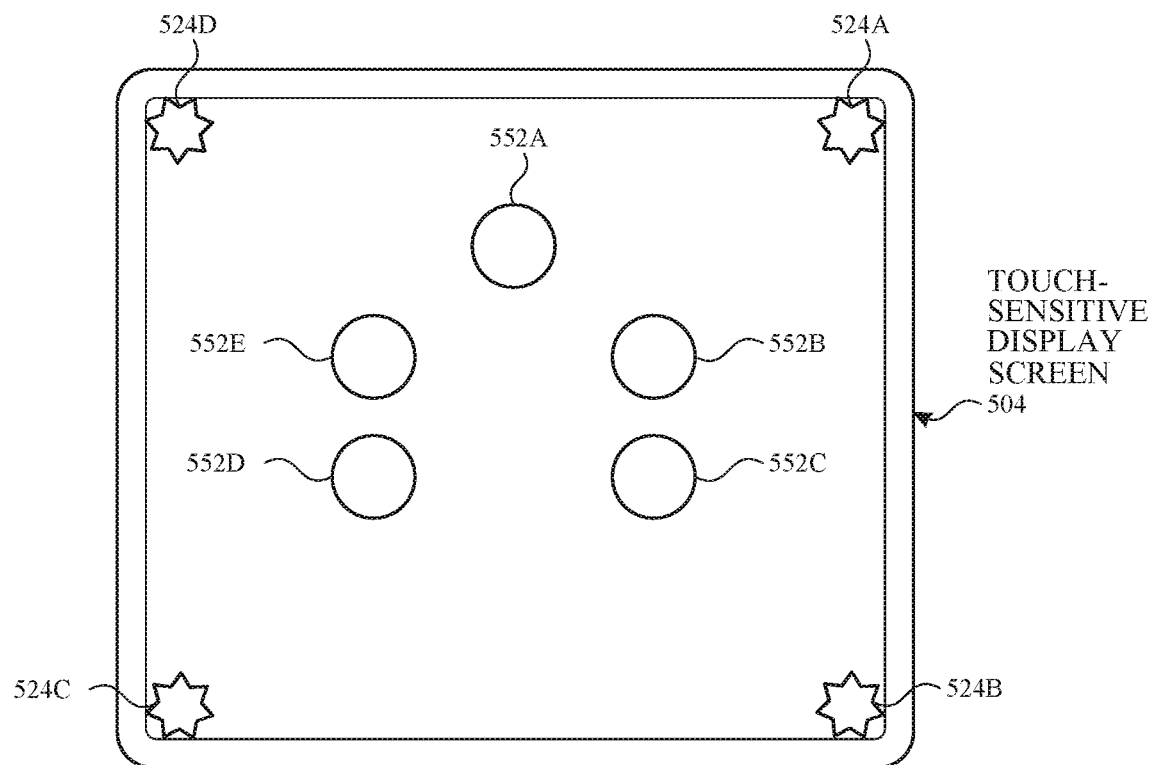
FIGS. 5C-5D illustrate exemplary components of a personal electronic device having a touch-sensitive display and intensity sensors in accordance with some embodiments.
Figure 5C:
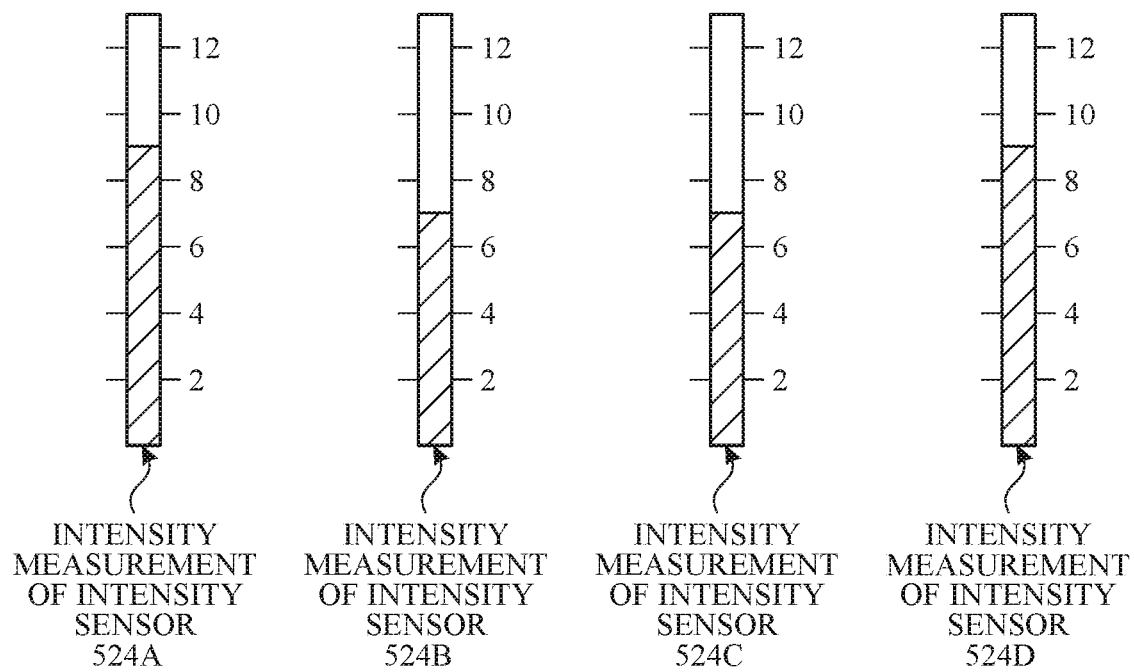
Figure 5D:
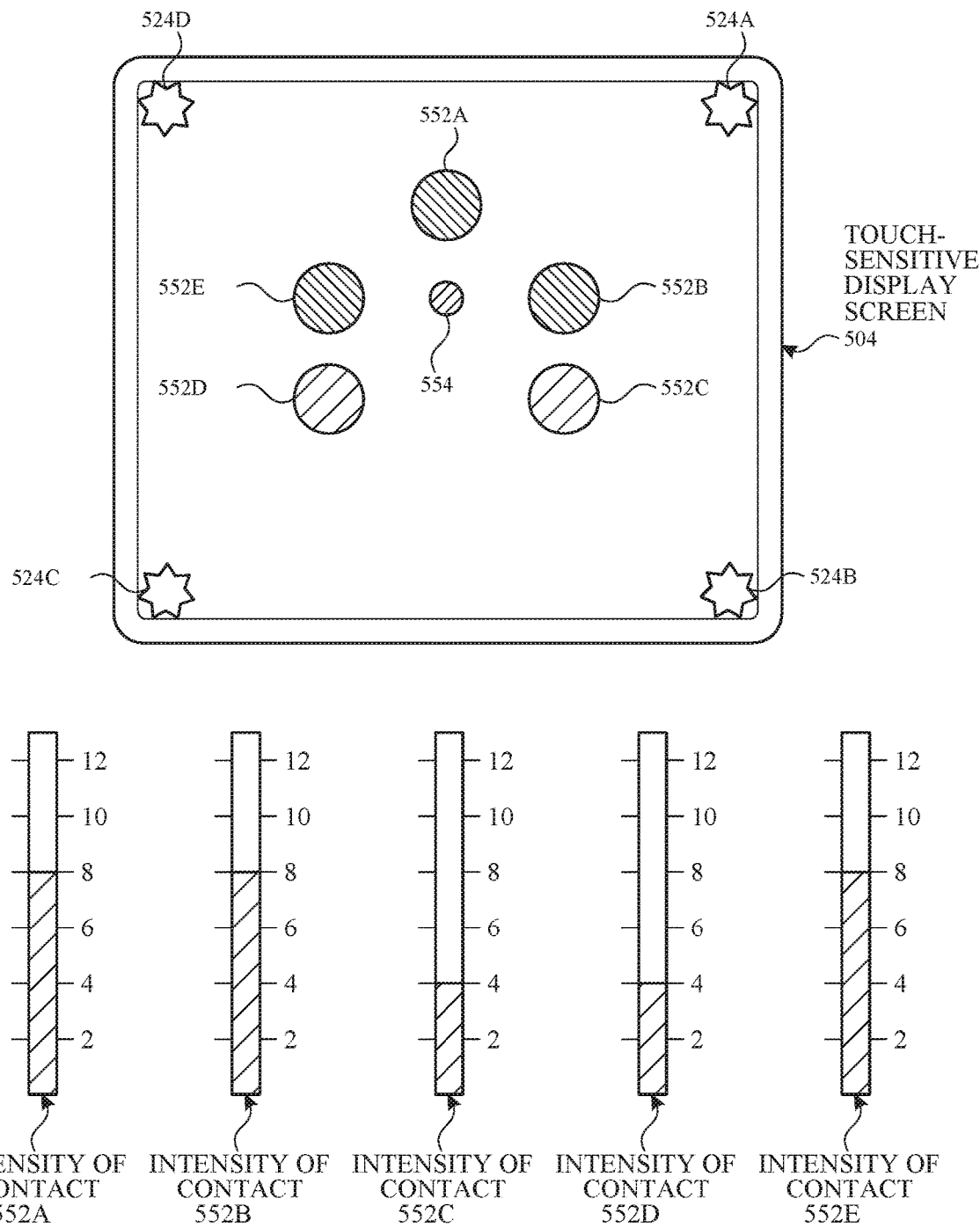

FIG. 5C illustrates detecting a plurality of contacts 552A-552E on touch-sensitive display screen 504 with a plurality of intensity sensors 524A-524D. FIG. 5C additionally includes intensity diagrams that show the current intensity measurements of the intensity sensors 524A-524D relative to units of intensity. In this example, the intensity measurements of intensity sensors 524A and 524D are each 9 units of intensity, and the intensity measurements of intensity sensors 524B and 524C are each 7 units of intensity. In some implementations, an aggregate intensity is the sum of the intensity measurements of the plurality of intensity sensors 524A-524D, which in this example is 32 intensity units. In some embodiments, each contact is assigned a respective intensity that is a portion of the aggregate intensity. FIG. 5D illustrates assigning the aggregate intensity to contacts 552A-552E based on their distance from the center of force 554. In this example, each of contacts 552A, 552B, and 552E are assigned an intensity of contact of 8 intensity units of the aggregate intensity, and each of contacts 552C and 552D are assigned an intensity of contact of 4 intensity units of the aggregate intensity. More generally, in some implementations, each contact j is assigned a respective intensity Ij that is a portion of the aggregate intensity, A, in accordance with a predefined mathematical function, Ij=A·(Dj/ΣDi), where Dj is the distance of the respective contact j to the center of force, and ΣDi is the sum of the distances of all the respective contacts (e.g., i=1 to last) to the center of force. The operations described with reference to FIGS. 5C-5D can be performed using an electronic device similar or identical to device 100, 300, or 500. In some embodiments, a characteristic intensity of a contact is based on one or more intensities of the contact. In some embodiments, the intensity sensors are used to determine a single characteristic intensity (e.g., a single characteristic intensity of a single contact). It should be noted that the intensity diagrams are not part of a displayed user interface, but are included in FIGS. 5C-5D to aid the reader.

In some embodiments, a portion of a gesture is identified for purposes of determining a characteristic intensity. For example, a touch-sensitive surface optionally receives a continuous swipe contact transitioning from a start location and reaching an end location, at which point the intensity of the contact increases. In this example, the characteristic intensity of the contact at the end location is, optionally, based on only a portion of the continuous swipe contact, and not the entire swipe contact (e.g., only the portion of the swipe contact at the end location). In some embodiments, a smoothing algorithm is, optionally, applied to the intensities of the swipe contact prior to determining the characteristic intensity of the contact. For example, the smoothing algorithm optionally includes one or more of: an unweighted sliding-average smoothing algorithm, a triangular smoothing algorithm, a median filter smoothing algorithm, and/or an exponential smoothing algorithm. In some circumstances, these smoothing algorithms eliminate narrow spikes or dips in the intensities of the swipe contact for purposes of determining a characteristic intensity.

The intensity of a contact on the touch-sensitive surface is, optionally, characterized relative to one or more intensity thresholds, such as a contact-detection intensity threshold, a light press intensity threshold, a deep press intensity threshold, and/or one or more other intensity thresholds. In some embodiments, the light press intensity threshold corresponds to an intensity at which the device will perform operations typically associated with clicking a button of a physical mouse or a trackpad. In some embodiments, the deep press intensity threshold corresponds to an intensity at which the device will perform operations that are different from operations typically associated with clicking a button of a physical mouse or a trackpad. In some embodiments, when a contact is detected with a characteristic intensity below the light press intensity threshold (e.g., and above a nominal contact-detection intensity threshold below which the contact is no longer detected), the device will move a focus selector in accordance with movement of the contact on the touch-sensitive surface without performing an operation associated with the light press intensity threshold or the deep press intensity threshold. Generally, unless otherwise stated, these intensity thresholds are consistent between different sets of user interface figures.

An increase of characteristic intensity of the contact from an intensity below the light press intensity threshold to an intensity between the light press intensity threshold and the deep press intensity threshold is sometimes referred to as a "light press" input. An increase of characteristic intensity of the contact from an intensity below the deep press intensity threshold to an intensity above the deep press intensity threshold is sometimes referred to as a "deep press" input. An increase of characteristic intensity of the contact from an intensity below the contact-detection intensity threshold to an intensity between the contact-detection intensity threshold and the light press intensity threshold is sometimes referred to as detecting the contact on the touch-surface. A decrease of characteristic intensity of the contact from an intensity above the contact-detection intensity threshold to an intensity below the contact-detection intensity threshold is sometimes referred to as detecting liftoff of the contact from the touch-surface. In some embodiments, the contact-detection intensity threshold is zero. In some embodiments, the contact-detection intensity threshold is greater than zero.

In some embodiments described herein, one or more operations are performed in response to detecting a gesture that includes a respective press input or in response to detecting the respective press input performed with a respective contact (or a plurality of contacts), where the respective press input is detected based at least in part on detecting an increase in intensity of the contact (or plurality of contacts) above a press-input intensity threshold. In some embodiments, the respective operation is performed in response to detecting the increase in intensity of the respective contact above the press-input intensity threshold (e.g., a "down stroke" of the respective press input). In some embodiments, the press input includes an increase in intensity of the respective contact above the press-input intensity threshold and a subsequent decrease in intensity of the contact below the press-input intensity threshold, and the respective operation is performed in response to detecting the subsequent decrease in intensity of the respective contact below the press-input threshold (e.g., an "up stroke" of the respective press input).

Figure 5E:
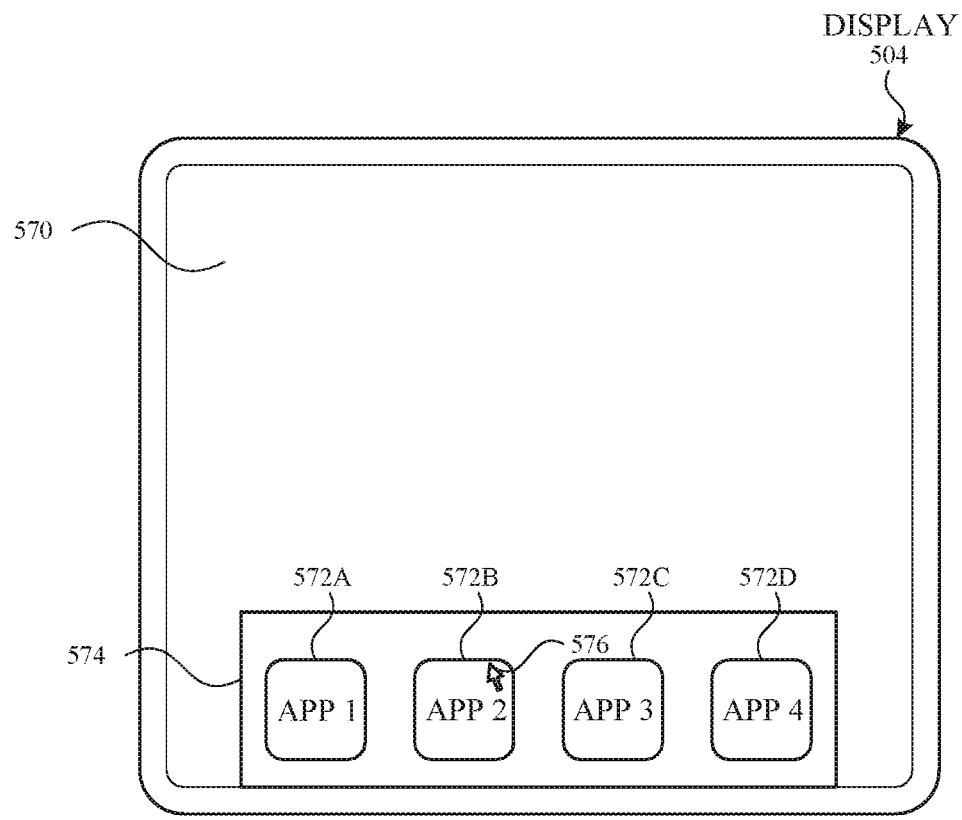
FIGS. 5E-5H illustrate exemplary components and user interfaces of a personal electronic device in accordance with some embodiments.
Figure 5E:
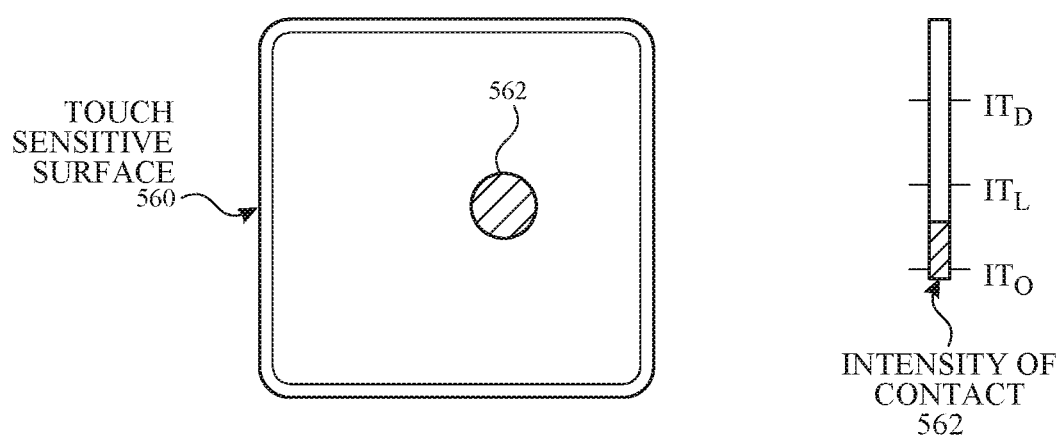
Figure 5F:
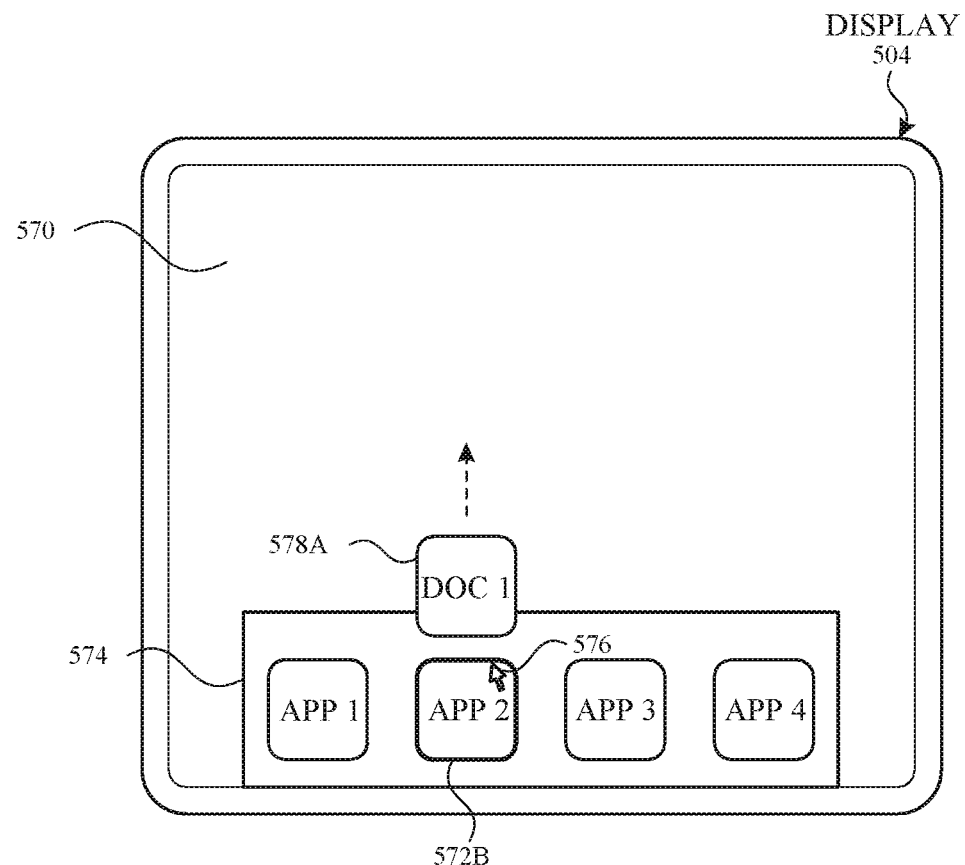
Figure 5F:
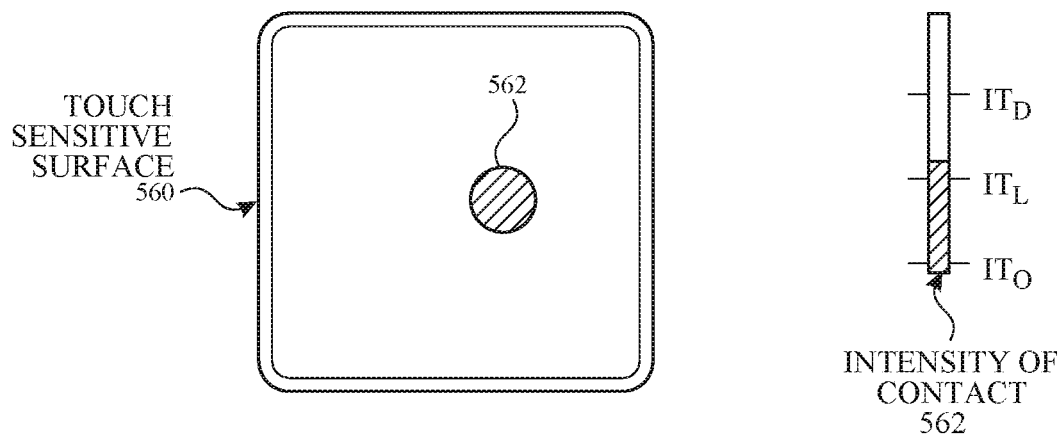
Figure 5G:
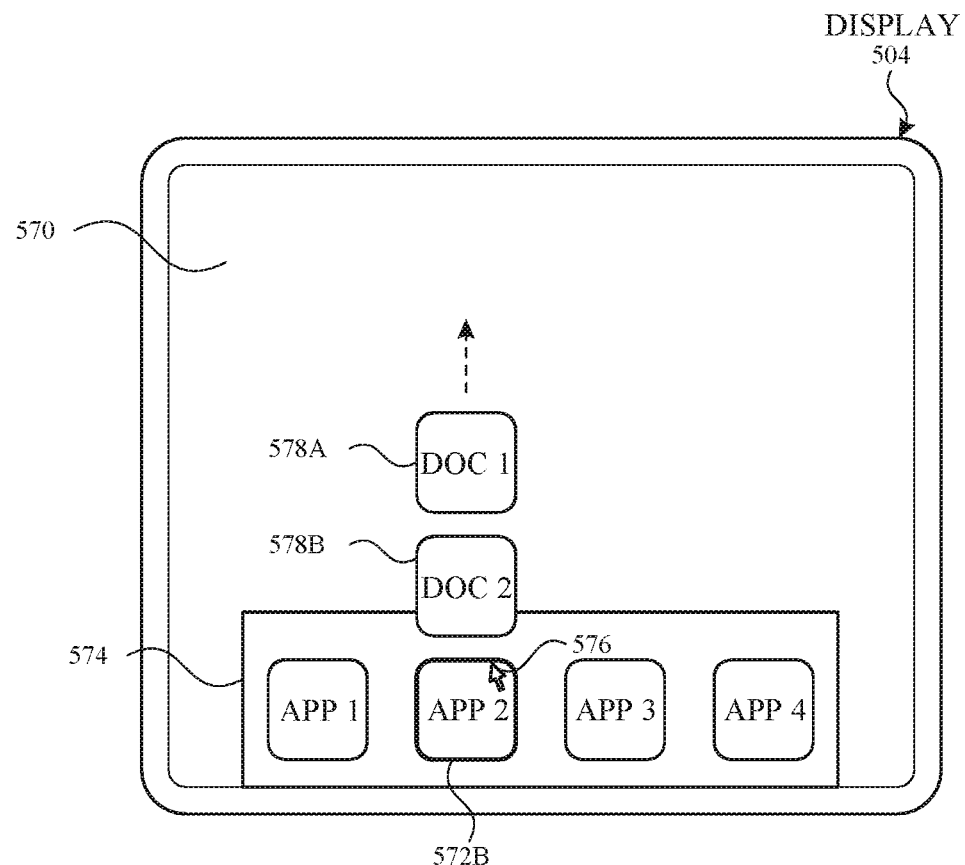
Figure 5G:
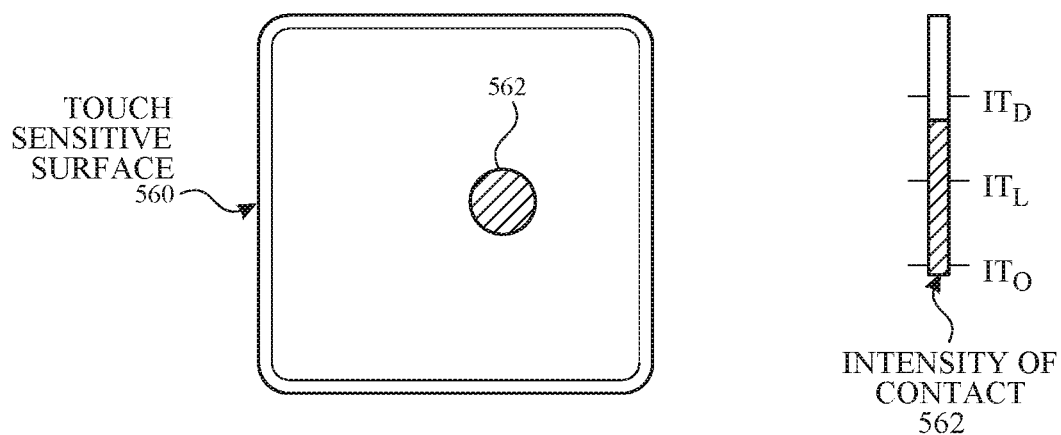
Figure 5H:
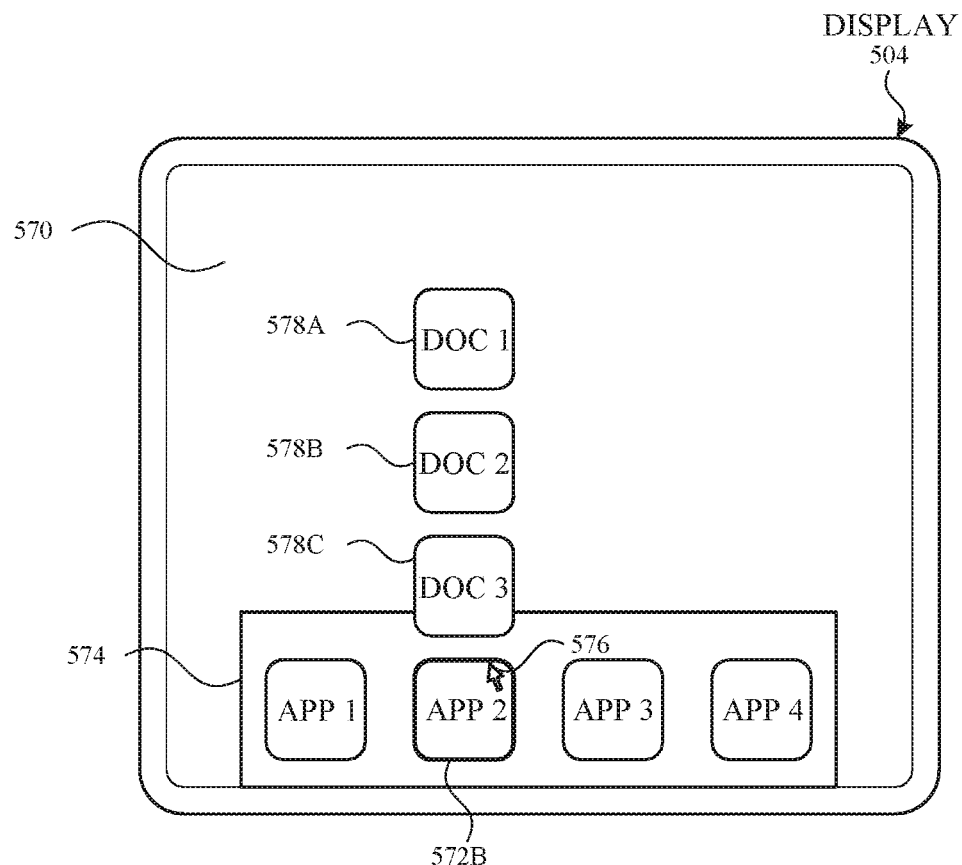
Figure 5H:
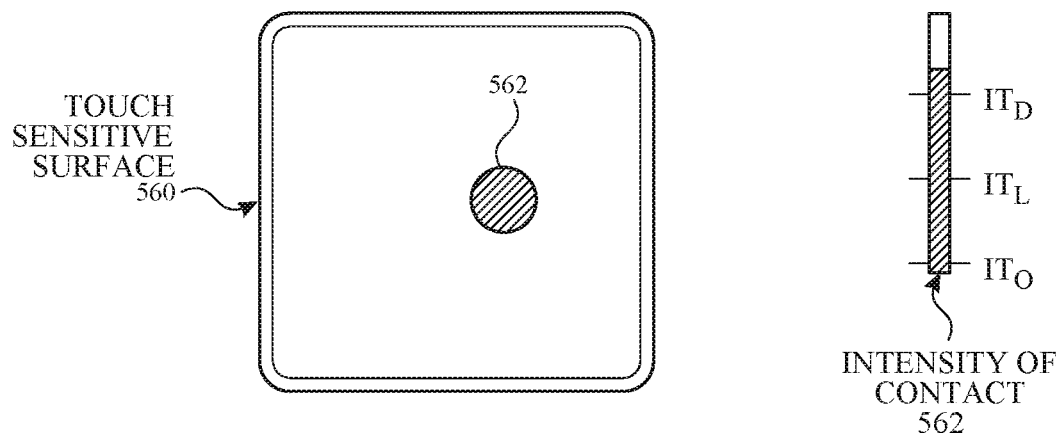

FIGS. 5E-5H illustrate detection of a gesture that includes a press input that corresponds to an increase in intensity of a contact 562 from an intensity below a light press intensity threshold (e.g., "$IT_L$") in FIG. 5E, to an intensity above a deep press intensity threshold (e.g., "$IT_D$") in FIG. 5H. The gesture performed with contact 562 is detected on touch-sensitive surface 560 while cursor 576 is displayed over application icon 572B corresponding to App 2, on a displayed user interface 570 that includes application icons 572A-572D displayed in predefined region 574. In some embodiments, the gesture is detected on touch-sensitive display 504. The intensity sensors detect the intensity of contacts on touch-sensitive surface 560. The device determines that the intensity of contact 562 peaked above the deep press intensity threshold (e.g., "$IT_D$"). Contact 562 is maintained on touch-sensitive surface 560. In response to the detection of the gesture, and in accordance with contact 562 having an intensity that goes above the deep press intensity threshold (e.g., "$IT_D$") during the gesture, reduced-scale representations 578A-578C (e.g., thumbnails) of recently opened documents for App 2 are displayed, as shown in FIGS. 5F-5H. In some embodiments, the intensity, which is compared to the one or more intensity thresholds, is the characteristic intensity of a contact. It should be noted that the intensity diagram for contact 562 is not part of a displayed user interface, but is included in FIGS. 5E-5H to aid the reader.

In some embodiments, the display of representations 578A-578C includes an animation. For example, representation 578A is initially displayed in proximity of application icon 572B, as shown in FIG. 5F. As the animation proceeds, representation 578A moves upward and representation 578B is displayed in proximity of application icon 572B, as shown in FIG. 5G. Then, representations 578A moves upward, 578B moves upward toward representation 578A, and representation 578C is displayed in proximity of application icon 572B, as shown in FIG. 5H. Representations 578A-578C form an array above icon 572B. In some embodiments, the animation progresses in accordance with an intensity of contact 562, as shown in FIGS. 5F-5G, where the representations 578A-578C appear and move upwards as the intensity of contact 562 increases toward the deep press intensity threshold (e.g., "$IT_D$"). In some embodiments, the intensity, on which the progress of the animation is based, is the characteristic intensity of the contact. The operations described with reference to FIGS. 5E-5H can be performed using an electronic device similar or identical to device 100, 300, or 500.

In some embodiments, the device employs intensity hysteresis to avoid accidental inputs sometimes termed "jitter," where the device defines or selects a hysteresis intensity threshold with a predefined relationship to the press-input intensity threshold (e.g., the hysteresis intensity threshold is X intensity units lower than the press-input intensity threshold or the hysteresis intensity threshold is 75%, 90%, or some reasonable proportion of the press-input intensity threshold). Thus, in some embodiments, the press input includes an increase in intensity of the respective contact above the press-input intensity threshold and a subsequent decrease in intensity of the contact below the hysteresis intensity threshold that corresponds to the press-input intensity threshold, and the respective operation is performed in response to detecting the subsequent decrease in intensity of the respective contact below the hysteresis intensity threshold (e.g., an "up stroke" of the respective press input). Similarly, in some embodiments, the press input is detected only when the device detects an increase in intensity of the contact from an intensity at or below the hysteresis intensity threshold to an intensity at or above the press-input intensity threshold and, optionally, a subsequent decrease in intensity of the contact to an intensity at or below the hysteresis intensity, and the respective operation is performed in response to detecting the press input (e.g., the increase in intensity of the contact or the decrease in intensity of the contact, depending on the circumstances).

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

As used herein, an "installed application" refers to a software application that has been downloaded onto an electronic device (e.g., devices 100, 300, and/or 500) and is ready to be launched (e.g., become opened) on the device. In some embodiments, a downloaded application becomes an installed application by way of an installation program that extracts program portions from a downloaded package and integrates the extracted portions with the operating system of the computer system.

As used herein, the terms "open application" or "executing application" refer to a software application with retained state information (e.g., as part of device/global internal state 157 and/or application internal state 192). An open or executing application is, optionally, any one of the following types of applications:

an active application, which is currently displayed on a display screen of the device that the application is being used on;
 a background application (or background processes), which is not currently displayed, but one or more processes for the application are being processed by one or more processors; and
 a suspended or hibernated application, which is not running, but has state information that is stored in memory (volatile and non-volatile, respectively) and that can be used to resume execution of the application.

As used herein, the term "closed application" refers to software applications without retained state information (e.g., state information for closed applications is not stored in a memory of the device). Accordingly, closing an application includes stopping and/or removing application processes for the application and removing state information for the application from the memory of the device. Generally, opening a second application while in a first application does not close the first application. When the second application is displayed and the first application ceases to be displayed, the first application becomes a background application.

Attention is now directed towards embodiments of user interfaces ("UI") and associated processes that are implemented on an electronic device, such as portable multifunction device 100, device 300, or device 500.

FIGS. 6A-6BN illustrate exemplary user interfaces associated with a physical activity application, in accordance with some embodiments. The user interfaces in these figures are used to illustrate the processes described below, including the processes in FIG. 7.

FIG. 6A illustrates device 600 with touch sensitive display 602. User interface 610A of a workout application is displayed on touch sensitive display 602. Device 600 includes various input mechanisms that receive user input, such as rotatable input mechanism 603, which is able to receive a rotatable input (and may also receive a push input), and input mechanism 604, which is able to receive a push user input. In some embodiments, device 600 includes some or all of the features of device 100, device 300, or device 500.

User interface 610A includes a scrollable list of affordances 620, which are associated with respective physical activity tracking functions for a physical activity. For example, the scrollable list of affordances includes affordance 621, which corresponds to a physical activity tracking function for an outdoor run, and affordance 622, which corresponds to a physical activity tracking function for a pool swim. It is noted that the scrollable list of affordances 620 includes additional affordances corresponding to other physical activity tracking functions that are not currently displayed but can be displayed in response to a scrolling input (e.g., rotation of rotational mechanism 603).

In some embodiments, one or more of the affordances in the scrollable list of affordances 620 includes a respective change workout metrics affordance, which will be described in further detail below (see at least FIG. 6J). For example, affordance 621 includes change workout metrics affordance 631, and affordance 622 includes change workout metrics affordance 632.

In some embodiments, one or more affordances in the scrollable list of affordances 620 includes a physical activity icon corresponding to a physical activity associated with the affordance. For example, affordance 621 includes physical activity icon 621-1 (e.g., icon of a runner). Similarly, affordance 622 includes physical activity icon 622-1 (e.g., icon of a swimmer). In various embodiments, the physical activity icons (e.g., physical activity icon 621-1) are displayed in a first state (e.g., static state).

In some embodiments, one or more affordances in the scrollable list of affordances includes a workout identifier. For example, affordance 621 includes workout identifier 621-2 that indicates that affordance 621 is associated with an outdoor run workout. Similarly, affordance 622 includes workout identifier 622-2 that indicates that affordance 622 is associated with a pool swim workout.

In some embodiments, one or more affordances in the scrollable list of affordances includes workout goal information. For example, affordance 622 includes workout goal information 622-3 that indicates that the pool swim workout associated with affordance 622 has a predetermined goal of three miles. That is, when affordance 622 is selected, the associated physical activity tracking function will automatically track the distance of the pool swim workout with a preset goal of three miles. Affordance 621 includes goal workout affordance 621-3 that indicates that the outdoor run associated with affordance 621 is an "open goal." An open goal indication indicates to the user that the associated workout does not currently have any preset goals. Accordingly, when affordance 621 is selected, various metrics will be tracked by the associated physical activity tracking function, wherein the metrics do not include any preset goal values.

Referring to FIG. 6B, touch input (e.g., tap input) 615A is received, wherein touch input 615A corresponds to selection of affordance 621. In accordance with a determination that user input 615A is detected at first affordance 621 in the scrollable list of affordances, a physical activity tracking function associated with affordance 621 is launched. That is, execution of the physical activity tracking function starts in accordance to the selection of affordance 621. Moreover, in some embodiments, selection of another affordance (e.g., affordance 622) in the scrollable list of affordances 620 will launch another associated physical activity tracking function, which will be described in further detail below.

Figure 6F:
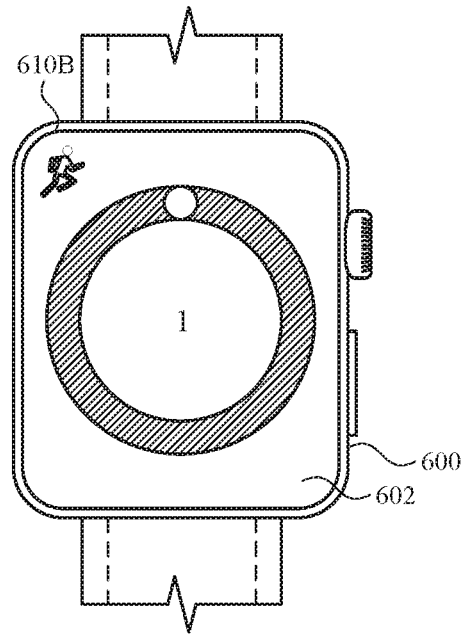

Referring to FIGS. 6C-6F, in response to selection of affordance 621, user interface 610B displays a countdown prior to tracking metrics by the physical activity tracking function. For example, user interface 610B displays "Ready" (FIG. 6C), then a numerical countdown by displaying "3" (FIG. 6D), then "2" (FIG. 6E), and then "1" (FIG. 6F).

Figure 6G:
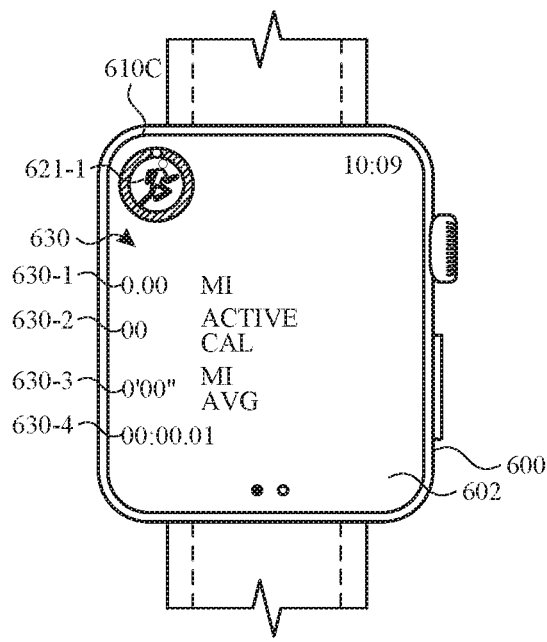
Figure 6H:
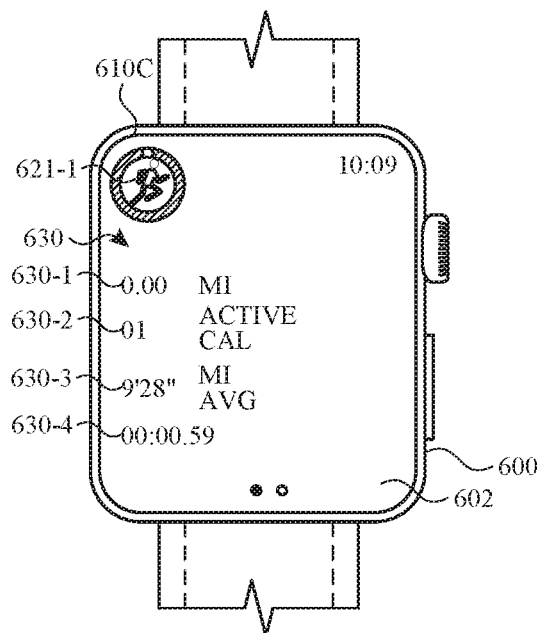
Figure 6I:
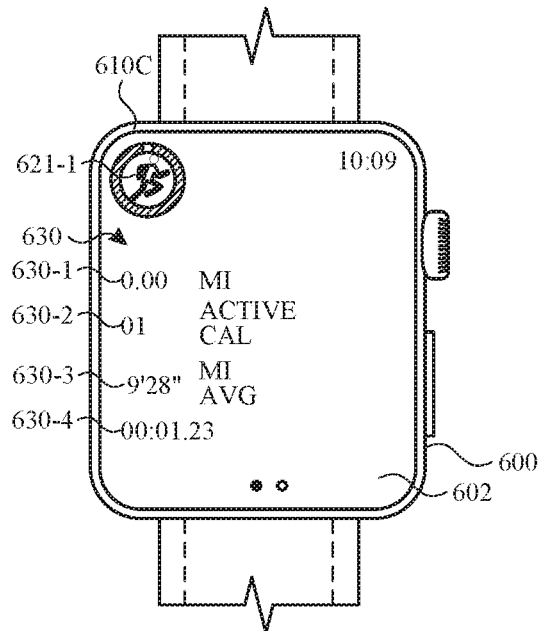

In response to the completion of the countdown, user interface 610C is displayed (FIGS. 6G-6I). User interface 610 displays the tracked metrics 630 (which are tracked by the physical activity tracking function) associated with the workout (e.g., outdoor run) corresponding to the selected affordance 621. For example, user interface 610C includes the tracking of various metrics (e.g., miles 630-1, active calories 630-2, average miles 630-3, and time 630-4). As shown in FIGS. 6G-6I, user interface 610C displays tracked metrics 630 of the outdoor run workout at time of 0.01 seconds into the outdoor run (FIG. 6G), at a time of 0.59 seconds into the outdoor run (FIG. 6H), and a time of 1.23 seconds into the outdoor run (FIG. 6H). In some embodiments, in response to selection of affordance 621, user interface 610C is displayed without displaying (or bypassing) user interface 610C.

Displaying a scrollable list of workout affordances and launching the physical activity tracking function for tracking metrics associated with a selected workout affordance allows a user to quickly select a workout and launch the tracking function to track the metrics associated with the selected workout. Reducing the number of inputs needed to perform tracking of workout metrics enhances the operability of the device and makes the user-device interface more efficient (e.g., by helping the user to provide proper inputs and reducing user mistakes when operating/interacting with the device), which, additionally, reduces power usage and improves battery life of the device by enabling the user to use the device more quickly and efficiently.

In some embodiments, while the physical activity tracking function associated with the affordance is running, the physical activity icon is displayed in an animated state. For example, referring to FIGS. 6G-6I, while the physical activity tracking function is tracking metrics 630, physical activity icon 621-1 is animated (e.g., the runner in the physical activity icon 621-1 moves in a running motion). It should be appreciated that physical activity icon 621-1 ceases to be animated when the physical activity tracking function associated with the affordance stops running (e.g., stops tracking metrics 630).

In some embodiments, the tracking of the metrics is performed by one or more tracking sensors of the device. For example, device 600 tracks the physical activity via tracking sensors (or workout sensors) that communicate with workout support module 142 (as shown in FIG. 3).

Figure 6J:
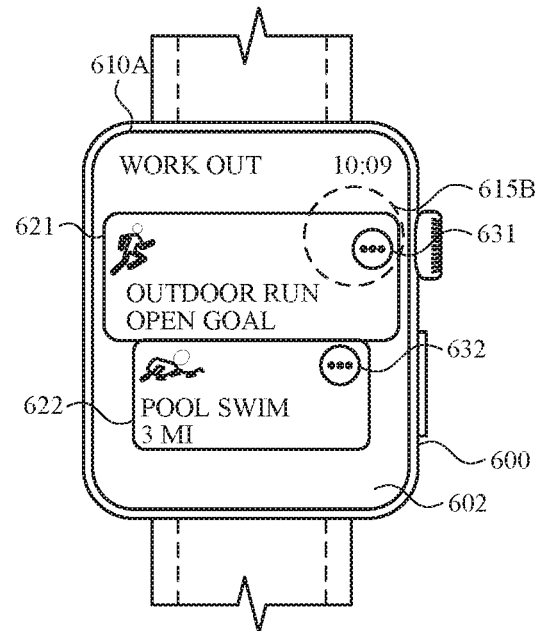

Referring to FIG. 6J, user interface 610A displays scrollable list of affordances 620 (similar to FIG. 6A). User input 615B (e.g., tap gesture) is received at change workout metrics affordance 631.

Figure 6K:
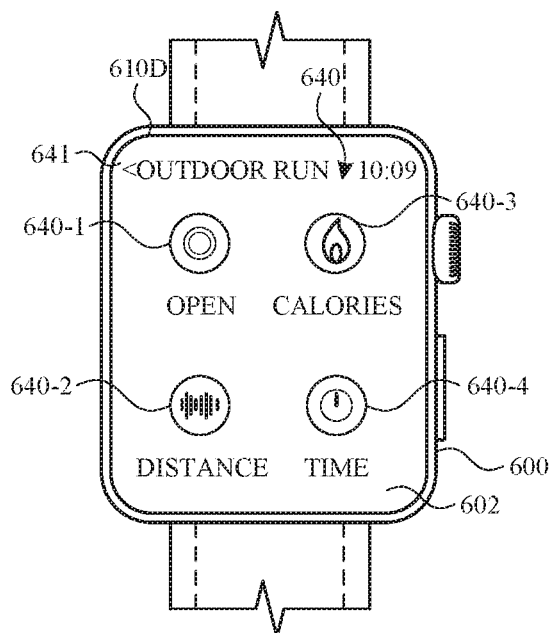

Referring to FIG. 6K, in accordance to a determination that user input 615B is detected at change workout metrics affordance 631, user interface 610D is displayed, wherein user interface 610D is configured to change workout metrics associated with a physical activity (e.g., outdoor run) corresponding to affordance 621. In particular, user interface 610D includes metric affordances 640 (e.g., open goal affordance 640-1, distance affordance 640-2, calories affordance 640-3, and time affordance 640-4) that are associated with workout metrics corresponding with the outdoor run workout. User interface 610D also includes affordance 641, which when selected, is configured to display previous UI 610A (FIG. 6J). In some embodiments, in accordance to a determination that user input 615B is detected at change workout metrics affordance 631, user interface 610D is displayed with launching the physical activity tracking function associated with affordance 621.

Displaying a change workout metrics affordance with the scrollable list of workouts allows a user to quickly change goal values of a metric and launch the tracking function to track metrics associated with a workout. Reducing the number of inputs needed to change goal values and perform tracking of workout metrics enhances the operability of the device and makes the user-device interface more efficient (e.g., by helping the user to provide proper inputs and reducing user mistakes when operating/interacting with the device), which, additionally, reduces power usage and improves battery life of the device by enabling the user to use the device more quickly and efficiently.

Figure 6L:
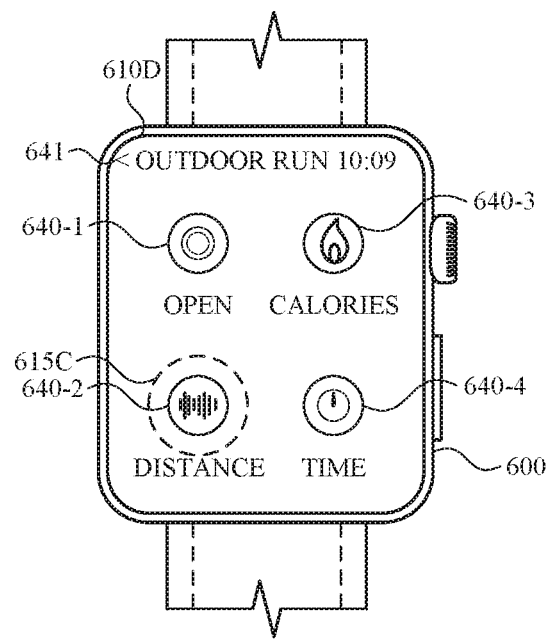
Figure 6M:
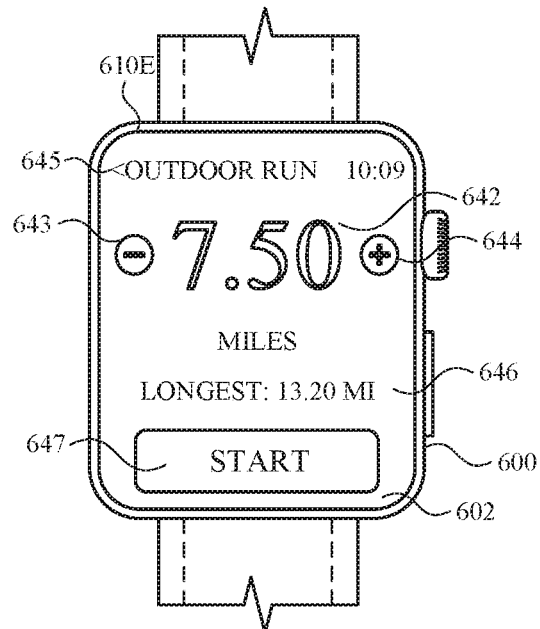

Referring to FIG. 6L, user input 615C (e.g., tap gesture) is received at distance affordance 640-2.

Referring to FIGS. 6M-6R, in response to receiving user input 615C at distance affordance 640-2, goal value user interface 610E is displayed. Goal value user interface 610E includes goal value 642 (e.g., 7.5 miles) corresponding to the selected distance affordance 640-2 of the outdoor run workout. The initial goal value of 7.50 miles is the current value associated with the distance metric of the outdoor run. That is, if the outdoor run workout was launched (with the distance goal value of 7.50 miles) then the tracking of the distance metric would be set at 7.50 miles.

Figure 6N:
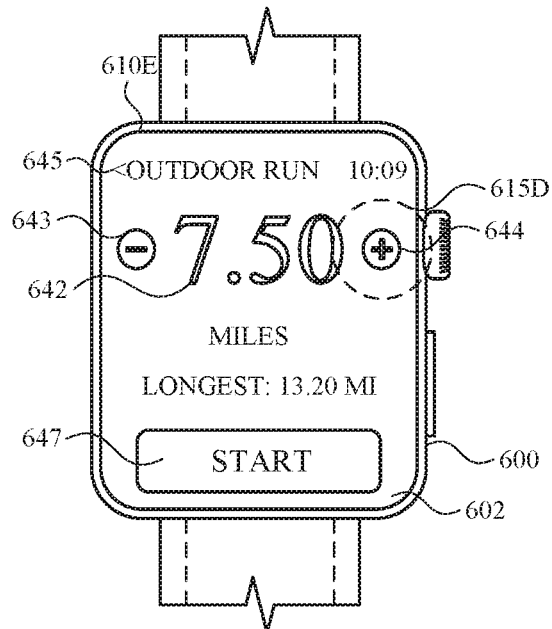
Figure 6O:
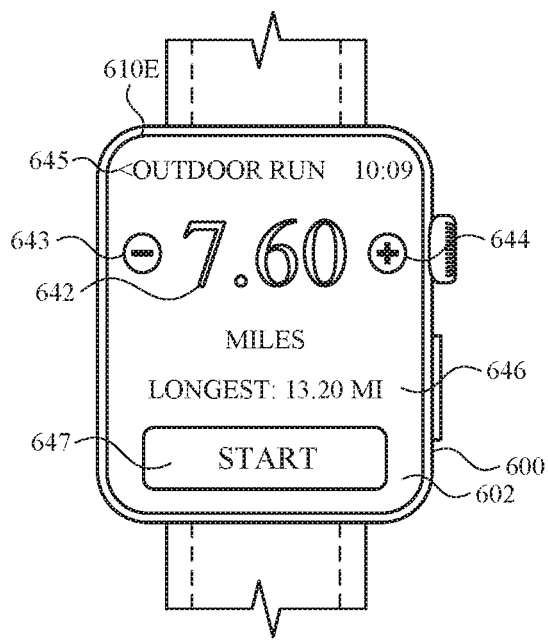
Figure 6P:
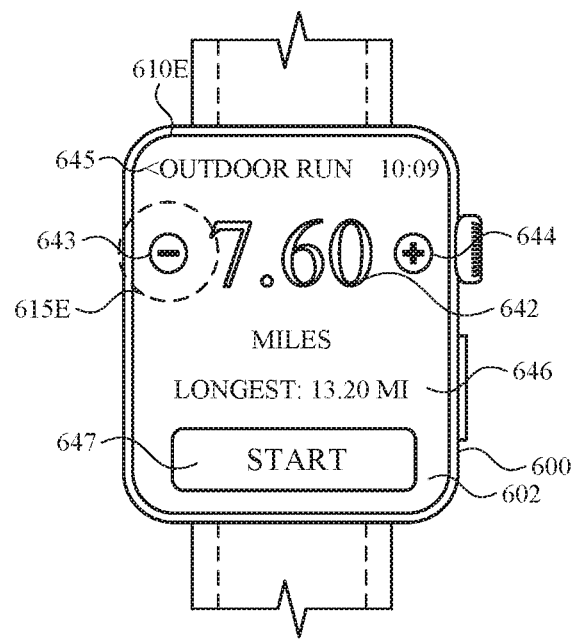

In some embodiments, the goal value 642 (e.g., 7.50 miles) can be adjusted via goal change affordance 643 (e.g., "−" affordance) and/or goal change affordance 644 (e.g., "+" affordance). For example, user input 615D is received at goal change affordance 644 (FIG. 6N). In response to receiving user input 615D at goal change affordance 644, goal value of 7.50 miles is changed to 7.60 miles (FIG. 6O). Similarly, user input 615E is received at goal change affordance 643 (FIG. 6P). In response to receiving user input 615E at goal change affordance 643, goal value of 7.60 miles is changed to 7.50 miles (FIG. 6Q).

Figure 6Q:
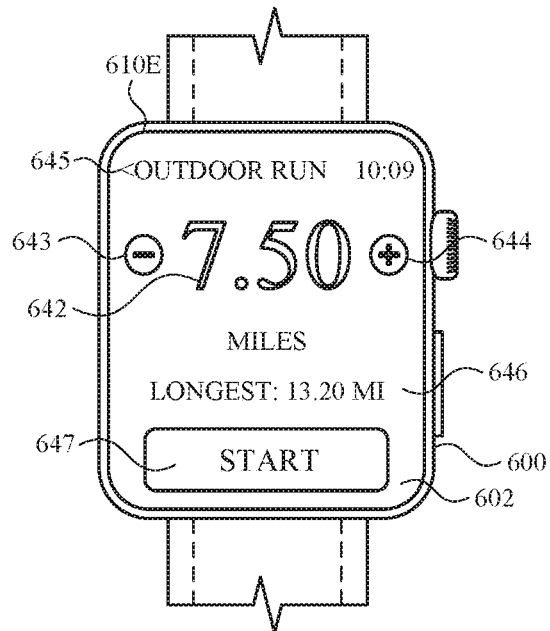

As shown in FIG. 6Q, goal value user interface 610E includes goal information 646. For example, goal information 646 is information identifying a previous longest distance (associated with the outdoor run workout) that the physical activity tracking function has tracked. Accordingly, the user may adjust the goal value 642 (by increasing or decreasing the goal value, as described above) based, at least in part, on goal information 646. Goal value user interface 610E also includes affordance 645, which when selected, is configured to display previous UI 610D (FIG. 6L).

Figure 6R:
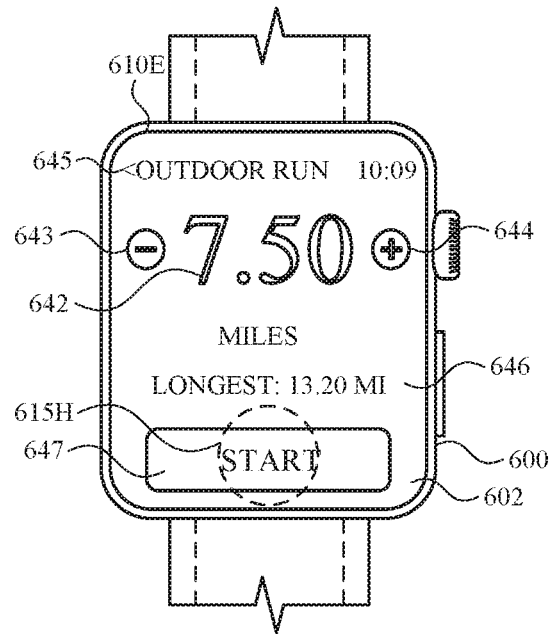

Referring to FIG. 6R, goal value user interface 610E includes start affordance 647 configured to launch a physical activity tracking function associated with affordance 621. For example, user input 615H is received at start affordance 647. In response to user input 615H selecting affordance 647, the physical activity tracking function associated with affordance 621 (e.g., outdoor run) is launched. Specifically, the physical activity tracking function tracks distance traveled of the outdoor run based on the goal value of 7.50 miles. In some embodiments, the launching of the physical activity tracking function associated with affordance 621, via start affordance 647, is similar to the launching of the physical activity tracking function by user input 615A at affordance 621 (e.g., FIGS. 6C-6I).

Figure 6S:
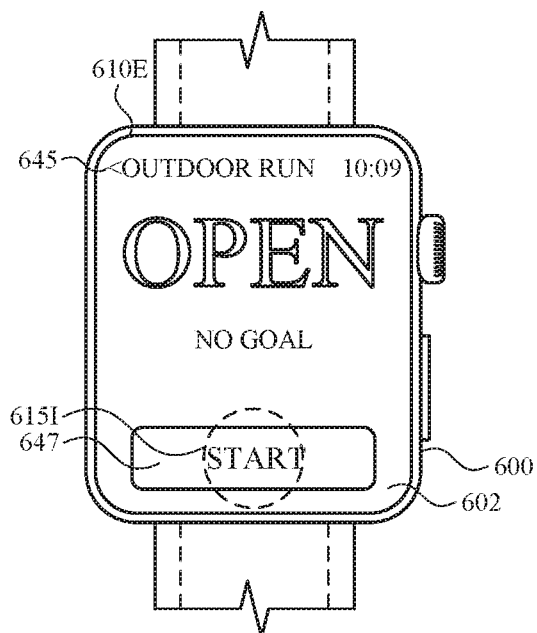
Figure 6T:
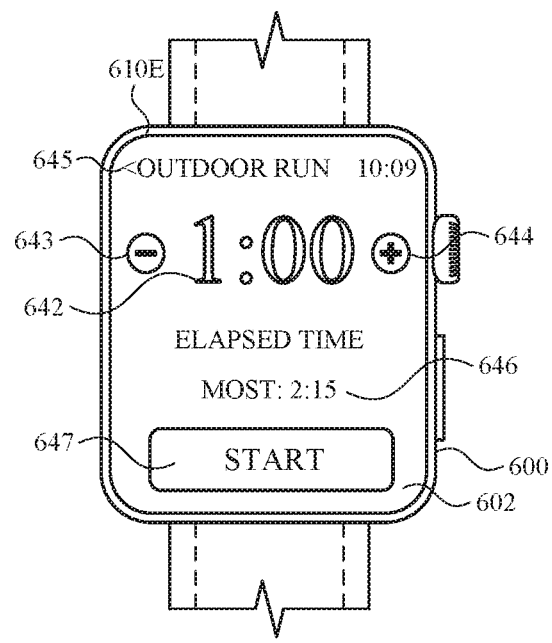
Figure 6U:
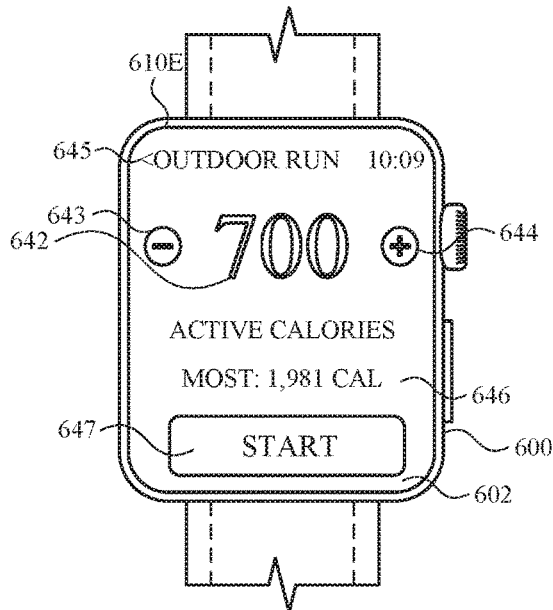

FIGS. 6S-6U depict various embodiments of goal value user interface 610E. FIG. 6S depicts of user interface 610E displayed in response to a user input at open goal affordance 640-1 (FIG. 6K). The open goal feature does not include any goal values associated with the physical activity (e.g., outdoor run). Accordingly, goal value user interface 610E (when displayed in response to the selection of open goal affordance 640-1) does not display any goal values. In response to receiving user input 615I, at start affordance 647, the physical activity tracking function associated with affordance 621 (e.g., outdoor run) is launched. The launched physical tracking function tracks various metrics (e.g., distance, calories, time) but does not track the metrics with respect to goal values. In some embodiments, the launching of the physical activity tracking function associated with affordance 621, via start affordance 647, is similar to the launching of the physical activity tracking function by user input 615A at affordance 621 (e.g., FIGS. 6C-6I).

FIG. 6T depicts goal value user interface 610E displayed in response to user input at time goal affordance 640-4 (FIG. 6K). Goal user interface 610E (when displayed in response to the selection of time goal affordance 640-4) includes goal value 642 (e.g., elapsed time of one hour), goal change affordances 643 and 644, goal information 646 (e.g., information identifying a previous longest time duration that the physical activity tracking function has tracked for the outdoor run), and start affordance 647. Goal value 642 can be adjusted via selection of goal change affordance 643 and/or goal change affordance 644 as described above (FIGS. 6M-6Q). Additionally, in response to a user input (e.g., tap gesture) selecting affordance 647, the physical activity tracking function associated with affordance 621 (e.g., outdoor run) is launched. Specifically, the physical activity tracking function tracks time duration of the outdoor run based on the goal value of one hour. In some embodiments, the launching of the physical activity tracking function associated with affordance 621, via start affordance 647, is similar to the launching of the physical activity tracking function by user input 615A at affordance 621 (e.g., FIGS. 6C-6I).

FIG. 6U depicts user interface 610E displayed in response to a user input at calories affordance 640-3 (FIG. 6K). Goal user interface 610E (when displayed in response to the selection of calories affordance 640-3) includes goal value 642 (e.g., active calories burned), goal change affordances 643 and 644, goal information 646 (e.g., information identifying the most calories burned that the physical activity tracking function has tracked from a previous outdoor run workout), and start affordance 647. Goal value 642 can be adjusted via selection of goal change affordance 643 and/or goal change affordance 644 as described above (FIGS. 6M-6Q). Additionally, in response to a user input (e.g., tap gesture) selecting affordance 647, the physical activity tracking function associated with affordance 621 (e.g., outdoor run) is launched. Specifically, the physical activity tracking function tracks calories burned during the outdoor run based on the goal value of 700 calories. In some embodiments, the launching of the physical activity tracking function associated with affordance 621, via start affordance 647, is similar to the launching of the physical activity tracking function by user input 615A at affordance 621 (e.g., FIGS. 6C-6I).

Figure 6V:
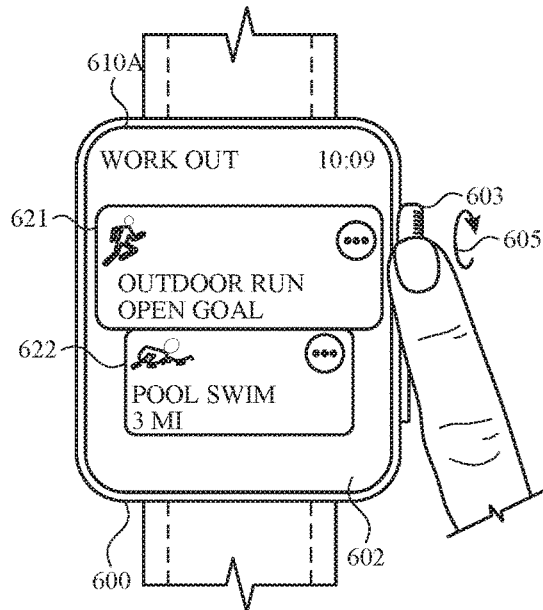
Figure 6W:
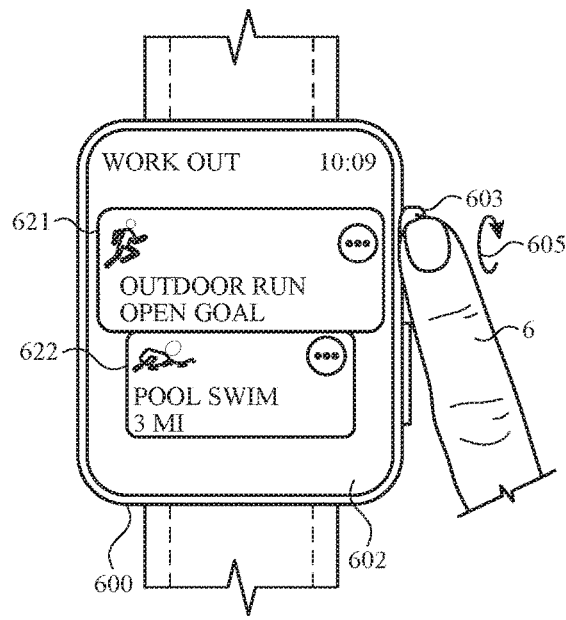
Figure 6X:
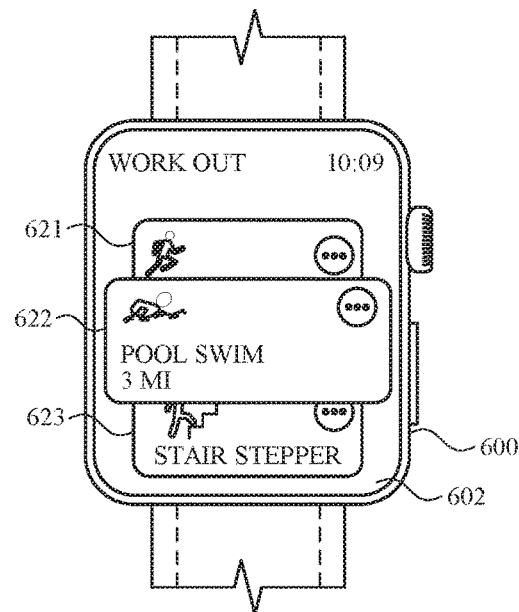

FIGS. 6V-6AB depict an embodiment of user interface 610A displaying scrolling of the scrollable list of affordances 620 and selecting of an affordance. For example, a rotational input 605 is received at rotatable input mechanism 603 (FIGS. 6V-6W). In response to the rotational input 605, the list of affordances 620 are scrolled in an upward direction such that affordance 622 is fully displayed, affordance 621 is partially displayed, and affordance 623 (associated with a stair stepper workout) is partially displayed (FIG. 6X).

Figure 6Y:
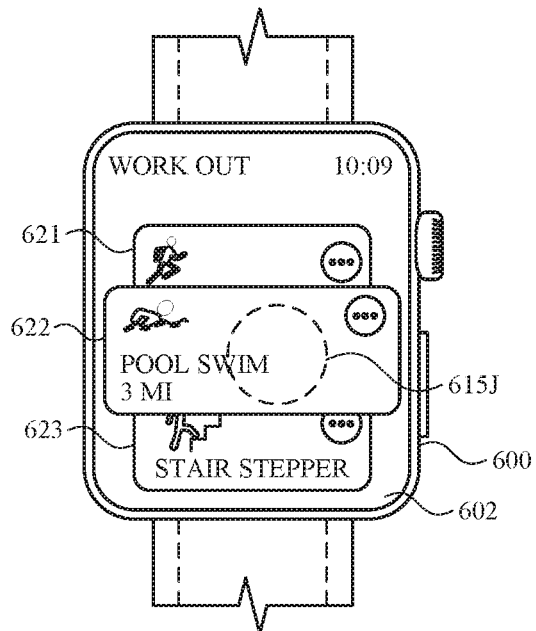
Figure 6Z:
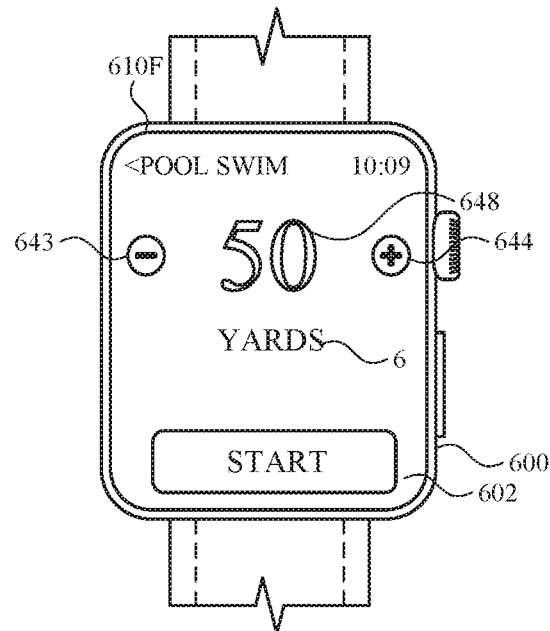
Figure 6A:
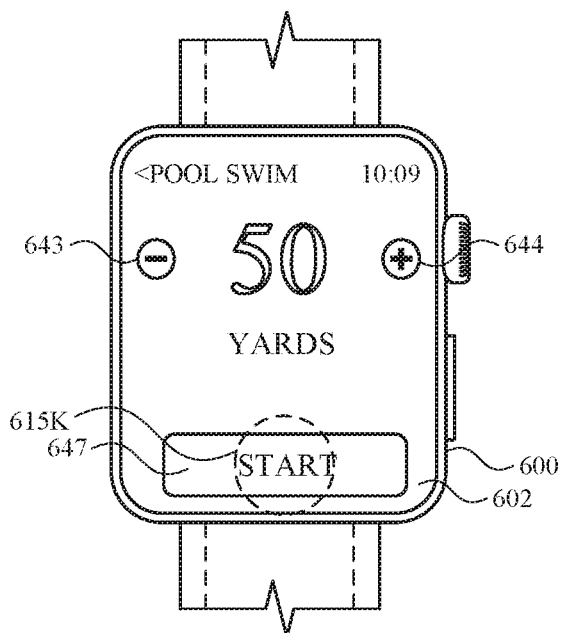
Figure 6A:
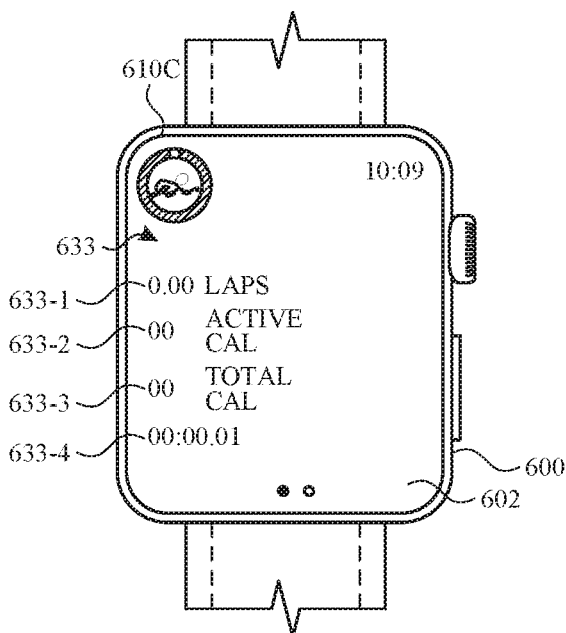
Figure 6A:
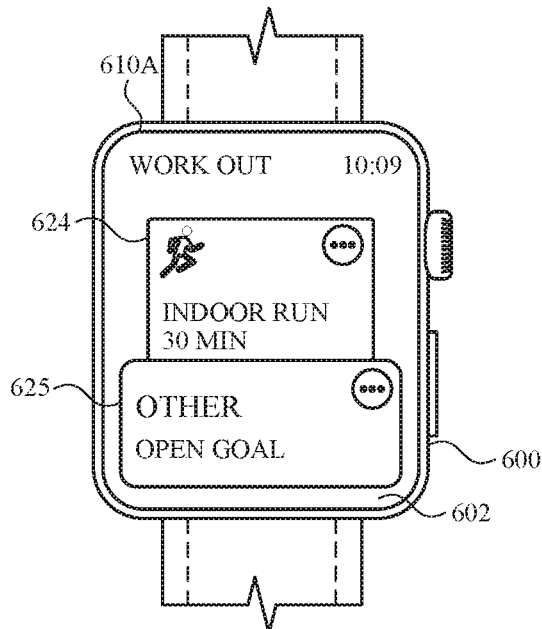
Figure 6A:
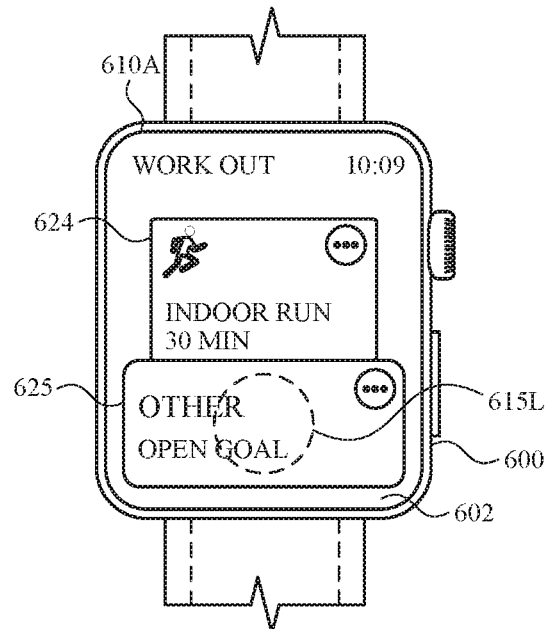
Figure 6A:
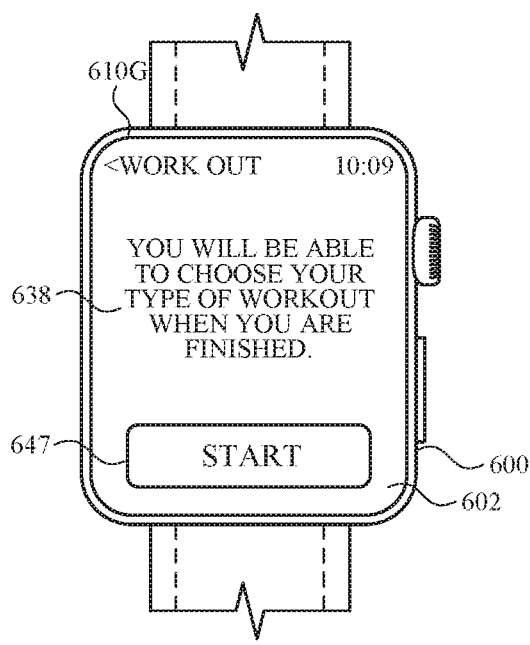
Figure 6A:
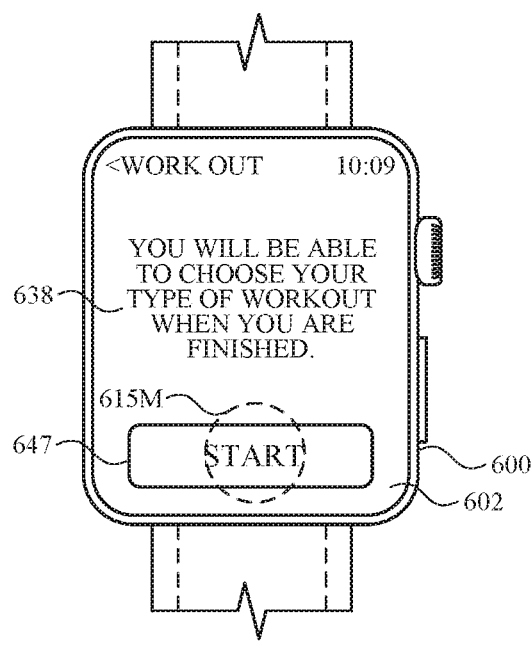
Figure 6A:
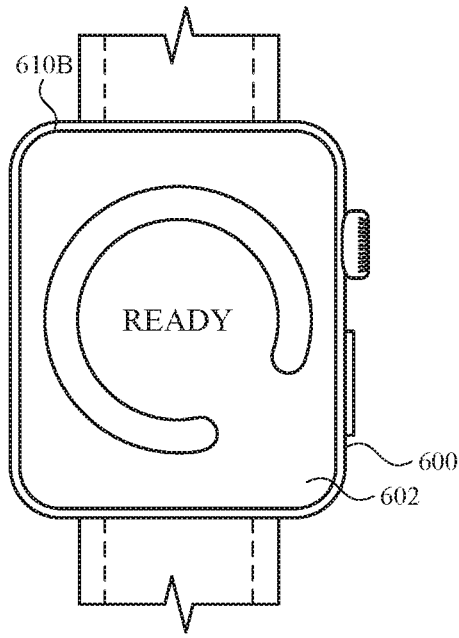
Figure 6A:
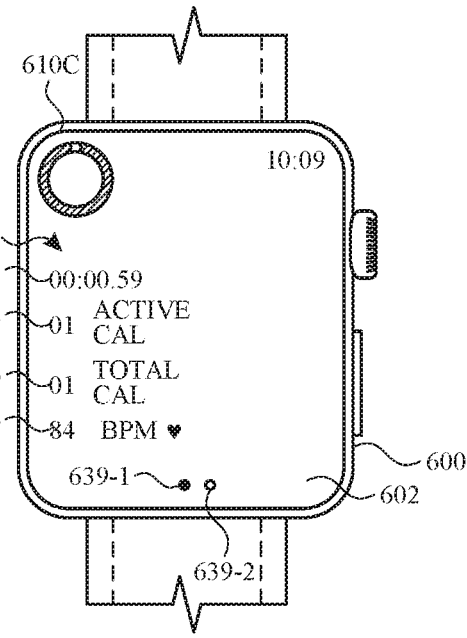
Figure 6A:
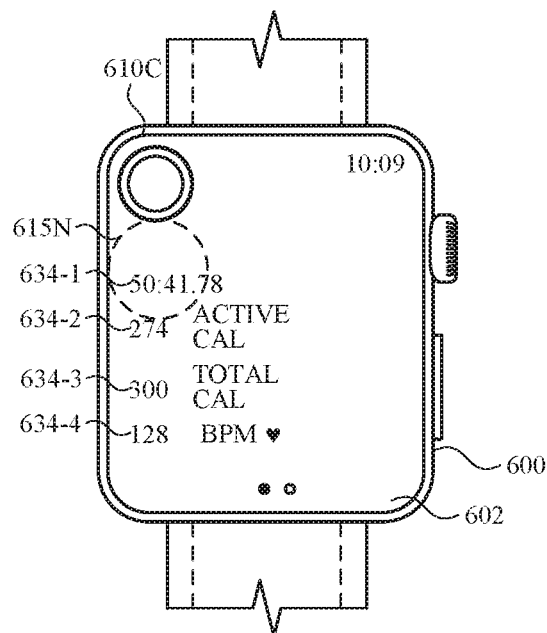
Figure 6A:
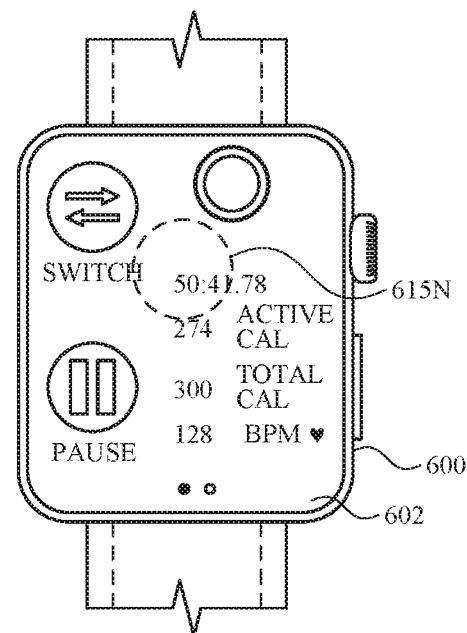
Figure 6A:
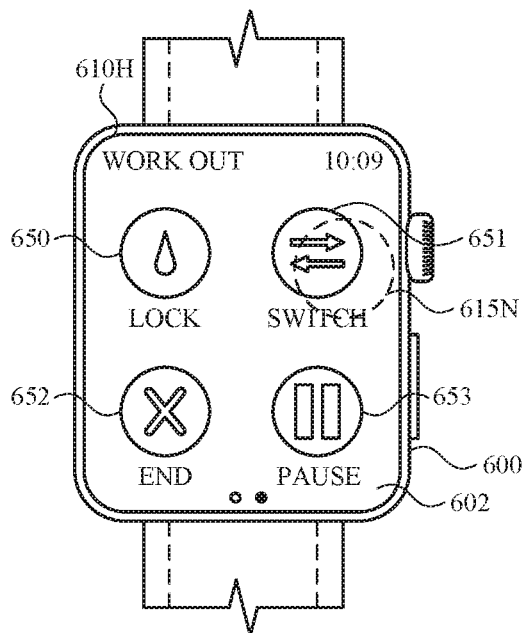
Figure 6A:
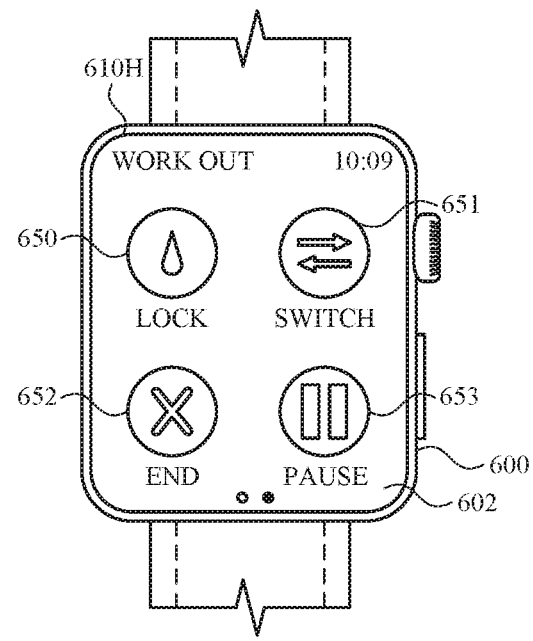
Figure 6A:
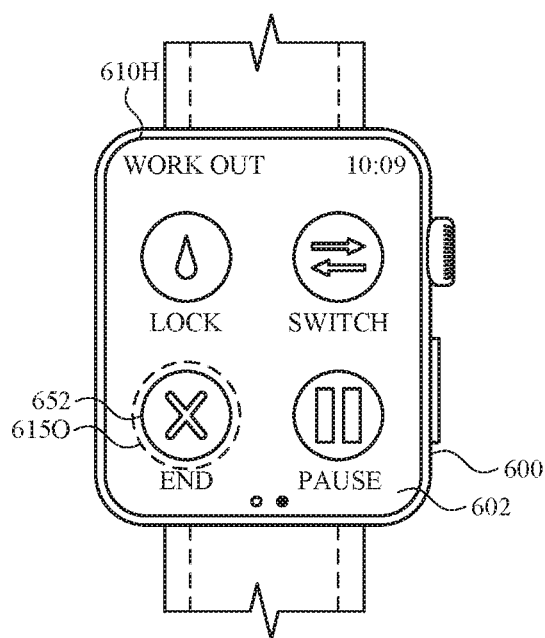
Figure 6A:
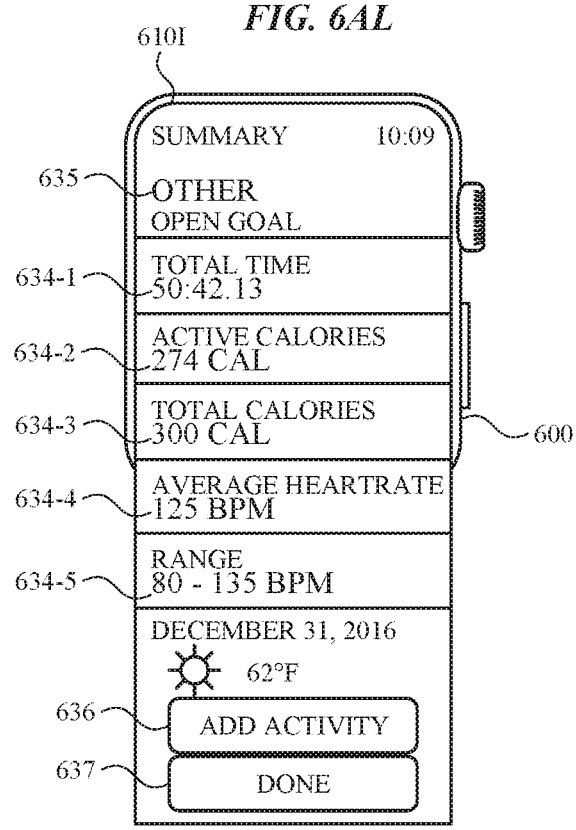
Figure 6A:
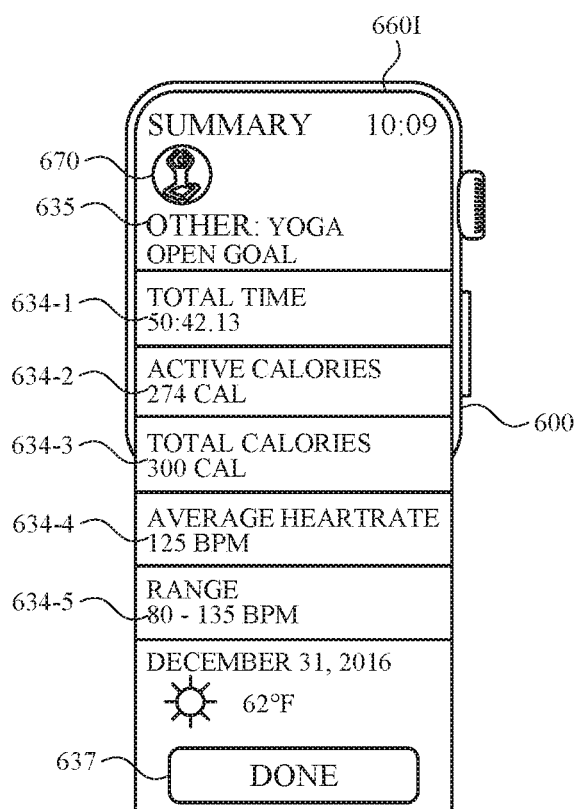
Figure 6A:
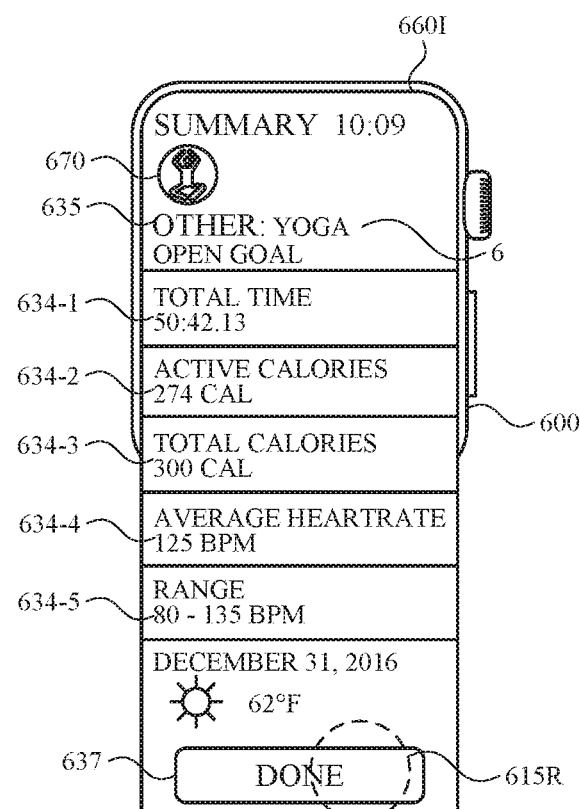
Figure 6A:
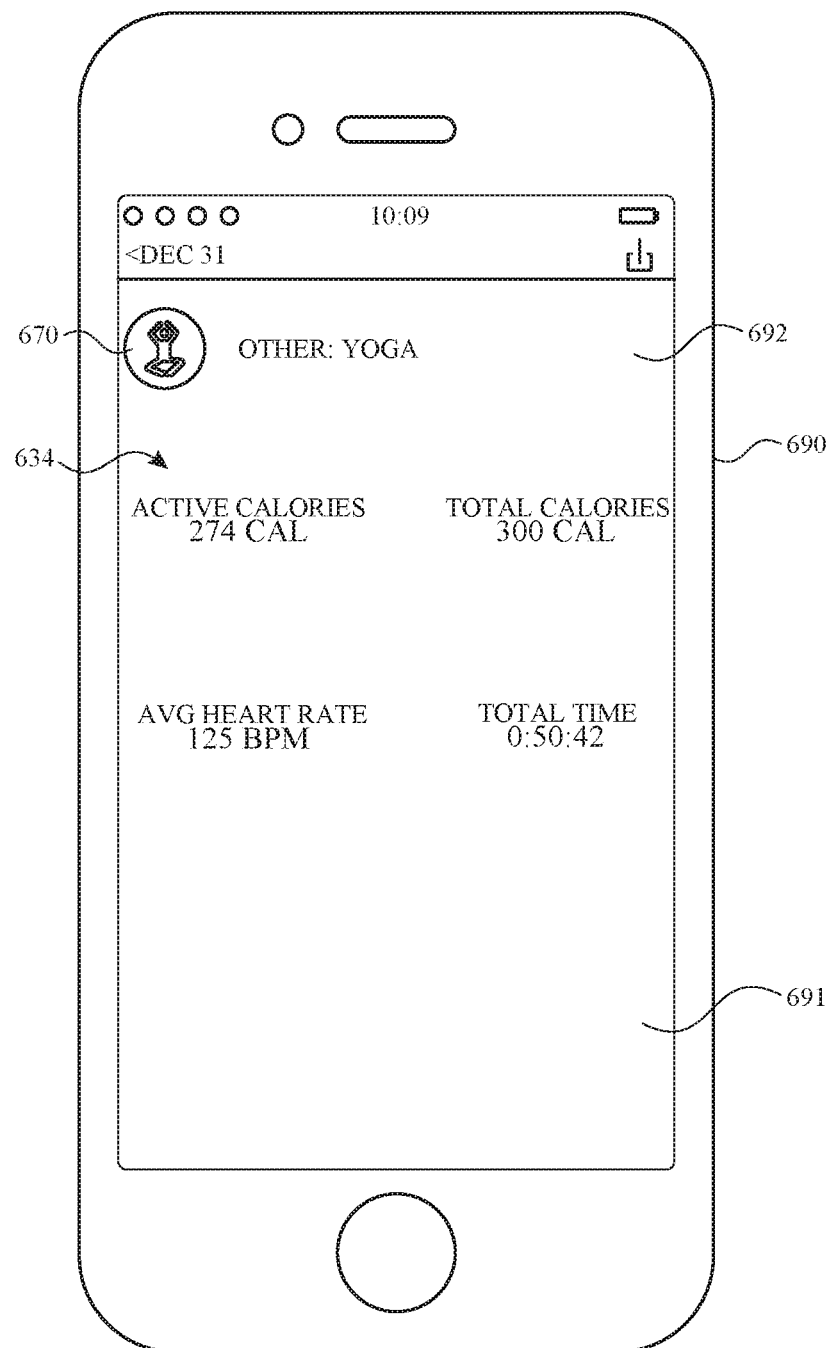
Figure 6A:
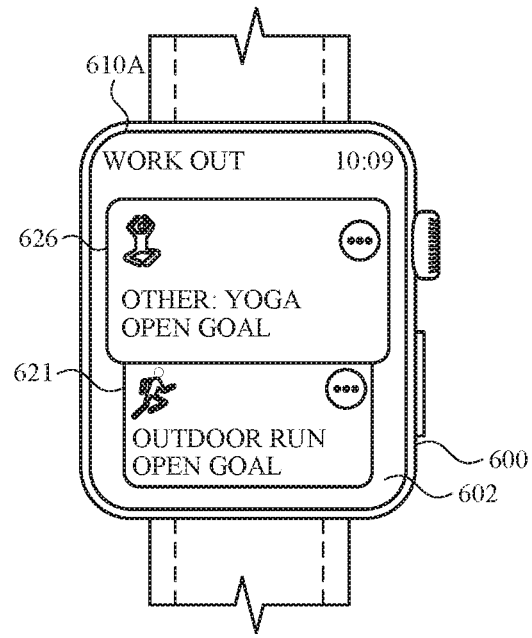
Figure 6A:
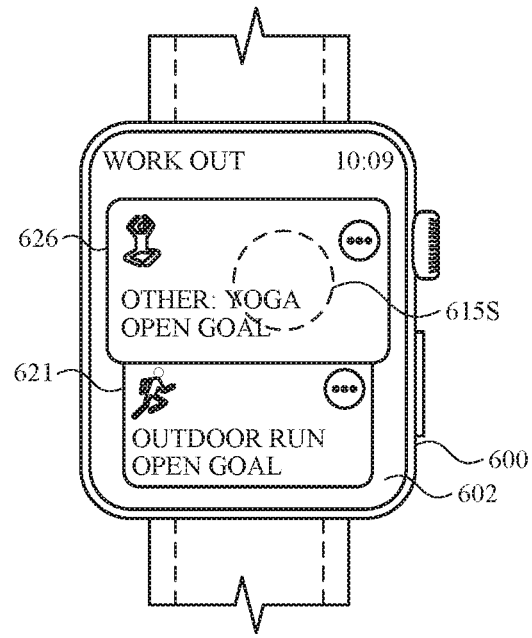
Figure 6A:
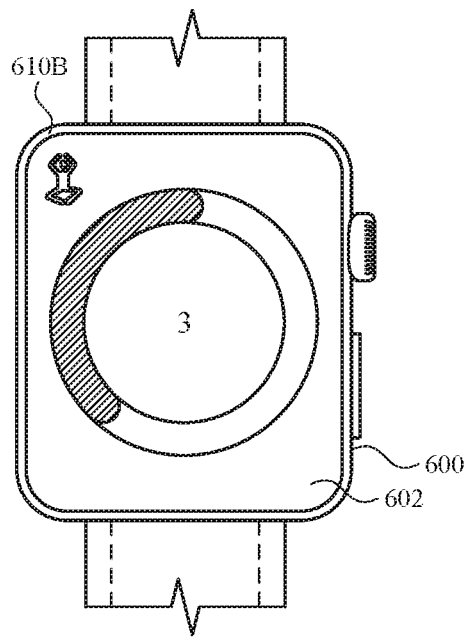
Figure 6A:
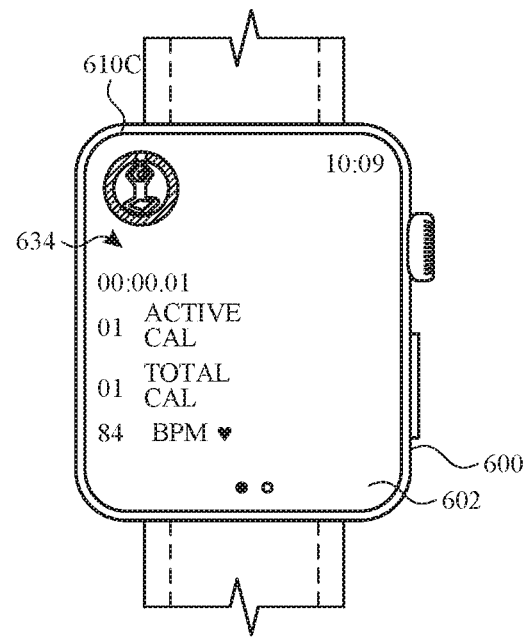
Figure 6A:
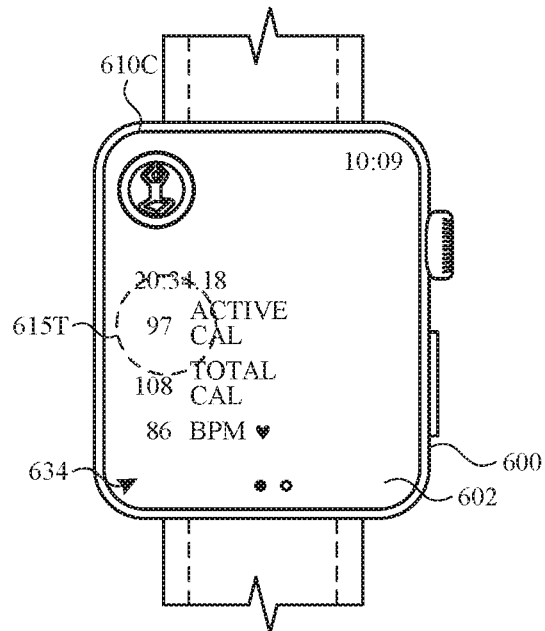
Figure 6A:
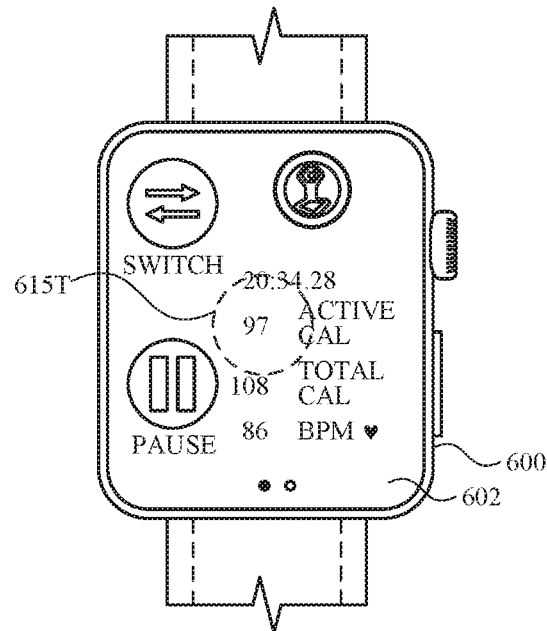
Figure 6B:
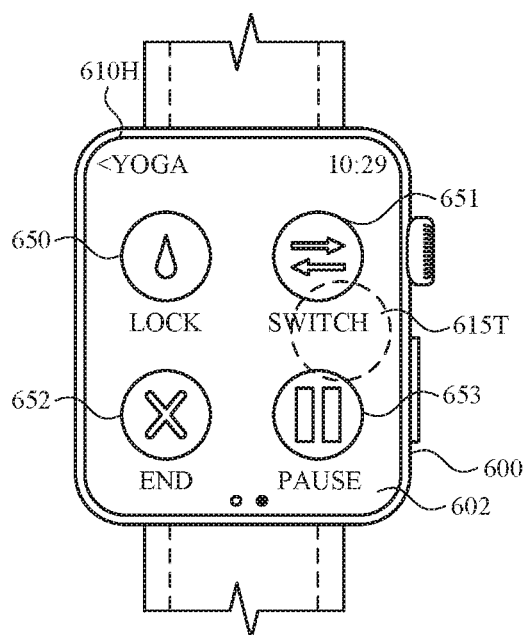
Figure 6B:
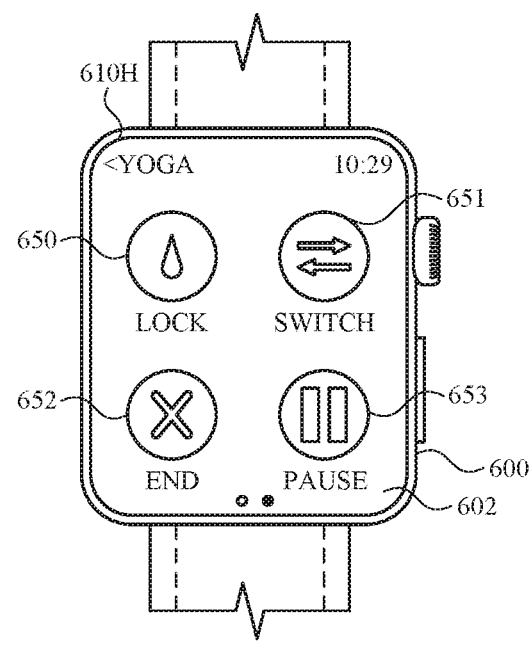
Figure 6B:
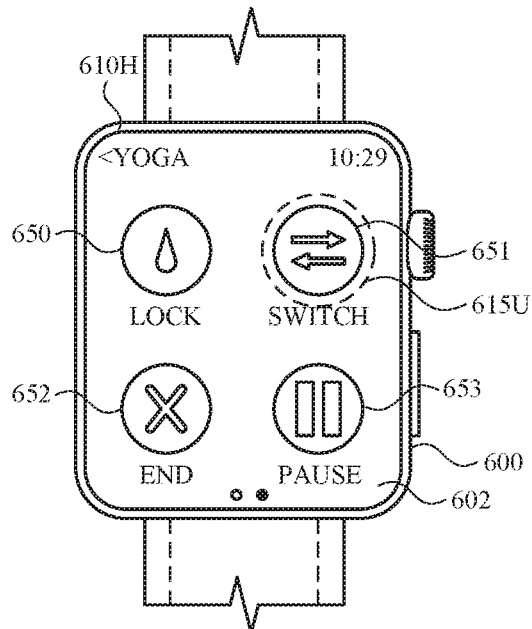
Figure 6B:
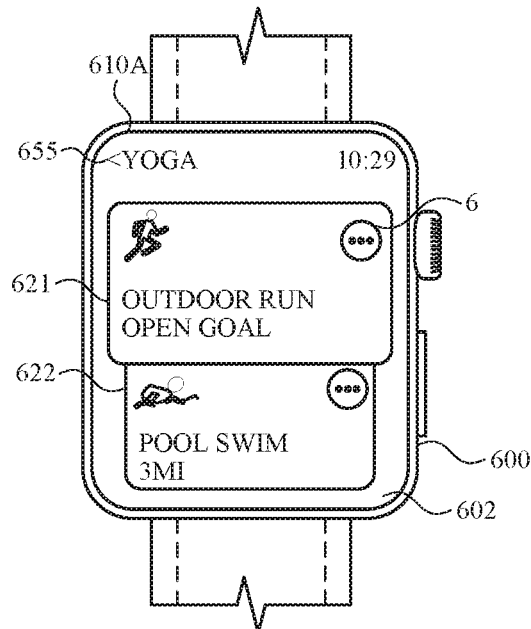
Figure 6B:
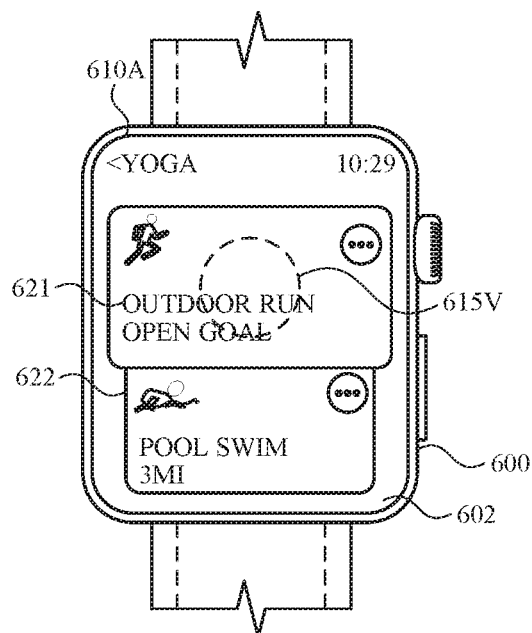
Figure 6B:
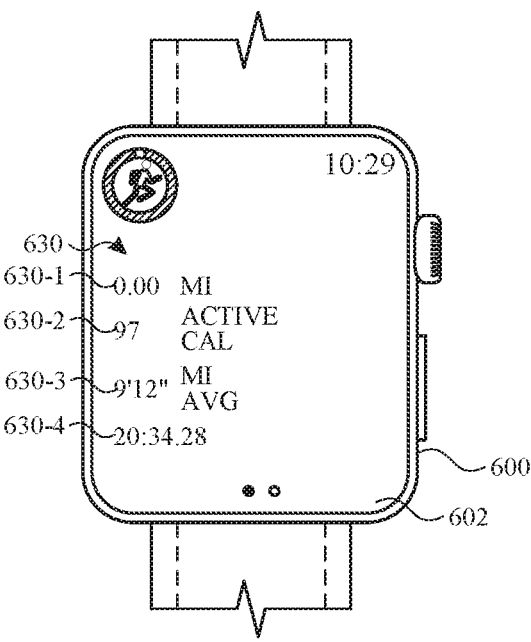
Figure 6B:
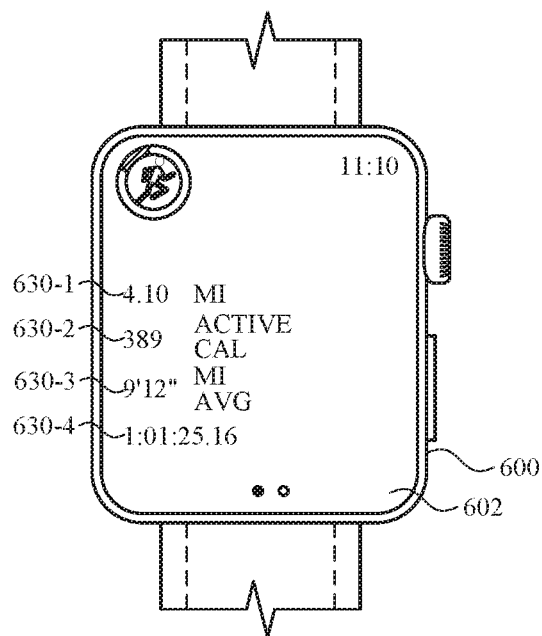
Figure 6B:
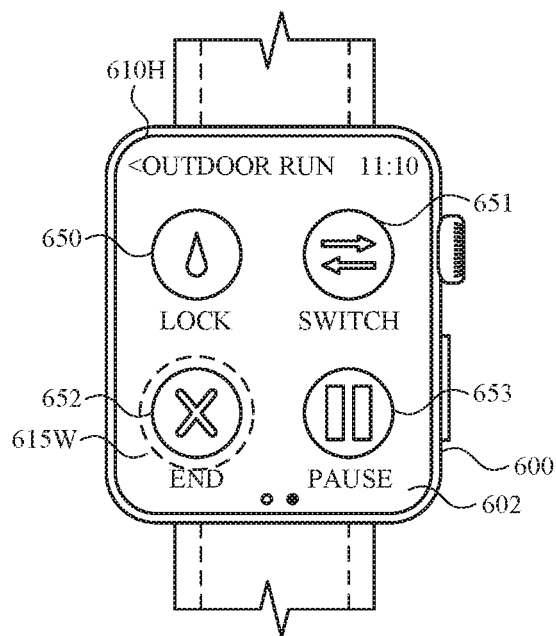
Figure 6B:
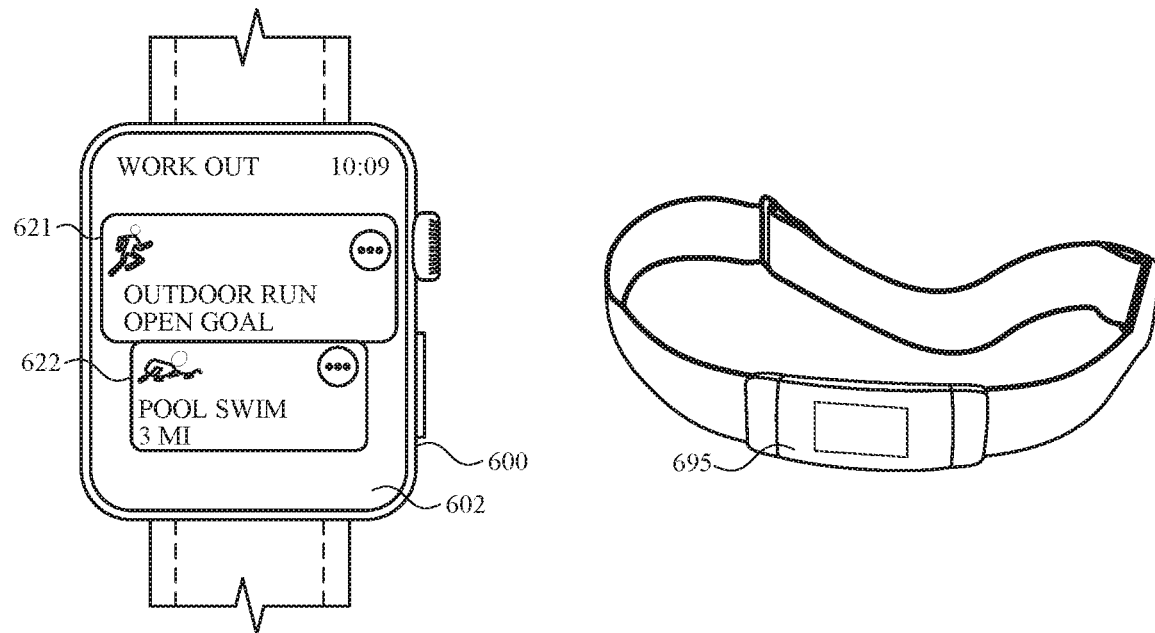
Figure 6B:
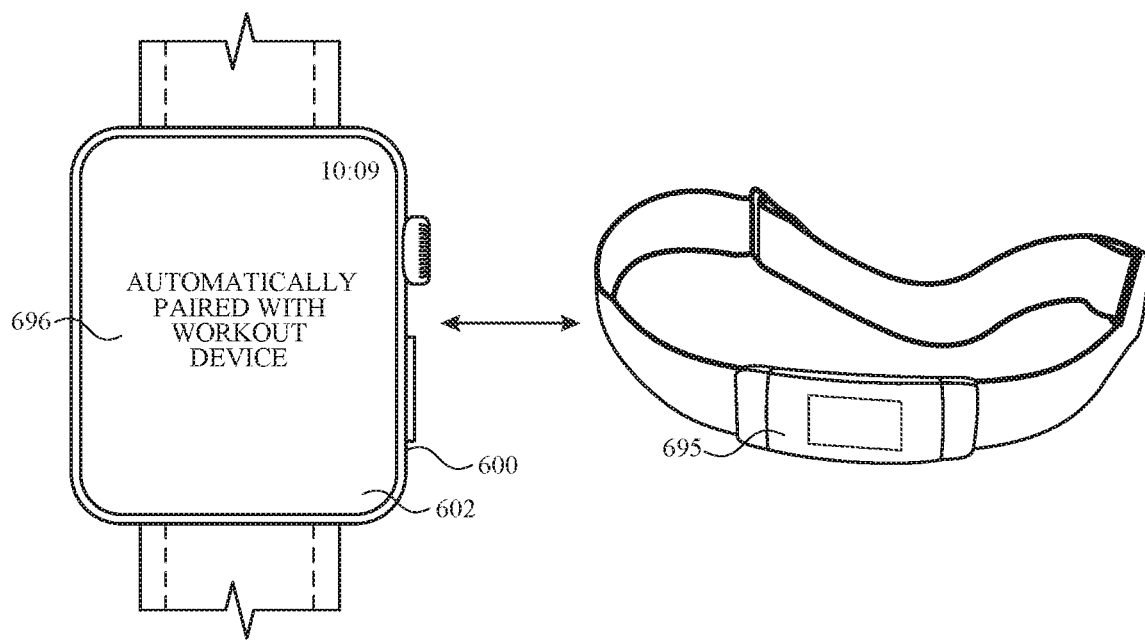
Figure 6B:
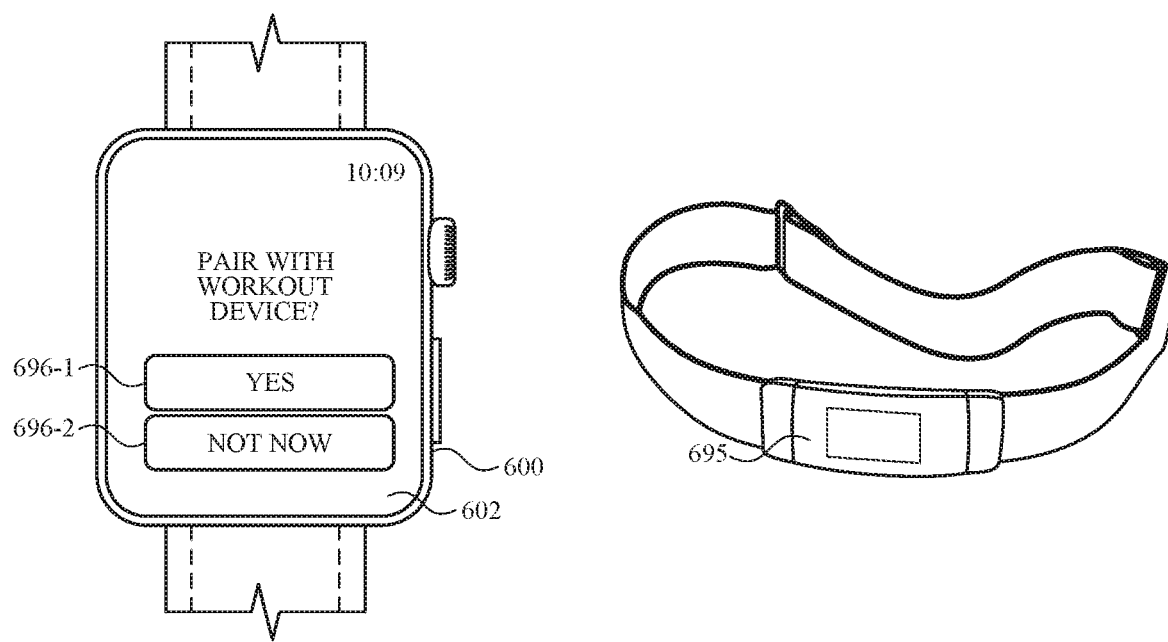

User input 615J is received at affordance 622 (FIG. 6Y). In response to user input 615J at affordance 622 (associated with a pool swim workout), user interface 610F is displayed (FIG. 6Z). User interface 610F includes pool length value 648, value change affordance 643 and/or value change affordance 644. Pool length value 648 may be changed (e.g., from 50 yards to 100 yards, from 50 yards to 25 yards, etc.) via the one or more of the value change affordances. In particular, user interface 610F is configured to receive a pool length value (e.g., 50 yards) for the pool swim workout such that the physical activity tracking function can track the number of pool lengths that the user swims during the pool swim workout.

User input 615K is received at start affordance 647 (FIG. 6AA). In response to user input 615K, the physical activity tracking function associated with affordance 622 (e.g., pool swim) is launched. For example, in response to the selection of affordance 647, user interface 610C is displayed (FIG. 6AB). User interface 610C includes tracking of various metrics 633 (e.g., number of laps metric 633-1, active calories 633-2, total calories 633-3, and time elapsed 633-4). It should be appreciated that a comparison between FIG. 6G (depicting tracked metrics 630 associated with an outdoor run) and FIG. 6AB (depicting tracked metrics 633 associated with a pool swim) shows that different physical activities can be tracked using different metrics. For example, for a running activity it is often desirable to track the total length of the run (in miles), and for a pool swim it is often desirable to track the number laps completed.

FIGS. 6AC-6AD depict an embodiment of user interface 610A. User interface 610A displays affordances 624 and 625 in the scrollable list of affordances 620. In one embodiment, affordance 625 is not associated with a specific physical activity and is labeled "OTHER, Open Goal." Additionally, in one embodiment, affordance 625 is the last (or bottom) affordance in the scrollable list of affordances 620. As will be described in further detail below, affordance 625 facilitates in updating the scrollable list of affordances 220 with an additional specific activity affordance, wherein the user is able to select the specific physical activity (e.g., yoga) associated with the additional specific activity affordance.

User input 615L is received at affordance 625 (FIG. 6AD). In response to user input 615L, user interface 610G is displayed (FIG. 6AE). User interface 610G displays information 638 indicating that the user is able to select a workout associated with the metrics that will be tracked by a physical activity tracking function. User interface 610G includes affordance 647 configured to launch the physical activity tracking function.

User input 615M is received at affordance 647 (FIG. 6AF). In response to user input 615M, user interface 61B is displayed (FIG. 6AG). User interface 610B displays a countdown prior to tracking metrics by the physical activity tracking function, as described above (e.g., FIGS. 6C-6F).

Upon completion of the countdown, user interface 610C is displayed (FIGS. 6AH-6AI). User interface 610C is configured to display a plurality of metrics 634 (e.g., duration 634-1, active calories 634-2, total calories 634-3, and heart rate 634-4) tracked by the physical activity tracking function during the physical activity (e.g., yoga). In some embodiments, user interface 610C is displayed in response to user input 615M without display of intermediary user interface 610B. It is noted that user interface 610C, as illustrated in FIGS. 6AH-6AI, does not include a physical activity icon (e.g., physical activity icon 621-1) because affordance 625 is not associated with a physical activity.

User input 615N (e.g., a swipe gesture) is received on touch sensitive display 602 (FIG. 6AI-6AK). In response to user input 615N, user interface 610H is displayed (FIG. 6AL). User interface 610H includes affordances to control various functionalities of the workout application. For example, user interface 610H includes lock screen affordance 650 (configured to lock the screen and not receive user input), switch workout affordance 651 (described in further detail below), end workout affordance 652 (configured to end a currently running workout), and pause workout affordance 653 (configured to pause a currently running workout).

User interface 610C includes paging dots 639-1 and paging dot 639-2. The paging dots correspond to successive pages (or user interfaces) in the workout application. For example, paging dot 639-1 corresponds to user interface 610C, and paging dot 639-2 corresponds to user interface 610H. In response to user input, such as a swipe gesture (e.g., 610H), the currently displayed page (e.g., user interface 610C in FIG. 6AH) is replaced with display of the corresponding successive page (e.g., user interface 610H in FIG. 6AL). It is noted that, when user interface 610C is displayed, paging dot 639-1 is highlighted (FIG. 6AH). Similarly, when user interface 610H is displayed, paging dot 639-2 is highlighted (FIG. 6AL).

User input 6150 is received at end workout affordance 652 (FIG. 6AM). For example, upon completion of the user's yoga workout, the user selects end workout affordance 652 to stop tracking metrics 634. In response to user input 6150 at end workout affordance 652, user interface 610I is displayed (FIG. 6AN).

User interface 610I includes a summary of the tracked metrics 634 associated with affordance 625. For example, user interface 610I includes physical activity information 635 associated with metrics 634. Because tracked metrics 634 were tracked via selection of affordance 625 (e.g., Other, Open Goal affordance), there is no physical activity (e.g., yoga) currently assigned or associated with tracked metrics 634 of the completed workout. User interface 610I also includes duration 634-1, active calories 634-2, total calories 634-3, average heart rate 634-4, and range of heart rate 634-5. Additionally, user interface 610I includes add activity affordance 636 and done affordance 637. In some embodiments, user interface 610I includes the date and weather information associated with the physical activity.

Note that the entirety of user interface 610I (including off-screen portions) is depicted in FIG. 6AN, for ease of discussion. However, it should be appreciated the entirety of user interface 610I may not be able to be displayed on the limited display size of touch sensitive display 602. As a result, a user may scroll through the user interface via user input (e.g., a rotatable input) received at rotatable input mechanism 603.

User input 615P (e.g., tap gesture) is received at affordance 636 (FIG. 6AO). Referring to FIG. 6AP, user interface 610I is displayed in response to user input 615P at affordance 636. User interface 610I displays a predefined list of selectable physical activities 660. Predefined list of selectable physical activities 660 is configured to be selected and subsequently associated with the tracked metrics 634 corresponding to affordance 625 (e.g., Other, Open Goal affordance). Predefined list of selectable physical activities 660 includes soccer 660-1, yoga 660-2, strength 660-3, archery 660-4, basketball 660-5, and curling 660-6. It is noted that the predefined list of selectable physical activities 660 may include additional physical activities that are not currently displayed but can be displayed in response to a scrolling input (e.g., rotation of rotational mechanism 603).

In some embodiments, the predefined list of selectable physical activities 660 includes a first set of physical activities (e.g., soccer 660-1, yoga 660-2, and strength 660-3). The first set of physical activities, in some embodiments, is a predefined list of popular activities and displayed at the top of the predefined list of selectable physical activities 660. Additionally, the predefined list of selectable physical activities 660 includes a second set of physical activities (e.g., archery 660-4, basketball 660-5, and curling 660-6) that is listed in alphabetical order.

Referring to FIGS. 6AQ and 6AR, user input 615Q is received at yoga activity 660-2. In response to user input 615Q at yoga activity 660-2, metrics 634 of the completed workout are associated with a yoga workout. Accordingly, physical activity information 635 (in user interface 6601) indicates that metrics 634 are associated with a yoga workout via selection of affordance 625. Additionally, in response to user input 615Q at yoga activity 660-2, user interface 6601 includes icon 670 that corresponds to a yoga workout.

FIG. 6AT illustrates companion device 690 that is paired to device 600. In some embodiments, companion device 690 may be device 100, device 300, device 500, or a device that includes one or more features of those devices. Companion device 690 includes touch sensitive display 691. User interface 692 is displayed on touch sensitive display 691. Companion device 690, in some embodiments, when paired to device 600 is able to display the application views and perform at least some of the same processes as device 600, as described, herein. In response to user input 615R at affordance 637 (FIG. 6AS), summary information of the yoga workout is displayed on user interface 692 of companion device 690. For example, user interface 692 includes icon 670 and metrics 634 associated with the completed yoga workout.

FIGS. 6AU-6AV illustrate an embodiment of user interface 610A. In response to user input 615R at affordance 637 (FIG. 6AS), affordance 626 is added to the scrollable list of affordances 620. For example, affordance 626 is a new affordance associated with a yoga workout. Affordance 626 is an open goal affordance associated with a yoga workout. An open goal affordance is not associated with any predefined goal values. As such, in some embodiments, a physical activity tracking function tracks various metrics associated with the open goal affordance and tracks the metrics without consideration of any predefined goal values. Affordance 626 is listed at the top or beginning of the scrollable list of affordances 620. In one embodiment, affordance 626 is listed at the bottom or end of the scrollable list of affordances 620. In various embodiments, affordance 625 remains listed in the scrollable list of affordances upon adding a new affordance (e.g., affordance 626), wherein the new affordance is created, based, in part, on the selection of affordance 625, as described herein.

User input 615S is received at affordance 626 (FIG. 6AV). In response to user input 615S, user interface 610B displays a countdown prior to tracking metrics by the physical activity tracking function, as described above (e.g., FIGS. 6C-6F). Upon completion of the countdown displayed in user interface 610B, a physical activity tracking function is launched to track metrics 634 associated with a yoga workout (e.g., duration 634-1, active calories 634-2, total calories 634-3, and heart rate 634-4) tracked by the physical activity tracking function during the physical activity (FIG. 6AX).

Referring to FIGS. 6AY-6BB, user input 615T (e.g., swipe gesture) is received on touch sensitive display 602. In accordance to user input 615T, user interface 610H is displayed (FIG. 6BB). User interface 610H includes affordances to control various functionality of the workout application. For example, user interface 610H includes lock screen affordance 650, switch workout affordance 651, end workout affordance 652, and pause workout affordance 653.

User input 615U is received at switch workout affordance 651 (FIG. 6BC). For example, while the physical activity tracking function is tracking metrics 634 during the user's yoga workout, the user selects switch workout affordance 651 to switch to a different workout. In response to user input 615U at switch workout affordance 651, user interface 610A is displayed (FIG. 6BD) displaying the scrollable list of affordances 620 (e.g., affordance 621 and affordance 622). Additionally, in response to user input 615U at switch workout affordance 651, the physical activity tracking function tracking metrics 634 is paused.

FIG. 6BD illustrates user interface 610A that includes paused physical activity affordance 655. In one embodiment, user input at affordance 655 is configured to continue the paused workout (e.g., paused yoga workout). For example, in response to user input at affordance 655, the paused physical activity tracking function associated with the yoga workout resumes tracking metrics 634 (e.g., FIG. 6AY).

Referring to FIGS. 6BE-6BG, user input 615V is received at affordance 621 (FIG. 6BE). In response to user input 615V at affordance 621, a physical activity tracking function is launched to track metrics 630 (e.g., miles 630-1, active calories 630-2, average miles 630-3, and time 630-4) of the corresponding physical activity (e.g., outdoor run). Additionally, in response to user input 615V at affordance 621 (FIG. 6BE), the paused workout (e.g., paused yoga workout) is cancelled. Specifically, the physical activity tracking function associated with tracking metrics 634 is cancelled.

Referring to FIG. 6BH, user interface 610H is displayed. For example, user interface 610H is displayed in response a swipe gesture on touch sensitive display 602 in FIG. 6BG.

User input 615W is received at end workout affordance 652 (FIG. 6BH). In response to user input 615W at end workout affordance 652, tracking of metrics 630 is ended, and user interface 610J is displayed (FIG. 6BI). User interface 610J is configured to display a summary of aggregated metrics of at least two previously completed workouts. For example, user interface 610J includes aggregated metrics 680 (e.g., total time 680-1, active calories 680-2, total calories 680-3, average heart rate 680-4, and heart rate range 680-5) that include an aggregation of the metrics 630 associated with the outdoor run workout and metrics 634 associated with the yoga workout. In one embodiment, a user switched from the yoga workout to the outdoor run workout via selection of switch affordance 651 (FIG. 6BC).

User interface 610J includes workout affordance 681 associated with the yoga workout and affordance 682 associated with the outdoor run workout. User input 615W is received at affordance 682 corresponding to the outdoor run workout. In response to user input 615W at affordance 682, user interface 610K is displayed (FIG. 6BK). User interface 610K includes metrics 630 (e.g., total time, average pace, active calories, total calories, average heart rate, and heart rate range) associated with the outdoor run. Similarly, in some embodiments, in response to user input at affordance

681, metrics 634 associated with the yoga workout would be displayed (e.g., similar to displayed metrics 634 in FIG. 6AS).

Referring to FIGS. 6BL-6BM, device 600 is in proximity to pairable workout device 695 (e.g., external heart rate monitor, treadmill, stair stepper). Device 600 and device 695 are communicatively pairable. For example, device 600 and device 695 are pairable via a wireless communication (e.g., near-field communication (NFC), Bluetooth). It should be appreciated that device 690 may also be pairable to workout device 695.

Device 600 detects pairable workout device 695 when device 600 is in close proximity to device 695. In response to detecting pairable workout device 695 and in accordance with a determination that an automatic workout device pairing criteria is satisfied, device 600 is automatically paired (e.g., without additional user input) with pairable workout device 695 (FIG. 6BM). For example, device 695 is automatically paired with device 695 (e.g., external heart rate monitor). Accordingly, device 600 displays information 696 indicating that device 600 and device 695 have been automatically paired with one another.

In one embodiment, the automatic workout device pairing criteria is satisfied when a workout (e.g., outdoor run workout) has been completed on device 600. In another embodiment, the automatic workout device pairing criteria is satisfied when device 600 has been paired with pairable workout device 695 within a predetermined time (e.g., within the past 90 days). In a further embodiment, the automatic workout device pairing criteria is satisfied when a user affirmatively enables a setting for automatic pairing with pairable workout devices.

In some embodiments, in response to detecting pairable workout device 695 and in accordance with a determination that an automatic workout device pairing criteria is not satisfied, device 600 is not automatically paired with pairable workout device. In one embodiment, the automatic workout device pairing criteria is not satisfied when a workout (e.g., outdoor run workout) has not been previously completed on device 600. In another embodiment, the automatic workout device pairing criteria is not satisfied when device 600 has not been paired with pairable workout device 695 within a predetermined time (e.g., within the past 90 days). In a further embodiment, the automatic workout device pairing criteria is not satisfied when a user does not affirmatively enable a setting for automatic pairing with pairable workout devices. In another embodiment, the automatic workout device pairing criteria is not satisfied when a user selects a workout affordance (e.g., affordance 621) and the user is prompted to provide user input to connect with the pairable workout device 695 (e.g., heart monitor). For example, referring to FIG. 6BN, accept pairing affordance 696-1 (e.g., Yes), and decline pairing affordance 696-2 (e.g., not now) are displayed. Devices 600 and 695 will be paired in accordance to user selection of accept pairing affordance 696-1. Alternatively, devices 600 and 695 will not be paired in accordance to user selection of decline pairing affordance 696-2.

FIG. 7 is a flow diagram illustrating a method for displaying a scrollable list of affordances associated with physical activities using an electronic device in accordance with some embodiments. Method 700 is performed at a device (e.g., 100, 300, 500, 600) with one or more processors, memory and a physical activity tracking sensor. Some operations in method 700 are, optionally, combined, the order of some operations are, optionally, changed, and some operations are, optionally, omitted.

As described below, method 700 provides, among other things, an intuitive way for launching a physical activity tracking function in accordance with a determination that the user input is detected at a first affordance in the scrollable list of affordances. The method reduces the cognitive burden on a user by selecting a workout from a list of workouts and launching a physical activity tracking function, thereby creating a more efficient human-machine interface. For battery-operated computing devices, enabling a user to select a workout from a list of workouts and launch a physical activity tracking function faster and more efficiently conserves power and increases the time between battery charges.

At block 710, the device (e.g., 600) displays a scrollable list of affordances (e.g., 620) associated with physical activities.

At block 720, the device displays a first change workout metrics affordance (e.g., 631) corresponding to a first affordance (e.g., 621) of the scrollable list of affordances (e.g., 620).

At block 730, the device (e.g., 600) receives a user input (e.g., 615A).

At block 740, in accordance with a determination that the user input (e.g., 615A) is detected at the first affordance (e.g., 221) in the scrollable list of affordances (e.g., 220), a physical activity tracking function associated with the selected first affordance is launched (e.g., the physical activity tracking function tracks metrics 630).

At block 750, in accordance with a determination that the user input (e.g., 615B) is detected at the first change workout metrics affordance (e.g., 631), a user interface (e.g., 610D) configured to change a workout metric is displayed.

In some embodiments, user input (e.g., 615L) is received at a second affordance (e.g., 625) in the scrollable list of affordances. In response to the user input at the second affordance, the device (e.g., 600) launches a physical activity tracking function associated with the selected second affordance. Subsequent to completion of the tracking function, the device displays a predefined list of selectable physical activities (e.g., 660). User input (e.g., 615Q) is received at a selectable physical activity (e.g., 660-2) of the predefined list of selectable physical activities. Subsequent the selection of the physical activity in the predefined list of selectable physical activities, the device updates the scrollable list of affordances (e.g., 220) with an additional affordance (e.g., 626) associated with the selected physical activity.

In accordance with some embodiments, in accordance with a determination that the user input (e.g., 615B) is detected at the first change workout metrics affordance (e.g., 631), the device forgoes launching of the physical activity tracking function associated with the first affordance (e.g., 621).

In some embodiments, user input (e.g., 615C) corresponding with selecting a metric affordance (e.g., 640-2) of the plurality of metric affordances (e.g., 640) is received. In response to receiving the user input corresponding with selecting the metric affordance, the device (e.g., 600) displays a first goal value (e.g., 642) corresponding to the selected metric affordance.

In some embodiments, in response to receiving the user input corresponding with selecting the metric affordance (e.g., 615C), the device (e.g., 600) displays at least one goal change affordance (e.g., 643 or 644). User input (e.g., 615D) corresponding with selecting the at least one goal change affordance in received. In response to receiving the user input corresponding with the at least one goal change affordance, the first goal value (e.g., goal value of 7.50 miles) is replaced with a second goal value (e.g., goal value of 7.60 miles).

In some embodiments, further in response to receiving the user input (e.g., 615C) corresponding with selecting the metric affordance (e.g., 640-2), the device (e.g., 600) displays a start physical activity tracking affordance (e.g., 647) corresponding with launching a physical activity tracking function associated with the selected first affordance. User input (e.g., 615H) is received corresponding with selecting the start physical activity tracking function affordance. In response to receiving the user input corresponding with selecting the start physical activity tracking function affordance, a physical activity tracking function associated with the selected first affordance is launched (e.g., device 600 tracks metrics 630 associated with an outdoor run workout).

In some embodiments, launching the physical activity tracking function associated with the selected first affordance (e.g., 621) includes tracking a first set of metrics (e.g., 630) associated with a first type of physical activity (e.g., outdoor run). In accordance with a determination that the user input is detected at a second affordance (e.g., 622) in the scrollable list of affordances (e.g., 620), a physical activity tracking function associated with the selected second affordance is launched, including tracking a second set of metrics (e.g., 633) associated with a second type of physical activity (e.g., pool swim). The second set of metrics (e.g., 633) is different than the first set of metrics (e.g., 630).

In some embodiments, an affordance (e.g., 621) in the scrollable list of affordances includes a physical activity icon (e.g., 621-1) corresponding to a physical activity (e.g., outdoor run) associated with the affordance. In some embodiments, while a physical activity tracking function associated with the affordance is running, the physical activity icon (e.g., 621-1) is displayed in an animated state.

In some embodiments, while a physical activity tracking function associated with an affordance (e.g., 626) is running, user input (e.g., 615T) is received corresponding to a request to display a user interface (e.g., 610H) configured to switch workouts. In response to receiving the user input corresponding to a request to display a user interface configured to switch workouts, the physical activity tracking function is paused, and a switch workout affordance (e.g., 651) is displayed. User input (e.g., 615U) corresponding to selecting the switch workout affordance is received. In response to receiving the user input corresponding to selecting the switch workout affordance, the scrollable list of affordances (e.g., 620) is displayed, and a paused physical activity affordance (e.g., 655) associated with the paused physical tracking function is displayed.

In some embodiments, subsequent to pausing the physical activity tracking function, user input (e.g., 615V) corresponding to selection of an affordance (e.g., 621) in the scrollable list of affordances (e.g., 620) is received. In response to receiving the user input corresponding to the selection of the affordance in the scrollable list of affordances, the paused physical activity tracking function is cancelled (e.g., stop tracking metrics 634 for a yoga workout), and a different physical activity tracking function associated with the selected affordance is launched (e.g., start tracking metrics 630 for an outdoor run).

In some embodiments, user input corresponding to selection of the paused physical activity affordance (e.g., 655) is received. In response to receiving the user input corresponding to selection of the paused physical activity affordance, the paused physical activity tracking function is resumed (e.g., tracking of metrics 634 resumes).

In some embodiments, subsequent completion of a first workout tracking function and a second workout tracking function, a scrollable workout summary (e.g., summary of aggregated metrics 680) of a first physical activity associated with the first workout tracking function and a second physical activity associated with the second workout tracking function is displayed. The scrollable workout summary includes a set of aggregated metrics (e.g., 680) of the first workout tracking function and the second workout tracking function, a first affordance associated with the first physical activity (e.g., 681), and a second affordance associated with the second physical activity (e.g., 682). User input is received (e.g., 615W). In accordance to determination that the user input (e.g., 615W) corresponds to selection of the first affordance associated with the first physical activity (e.g., 681), a set of metrics associated with the first physical activity is displayed (e.g., 630 in FIG. 6BK). In accordance to determination that the user input (e.g., 615W) corresponds to selection of the second affordance associated with the second physical activity (e.g., 682), a set of metrics associated with the second physical activity is displayed (e.g., 634).

In some embodiments, a pairable workout device (e.g., 695) is detected. In response to detecting the pairable workout device and in accordance with a determination that an automatic workout device pairing criteria is satisfied (e.g., a workout has been completed on device 600, device 600 has been paired with pairable workout device 695 within a predetermined time, or the user affirmatively enables a setting for automatic pairing with pairable workout devices), the device (e.g., 600) is automatically paired with the pairable workout device. In response to detecting the pairable workout device (e.g., 695) and in accordance with a determination that an automatic workout device pairing criteria is not satisfied (e.g., a workout has not been previously completed on device 600, device 600 has not been paired with pairable workout device 695 within a predetermined time, a user does not affirmatively enable a setting for automatic pairing, or the user is prompted to provide user input to connect with the pairable workout device), forgo automatic pairing the device with the pairable workout device (FIG. 6BN).

In some embodiments, the user interface configured to change a workout metric (e.g., 610D) includes a plurality of metric affordances (e.g., 640-1, 640-2, 640-3, and 64-4) corresponding to the physical activity associated with the first affordance (e.g., 621). In some embodiments, the physical activity tracking function tracks metrics (e.g., 630) corresponding to data received from the physical activity tracking sensor (e.g., sensors of workout support module 142). In some embodiments, the first affordance (e.g., 621) in the scrollable list of affordances (e.g., 620) is the most recently selected affordance.

Note that details of the processes described above with respect to method 700 (e.g., FIG. 7) are also applicable in an analogous manner to the methods described below. For example, method 900 optionally includes one or more of the characteristics of the various methods described above with reference to method 700. For example, method 900, in some embodiments, may include launching a physical activity tracking function or displaying a user interface configured to change a workout metric. For brevity, these details are not repeated below.

FIGS. 8A-8T illustrates exemplary user interfaces associated with a physical activity application and an audio application, in accordance with some embodiments. The user interfaces in these figures are used to illustrate the processes described below, including the processes in FIG. 9.

FIG. 8A illustrates device 800 with touch sensitive display 802. Device 800 includes various input mechanisms that receive user input, such as rotatable input mechanism 803, that is able to receive a rotatable input (and may also receive a push input), and input mechanism 804 that is able to receive a push user input. In some embodiments, device 800 includes some or all of the features of device 100, device 300, device 500, or device 600.

Referring to FIG. 8A, user interface 810A, displayed on touch sensitive display 802, is an audio application control user interface configured to control audio content playing on the audio application. User interface 810A includes audio content information 811 and audio content controls 812. For example, audio content information 811 includes, but is not limited to, the title of the currently playing audio content (e.g., "Across the Land") and the name of the group (e.g., "Awe Singers") performing the song. Audio content controls 812 includes but are not limited to, jump forward to next song, pause/play, jump backward to previous song, and volume control.

User input 815A (e.g., push input via finger 816) is received at rotatable input mechanism 803 (FIG. 8B). In response to user input 815A and while audio content is playing on the audio application, user interface 810B is displayed (FIG. 8C). User interface 810B includes a plurality of application affordances 805 associated with applications. For example, affordance 805-1 is associated with a workout application, and affordance 805-2 is associated with the audio application currently playing the audio content.

User input 815B (e.g., tap gesture) is received at affordance 805-1 (FIG. 8D). In response to user input 815B at affordance 805-1 and while the audio content is playing on the audio application, user interface 810C is displayed (FIG. 8E). User interface 810C includes a scrollable list of affordances 820 that are associated with respective physical activity tracking functions for a physical activity. For example, the scrollable list of affordances includes affordance 821, which corresponds to a physical activity tracking function for an outdoor run, and affordance 822, which corresponds to a physical activity tracking function for a pool swim. It is noted that the list of affordances 820 includes additional affordances corresponding to other physical activity tracking functions that are not currently displayed but can be displayed in response to a scrolling input (e.g., rotation of rotational mechanism 803).

In some embodiments, one or more of the affordances in the scrollable list of affordances 820 includes a respective change workout metrics affordance. For example, affordance 821 includes change workout metrics affordance 831, and affordance 822 includes change workout metrics affordance 832. In one embodiment, user interface 810C is the same as user interface 610A (FIG. 6A). Accordingly, user interface 810C includes the same features and functionality as user interface 610A, as described above.

In some embodiments, while the audio content is currently playing on device 800, device 800 receives an enabled setting of the workout audio playlist setting from an external device (e.g., companion device 890), which will be described in further detail below (FIGS. 8N-8T). When the workout audio playlist setting is enabled, a workout playlist will automatically play in response to selection of a workout affordance. In one embodiment, a workout audio playlist is a list of audio content (e.g., a list of songs) selected by the user to be played during a workout.

User input 815C is received at affordance 821 (FIG. 8F). In response to user input 815C, user interface 810D is displayed (FIG. 8G). User interface 810D (similar to user interface 610B) displays a countdown prior to tracking metrics by the physical activity tracking function associated with affordance 821. In one embodiment, user interface 810D is the same as user interface 610B (FIGS. 6C-6F). Accordingly, user interface 810D includes the same features and functionality as user interface 610B, as described above.

In response to completion of the countdown, user interface 810E is displayed (FIG. 8H). User interface 810E is configured to display a plurality of metrics 830 (e.g., miles 830-1, active calories 830-2, average miles 830-3, and time 830-4) tracked by the physical activity tracking function during the physical activity (e.g., outdoor run). In one embodiment, user interface 810E is the same as user interface 610C (FIGS. 6G-6I). Accordingly, user interface 810E includes the same features and functionality as user interface 610C, as described above. In one embodiment, user interface 810E is displayed in response to user input 815C without display of intermediary user interface 610D.

Additionally, in response to user input 815C (FIG. 8F), the audio application stops playing the currently playing song (e.g., "Across the Land") and initiates playing the workout audio playlist. For example, the currently playing song (e.g., "Across the Land") is not a song listed in the workout playlist. Accordingly, the currently playing song is canceled and replaced with playing of a song in the workout playlist.

Referring to FIGS. 8I-8L, user input 815D (e.g., swipe gesture) is received on touch sensitive display 802 while the physical activity tracking function is running (e.g., tracking metrics associated with the outdoor run workout) and the audio application is playing audio content. In response to user input 815D, user interface 810A is displayed. User interface 810A displays audio content from the workout audio playlist because playing of the workout audio playlist was initiated in response to user input 815C (as described above). In particular, user interface 810A includes audio content information 811 corresponding to the song "Feel the Burn" performed by "Drill Sergeant" from the workout audio playlist. It is noted that user interface 810A includes volume control 813 configured to control the volume of the currently playing song.

In some embodiments, when the setting is not enabled, the currently playing song continues to play, as seen in FIG. 8M.

Referring to FIGS. 8I-8K, user interface 810E includes paging dots 839-1, 839-2, and 839-3. The paging dots correspond to successive pages (or user interfaces). For example, paging dot 839-1 corresponds to a workout control user interface (e.g., similar to user interface 610H), paging dot 839-2 corresponds to user interface 810E, and paging dot 839-3 corresponds to user interface 810A. In response to user input, such as swipe gesture 815D, the currently displayed user interface 610E (FIG. 8I) is replaced with a display of the corresponding successive user interface 810A (FIG. 8K). It is noted, that when user interface 810E is displayed, paging dot 839-2 is highlighted (FIG. 8I). Similarly, when user interface 810A is displayed, paging dot 839-3 is highlighted (FIG. 8L).

FIGS. 8N-8T illustrate embodiments of companion device 890 that is paired to device 800. In some embodiments, companion device 890 may be device 100, device 300, device 500, or a device that includes one or more features of those devices. Companion device 890 includes touch sensitive display 891. User interface 892A is displayed on touch sensitive display 891. Companion device 890, in some embodiments, when paired to device 800, is able to display the application views and perform at least some of the same processes as device 800, as described herein. In some embodiments, a setting (e.g., enabled or disabled) of the workout audio playlist setting is received from companion device 890 (as described above).

Referring to FIG. 8N, user interface 892A includes a plurality of affordances 893 associated with respective applications (e.g., watch application, camera application, weather application, clock application, phone application, message application, mail application, and browser application). In one embodiment, affordance 893-1 is associated with a watch application (e.g., watch application for controlling various features and functionality of device 800).

User input 815F is received at affordance 893-1 (FIG. 8O). In response to user input 815F at affordance 893-1, user interface 892B is displayed (FIG. 8P). User interface 892B includes device information 860 (e.g., information related to device 800 that is paired with device 892), watch faces 861 (e.g., various watch faces that are enabled to be displayed on device 800), and a list of application affordances 862 that correspond to applications installed on device 800. The list of application affordances 862, in some embodiments, corresponds, at least in part, to the plurality of application affordances 805 displayed on user interface 810B on device 800 (FIG. 8C). List of application affordances 862 includes affordance 862-1 that corresponds to a workout application installed on device 800.

User input 815G (e.g., tap gesture) is received at affordance 862-1 (FIG. 8Q). In response to user input 815G at affordance 862-1, user interface 892C is displayed (FIG. 8R). User interface 892C includes various workout application settings associated with the workout application installed on device 800. In one embodiment, user interface 892C includes workout audio playlist setting 870 (e.g., "Workout Playlist Auto Play"). As illustrated in FIG. 8R, the setting of workout audio playlist setting 870 is enabled. Accordingly, when workout audio playlist setting 870 is enabled (at device 890) the workout audio playlist is automatically played by the audio application (at device 800) in response to selection of an affordance (e.g., affordance 821) in the scrollable list of affordances 820, as described above. In one embodiment, the setting of workout audio playlist setting 870 (e.g., enabled setting) corresponds to a default setting at device 890. In another embodiment, the setting of workout audio playlist setting 870 (e.g., enabled setting) corresponds to user-selected settings at device 890.

User interface 892C includes running auto pause setting 871. For example, when it is determined that running auto pause setting 871 is enabled, tracking of metrics associated with a running workout is automatically paused when it is determined that the user has stopped running for a predetermined amount of time (e.g., three seconds). Alternatively, when it is determined that running auto pause setting 871 is disabled, tracking of metrics associated with a running workout continues (not automatically paused) when it is determined that the user has stopped running for a predetermined amount of time (e.g., three seconds).

Automatically stopping a song playing on a device and initiating playing of a workout audio playlist on the device in response to selection of a workout when workout playlist setting is enabled provides the user with more control of the device by simultaneously allowing the user to stop a currently playing song and automatically initiate playing the workout playlist. Automatically stopping a song playing on a device and initiating playing of a workout audio playlist on the device in response to selection of a workout when workout playlist setting is enabled without requiring further user input enhances the operability of the device and makes the user-device interface more efficient (e.g., by helping the user to provide proper inputs and reducing user mistakes when operating/interacting with the device), which, additionally, reduces power usage and improves battery life of the device by enabling the user to use the device more quickly and efficiently.

Referring to FIG. 8S, user input 815H is received at workout audio playlist setting 870. User input 815H is to switch the workout audio playlist setting from enabled to disabled (or from disabled to enabled). Referring to FIG. 8T, in response to user input 815H, workout audio playlist setting 870 is set to disabled. Accordingly, when workout audio playlist setting 870 is disabled (at device 890), the workout audio playlist is not automatically played by the audio application (at device 800) in response to selection of an affordance (e.g., affordance 821) in the scrollable list of affordances 820, as described above. For example, when workout audio playlist setting 870 is disabled (at device 890), a song (e.g., "Across the Land") currently playing by the audio application (at device 800) remains playing without interruption in response to selection of an affordance (e.g., affordance 821) in the scrollable list of affordances 820, as described above. In one embodiment, the setting of workout audio playlist setting 870 (e.g., disabled setting) corresponds to a default setting at device 890.

FIG. 9 is a flow diagram illustrating a method for, in response to selecting a workout affordance, automatically playing a workout playlist based on a workout playlist setting. Method 900 is performed at a device (e.g., 100, 300, 500, 600, and 800) with one or more processors and memory. Some operations in method 900 are, optionally, combined, the order of some operations are, optionally, changed, and some operations are, optionally, omitted.

As described below, method 900 provides, among other things, an intuitive way for, in response to selecting a workout affordance, automatically playing a workout playlist based on a workout playlist setting. The method reduces the cognitive burden on a user by automatically playing a workout playlist based on a workout playlist setting, thereby creating a more efficient human-machine interface. For battery-operated computing devices, enabling a user to select a workout from a list of workouts and launch a physical activity tracking function faster and more efficiently conserves power and increases the time between battery charges.

At block 910, while an audio application is playing audio content (e.g., "Across the Land"), the device 800 displays a scrollable list of affordances (e.g., 820) associated with physical activities.

At block 920, while the audio application is playing the audio content, a user input (e.g., 815C) is received at an affordance (e.g., 821) of the scrollable list of affordances.

At block 930, in response to receiving the user input at the affordance, a physical activity tracking function associated with the selected affordance is launched, and it is determined whether a workout audio playlist setting is enabled (e.g., enabled setting is received from device 890).

At block 940, in accordance with a determination that the workout audio playlist setting is enabled, the audio content currently playing on the device (e.g., "Across the Land") is stopped, and playing a workout audio playlist is initiated (e.g., playing of "Feel the Burn") on the device (e.g., device 800). At block 950, in accordance with a determination that the workout audio playlist setting is disabled (e.g., disabled setting is received from device 890), the audio content currently playing on the device is continued (e.g., "Across the Land").

In some embodiments, while the physical activity tracking function is running (e.g., tracking metrics 830) and the audio application is playing audio content (e.g., "Across the Land" is playing), user input (e.g., 815D) is received corresponding to a request to display an audio application control user interface (e.g., 810A), and, in response to the user input (e.g., 815D), the audio application control user interface (e.g., 810A) of the audio application playing the audio content is displayed.

In some embodiments, prior to receiving user input (e.g., 815C) at an affordance (e.g., 821), a setting of the workout audio playlist setting (e.g., enabled or disabled) is received from an external device (e.g., 890).

Note that details of the processes described above with respect to method 900 (e.g., FIG. 9) are also applicable in an analogous manner to the methods described below. For example, method 900 optionally includes one or more of the characteristics of the various methods described above with reference to method 1300. For example, the tracking of metrics by a physical activity tracking function in method 900 may also track heart rate information, as described in method 1300. For brevity, these details are not repeated below.

FIGS. 10A-10N illustrate exemplary user interfaces associated with a messaging application, in accordance with some embodiments. The user interfaces in these figures are used to illustrate the processes described below, including the processes in FIG. 11.

FIG. 10A illustrates device 1000 with touch sensitive display 1002. Device 1000 includes various input mechanisms that receive user input, such as rotatable input mechanism 1003, that is able to receive a rotatable input (and may also receive a push input), and input mechanism 1004 that is able to receive a push user input. In some embodiments, device 1000 includes some or all of the features of device 100, device 300, device 500, device 600, or device 800.

FIG. 10A includes user interface 1010A. User interface 1010A includes a message 1020 (e.g., text message or email) received from an external device. Message 1020 includes workout information. For example, workout information includes information identifying a person 1020-1 (e.g., "John completed a workout!"), type of workout 1020-2 (e.g., "Outdoor Run"), and workout metrics 1020-3 (e.g., 3.00 miles, 326 active calories, and 351 total calories).

In some embodiments, the external device (that sent message 1020) includes some or all of the features of device 1000 (or device 100, device 300, or device 500). In one embodiment, the external device is a device that is a companion device to another external device (e.g., companion device 690 described above). In one embodiment, message 1020 is composed by a workout application (or workout tracking application) on the external device, wherein the workout application generates the workout information contained in message 1020. Further, in one embodiment, the workout application on the external device includes some or all of the features as a workout application described herein (e.g., workout application as shown in at least FIG. 6A).

User interface 1010A also includes reply affordance 1022-1 (e.g., configured to enable a user to generate a reply message), mute affordance 1022-1 (e.g., configured to mute subsequent messages from the external device), and dismiss affordance 1022-3 (e.g., configured to dismiss message 1020 without sending a reply message).

User input 1015A is received at reply affordance 1022-1 (FIG. 10B). Referring to FIGS. 10C-10D, in response to user input 1015A at reply affordance 1022-1 and in accordance with a determination that message 1020 contains workout information, user interface 1010B is displayed. User interface 1010B is configured to enable a user to compose a reply message to message 1020. User interface 1010B includes a list of predefined responses 1030 corresponding to message 1020 that includes workout information. Predefined responses 1030, in some embodiments, includes predefined response 1030-1 (e.g., "how'd you get so good"), predefined response 1030-2 (e.g., "#goals"), predefined response 1030-3 (e.g., "Hands down, you're the best"), predefined response 1030-4 (e.g., "what's your secret?"), predefined response 1030-5 (e.g., "Hello!"), predefined response 1030-6 (e.g., "what's up?"), predefined response 1030-7 (e.g., "on my way"), and predefined response 1030-8 (e.g., "ok").

Additionally, user interface 1010B includes affordance 1031 configured to enable a user to record an audio reply to message 1020, affordance 1032 configured to enable a user to select emojis for a reply message to message 1020, affordance 1033 configured to enable a user to send a handwritten reply message (or sticker) to message 1020, and affordance 1034 configured to enable a user to send a reply message (that includes text generated from handwriting input) to message 1020.

In one embodiment, in accordance to a determination that message 1020 does not contain workout information (e.g., a text that includes "Hi Jane"), the message is displayed at device 1000. However, predefined responses 1030 are not displayed at device 1000.

As shown in FIG. 10D, user input 1015B is received at predefined response 1030-2. In response to user input 1015B at predefined response 1030-2, a reply message to message 1020 is composed (e.g., reply message 1050 in FIG. 10E). In one embodiment, subsequent to receiving user input 1015B at predefined response 1030-2, an intermediary user interface is displayed that prompts the user to compose the reply message. In response to user input to compose the reply message, the reply message is composed.

FIGS. 10E-10F depict user interface 1010C (e.g., text message user interface) displayed at companion device 1065 (e.g., companion device to device 1000) and external device 1090. Referring to FIG. 10E, reply message 1050 is displayed at companion device 1065. In one embodiment, reply message 1050 is displayed at device 1000. Reply message 1050 includes selected predefined message 1030-2 (e.g., "#goals" selected at device 1000, FIG. 10C) and workout information, such as information identifying a person 1020-1 (e.g., "John"), type of workout 1020-2 (e.g., "Outdoor Run"), and workout metrics 1020-3 (e.g., 3.00 miles). At companion device 1065, reply message 1050 is displayed in-line with other messages (from external device 1090). Referring to FIG. 10F, reply message 1050 is received at external device 1090 and displayed at external device 1090. At external device 1090, reply message 1050 is displayed in-line with other messages (from companion device 1065).

Generating a reply message that includes a selected predefined response and workout information from a received message allows a user to quickly compose the reply message that automatically includes the workout information (from the received message) and enables the user to generate the reply message with minimal user input. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

FIG. 10G depicts user interface 1010C displayed on device 1000. User interface 1010C includes information identifying a person 1020-1 (e.g., "John completed a workout!"), selected predefined message 1030-2 (e.g., "#goals"), and reply message delivery indication 1051 (e.g., "Delivered"). Reply message delivery indication 1051 indicates that reply message 1050 (to message 1020) has been sent to external device 1090.

FIG. 10H includes user interface 1010A. User interface 1010A includes a message 1040 (e.g., text message or email) received from an external device. Message 1040 includes workout information. For example, workout information includes information identifying a person 1040-1 (e.g., "John earned an achievement"), type of workout 1040-2 (e.g., "Outdoor Run"), and achievement sticker 1040-3 indicating a workout achievement was accomplished by a user (e.g., John) of the external device. In one embodiment, message 1040 is composed by a workout application on the external device, wherein the workout application generates the workout information contained in message 1040. Further, in one embodiment, the workout application on the external device includes some or all of the features as a workout application, described herein (e.g., workout application as shown in at least FIG. 6A).

User interface 1010A also includes reply affordance 1042-1 (e.g., configured to enable a user to generate a reply message), mute affordance 1042-1 (e.g., configured to mute subsequent messages from the external device), and dismiss affordance 1042-3 (e.g., configured to dismiss message 1020 without sending a reply message).

User input 1015C is received at reply affordance 1042-1 (FIG. 10I). Referring to FIGS. 10J-10K, in response to user input 1015C at reply affordance 1042-1 and in accordance with a determination that message 1040 contains workout information, user interface 1010B is displayed. User interface 1010B is configured to enable a user to compose a reply message to message 1040. User interface 1010B includes a list of predefined responses 1043 corresponding to message 1040 that includes workout information. Predefined responses 1043 include predefined response 1043-1 (e.g., "you're on fire!"), predefined response 1043-2 (e.g., "INCREDIBLE"), predefined response 1043-3 (e.g., "keep it up!"), predefined response 1043-4 (e.g., "you inspire me"), predefined response 1043-5 (e.g., "Hello!"), predefined response 1043-6 (e.g., "what's up?"), predefined response 1043-7 (e.g., "on my way"), and predefined response 1043-8 (e.g., "ok").

Additionally, user interface 1010B includes affordance 1031 configured to enable a user to record an audio reply to message 1040, affordance 1032 configured to enable a user to select emojis for a reply message to message 1040, affordance 1033 configured to enable a user to send a handwritten reply message (or sticker) to message 1040, and affordance 1034 configured to enable a user to send a reply message (that includes text generated from handwriting input) to message 1040.

In one embodiment, in accordance with a determination that message 1040 does not contain workout information (e.g., a text that includes "Hi Jane"), the message is displayed at device 1000. However, predefined responses 1043 are not displayed at device 1000.

User input 1015D is received at predefined response 1043-4. In response to user input 1015D at predefined response 1043-4, a reply message to message 1040 is composed (e.g., reply message 1060 in FIG. 10L). In one embodiment, subsequent to receiving user input 1015D at predefined response 1043-4, an intermediary user interface is displayed that prompts the user to compose the reply message. In response to user input to compose the reply message, the reply message to message 1040 is composed.

FIGS. 10L-10M depict user interface 1010C (e.g., text message user interface) displayed at companion device 1065 (e.g., companion device to device 1000) and external device 1090. Referring to FIG. 10L, reply message 1060 is displayed at companion device 1065. In one embodiment, reply message 1060 is displayed at device 1000. Reply message 1060 includes selected predefined message 1043-4 (e.g., "You inspire me" selected at device 1000, FIG. 10K) and workout information, such as information identifying a person 1040-1 (e.g., "John earned an achievement"), and achievement sticker 1040-3. At companion device 1065, reply message 1060 is displayed in-line with other messages (from external device 1090). Referring to FIG. 10M, reply message 1060 is received at external device 1090 and displayed at external device 1090. At external device 1090, reply message 1060 is displayed in-line with other messages (from companion device 1065).

FIG. 10N depicts user interface 1010C displayed on device 1000. User interface 1010C includes information identifying a person 1040-1 (e.g., "John earned an achievement"), selected predefined message 1043-4 (e.g., "you inspire me"), and reply message delivery indication 1051 (e.g., "Delivered"). Reply message delivery indication 1051 indicates that reply message 1060 (to message 1020) has been sent to external device 1090.

FIG. 11 is a flow diagram illustrating a method for composing a reply message that includes a selected predefined response, and workout information. Method 1100 is performed at a device (e.g., 100, 300, 500, 600, 800, or 1000) with one or more processors, and memory. Some operations in method 1100 are, optionally, combined, the order of some operations are, optionally, changed, and some operations are, optionally, omitted.

As described below, method 1100 provides, among other things, an intuitive way for, a user to quickly compose a reply message that automatically includes workout information (from the received message) and enables the user to generate the reply message with minimal user input. The method reduces the cognitive burden on a user by automatically including, in the reply message, the workout information from the received message. For battery-operated computing devices, enabling a user to select a workout from a list of workouts and launch a physical activity tracking function faster and more efficiently conserves power and increases the time between battery charges.

At block 1110, a message (e.g., 1020) is received at the device (e.g., 1000) from an external device (e.g., 1090).

At block 1120, in accordance with a determination that the message (e.g., 1020) contains workout information (e.g., 1020-1, 1020-2, or 1020-3), one or more predefined responses (e.g., 1030) to the received message are displayed.

At block 1130, user input (e.g., 1015B) is received corresponding to selecting a predefined response of the one or more predefined responses (e.g., 1030-2).

At block 1140, subsequent to receiving the user input (e.g., 1015B), a reply message (e.g., 1050) is composed, wherein the reply message comprises the selected predefined response (e.g., 1030-2) and the workout information (e.g., 1020-1, 1020-2, or 1020-3).

In some embodiments, the message (e.g., 1020) is displayed at the device (e.g., 1000). In some embodiments, the composed message (e.g., 1050) is sent to an external device (e.g., 1090) in response to user input (e.g., 1015B) for selecting a predefined response (e.g., 1030-2). In some embodiments, in accordance with a determination that the message (e.g., 1020) does not contain workout information, the message is displayed (e.g., displayed at device 1000) without subsequently displaying the one or more predefined responses (e.g., 1030).

In some embodiments, the workout information includes information identifying a person (e.g., 1020-1), workout metrics (e.g., 1020-3), type of workout (e.g., 1020-2), or an achievement sticker (e.g., 1040-3).

Note that details of the processes described above with respect to method 1100 (e.g., FIG. 11) are also applicable in an analogous manner to the methods described above. For example, method 1100 optionally includes one or more of the characteristics of the various methods described above with reference to method 700. For example, method 1100 includes workout metrics similar to workout metrics described with respect to method 700. For brevity, these details are not repeated below.

FIGS. 12A-12M illustrate exemplary user interfaces associated with a heart rate tracking application, in accordance with some embodiments. The user interfaces in these figures are used to illustrate the processes described below, including the processes in FIG. 13.

Figure 12A:
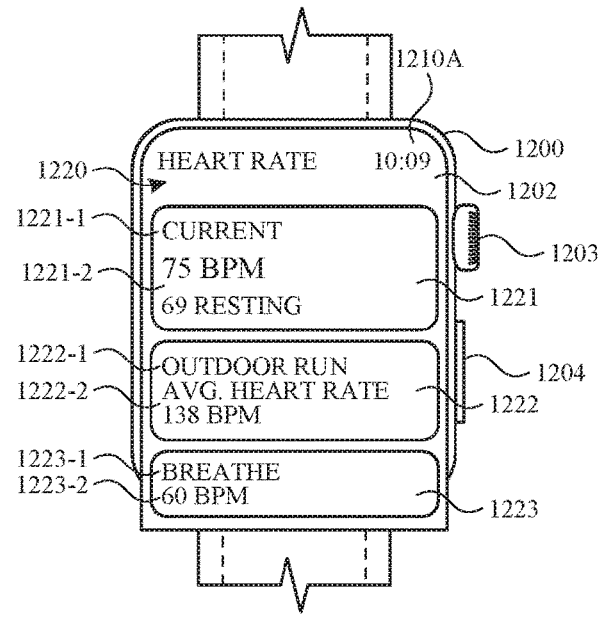
Figure 13:
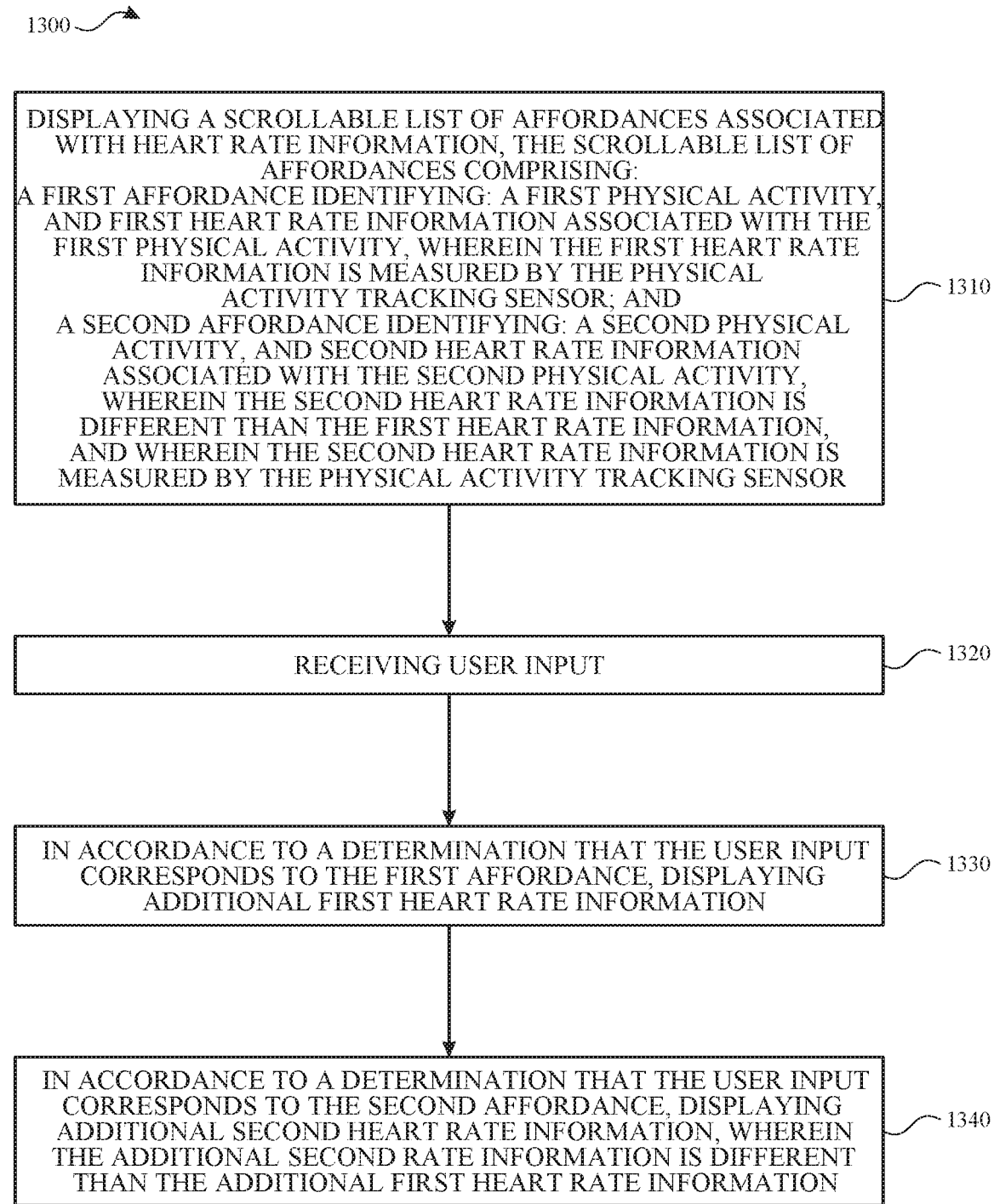
FIG. 13 is a flow diagram illustrating a method for operating an electronic device in accordance with some embodiments.

FIG. 12A illustrates device 1200 with touch sensitive display 1202. Device 1200 includes various input mechanisms that receives user input, such as, rotatable input mechanism 1203, that is able to receive a rotatable input (and may also receive a push input), and input mechanism 1204 that is able to receive a push user input. In some embodiments, device 1200 includes some or all of the features of device 100, device 300, device 500, device 600, device 800, or device 1000.

Figure 12B:
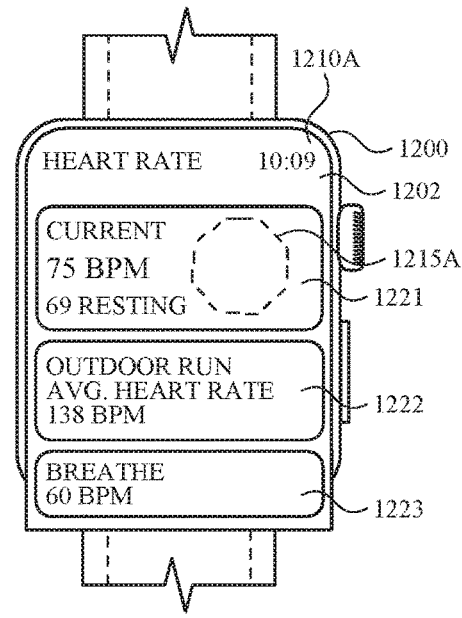

Referring to FIGS. 12A-12B, user interface 1210A of a heart rate application is displayed on touch sensitive display 1202. User interface 1210A includes a list of affordances 1220. List of affordances 1220 include affordance 1221 associated with a current heart rate (of the user of device 1200), affordance 1222 associated with a heart rate during a physical activity (e.g., outdoor run), and affordance 1223 associated with a heart rate during a breathe session of a breathe application.

One or more affordances in the list of affordances 1220 identifies a physical activity associated with the affordance. For example, affordance 1221 identifies activity 1221-1 (e.g., user's activity associated with current heart rate), affordance 1222 identifies activity 1222-1 (e.g., outdoor run), and affordance 1223 identifies activity 1223-1 (e.g., breathe session).

One or more affordances in the list of affordances 1220 identifies heart rate information associated with a physical activity. For example, affordance 1221 identifies heart rate information 1221-2 (e.g., 75 BPM, 69 resting). Affordance 1222 identifies heart rate information 1222-2 (e.g., avg. heart rate 138 BPM), and affordance 1223 identifies heart rate information 1223-2 (e.g., 60 BPM). In one embodiment, the heart rate information is measured by a physical activity tracking sensor of device 1200.

Displaying a list of affordances that identify a physical activity and associated heart rate information enables a user to quickly view the physical activity and associated heart rate information and select an affordance to view additional heart rate information associated with the physical activity. Reducing the number of inputs to view additional heart rate information enhances the operability of the device and makes the user-device interface more efficient (e.g., by helping the user to provide proper inputs and reducing user mistakes when operating/interacting with the device), which, additionally, reduces power usage and improves battery life of the device by enabling the user to use the device more quickly and efficiently.

Figure 12C:
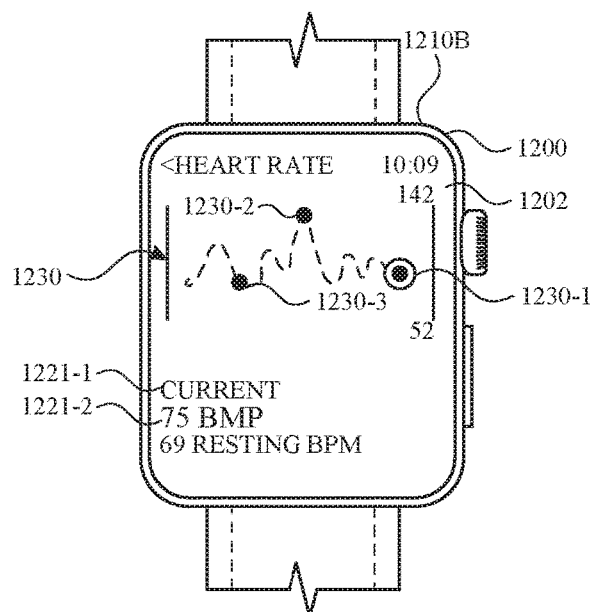

User input 1215A is received at affordance 1220-1 (FIG. 12B). In response to user input 1215A at affordance 1220-1, user interface 1210B is displayed (FIG. 12C). User interface 1210B includes graph 1230. Graph 1230 is a graph of the current heart rate of the user over a period of time (e.g., today's heart rate). User interface 1210B also includes activity 1221-1 (e.g., user's activity associated with current heart rate) and heart rate information 1221-2 (e.g., 75 BPM, 69 resting).

Graph 1230 includes physical activity points corresponding to a heart rate of various physical activities. For example, graph 1230 includes physical activity point 1230-1 that corresponds to the current heart rate, physical activity point 1230-2 that corresponds to the outdoor run, and physical activity point 1230-3 that corresponds to the breathe session. As shown in FIG. 12C, physical activity point 1230-1 that corresponds to the current heart rate is highlighted because the current heart rate information corresponds to selected affordance 1221.

Figure 12D:
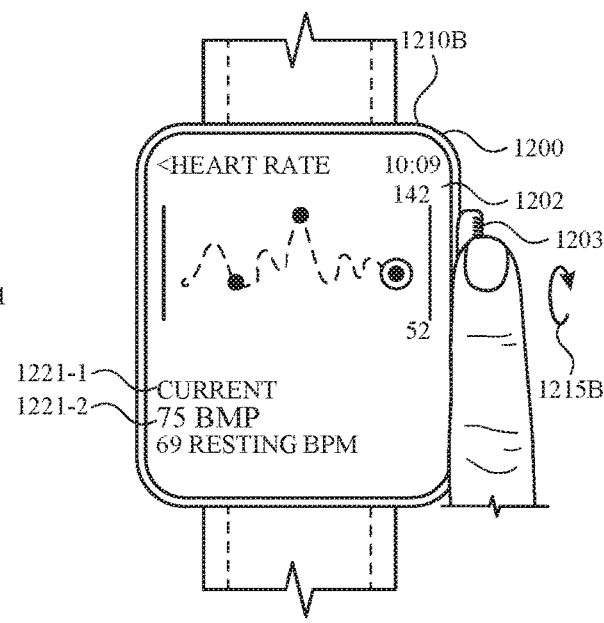

User input 1215B (e.g., rotational input) is received at rotatable input mechanism 1203 (FIG. 12D). In response to user input 1215B at rotatable input mechanism 1203, activity 1222-1 (e.g., outdoor run) and corresponding metrics (e.g., 142 High BPM, 138 BPM avg.) are displayed (FIG. 12E). Additionally, physical activity point 1230-2 that corresponds to the outdoor run is highlighted.

In response to further user input 1215B at rotatable input mechanism 1203, activity 1222-3 (e.g., breath session) and corresponding metrics (e.g., 60 BPM) are displayed (FIG. 12F). Additionally, physical activity point 1230-3 that corresponds to the breathe session is highlighted.

Referring to FIGS. 12G-12H, user input 1215C is received at affordance 1231. In response to user input 1215C at affordance 1231, the previous user interface 1210A is displayed (FIG. 12H).

Figure 12I:
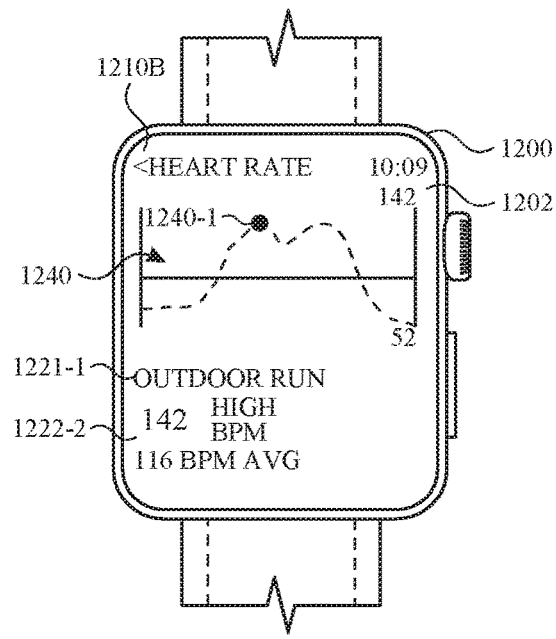
Figure 12J:
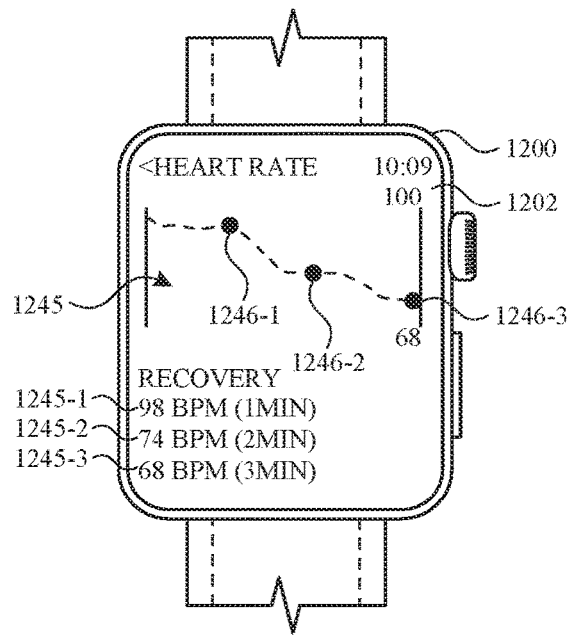

User input 1215D is received at affordance 1222 (FIG. 12H). In response to user input 1215D at affordance 1222, user interface 1210B is displayed (FIG. 12I). User interface 1210B includes graph 1240. Graph 1240 is a graph of the heart rate of the user during the outdoor run over the duration of the outdoor run. User interface 1210B also includes activity 1221-2 (e.g., outdoor run) and corresponding metrics (e.g., 142 High BPM and 116 BPM avg.). Graph 1240 also includes average heart rate 1240-1 (e.g., 116 BPM) over the duration of the outdoor run.

In some embodiments, user input (e.g., tap gesture) is received on touch sensitive display 1202 (FIG. 12I). In response to the user input on touch sensitive display 1202, user interface 1210B displays graph 1245. Graph 1245 is a graph of the heart rate of the user during a recovery period (or cool down period) after completion of a physical activity (e.g., outdoor run). For example, graph 1245 includes heart rate information 1245-1 at a first duration after the outdoor run (e.g., 98 BPM at one minute after the outdoor run), heart rate information 1245-2 at a second duration after the outdoor run (e.g., 74 BPM at two minutes after the outdoor run), and heart rate information 1245-3 at a third duration after the outdoor run (e.g., 68 BPM at three minutes after the outdoor run). Additionally, graph 1245 includes a first heart rate point 1246-1 that corresponds with the heart rate information 1245-1 (e.g., 98 BPM), a second heart rate point 1246-2 that corresponds with heart rate information 1245-2 (e.g., 74 BPM), and a third heart rate point 1246-3 that corresponds with heart rate information 1245-3 (e.g., 68 BPM).

Figure 12K:
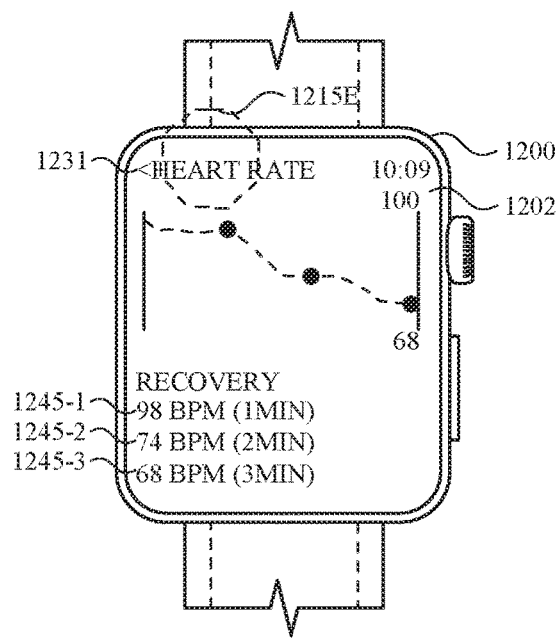
Figure 12L:
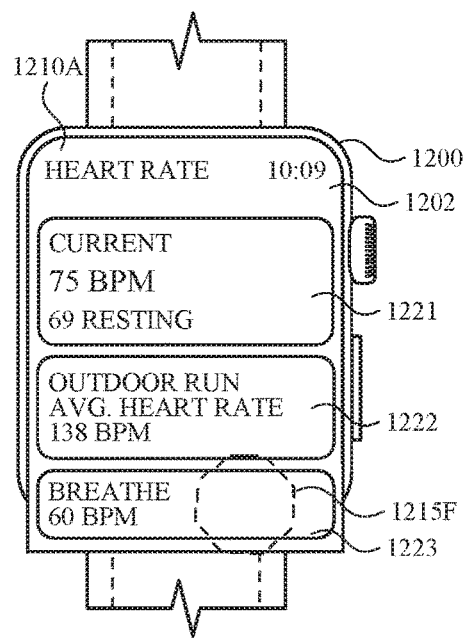

Referring to FIGS. 12K-12L, user input 1215E is received at affordance 1231. In response to user input 1215E at affordance 1231, the previous user interface 1210A is displayed (FIG. 12L).

Figure 12M:
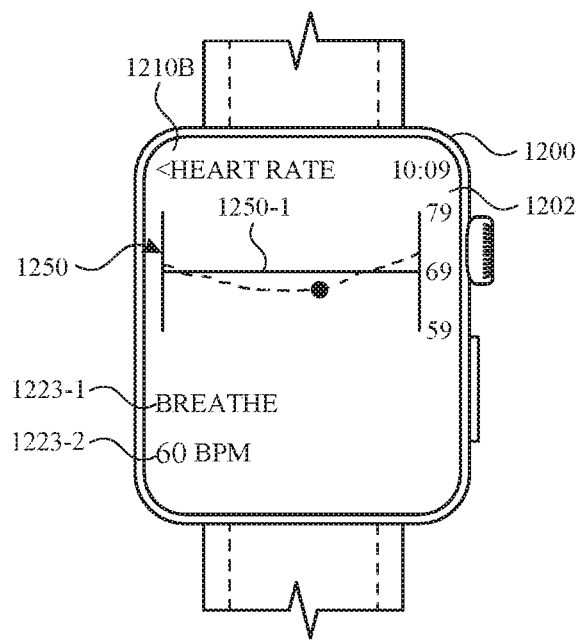

User input 1215F is received at affordance 1223 (FIG. 12L). In response to user input 1215F at affordance 1223, user interface 1210B is displayed (FIG. 12M). User interface 1210B includes graph 1250. Graph 1250 is a graph of the heart rate of the user during the breathe session over the duration of the breath session. User interface 1210B also includes activity 1223-1 (e.g., breathe session) and heart rate information 1223-2 (e.g., 60 BPM) associated with the breathe session. Graph 1250 includes average heart rate 1250-1 over the duration of the breathe session.

FIG. 13 is a flow diagram illustrating a method for displaying a scrollable list of affordances associated with heart rate information. Method 1300 is performed at a device (e.g., 100, 300, 500, 600, 800, 1000, or 1200) with one or more processors, and memory. Some operations in method 1300 are, optionally, combined, the order of some operations are, optionally, changed, and some operations are, optionally, omitted.

As described below, method 1300 provides, among other things, an intuitive way for selecting an affordance to view additional heart rate information. The method reduces the cognitive burden on a user by enabling a user to quickly view multiple physical activities and associated heart rate information. For battery-operated computing devices, enabling a user to view multiple physical activities and associated heart rate information faster and more efficiently conserves power and increases the time between battery charges.

At block 1310, a scrollable list of affordances (e.g., 1220) associated with heart rate information is displayed. The scrollable list of affordances includes at least a first affordance (e.g., 1221) and a second affordance (e.g., 1222). The first affordance (e.g., 1221) identifies a first physical activity (e.g., 1221-1), and a first heart rate information (e.g., 1221-2), wherein the first heart rate information is measured by the physical activity tracking sensor. The second affordance (e.g., 1222) identifies a second physical activity (e.g., 1222-1), and a second heart rate information (e.g., 1222-2), wherein the second heart rate information is measured by the physical activity tracking sensor. The second heart rate information (e.g., 1222-2) is different than the first heart rate information (e.g., 1221-2).

At block 1320, user input (e.g., 1215A) is received.

At block 1330, in accordance to a determination that the user input corresponds to the first affordance (e.g., 1221), additional first heart rate information (e.g., 1230) is displayed.

At block 1340, in accordance to a determination that the user input corresponds to the second affordance, additional second heart rate information (e.g., 1240) is displayed, wherein the additional second heart rate information (e.g., 1240) is different than the additional first heart rate information (e.g., 1230).

In some embodiments, the additional first heart rate information or the additional second heart rate information includes a graph of heart rate over time (e.g., 1240), and a graph of average heart rate over the time (e.g., 1240-1), a graph of a breathing heart rate over time (e.g., 1250), a graph of a current heart rate over a predetermined time period (e.g., 1230), a graph of a workout heart rate over time (e.g., 1240), or a graph of a heart rate subsequent completion of a workout over a predetermined period of time (e.g., 1245). In one embodiment, the additional first heart rate information is concurrently displayed with the first heart rate information (e.g., 1210B).

Note that details of the processes described above with respect to method 1300 (e.g., FIG. 13) are also applicable in an analogous manner to the methods described below. For example, method 1300 optionally includes one or more of the characteristics of the various methods described below with reference to method 1500. For example, method 1300, in some embodiments, includes displaying a heart rate affordance in accordance to determining that heart rate data satisfies a heart rate alert criteria. For brevity, these details are not repeated below.

FIGS. 14A-14O illustrates exemplary user interfaces associated with a heart rate tracking application, in accordance with some embodiments. The user interfaces in these figures are used to illustrate the processes described below, including the processes in FIG. 15.

FIG. 14A illustrates device 1400 with touch sensitive display 1402. Device 1400 includes various input mechanisms that receives user input, such as, rotatable input mechanism 1403, that is able to receive a rotatable input (and may also receive a push input), and input mechanism 1404 that is able to receive a push user input. In some embodiments, device 1400 includes some or all of the features of device 100, device 300, device 500, device 600, device 800, device 1000, or device 1200.

Referring to FIG. 14A, user interface 1410A is displayed on touch sensitive display 1402. User interface 1410A includes heart rate information 1420 (e.g., 75 BPM, 2 min ago). Heart rate information 1420 is a current heart rate of the user of device 1400. User interface 1410A includes one or more affordances associated with respective applications (e.g., affordance 1421 associated with a workout application, and affordance 1422 associated with an activity tracking application). Additionally, user interface 1410A includes time, date, temperature, etc.

User input 1415A is received at touch sensitive display 1402 corresponding to heart rate information 1420 (FIG. 14B). In response to user input 1415A at touch sensitive display 1402, user interface 1415B is displayed (FIG. 14C). User interface 1410B, in some embodiments, is similar to user interface 1210A (FIG. 12A), described above. User interface 1410B includes affordance 1421 associated with a current heart rate of the user of device 1400. Affordance 1421 identifies a physical activity 1421-1 (e.g., user's current activity associated with current heart rate), and heart rate information 1421-2 (e.g., 75 BPM measured 2 min ago (from current time)).

While tracking heart rate data (e.g., user's current heart rate) corresponding to data received from a physical active tracking sensor of device 1400, it is determined that the heart rate data satisfies a heart rate alert criteria (e.g., tracked heart rate data is arrhythmic). In response to determining that the heart rate data satisfies the heart rate alert criteria (e.g., tracked heart rate data is determined to be arrhythmic), user interface 1410C is displayed (FIG. 14D). User interface 1410C includes a heart rate alert affordance 1430 that alerts the user that the user's tracked heart rate data satisfies a heart rate alert criteria (e.g., "Heart Health, Possible Arrhythmia Detected").

In one embodiment, the heart rate alert criteria includes a criterion based on the heart rate exceeding a heart rate threshold. For example, an instantaneous heart rate exceeds a predetermined heart rate threshold (e.g., heart rate is above 100 BPM, or a heart rate that is below 60 BPM), wherein the exceeding the predetermined heart rate threshold indicates arrhythmia. An instantaneous heart rate may be determined by measuring the inter-beat-interval between two successive heart rates. The instantaneous heart rate is based on a single interval (between successive heart beats). The instantaneous heart rate may be converted to beats per minute, and such instantaneous heart rates can therefore differ between successive beats (intervals).

In one embodiment, the heart rate alert criteria includes a criterion that is satisfied when the heart rate pattern matches a heart rate alert pattern. For example, a pattern of the instantaneous heart rate (e.g., irregular instantaneous heart rate between successive beats) matches a heart rate alert pattern that is indicative of an arrhythmia.

Displaying a heart rate alert icon when it is determined that the user's tracked heart information indicates that the user may have an arrhythmia, promptly alerts the user that they may have a heart condition that should be diagnosed by a medical professional. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

User input 1415B is received at heart rate alert affordance 1430 (FIG. 14D). In response to receiving user input 1415B at heart rate alert affordance 1430, user interface 1410D is displayed (FIG. 14E). User interface 1410D provides information directing the user that further details associated with the heart rate data can be accessed at a companion device to device 1400.

FIGS. 14F-14O depicts companion device 1490 that is paired to device 1400. Companion device 1490 includes touch sensitive display 1491. Companion device 1490, in some embodiments, when paired to device 1400 is able to display the application views and perform at least some of the same processes as device 1400, as described, herein.

Referring to FIG. 14F, user interface 1492A includes a list of affordances 1493 associated with respective applications (e.g., watch application, camera application, weather application, clock application, and health application). Affordance 1493-1 is associated with a health application. The health application displays heart rate data, which will be described in further detail below. Additionally, in some embodiments, the health application on companion device 1490 is configured to control various features and functionality of a corresponding health application on device 1400.

User input 1415C is received at affordance 1493-1 associated with the health application (FIG. 14G). In response to user input 1415C, user interface 1492B is displayed (FIG. 14H). User interface 1492B includes various affordances 1494 associated with health data. For example, user interface 1492B includes affordance 1494-1 associated with activity data, affordance 1494-2 associated with heart health data, affordance 1494-3 associated with mindfulness data, affordance 1494-4 associated with nutrition data, and affordance 1494-5 associated with sleep data.

User input 1415D is received at affordance 1494-2. User input 1415D is received at affordance 1494-2 (FIG. 14I). In response to user input 1415D, user interface 1492C is displayed (FIG. 14J). User interface 1492C includes graph 1495. Graph 1495 includes the heart rate data that satisfies the heart rate alert criteria over a period of time. For example, graph 1495 is a tachogram of the heart rate data (that satisfies the heart rate alert criteria) over a predetermined period of time (e.g., 21 seconds). Graph 1495 includes normal heart rate 1495-1 over the same time period. Graph 1495 is displayed subsequent receiving user input 1415B at heart alert affordance 1430 (FIG. 14D).

User interface 1492C includes graph type 1496-1 (e.g., tachogram), heart rate data tracking period 1496-2 (e.g., 21 seconds), additional graph information 1496-3, user instructions 1496-4, and heart alert setting 1496-5 (e.g., enabled or disabled). In one embodiment, the setting of heart rate alert setting 1496-5 corresponds to a user-selected setting at device 1490. In another embodiment, the setting of heart rate alert setting 1496-5 corresponds to a default setting at device 1490.

User interface 1492C includes scrollable heart data affordances 1497-1, 1497-2, and 1497-3. The scrollable heart data affordances are associated with a set heart rate data corresponding to data received from the physical activity tracking sensor. The scrollable heart data affordances identify the date and time that the heart rate data was received from the physical activity tracking sensor. For example, heart data affordance 1497-1 identifies the date 1498-1 (e.g., Today, Nov. 16, 2016), and time 1498-2 (e.g., 5:21 pm) that the associated data was received from the physical activity tracking sensor.

Graph 1495 corresponds with heart rate data associated with affordance 1497-1 (FIG. 14J). Accordingly, affordance 1497-1 is highlighted with respect to affordances 1497-2 and 1497-3.

Referring to FIGS. 14K-14M, user input 1415E (e.g., swipe gesture) is received near scrollable heart data affordances 1497-1, 1497-2, and 1497-3. In response to user input 1415E, heart data affordances 1497-1, 1497-2, and 1497-3 are scrolled to a new position. For example, the affordances are translated to the left such that at least affordance 1497-3 is fully displayed.

Referring to FIGS. 14N-14O, user input 1415F is received at affordance 1497-3. In response to user input 1415F received at affordance 1497-3, graph 1495 is replaced by graph 1499 (FIG. 14O). Graph 1499 corresponds with heart rate data associated with affordance 1497-3. Accordingly, affordance 1497-3 is highlighted with respect to affordances 1497-1 and 1497-2. It should be appreciated that heart rate data associated with at least one affordance (e.g., affordance 1497-1, 1497-2, or 1497-3) is heart rate data that satisfies the heart rate alert criteria. In some embodiments, heart rate data associated with at least one affordance (e.g., affordance 1497-1, 1497-2, or 1497-3) is heart rate data that does not satisfy the heart rate alert criteria.

It should be appreciated that heart rate data (e.g., heart rate data that satisfies the heart rate alert criteria) can be transmitted to an external device. For example, the heart rate data can be sent (e.g., email or text) to a device of a medical professional such that the medical professional can access/view the heart rate data.

FIG. 15 is a flow diagram illustrating a method for displaying a heart rate alert affordance. Method 1500 is performed at a device (e.g., 100, 300, 500, 600, 800, 1000, 1200, or 1400) with one or more processors, and memory. Some operations in method 1500 are, optionally, combined, the order of some operations are, optionally, changed, and some operations are, optionally, omitted.

As described below, method 1500 provides, among other things, an intuitive way for promptly alerting a user of a possible heartbeat irregularity. The method reduces the cognitive burden on a user by enabling a user to quickly view a heart rate alert and subsequently view the heart rate data that satisfies the heart rate alert criteria. For battery-operated computing devices, enabling a user to view heart rate data that satisfies the heart rate alert criteria faster and more efficiently conserves power and increases the time between battery charges.

At block 1510, while tracking heart rate data corresponding to data received from the physical activity tracking sensor (e.g., tracking current heart rate data), it is determined whether the heart rate data satisfies a heart rate alert criteria (e.g., heart rate data matches an irregular heart beat pattern).

At block 1520, in accordance to determining that the heart rate data satisfies the heart rate alert criteria, a heart rate alert affordance is displayed (e.g., 1430).

At block 1530, user input (e.g., 1415B) corresponding to the heart rate alert affordance is received.

At block 1540, subsequent to receiving the user input corresponding to the heart rate alert affordance, a graph (e.g. 1495) comprising the heart rate data that satisfies the heart rate alert criteria over a period of time is displayed. At block 1550, in accordance to determining that the heart rate data (e.g., user's current heart rate data) does not satisfy the heart rate alert criteria, forgoing display of the heart rate alert affordance (e.g., 1430 is not displayed).

In some embodiments, the graph 1495 includes expected or normal heart rate over a period of time 1495-1. In some embodiments, the heart rate alert criteria includes a criterion based on the heart rate exceeding a heart rate threshold. In some embodiments, the heart rate alert criteria includes a criterion that is satisfied when the heart rate pattern matches a heart rate alert pattern. In some embodiments, the heart rate data is instantaneous heart beat acceleration. In some embodiments, the graph 1495 of the heart rate data is a tachogram.

In some embodiments, the heart rate data is transmitted to an external device. For example, the heart rate data is sent to (e.g., email, text) a device of a medical professional.

Note that details of the processes described above with respect to method 1500 (e.g., FIG. 15) are also applicable in an analogous manner to the methods described below. For example, method 1500 optionally includes one or more of the characteristics of the various methods described above with reference to method 700. For example, method 1500, in some embodiments, includes launching a physical activity tracking function in response to selection of an affordance in scrollable list of affordances. For brevity, these details are not repeated below.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to improve the delivery to users of invitational content or any other content that may be of interest to them. The present disclosure contemplates that in some instances, this gathered data may include personal information data that uniquely identifies or can be used to contact or locate a specific person. Such personal information data can include demographic data, location-based data, telephone numbers, email addresses, home addresses, or any other identifying information.

The present disclosure recognizes that the use of such personal information data, in the present technology, can be used to the benefit of users. For example, the personal information data can be used to deliver targeted content that is of greater interest to the user. Accordingly, use of such personal information data enables calculated control of the delivered content. Further, other uses for personal information data that benefit the user are also contemplated by the present disclosure.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services. In another example, users can select not to provide location information for targeted content delivery services. In yet another example, users can select to not provide precise location information, but permit the transfer of location zone information.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publically available information.

What is claimed is:

1. An electronic device, comprising:
   a display;
   a touch-sensitive surface;
   a physical activity tracking sensor;
   one or more processors; and
   memory storing one or more programs configured to be executed by the one or more processors, the one or more programs including instructions for:
   while tracking heart rate data corresponding to data received from the physical activity tracking sensor:
      in accordance with a determination that a heart alert setting is enabled:
         determining whether the heart rate data satisfies a heart rate alert criteria wherein the heart rate alert criteria includes a criterion that is satisfied when a heart rate pattern matches a heart alert pattern;
         in accordance to determining that the heart rate data satisfies the heart rate alert criteria:
            displaying a heart rate alert affordance on the display of the electronic device;
            receiving user input corresponding to the heart rate alert affordance; and
            subsequent to receiving the user input corresponding to the heart rate alert affordance:
               transmitting the heart rate data to an external device; and
               causing display of a graph, on a display of the external device, comprising the heart rate data that satisfies the heart rate alert criteria over a period of time; and
         in accordance to determining that the heart rate data does not satisfy the heart rate alert criteria, forgo causing display of the heart rate alert affordance.

2. The electronic device of claim 1, wherein the graph further comprises expected heart rate over the period of time.

3. The electronic device of claim 1, wherein the heart rate alert criteria includes a criterion based on a heart rate exceeding a heart rate threshold.

4. The electronic device of claim 1, wherein the heart rate data is instantaneous heart beat acceleration.

5. The electronic device of claim 1, wherein the graph of the heart rate data is a tachogram.

6. A method, comprising:
   at an electronic device with a display, a touch-sensitive surface, and a physical activity tracking sensor:
      while tracking heart rate data corresponding to data received from the physical activity tracking sensor:
         in accordance with a determination that a heart alert setting is enabled:
            determining whether the heart rate data satisfies a heart rate alert criteria wherein the heart rate alert criteria includes a criterion that is satisfied when a heart rate pattern matches a heart rate alert pattern;
            in accordance to determining that the heart rate data satisfies the heart rate alert criteria:
               displaying a heart rate alert affordance on the display of the electronic device;
               receiving user input corresponding to the heart rate alert affordance; and
               subsequent to receiving the user input corresponding to the heart rate alert affordance:
                  transmitting the heart rate data to an external device; and
                  causing display of a graph, on a display of the external device, comprising the heart rate data that satisfies the heart rate alert criteria over a period of time; and
            in accordance to determining that the heart rate data does not satisfy the heart rate alert criteria, forgo causing display of the heart rate alert affordance.

7. The method of claim 6, wherein the graph further comprises expected heart rate over the period of time.

8. The method of claim 6, wherein the heart rate alert criteria includes a criterion based on a heart rate exceeding a heart rate threshold.

9. The method of claim 6, wherein the heart rate data is instantaneous heart beat acceleration.

10. The method of claim 6, wherein the graph of the heart rate data is a tachogram.

11. A non-transitory computer-readable storage medium storing one or more programs configured to be executed by one or more processors of an electronic device with a display, a touch-sensitive surface, a physical activity tracking sensor, and the one or more programs including instructions for:
   while tracking heart rate data corresponding to data received from the physical activity tracking sensor:
      in accordance with a determination that a heart alert setting is enabled:
         determining whether the heart rate data satisfies a heart rate alert criteria, wherein the heart rate alert criteria includes a criterion that is satisfied when a heart rate pattern matches a heart rate alert pattern;
         in accordance to determining that the heart rate data satisfies the heart rate alert criteria:
            displaying a heart rate alert affordance on the display of the electronic device;
            receiving user input corresponding to the heart rate alert affordance; and
            subsequent to receiving the user input corresponding to the heart rate alert affordance:
               transmitting the heart rate data to an external device; and
               causing display of a graph, on a display of the external device, comprising the heart rate data that satisfies the heart rate alert criteria over a period of time; and
         in accordance to determining that the heart rate data does not satisfy the heart rate alert criteria, forgo causing display of the heart rate alert affordance.

12. The computer-readable storage medium of claim 11, wherein the graph further comprises expected heart rate over the period of time.

13. The computer-readable storage medium of claim 11, wherein the heart rate alert criteria includes a criterion based on a heart rate exceeding a heart rate threshold.

14. The computer-readable storage medium of claim 11, wherein the heart rate data is instantaneous heart beat acceleration.

15. The computer-readable storage medium of claim 11, wherein the graph of the heart rate data is a tachogram.

\* \* \* \* \*